(12) United States Patent
Rennie et al.

(10) Patent No.: US 10,844,064 B2
(45) Date of Patent: *Nov. 24, 2020

(54) SGC STIMULATORS

(71) Applicant: Cyclerion Therapeutics, Inc., Cambridge, MA (US)

(72) Inventors: Glen Robert Rennie, Somerville, MA (US); Nicholas Perl, Somerville, MA (US); Ara Mermerian, Waltham, MA (US); Joon Jung, Newton, MA (US); Lei Jia, San Diego, CA (US); Rajesh R. Iyengar, West Newton, MA (US); G-Yoon Jamie Im, Cambridge, MA (US); Timothy Claude Barden, Salem, MA (US); James Edward Sheppeck, Newtown, PA (US); Paul Allan Renhowe, Sudbury, MA (US); Takashi Nakai, Newton, MA (US); Thomas Wai-Ho Lee, Lexington, MA (US); Karthik Iyer, Cambridge, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/511,888

(22) PCT Filed: Sep. 16, 2015

(86) PCT No.: PCT/US2015/050467
§ 371 (c)(1),
(2) Date: Mar. 16, 2017

(87) PCT Pub. No.: WO2016/044446
PCT Pub. Date: Mar. 24, 2016

(65) Prior Publication Data
US 2018/0155345 A1 Jun. 7, 2018

Related U.S. Application Data

(60) Provisional application No. 62/204,698, filed on Aug. 13, 2015, provisional application No. 62/051,576, filed on Sep. 17, 2014.

(51) Int. Cl.
*C07D 487/04* (2006.01)
*C07D 413/14* (2006.01)
(Continued)

(52) U.S. Cl.
CPC .............. *C07D 487/04* (2013.01); *A61P 9/10* (2018.01); *A61P 15/00* (2018.01); *A61P 29/00* (2018.01); *C07D 401/04* (2013.01); *C07D 401/14* (2013.01); *C07D 405/14* (2013.01); *C07D 413/14* (2013.01); *C07D 417/14* (2013.01); *C07D 498/04* (2013.01)

(58) Field of Classification Search
CPC .. C07D 487/04; C07D 401/04; C07D 401/14; C07D 405/14; C07D 413/14; C07D 417/14; C07D 498/04; A61P 9/10; A61P 15/00; A61P 29/00
USPC ........................................................ 514/243
See application file for complete search history.

(56) References Cited

U.S. PATENT DOCUMENTS 8,748,442 B2 * 6/2014 Kim ................... A61K 31/4155
514/269
9,139,564 B2 * 9/2015 Kim ..................... C07D 413/14
(Continued)

FOREIGN PATENT DOCUMENTS

WO    2012003405 A1    1/2012
WO    2013101830 A1    7/2013
(Continued)

OTHER PUBLICATIONS

Chemical Abstracts STN Registry Database, record for RN 1604827-89-5, Entered into STN on May 14, 2014. (Year: 2014).*
(Continued)

*Primary Examiner* — Daniel R Carcanague
(74) *Attorney, Agent, or Firm* — McCarter & English, LLP; Steven G. Davis; Xin Zhang

(57) ABSTRACT

The present patent application discloses at least the compounds according to Formula I' shown below, or pharmaceutically acceptable salts thereof,

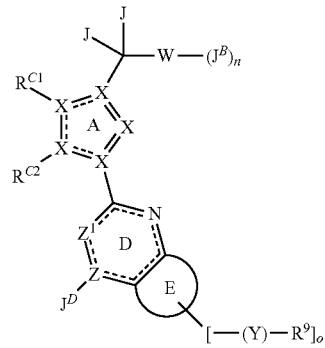

Formula I' wherein ring D, ring A, ring E, $J^B$, n, $J^D$, J, X, Z, $Z^1$, $R^{C1}$, $R^{C2}$, Y, $R^9$, o and W are as defined herein.

9 Claims, No Drawings

(51) Int. Cl.
*C07D 401/14* (2006.01)
*C07D 417/14* (2006.01)
*C07D 405/14* (2006.01)
*C07D 401/04* (2006.01)
*A61P 9/10* (2006.01)
*A61P 15/00* (2006.01)
*A61P 29/00* (2006.01)
*C07D 498/04* (2006.01)

(56) References Cited

U.S. PATENT DOCUMENTS

| | | | | |
|---|---|---|---|---|
| 8,748,442 C1* | 4/2016 | Kim | ............ | A61K 31/4155 |
| | | | | 514/269 |
| 9,481,689 B2* | 11/2016 | Nakai | ............ | C07D 413/14 |
| 9,487,508 B2* | 11/2016 | Nakai | ............ | A61K 45/06 |
| 9,586,937 B2* | 3/2017 | Nakai | ............ | C07D 413/14 |
| 10,047,095 B2* | 8/2018 | Perl | ............ | C07D 471/04 |
| 2011/0166152 A1* | 7/2011 | Leclerc | ............ | C07D 403/04 |
| | | | | 514/249 |
| 2012/0184516 A1* | 7/2012 | Kim | ............ | A61K 31/4155 |
| | | | | 514/171 |
| 2013/0178475 A1* | 7/2013 | Moore | ............ | C07D 401/04 |
| | | | | 514/245 |
| 2013/0210768 A1* | 8/2013 | Arrington | ............ | C07D 471/04 |
| | | | | 514/63 |
| 2014/0088071 A1* | 3/2014 | Nakai | ............ | C07D 401/04 |
| | | | | 514/210.2 |
| 2014/0323448 A1* | 10/2014 | Kim | ............ | A61K 31/4155 |
| | | | | 514/171 |
| 2015/0018353 A1* | 1/2015 | Kim | ............ | C07D 413/14 |
| | | | | 514/236.5 |
| 2015/0232461 A1* | 8/2015 | Nakai | ............ | C07D 413/14 |
| | | | | 514/236.5 |
| 2015/0274712 A1* | 10/2015 | Im | ............ | C07D 413/14 |
| | | | | 514/269 |
| 2015/0342954 A1* | 12/2015 | Kim | ............ | C07D 413/14 |
| | | | | 514/236.5 |
| 2016/0031903 A1* | 2/2016 | Nakai | ............ | C07D 413/14 |
| | | | | 514/210.18 |
| 2016/0311826 A1* | 10/2016 | Renhowe | ............ | C07D 405/14 |
| 2016/0324856 A1* | 11/2016 | Long | ............ | A61K 31/4439 |
| 2016/0347738 A1* | 12/2016 | Nakai | ............ | C07D 413/14 |
| 2016/0375022 A1* | 12/2016 | Nakai | ............ | C07D 413/14 |
| | | | | 514/256 |
| 2017/0065586 A1* | 3/2017 | Nakai | ............ | A61K 45/06 |
| 2017/0112845 A1* | 4/2017 | Kim | ............ | C07D 401/04 |
| 2017/0136019 A1* | 5/2017 | Nakai | ............ | A61K 31/506 |
| 2017/0137439 A1* | 5/2017 | Nakai | ............ | C07D 498/04 |
| 2017/0291889 A1* | 10/2017 | Barden | ............ | C07D 401/14 |
| 2017/0291902 A1* | 10/2017 | Perl | ............ | C07D 471/04 |
| 2017/0298055 A1* | 10/2017 | Rennie | ............ | C07D 413/14 |
| 2017/0305878 A1* | 10/2017 | Kim | ............ | A61K 31/4155 |
| 2018/0065971 A1* | 3/2018 | Rennie | ............ | A61K 31/437 |

FOREIGN PATENT DOCUMENTS

| | | | | |
|---|---|---|---|---|
| WO | WO 2014047325 | * | 3/2014 | |
| WO | WO 2014060112 | * | 4/2014 | |
| WO | 2014144100 A2 | | 9/2014 | |
| WO | WO 2015021358 | * | 2/2015 | |
| WO | 2015089182 A1 | | 6/2015 | |
| WO | WO 2017106175 | * | 6/2017 | |
| WO | WO 2017136309 | * | 8/2017 | |
| WO | WO-2018111795 A2 | * | 6/2018 | ............ A61K 31/165 |

OTHER PUBLICATIONS

Cosyn; Journal of Medicinal Chemistry 2006, 49, 7373-7383. (Year: 2006).*
International Search Report and Written Opinion issued in PCT/US2015/050467, dated Mar. 5, 2016.

* cited by examiner

SGC STIMULATORS

CROSS REFERENCE TO RELATED APPLICATIONS

This application is a U.S. National Phase filing under 35 U.S.C. § 371 of International Application PCT/US2015/050467, filed Sep. 16, 2015, and published as WO 2016/044446 on Mar. 24, 2016. PCT/US2015/050467 claims priority from U.S. provisional application Nos. 62/051,576, filed Sep. 17, 2014, and 62/204,698, filed Aug. 13, 2015. The entire contents of each of these applications are hereby incorporated herein by reference.

FIELD OF THE INVENTION

The present disclosure relates to stimulators of soluble guanylate cyclase (sGC), pharmaceutical formulations comprising them and their uses thereof, alone or in combination with one or more additional agents, for treating and/or preventing various diseases, wherein an increase in the concentration of nitric oxide (NO) or an increase in the concentration of cyclic Guanosine Monophosphate (cGMP) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure. Experimental and clinical evidence indicates that reduced bioavailability and/or responsiveness to endogenously produced NO contributes to the development of cardiovascular, endothelial, renal and hepatic disease, as well as erectile dysfunction and other sexual disorders (e.g. female sexual disorder or vaginal atrophy).

In particular, the NO signaling pathway is altered in cardiovascular diseases, including, for instance, systemic and pulmonary hypertension, heart failure, angina, stroke, thrombosis and other thromboembolic diseases, peripheral arterial disease, fibrosis of the liver, lung or kidney and atherosclerosis. sGC stimulators are also useful in the treatment of lipid related disorders such as e.g., dyslipidemia, hypercholesterolemia, hypertriglyceridemia, sitosterolemia, fatty liver disease, and hepatitis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They are potentially useful in the prevention, management and treatment of disorders such as pulmonary hypertension, arterial hypertension, heart failure, atherosclerosis, inflammation, thrombosis, renal fibrosis and failure, liver cirrhosis, lung fibrosis, erectile dysfunction, female sexual arousal disorder and vaginal atrophy and other cardiovascular disorders; they are also potentially useful for the prevention, management and treatment of lipid related disorders.

SUMMARY OF THE INVENTION

A compound of Formula I', or a pharmaceutically acceptable salt thereof:

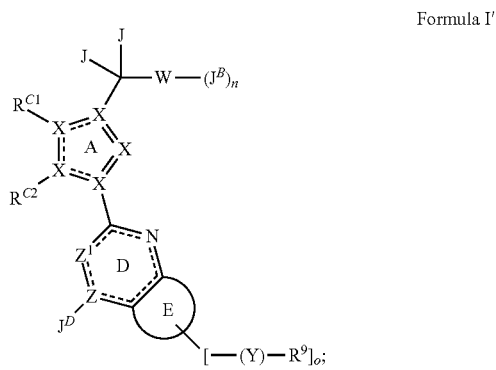

Formula I' wherein:

ring A is a 5-membered heteroaryl ring; each instance of X is independently selected from C or N and the bond between each two instances of X is either a single or a double bond so as to make ring A an aromatic heterocycle; wherein a minimum of 2 instances of X and a maximum of 3 instances of X in ring A can simultaneously be N;

W is either i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and up to 9 instances of fluorine; wherein, optionally, one —CH$_2$— unit of said C$_{2-7}$ alkyl chain can be replaced by —O— or —S—.

ii) a ring B selected from phenyl, a 5 or 6-membered heteroaryl ring, containing 1 or 2 ring heteroatoms independently selected from N, O or S, a C$_{3-7}$ cycloalkyl ring and a 4 to 7-membered heterocyclic ring, containing up to 3 heteroatoms independently selected from O, N or S;

wherein when W is ring B each J is hydrogen;

n is 0 or an integer selected from 1, 2 or 3;

each J$^B$ is independently selected from halogen, —CN, a C$_{1-6}$ aliphatic, —OR$^B$ or a C$_{3-8}$ cycloaliphatic group; wherein each said C$_{1-6}$ aliphatic and each said C$_{3-8}$ cycloaliphatic group is optionally and independently substituted with up to 3 instances of R$^3$;

each R$^B$ is independently selected from hydrogen, a C$_{1-6}$ aliphatic or a C$_{3-8}$ cycloaliphatic; wherein each of said R$^B$ that is a C$_{1-6}$ aliphatic and each of said R$^B$ that is a C$_{3-8}$ cycloaliphatic ring is optionally and independently substituted with up to 3 instances of R$^{3a}$;

each R$^3$ is independently selected from halogen, —CN, C$_{1-4}$ alkyl, C$_{1-4}$ haloalkyl, —O(C$_{1-4}$ alkyl) or —O(C$_{1-4}$ haloalkyl);

each R$^{3a}$ is independently selected from halogen, —CN, C$_{1-4}$ alkyl, C$_{1-4}$ haloalkyl, —O(C$_{1-4}$ alkyl) or —O(C$_{1-4}$ haloalkyl);

Z$^1$ in ring D is selected from CH, CF or N; Z is selected from C or N; wherein if Z$^1$ is CH or CF, then Z must be C; and if Z$^1$ is N, then Z may be C or N;

each J$^D$ is independently selected from J$^A$, —CN, —NO$_2$, —OR$^D$, —SR$^D$, —C(O)R$^D$, —C(O)OR$^D$, —OC(O)R$^D$, —C(O)N(R$^D$)$_2$, —N(R$^D$)$_2$, —N(R$^d$)C(O)R$^D$, —N(R$^d$)C(O)OR$^D$, —N(R$^d$)C(O)N(R$^D$)$_2$, —OC(O)N(R$^D$)$_2$, —SO$_2$R$^D$, —SO$_2$N(R$^D$)$_2$, —N(R$^d$)SO$_2$R$^D$, —N(R$^d$)SO$_2$NHR$^D$, —N(R$^d$)SO$_2$NHC(O)OR$^D$, —N(R$^d$)SO$_2$NHC(O)R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said C$_{1-6}$ aliphatic, each said C$_{1-6}$ aliphatic portion of the —(C$_{1-6}$ aliphatic)-R$^D$ moiety, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of R$^{5d}$;

J$^A$ is selected from a lone pair on nitrogen, hydrogen, halogen, oxo, methyl, hydroxyl, methoxy, trifluoromethyl, trifluoromethoxy or —NR$^a$R$^b$; wherein R$^a$ and R$^b$ are each independently selected from hydrogen, C$_{1-6}$ alkyl or a 3-6 cycloalkyl ring; or wherein R$^a$ and R$^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;

each R$^D$ is independently selected from hydrogen, a C$_{1-6}$ aliphatic, —(C$_{1-6}$ aliphatic)-R$^f$, a C$_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 10-membered heterocyclic ring, each said phenyl and each said 5 to 6-membered heteroaryl ring is optionally and independently substituted with up to 5 instances of R$^{5a}$; wherein when any R$^D$ is one of a C$_{1-6}$ aliphatic or a —(C$_{1-6}$ aliphatic)-R$^f$ group, one or two —CH$_2$— units that form said C$_{1-6}$ aliphatic chains may, optionally, be replaced by a group independently selected from —N(R$^d$)—, —CO— or —O—;

each R$^d$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$; wherein when any R$^d$ is one of a C$_{1-6}$ aliphatic or a —(C$_{1-6}$ aliphatic)-R$^f$ group, one or two —CH$_2$— units that form said C$_{1-6}$ aliphatic chains may, optionally, be replaced by a group independently selected from —N(R$^{dd}$)—, —CO— or —O—;

each R$^{dd}$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$;

each R$^f$ is independently selected from a C$_{1-3}$ alkyl, a C$_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said C$_{3-8}$ cycloaliphatic ring, each said 4 to 10-membered heterocyclic ring, each said phenyl and each said 5 to 6-membered heteroaryl ring is optionally and independently substituted by up to 5 instances of R$^{5c}$;

when J$^D$ is —C(O)N(R$^D$)$_2$, —N(R$^D$)$_2$, —N(R$^d$)C(O)N(R$^D$)$_2$, —OC(O)N(R$^D$)$_2$ or —SO$_2$N(R$^D$)$_2$, the two R$^D$ groups together with the nitrogen atom attached to the two R$^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two R$^D$ groups are attached; and wherein each said 4 to 8-membered heterocyclic ring and each said 5-membered heteroaryl ring is optionally and independently substituted by up to 5 instances of R$^5$;

when J$^D$ is —N(R$^d$)C(O)R$^D$, the R$^D$ group together with the carbon atom attached to the R$^D$ group, with the nitrogen atom attached to the R$^d$ group, and with the R$^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)C(O)N($R^D$)$_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)SO$_2$$R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2$$R^6$, —N($R^6$)C(O)$R^6$, —N($R^6$)C(O)O$R^6$, —N($R^6$)C(O)N($R^6$)$_2$, —N($R^6$)$_2$, —SO$_2$$R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2$$R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —CONH$_2$, —OH or halogen; wherein R is hydrogen or a $C_{1-2}$ alkyl;

each $R^{5a}$ is independently selected from halogen, —CN, $C_{1-6}$ alkyl, —($C_{1-6}$ alkyl)$R^{6a}$, —S$R^{6a}$, —CO$R^{6a}$, —OC(O)$R^{6a}$, —C(O)O$R^{6a}$, —C(O)N($R^{6a}$)$_2$, —C(O)N($R^{6a}$)SO$_2$$R^{6a}$, —N($R^{6a}$)C(O)$R^{6a}$, —N($R^{6a}$)C(O)O$R^{6a}$, —N($R^{6a}$)C(O)N($R^{6a}$)$_2$, —N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, —N($R^{6a}$)SO$_2$$R^{6a}$, —(C=O)NHO$R^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$alkyl), —O($C_{1-4}$ alkyl), —O($C_{1-4}$ haloalkyl) or oxo;

each $R^{5b}$ is independently selected from halogen, —CN, $C_{1-6}$ alkyl, —($C_{1-6}$ alkyl)$R^{6a}$, —S$R^{6a}$, —CO$R^{6a}$, —OC(O)$R^{6a}$, —C(O)O$R^{6a}$, —C(O)N($R^{6a}$)$_2$, —C(O)N($R^{6a}$)SO$_2$$R^{6a}$, —N($R^{6a}$)C(O)$R^{6a}$, —N($R^{6a}$)C(O)O$R^{6a}$, —N($R^{6a}$)C(O)N($R^{6a}$)$_2$, —N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, —N($R^{6a}$)SO$_2$$R^{6a}$, —(C=O)NHO$R^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of R$^{5a}$ or two instances of R$^{5b}$ attached to the same or different atoms of R$^D$ or R$^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each R$^{5c}$ is independently selected from halogen, —CN, $C_{1-6}$ alkyl, —($C_{1-6}$ alkyl)-R$^{6b}$, —OR$^{6a}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of R$^{5c}$ attached to the same or different atoms of R$^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each R$^{5d}$ is independently selected from halogen, —CN, $C_{1-6}$ alkyl, —($C_{1-6}$ alkyl)-R$^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-R$^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of R$^{5d}$ attached to the same or different atoms of J$^D$, together with said atom or atoms of J$^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each R$^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), —C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

ring E is a 5 to 7-membered heterocycle or a 5-membered heteroaryl ring; said heterocycle or heteroaryl ring containing up to 4 heteroatoms independently selected from N, O and S;

o is 0 or an integer selected from 1, 2, 3 or 4;

Y is either absent or is a $C_{1-6}$ alkyl chain, optionally substituted by up to 6 instances of fluoro; and wherein in said Y that is a $C_{1-6}$ alkyl chain, up to 3 methylene units of this alkyl chain, can be replaced by a group selected from —O—, —C(O)— or —N(($Y^1$)—$R^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$ a $C_{3-6}$ cycloalkyl, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$; and when $Y^1$ is present, each $R^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$. —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each $R^9$ is independently selected from hydrogen, halogen, a $C_{1-6}$ alkyl, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each $R^{10}$ is independently selected from hydrogen, a $C_{1-6}$ alkyl, —($C_{1-6}$ alkyl)-R$^{13}$, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of R$^{11a}$;

each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of $R^{121}$;

each $R^{11a}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of $R^{121}$; and each $R^{11b}$ is independently selected from halogen, $C_{1-6}$ alkyl, oxo, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of $R^{121}$;

each $R^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ fluoroalkyl) or oxo;

each $R^{121}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ fluoroalkyl) or oxo;

$R^{C1}$ is either
i) a ring C; or
ii) is selected from a lone pair on a nitrogen atom, hydrogen, halogen, oxo, —CN, $C_{1-6}$ aliphatic, —(C$_{1-6}$ aliphatic)-R$^N$, —OR$^7$, —OC(O)R$^7$, —O(R$^7$)C(O)N(R$^7$)$_2$, —COR$^7$, —C(O)OR$^7$, —C(O)N(R$^7$)$_2$, —N(R$^7$)C(O)R$^7$, —N(R$^7$)C(O)OR$^7$, —N(R$^7$)C(O)N(R$^7$)$_2$, —N(R$^7$)$_2$, —SR$^7$, —S(O)R$^7$, —SO$_2$R$^7$, —SO$_2$N(R$^7$)$_2$, —C(O)N(R$^7$)SO$_2$R$^7$, —SO$_2$N(R$^7$)COOR$^7$, —SO$_2$N(R$^7$)C(O)R$^7$ or —N(R$^7$)SO$_2$R$^7$; wherein each said $C_{1-6}$ aliphatic, each $C_{1-6}$ aliphatic portion of said —(C$_{1-6}$ aliphatic)-R$^N$, is optionally and independently substituted with up to 6 instances of fluoro and up to 2 instances of —CN, —OR$^8$, oxo, —N(R$^8$)$_2$, —N(R$^8$)C(O)R$^8$, —N(R$^8$)C(O)OR$^8$, —N(R$^8$)C(O)N(R$^8$)$_2$, —SO$_2$R$^8$, —SO$_2$N(R$^8$)$_2$, —NHOR$^8$, —SO$_2$N(R$^8$)COOR$^8$, —SO$_2$N(R$^8$)C(O)R$^8$, —N(R$^8$)SO$_2$R$^8$;

wherein each $R^7$ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each $R^8$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —OR$^M$, —SR$^M$, —N(R$^M$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of $J^C$; wherein p is 0 or an integer selected from 1, 2 or 3.

each $J^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two $J^C$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of $R^H$ linked to the same nitrogen atom of —N(R$^H$)$_2$, together with said nitrogen atom of —N(R$^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each $R^{7c}$ is independently selected from halogen, —CN, —NO$_2$, $C_{1-4}$ alkyl, $C_{1-4}$ haloalkyl, $C_{3-8}$ cycloalkyl ring, —OR$^{8b}$, —SR$^{8b}$, —N(R$^{8b}$)$_2$, —C(O)O(C$_{1-4}$ alkyl), —C(O)OH, —NR(CO)CO(C$_{1-4}$ alkyl) or an oxo group; wherein each said cycloalkyl group is optionally and independently substituted with up to 3 instances of halogen;

each $R^{7d}$ is independently selected from halogen, —CN, —NO$_2$, $C_{1-4}$ alkyl, $C_{1-4}$ haloalkyl, $C_{3-8}$ cycloalkyl ring, —C(O)O(C$_{1-4}$ alkyl), —C(O)OH, —N(R$^{8c}$)$_2$, or an oxo group; wherein each said cycloalkyl group is optionally and independently substituted with up to 3 instances of halogen;

each $R^{8b}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each $R^{8c}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo; and $R^{C2}$ is selected from a lone pair on a nitrogen atom, hydrogen, halogen, —OH, —O(C$_{1-6}$ alkyl), —O(haloC$_{1-6}$ alkyl), —O(C$_{1-6}$ haloalkyl), —O(cyclopropyl), cyclopropyl, $C_{1-6}$ alkyl, $C_{1-6}$ haloalkyl and —CN;

provided that the compound is not one represented by any one of Formulae A-1 to Formula A-8 depicted below:

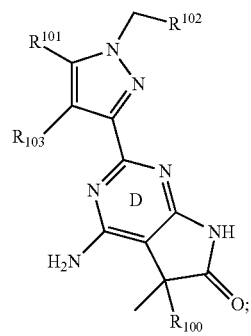

Formula A-1 wherein, $R^{100}$ is selected from —C(O)NH$_2$, —C(O)NH (cyclopropyl), —C(O)NH—NH$_2$, —C(O)NH—NH—C(O)Me or —C(O)OEt; $R^{101}$ is selected from isoxazole, —O(C$_{1-3}$ alkyl) or OH; $R^{102}$ is selected from 2-fluorophenyl or 2,2,2-trifluoroethyl; $R^{103}$ is selected from H, Me or —CN;

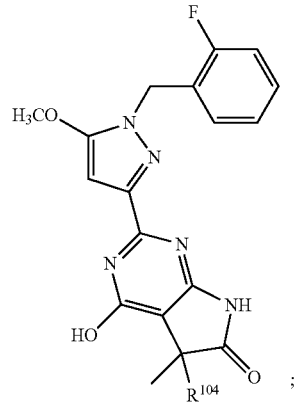

Formula A-2 wherein $R^{104}$ is selected from —NHC(O)OMe, —C(O)NH (cyclopropyl) or —C(O)OEt;

Formula A-3

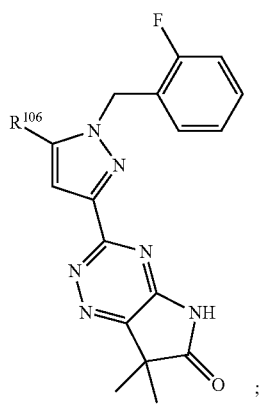

wherein $R^{106}$ is selected from isoxazole and —OCH$_3$;

Formula A-4

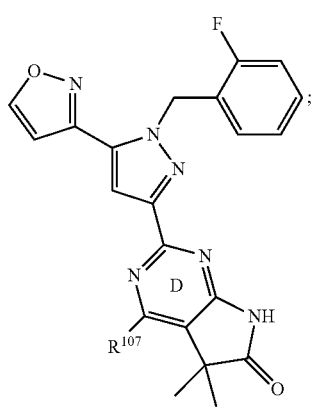

wherein $R^{107}$ is selected from hydrogen or —NH$_2$;

Formula A-5

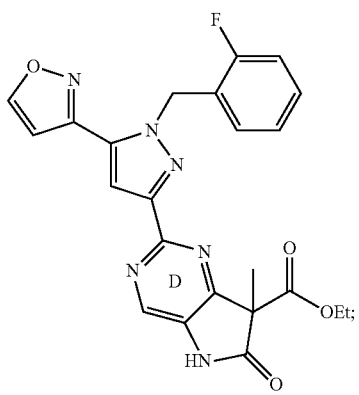

Formula A-6

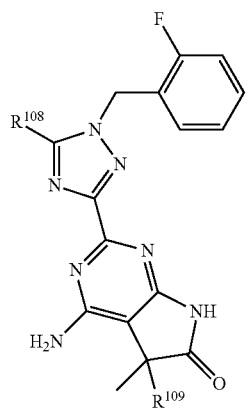

wherein $R^{108}$ is selected from OH or —OCH$_3$; wherein $R^{109}$ is selected from —C(O)NH$_2$, —C(O)NH(cyclopropyl) or —C(O)OEt;

Formula A-7

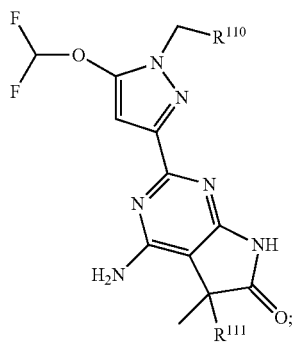

wherein $R^{110}$ is selected from a difluorinated benzyl ring or 3,3,3,2,2-pentafluoropropyl; wherein $R^{111}$ is selected from —CH$_3$, —C(O)NH$_2$, —C(O)NH(cyclopropyl) or —C(O)OEt;

Formula A-8

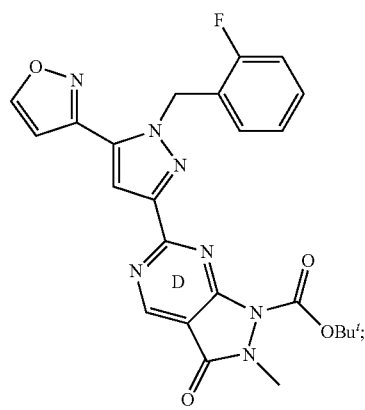

also, provided that the compound is not one represented by any one of Formula B-1 to Formula B-5 or a pharmaceutically acceptable salt thereof, Formula B-1

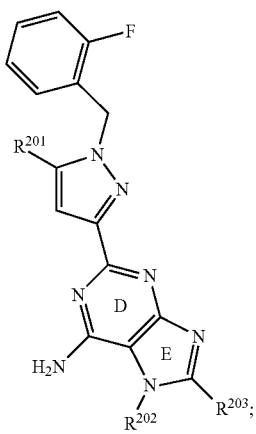

wherein $R^{201}$ is selected from thiazole or oxazole; $R^{202}$ is selected from hydrogen or methyl; $R^{203}$ is selected from —OH or —CH$_3$;

Formula B-2

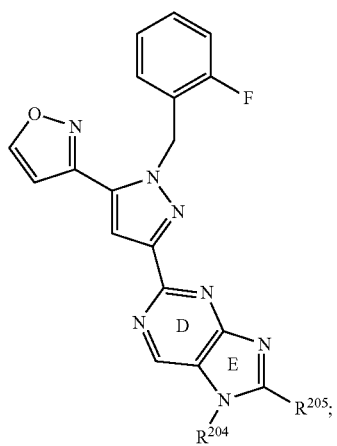

wherein $R^{204}$ is selected from hydrogen, methyl or —C(O)NH(Bu$^t$); $R^{205}$ is selected from hydrogen or —OH;

Formula B-3

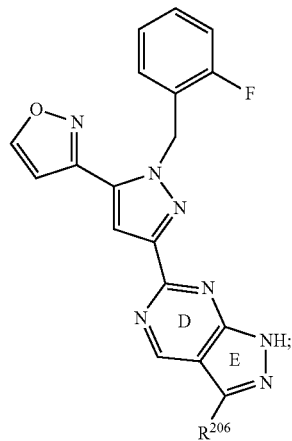

wherein $R^{206}$ is selected from —NH$_2$, —NHC(O)Me and hydrogen;

Formula B-4

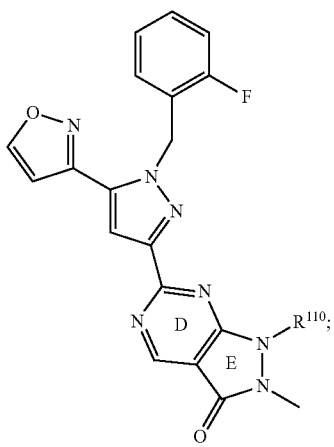

wherein $R^{110}$ is selected from hydrogen or a Boc protecting group;

Formula B-5

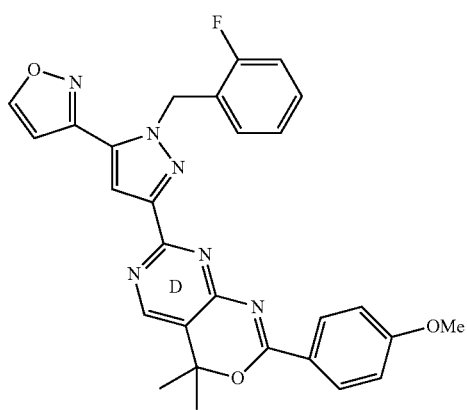

and provided the compound is not one of the compounds depicted below:

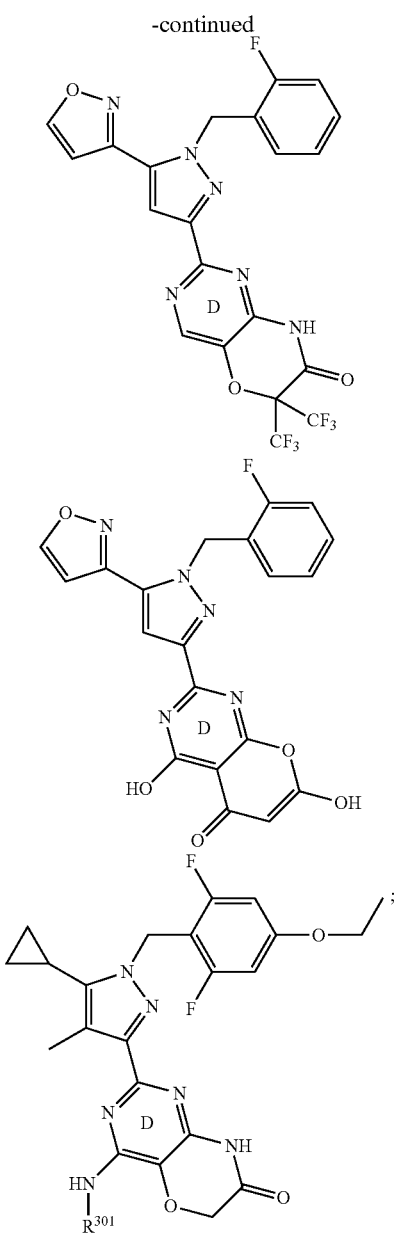

wherein R³⁰¹ is selected from pyridine, pyrimidine or hydrogen.

The invention is also directed to a pharmaceutical composition comprising a compound disclosed herein, or a pharmaceutically acceptable salt thereof, and at least one pharmaceutically acceptable excipient.

The invention is also directed to a pharmaceutical formulation or dosage form comprising the pharmaceutical composition and at least one excipient or carrier.

The invention also provides a method of treating or preventing a disease, health condition or disorder in a subject in need thereof, comprising administering, alone or in combination therapy, a therapeutically effective amount of a compound of Formula I', Formula I or Table I, or a pharmaceutically acceptable salt thereof, to the subject; wherein the disease, health condition or disorder is a peripheral, pulmonary, hepatic, kidney, cardiac or cerebral vascular/endothelial disorder or condition, a urogenital-gynecological or sexual disorder or condition, a thromboembolic disease, an ischemic disorder, a fibrotic disorder, a pulmonary or respiratory disorder, renal or hepatic disorder, ocular disorder, hearing disorder, CNS disorder, circulation disorder, topical or skin disorder, metabolic disorder, autoimmune disorder, inflammation mediated disorder, atherosclerosis, wound or bone healing, alopecia, certain cancers, or a lipid related disorder that benefits from sGC stimulation or from an increase in the concentration of NO or cGMP.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula I', Formula I or Table I may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as the compounds of Formula I', Formula I or Table I or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention. As an example, a substituent drawn as below:

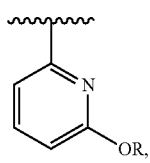

wherein R may be hydrogen, would include both compounds shown below:

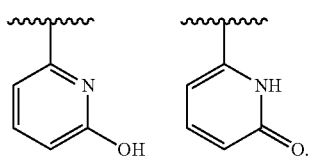 [SMILES: *c1cccc(O)n1 ; *c1cccc(=O)[nH]1]

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}$H, $^{3}$, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. To be perfectly clear, the term "aliphatic chain" may be used interchangeably with the term "aliphatic" or "aliphatic group".

The term "alkyl" (as in "alkyl chain" or "alkyl group"), as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" (as in "alkenyl chain" or "alkenyl group"), refers to a linear or branched-chain monovalent hydrocarbon radical with at least one site of unsaturation, i.e., a carbon-carbon, sp$^{2}$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" (as in "alkynyl chain" or "alkynyl group"), refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Cycloalkyl", as used herein, refers to a ring system in which is completely saturated and which has a single point of attachment to the rest of the molecule. Unless otherwise specified, a cycloalkyl group may be monocyclic, bicyclic, tricyclic, fused, spiro or bridged. In one embodiment, the term "cycloalkyl" refers to a monocyclic $C_3$-$C_{12}$ saturated hydrocarbon or a bicyclic $C_7$-$C_{12}$ saturated hydrocarbon. In some embodiments, any individual ring in a bicyclic or tricyclic ring system has 3-7 members. Suitable cycloalkyl groups include, but are not limited to, cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound of Formula I', Formula I or Table I. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0³,⁷]nonyl. "Spiro" bicyclic ring systems share only one ring atom (usually a quaternary carbon atom) between the two rings.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR⁺ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloaliphatic ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule. For example, where a phenyl group is substituted with two occurrences of —OR° as in Formula D1:

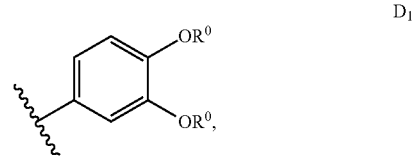

D₁ these two occurrences of —OR° are taken together with the carbon atoms to which they are bound to form a fused 6-membered oxygen containing ring as in Formula D2:

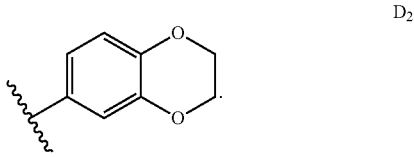 [SMILES: *c1ccc2c(c1)OCCO2]

D₂

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH. In another example, if the divalent linker —CH₂CH₂CH₂— were optionally interrupted with —O—, the resulting compound could be —OCH₂CH₂—, —CH₂OCH₂—, or —CH₂CH₂O—. The optional replacements can also completely replace all of the carbon atoms in a chain. For example, a $C_3$ aliphatic can be optionally replaced by —N(R')—, —C(O)—, and —N(R')— to form —N(R')C(O)N(R')-(a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

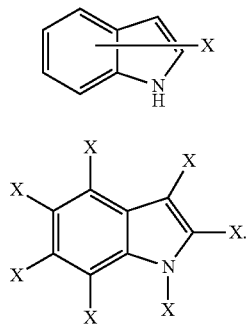

This also applies to multiple ring systems fused to optional ring systems (which would be represented by dotted lines). For example, in Formula D5, X is an optional substituent both for ring A and ring B.

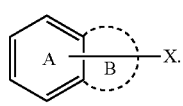

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

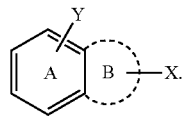

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms $C_{n-m}$ "alkoxyalkyl", $C_{n-m}$ "alkoxyalkenyl", $C_{n-m}$ "alkoxyaliphatic", and $C_{n-m}$ "alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4-6}$ alkoxyalkyl has a total of 4-6 carbons divided between the alkyl and alkoxy portion; e.g. it can be —CH₂OCH₂CH₂CH₃, —CH₂CH₂OCH₂CH₃ or —CH₂CH₂CH₂OCH₃.

When the moieties described in the preceding paragraph are optionally substituted, they can be substituted in either or both of the portions on either side of the oxygen or sulfur. For example, an optionally substituted $C_4$ alkoxyalkyl could be, for instance, CH₂CH₂OCH₂(Me)CH₃ or —CH₂(OH)OCH₂CH₂CH₃; a $C_5$ alkoxyalkenyl could be, for instance, —CH═CHO CH₂CH₂CH₃ or —CH═CHCH₂OCH₂CH₃.

The terms aryloxy, arylthio, benzyloxy or benzylthio, refer to an aryl or benzyl group attached to the molecule, or to another chain or ring, through an oxygen ("aryloxy", benzyloxy e.g., —O-Ph, —OCH₂Ph) or sulfur ("arylthio" e.g., —S-Ph, —S—CH₂Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1-4}$ alkyl) is a 5-6 membered aryl ring, attached via an oxygen atom to a $C_{1-4}$ alkyl chain which, in turn, is attached to the rest of the molecule via the terminal carbon of the $C_{1-4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH₂CHF₂ and a $C_{1-2}$ haloalkoxy could be —OC(Br)HCHF₂. This term includes perfluorinated alkyl groups, such as —CF₃ and —CF₂CF₃.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be =CHC(CN)H$_2$.

As used herein, an "amino" group refers to NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a $C_{1-3}$ aminoalkyl could be —CH(NH$_2$)CH$_2$CH$_2$NH$_2$ and a $C_{1-2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1-3}$ hydroxyalkyl could be —CH$_2$(CH$_2$OH)CH$_3$ and a $C_4$ hydroxyalkoxy could be OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$. When an "oxo" group is listed as a possible substituent on a ring or another moiety or group (e.g. an alkyl chain) it will be understood that the bond between the oxygen in said oxo group and the ring, or moiety it is attached to will be a double bond, even though sometimes it may be drawn generically with a single line. For example, in the example depicted below, $J^D$ attached to ring D below may be selected from a number of different substituents. When $J^D$ is oxo, it will be understood that the bond between $J^D$ and ring D is a double bond. When $J^D$ is a halogen, it will be understood that the bond between $J^D$ and ring D is a single bond. In some instances, for example when ring D contains an unsaturation or it has aromatic character, the compound may exist in two or more possible tautomeric forms. In one of them the bond between the oxo group and ring D will be a double bond. In the other one, a hydrogen bond will be exchanged between atoms and substituents in the ring, so that the oxo becomes a hydroxy and an additional double bond is formed in the ring. Whereas the compound is depicted as D7 or D8, both will be taken to represent the set of all possible tautomers for that particular compound.

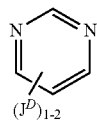

could be, for example:

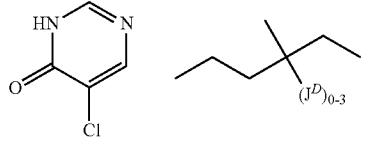

could be, for example:

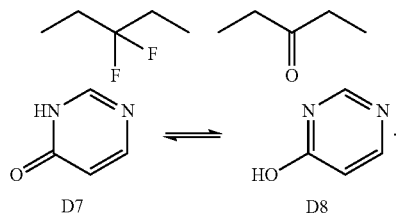

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be $C_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a $C_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a $C_3$ alkyl chain optionally interrupted by up to two —C(O)— or —NH— moieties. Cyclic groups can also form linkers: e.g. a 1,6-cyclohexanediyl can be a linker between two R groups, as in

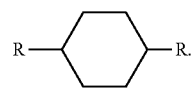

A linker can additionally be optionally substituted in any portion or position.

Divalent groups of the type R—CH= or R$_2$C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. Gin "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compound Embodiments

In a first aspect, the invention is directed to a compound according to Formula I', or a pharmaceutically acceptable salt thereof

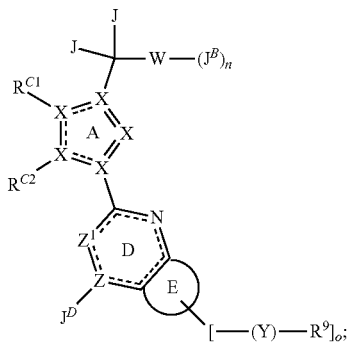

Formula I' wherein:
ring A is a 5-membered heteroaryl ring; each instance of X is independently selected from C or N and the bond between each two instances of X is either a single or a double bond so as to make ring A an aromatic heterocycle; wherein a minimum of 2 instances of X and a maximum of 3 instances of X in ring A can simultaneously be N;

W is either
i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and up to 9 instances of fluorine; wherein, optionally, one —$CH_2$— unit of said $C_{2-7}$ alkyl chain can be replaced by —O— or —S—.

ii) a ring B selected from phenyl, a 5 or 6-membered heteroaryl ring, containing 1 or 2 ring heteroatoms independently selected from N, O or S, a $C_{3-7}$ cycloalkyl ring and a 4 to 7-membered heterocyclic ring, containing up to 3 heteroatoms independently selected from O, N or S;

wherein when W is ring B
each J is hydrogen;
n is 0 or an integer selected from 1, 2 or 3;
each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);

$Z^1$ in ring D is selected from CH, CF or N; Z is selected from C or N; wherein if $Z^1$ is CH or CF, then Z must be C; and if $Z^1$ is N, then Z may be C or N;

each $J^D$ is independently selected from $J^A$, —CN, —$NO_2$, —$OR^D$, —$SR^D$, —C(O)$R^D$, —C(O)O$R^D$, —OC(O)$R^D$, —C(O)N($R^D$)$_2$, —N($R^D$)$_2$, —N($R^d$)C(O)$R^D$, —N($R^d$)C(O)O$R^D$, —N($R^d$)C(O)N($R^D$)$_2$, —OC(O)N($R^D$)$_2$, —$SO_2R^D$, —$SO_2N(R^D)_2$, —N($R^d$)$SO_2R^D$, —N($R^d$)$SO_2NHR^D$, —N($R^d$)$SO_2NHC(O)OR^D$, —N($R^d$)$SO_2NHC(O)R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$;

$J^A$ is selected from a lone pair on nitrogen, hydrogen, halogen, oxo, methyl, hydroxyl, methoxy, trifluoromethyl, trifluoromethoxy or —$NR^aR^b$; wherein $R^a$ and $R^b$ are each independently selected from hydrogen, $C_{1-6}$ alkyl or a 3-6 cycloalkyl ring; or wherein $R^a$ and $R^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —N($R^d$)—, —CO— or —O—;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —N($R^{dd}$)—, —CO— or —O—;

each $R^{dd}$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$;

each $R^f$ is independently selected from a $C_{1-3}$ alkyl, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said $C_{3-8}$ cycloaliphatic ring, each said 4 to 10-membered heterocyclic ring, each said phenyl and each said 5 to 6-membered heteroaryl ring is optionally and independently substituted by up to 5 instances of $R^{5c}$;

when $J^D$ is —C(O)N($R^D$)$_2$, —N($R^D$)$_2$, —N($R^d$)C(O)N($R^D$)$_2$, —OC(O)N($R^D$)$_2$ or —SO$_2$N($R^D$)$_2$, the two $R^D$ groups together with the nitrogen atom attached to the two $R^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two $R^D$ groups are attached; and wherein each said 4 to 8-membered heterocyclic ring and each said 5-membered heteroaryl ring is optionally and independently substituted by up to 5 instances of $R^5$;

when $J^D$ is —N($R^d$)C(O)$R^D$, the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)C(O)N($R^D$)$_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)SO$_2$$R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2$$R^6$, —N($R^6$)C(O)$R^6$, —N($R^6$)C(O)O$R^6$, —N($R^6$)C(O)N($R^6$)$_2$, —N($R^6$)$_2$, —SO$_2$$R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2$$R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —CONH$_2$, —OH or halogen; wherein R is hydrogen or a $C_{1-2}$ alkyl;

each $R^{5a}$ is independently selected from halogen, —CN, $C_{1-6}$ alkyl, —($C_{1-6}$ alkyl)$R^{6a}$, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)R$^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

each $R^{5b}$ is independently selected from halogen, —CN, $C_{1-6}$ alkyl, —($C_{1-6}$ alkyl)R$^{6a}$, —O$^{5a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)R$^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^{5b}$ is independently selected from halogen, —CN, $C_{1-6}$ alkyl, —($C_{1-6}$ alkyl)-R$^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5c}$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-R$^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

ring E is a 5 to 7-membered heterocycle or a 5-membered heteroaryl ring; said heterocycle or heteroaryl ring containing up to 4 heteroatoms independently selected from N, O and S;

o is 0 or an integer selected from 1, 2, 3 or 4;

Y is either absent or is a $C_{1-6}$ alkyl chain, optionally substituted by up to 6 instances of fluoro; and wherein in said Y that is a $C_{1-6}$ alkyl chain, up to 3 methylene units of this alkyl chain, can be replaced by a group selected from —O—, —C(O)— or —N((Y$^1$)—R$^{90}$)—, wherein Y$^1$ is either absent or is a $C_{1-6}$ alkyl chain, optionally substituted by up to 6 instances of fluoro; and:

when Y$^1$ is absent, each R$^{90}$ is independently selected from hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$ a $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$; and when Y$^1$ is present, each R$^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$), $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each R$^9$ is independently selected from hydrogen, halogen, a $C_{1-6}$ alkyl, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of R$^{11}$;

each R$^{10}$ is independently selected from hydrogen, a $C_{1-6}$ alkyl, —($C_{1-6}$ alkyl)-R$^{13}$, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of R$^{11a}$;

each R$^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of R$^{11b}$;

each R$^{11}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of R$^{121}$;

each R$^{11a}$ is independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of R$^{121}$; and each R$^{11b}$ is independently selected from halogen, $C_{1-6}$ alkyl, oxo, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of R$^{121}$;

each R$^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

each R$^{121}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

R$^{C1}$ is either
i) a ring C; or
ii) is selected from a lone pair on a nitrogen atom, hydrogen, halogen, oxo, —CN, $C_{1-6}$ aliphatic, —($C_{1-6}$ aliphatic)-R$^N$, —OR$^7$, —OC(O)R$^7$, —O(R$^7$)C(O)N(R$^7$)$_2$, —COR$^7$, —C(O)OR⁷, —C(O)N(R⁷)₂, —N(R⁷)C(O)R⁷, —N(R⁷)C(O)OR⁷, —N(R⁷)C(O)N(R⁷)₂, —N(R⁷)₂, —SR⁷, —S(O)R⁷, —SO₂R⁷, —SO₂N(R⁷)₂, —C(O)N(R⁷)SO₂R⁷, —SO₂N(R⁷)COOR⁷, —SO₂N(R⁷)C(O)R⁷ or —N(R⁷)SO₂R⁷; wherein each said $C_{1-6}$ aliphatic, each $C_{1-6}$ aliphatic portion of said —($C_{1-6}$ aliphatic)-$R^N$, is optionally and independently substituted with up to 6 instances of fluoro and up to 2 instances of —CN, —OR⁸, oxo, —N(R⁸)₂, —N(R⁸)C(O)R⁸, —N(R⁸)C(O)OR⁸, —N(R⁸)C(O)N(R⁸)₂, —SO₂R⁸, —SO₂N(R⁸)₂, —NHOR⁸, —SO₂N(R⁸)COOR⁸, —SO₂N(R⁸)C(O)R⁸, —N(R⁸)SO₂R⁸;

wherein each R⁷ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH₂, —NH($C_{1-4}$ alkyl), —N($C_{1-4}$ alkyl)₂, —CN, —COOH, —COO($C_{1-4}$ alkyl), —O($C_{1-4}$ alkyl), —O($C_{1-4}$ haloalkyl) or oxo;

each R⁸ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH₂, —NH($C_{1-4}$ alkyl), —N($C_{1-4}$ alkyl)₂, —CN, —COOH, —COO($C_{1-4}$ alkyl), —O($C_{1-4}$ alkyl), —O($C_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —OR^M, —SR^M, —N(R^M)₂, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances off; wherein p is 0 or an integer selected from 1, 2 or 3.

each $J^C$ is independently selected from halogen, —CN, —NO₂, a $C_{1-6}$ aliphatic, —OR^H, —SR^H, —N(R^H)₂, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two $J^C$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of R^H linked to the same nitrogen atom of —N(R^H)₂, together with said nitrogen atom of —N(R^H)₂, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each $R^{7c}$ is independently selected from halogen, —CN, —NO₂, $C_{1-4}$ alkyl, $C_{1-4}$ haloalkyl, $C_{3-8}$ cycloalkyl ring, —OR^{8b}, —SR^{8b}, —N(R^{8b})₂, —C(O)O($C_{1-4}$ alkyl), —C(O)OH, —NR(CO)CO($C_{1-4}$ alkyl) or an oxo group; wherein each said cycloalkyl group is optionally and independently substituted with up to 3 instances of halogen;

each $R^{7d}$ is independently selected from halogen, —CN, —NO₂, $C_{1-4}$ alkyl, $C_{1-4}$ haloalkyl, $C_{3-8}$ cycloalkyl ring, —C(O)O($C_{1-4}$ alkyl), —C(O)OH, —OR^{8c}, —SR^{8c}, —N(R^{8c})₂, or an oxo group; wherein each said cycloalkyl group is optionally and independently substituted with up to 3 instances of halogen;

each $R^{8b}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{8c}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; and $R^{C2}$ is selected from a lone pair on a nitrogen atom, hydrogen, halogen, —OH, —O($C_{1-6}$ alkyl), —O(halo$C_{1-6}$ alkyl), —O($C_{1-6}$ haloalkyl), —O(cyclopropyl), cyclopropyl, $C_{1-6}$ alkyl, $C_{1-6}$ haloalkyl and —CN;

provided that the compound is not one represented by any one of Formulae A-1 to Formula A-8 depicted below:

Formula A-1

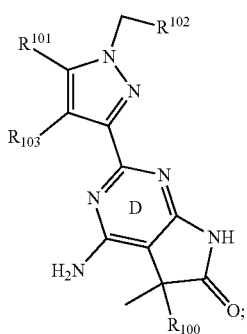

wherein, $R^{100}$ is selected from —C(O)NH$_2$, —C(O)NH(cyclopropyl), —C(O)NH—NH$_2$, —C(O)NH—NH—C(O)Me or —C(O)OEt; $R^{101}$ is selected from isoxazole, —O($C_{1-3}$ alkyl) or OH; $R^{102}$ is selected from 2-fluorophenyl or 2,2,2-trifluoroethyl; $R^{103}$ is selected from H, Me or —CN;

Formula A-2

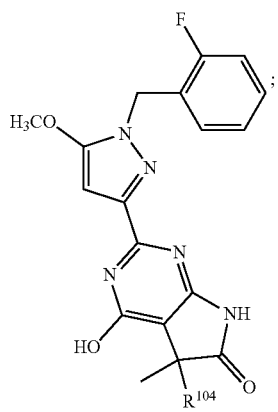

wherein $R^{104}$ is selected from —NHC(O)OMe, —C(O)NH(cyclopropyl) or —C(O)OEt;

Formula A-3

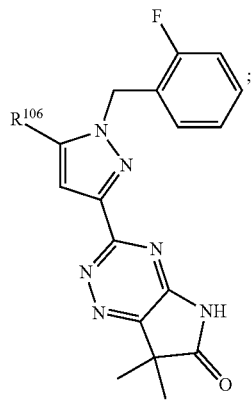

wherein $R^{106}$ is selected from isoxazole and —OCH$_3$;

Formula A-4

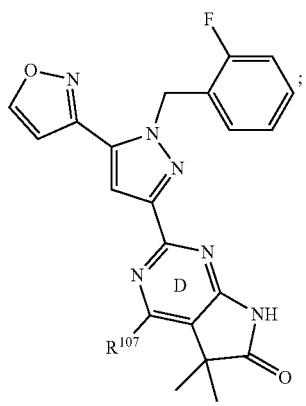

wherein $R^{107}$ is selected from hydrogen or —NH$_2$;

Formula A-5

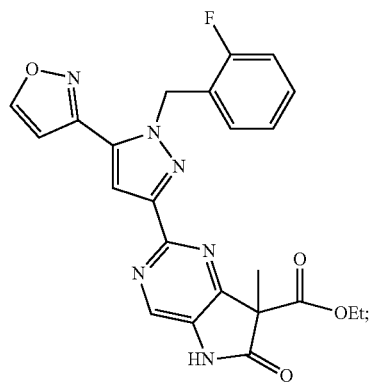

-continued

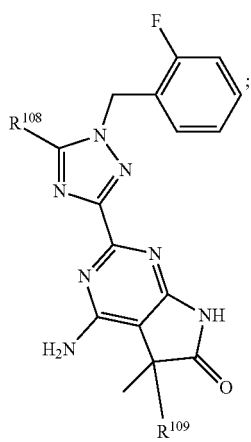

Formula A-6 wherein $R^{108}$ is selected from OH or —OCH$_3$; wherein $R^{109}$ is selected from —C(O)NH$_2$, —C(O)NH(cyclopropyl) or —C(O)OEt;

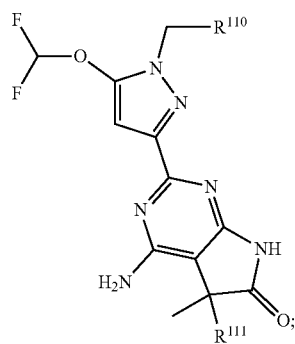

Formula A-7 wherein $R^{110}$ is selected from a difluorinated benzyl ring or 3,3,3,2,2-pentafluoropropyl; wherein $R^{111}$ is selected from —CH$_3$, —C(O)NH$_2$, —C(O)NH(cyclopropyl) or —C(O)OEt;

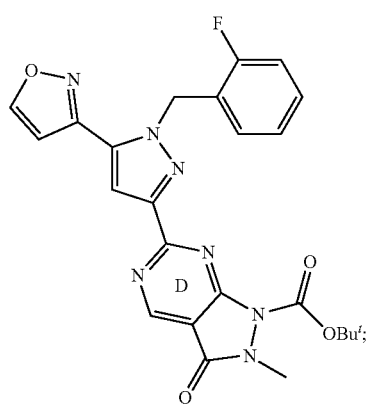

Formula A-8 also, provided that the compound is not one represented by any one of Formula B-1 to Formula B-5 or a pharmaceutically acceptable salt thereof,

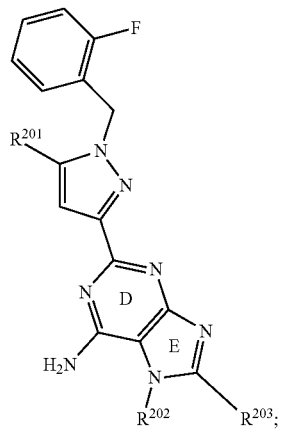

Formula B-1 wherein $R^{201}$ is selected from thiazole or oxazole; $R^{202}$ is selected from hydrogen or methyl; $R^{203}$ is selected from —OH or —CH$_3$;

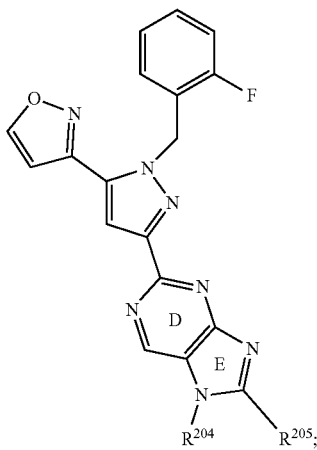

Formula B-2 wherein $R^{204}$ is selected from hydrogen, methyl or —C(O)NH(Bu$^t$); $R^{205}$ is selected from hydrogen or —OH;

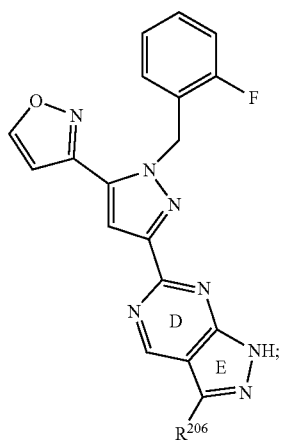

Formula B-3 wherein $R^{206}$ is selected from —$NH_2$, —NHC(O)Me and hydrogen;
Formula B-4
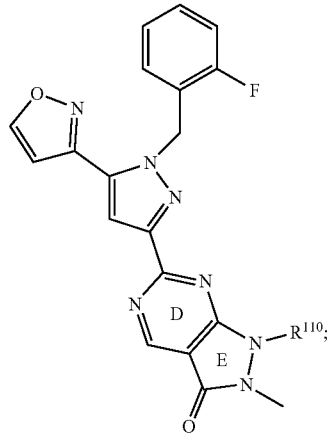
wherein $R^{110}$ is selected from hydrogen or a Boc protecting group;
Formula B-5
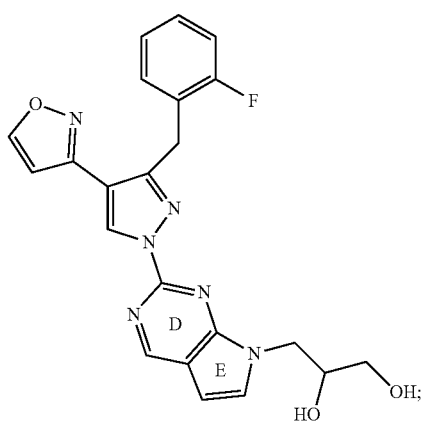
and provided the compound is not one of the compounds depicted below:
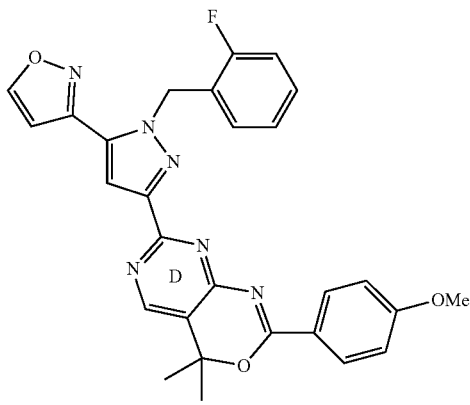
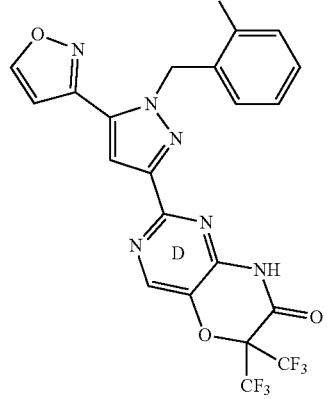
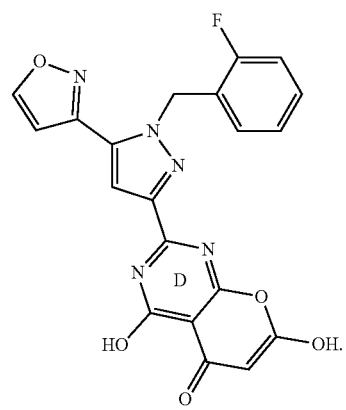
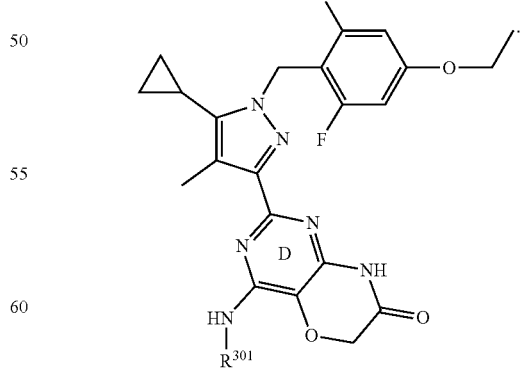
In some embodiments of the compounds of Formula I', the compound is of Formula I, or a pharmaceutically acceptable salt thereof:

Formula I

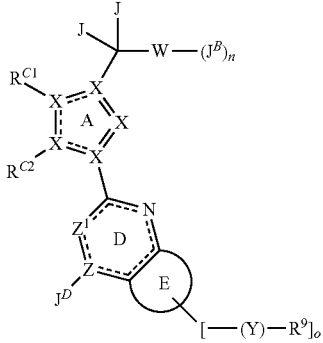

wherein:
ring A is a 5-membered heteroaryl ring; each instance of X is independently selected from C or N and the bond between each two instances of X is either a single or a double bond so as to make ring A an aromatic heterocycle; wherein a minimum of 2 instances of X and a maximum of 3 instances of X in ring A can simultaneously be N;
W is either
i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and 9 instances of fluorine; wherein, optionally, one —$CH_2$— unit of said $C_{2-7}$ alkyl chain can be replaced by —O— or —S—.
ii) a ring B selected from phenyl, a 5 or 6-membered heteroaryl ring, containing 1 or 2 ring heteroatoms independently selected from N, O or S, a $C_{3-7}$ cycloalkyl ring and a 4 to 7-membered heterocyclic compound, containing up to 3 heteroatoms independently selected from O, N or S;
wherein when W is ring B
each J is hydrogen;
n is 0 or an integer selected from 1, 2 or 3;
each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);
$Z^1$ in ring D is selected from CH or N; Z is selected from C or N; wherein if $Z^1$ is CH, then Z must be C; and if Z1 is N, then Z may be C or N;
each $J^D$ is independently selected from $J^A$, —CN, —$NO_2$, —$OR^D$, —$SR^D$, —C(O)$R^D$, —C(O)O$R^D$, —OC(O)$R^D$, —C(O)N($R^D$)$_2$, —N($R^D$)$_2$, —N($R^d$)C(O)$R^D$, —N($R^d$)C(O)O$R^D$, —N($R^d$)C(O)N($R^D$)$_2$, —OC(O)N($R^D$)$_2$, —$SO_2R^D$, —$SO_2$N($R^D$)$_2$, —N($R^d$)$SO_2R^D$, —N($R^d$)$SO_2NHR^D$, —N($R^d$)$SO_2$NHC(O)O$R^D$, —N($R^d$)$SO_2$NHC(O)$R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^D$ moiety, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of $R^{5d}$;
$J^A$ is selected from a lone pair on nitrogen, hydrogen, halogen, oxo, methyl, hydroxyl, methoxy, trifluoromethyl, trifluoromethoxy or $NR^aR^b$; wherein $R^a$ and $R^b$ are each independently selected from hydrogen, $C_{1-6}$ alkyl or a 3-6 cycloalkyl ring; or wherein $R^a$ and $R^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;
each $R^D$ is independently selected from hydrogen, a $C_{1-6}$ aliphatic, —($C_{1-6}$ aliphatic)-$R^f$, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 10-membered heterocyclic ring, each said phenyl and each said 5 to 6-membered heteroaryl ring is optionally and independently substituted with up to 5 instances of $R^{5a}$; wherein when any $R^D$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —N($R^d$)—, —CO— or —O—;
each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$; wherein when any $R^d$ is one of a $C_{1-6}$ aliphatic or a —($C_{1-6}$ aliphatic)-$R^f$ group, one or two —$CH_2$— units that form said $C_{1-6}$ aliphatic chains may, optionally, be replaced by a group independently selected from —N($R^{dd}$)—, —CO— or —O—;
each $R^{dd}$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 or 6-membered heteroaryl ring contains between 1 and 3 heteroatoms independently selected from O, N or S; and wherein each said $C_{1-6}$ aliphatic, each said $C_{1-6}$ aliphatic portion of the —($C_{1-6}$ aliphatic)-$R^f$ moiety, each said $C_{3-8}$ cycloaliphatic ring, each said 4 to 8-membered heterocyclic ring, each said phenyl and each said 5 to 6-membered heteroaryl ring is optionally and independently substituted by up to 5 instances of $R^{5b}$;

each $R^f$ is independently selected from a $C_{1-3}$ alkyl, a $C_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N or S; and wherein each said $C_{3-8}$ cycloaliphatic ring, each said 4 to 10-membered heterocyclic ring, each said phenyl and each said 5 to 6-membered heteroaryl ring is optionally and independently substituted by up to 5 instances of $R^{5c}$;

when $J^D$ is —C(O)N($R^D$)$_2$, —N($R^D$)$_2$, —N($R^d$)C(O)N($R^D$)$_2$, —OC(O)N($R^D$)$_2$ or —SO$_2$N($R^D$)$_2$, the two $R^D$ groups together with the nitrogen atom attached to the two $R^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O or S, in addition to the nitrogen atom to which the two $R^D$ groups are attached; and wherein each said 4 to 8-membered heterocyclic ring and each said 5-membered heteroaryl ring is optionally and independently substituted by up to 5 instances of $R^5$;

when $J^D$ is —N($R^d$)C(O)$R^D$, the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, in addition to the nitrogen atom to which the $R^d$ group is attached; and wherein each said 4 to 8-membered heterocyclic ring and each said 5-membered heteroaryl ring is optionally and independently substituted by up to 5 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with said $R^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)C(O)N($R^D$)$_2$, one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

when $J^D$ is —N($R^d$)SO$_2$$R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of $R^5$;

each $R^5$ is independently selected from halogen, —CN, $C_{1-6}$ alkyl, —($C_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2$$R^6$, —N($R^6$)C(O)$R^6$, —N($R^6$)C(O)O$R^6$, —N($R^6$)C(O)N($R^6$)$_2$, —N($R^6$)$_2$, —SO$_2$$R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2$$R^6$, —(C=O)NHO$R^6$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —CONH$_2$, —OH or halogen; wherein R is hydrogen or a $C_{1-2}$ alkyl;

each $R^{5a}$ is independently selected from halogen, —CN, $C_{1-6}$ alkyl, —($C_{1-6}$ alkyl)$R^{6a}$, —O$R^{6a}$, —S$R^{6a}$, —CO$R^{6a}$, —OC(O)$R^{6a}$, —C(O)O$R^{6a}$, —C(O)N($R^{6a}$)$_2$, —C(O)N($R^{6a}$)SO$_2$$R^{6a}$, —N($R^{6a}$)C(O)$R^{6a}$, —N($R^{6a}$)C(O)O$R^{6a}$, —N($R^{6a}$)C(O)N($R^{6a}$)$_2$, —N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, —N($R^{6a}$)SO$_2$$R^{6a}$, —(C=O)NHO$R^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl)

or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

each $R^{5b}$ is independently selected from halogen, —CN, $C_{1-6}$ alkyl, —($C_{1-6}$ alkyl)$R^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$OH, —SO$_2$NHOH, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, —(C=O)NHOR$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)R$^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^{5c}$ is independently selected from halogen, —CN, $C_{1-6}$ alkyl, —($C_{1-6}$ alkyl)-R$^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, or a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5c}$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-R$^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-R$^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR (CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH ($C_{1-4}$ alkyl), —N($C_{1-4}$ alkyl)$_2$, —CN, —COOH, —C(O) NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH ($C_{1-4}$ alkyl), —N($C_{1-4}$ alkyl)$_2$, —CN, —COOH, —C(O) NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH ($C_{1-4}$ alkyl), —N($C_{1-4}$ alkyl)$_2$, —CN, —COOH, —C(O) NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of $R^5$ or $R^{5d}$ respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

ring E is a 5 to 7-membered heterocycle or a 5-membered heteroaryl ring; said heterocycle or heteroaryl ring containing up to 4 heteroatoms independently selected from N, O and S;

o is 0 or an integer selected from 1, 2, 3 or 4;

Y is either absent or is a $C_{1-6}$ alkyl chain, optionally substituted by up to 6 instances of fluoro; and wherein in said Y that is a $C_{1-6}$ alkyl chain, up to 3 methylene units of this alkyl chain, can be replaced by a group selected from —O—, —C(O)— or —N(($Y^1$)—$R^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from hydrogen, —COR$^{10}$, —C(O)OR$^{10}$, —C(O)N (R$^{10}$)$_2$, —C(O)N(R$^{10}$)SO$_2$R$^{10}$, —SO$_2$R$^{10}$, —SO$_2$N (R$^{10}$)$_2$, —SO$_2$N(R$^{10}$)COOR$^{10}$, —SO$_2$N(R$^{10}$)C(O)R$^{10}$, —(C=O)NHOR$^{10}$ a $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and when $Y^1$ is present, each $R^{90}$ is independently selected from hydrogen, halogen, —CN, —OR$^{10}$, —COR$^{10}$, —OC(O)R$^{10}$, —C(O)OR$^{10}$, —C(O)N(R$^{10}$)$_2$, —C(O)N (R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$) C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from hydrogen, halogen, a $C_{1-6}$ alkyl, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N (R$^{10}$)$_2$, —N(R$^{10}$)$_2$, —SO$_2$R$^{10}$, —SO$_2$N(R$^{10}$)$_2$, —SO$_2$N (R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring or a 5-6 membered heteroaryl ring; wherein each said 4 to 8-membered heterocyclic ring or 5 to 6-membered heteroaryl ring contains up to 4 ring heteroatoms independently selected from N, O or S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^{10}$ is independently selected from hydrogen, a $C_{1-6}$ alkyl, —($C_{1-6}$ alkyl)-$R^{13}$, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{11a}$; each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, oxo, $C_{1-6}$ alkyl, —CN, —$OR^{12}$, —$COR^{12}$, —$C(O)OR^{12}$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})_2$, —$SO_2R^{12}$, —$SO_2N(R^{12})_2$ or —$N(R^{12})SO_2R^{12}$; wherein each of said $C_{1-6}$ alkyl is optionally and independently substituted by up to 6 instances of fluoro and/or 3 instances of $R^{121}$;

each $R^{11a}$ is independently selected from halogen, oxo, $C_{1-6}$ alkyl, —CN, —$OR^{12}$, —$COR^{12}$, —$C(O)OR^{12}$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})_2$, —$SO_2R^{12}$, —$SO_2N(R^{12})_2$ or —$N(R^{12})SO_2R^{12}$; wherein each of said $C_{1-6}$ alkyl is optionally and independently substituted by up to 6 instances of fluoro and/or 3 instances of $R^{121}$; and each $R^{11b}$ is independently selected from halogen, $C_{1-6}$ alkyl, oxo, —CN, —$OR^{12}$, —$COR^{12}$, —$C(O)OR^{12}$, —$C(O)N(R^{12})_2$, —$N(R^{12})C(O)R^{12}$, —$N(R^{12})C(O)OR^{12}$, —$N(R^{12})C(O)N(R^{12})_2$, —$N(R^{12})_2$, —$SO_2R^{12}$, —$SO_2N(R^{12})_2$ or —$N(R^{12})SO_2R^{12}$; wherein each of said $C_{1-6}$ alkyl is optionally and independently substituted by up to 6 instances of fluoro and/or 3 instances of $R^{121}$;

each $R^{12}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —$NH_2$, —$NH(C_{1-4}$ alkyl), —$N(C_{1-4}$ alkyl$)_2$, —CN, —COOH, —$CONH_2$, —$COO(C_{1-4}$ alkyl), —$O(C_{1-4}$ alkyl), —$O(C_{1-4}$ fluoroalkyl) or oxo;

each $R^{121}$ is selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —$NH_2$, —$NH(C_{1-4}$ alkyl), —$N(C_{1-4}$ alkyl$)_2$, —CN, —COOH, —$CONH_2$, —$COO(C_{1-4}$ alkyl), —$O(C_{1-4}$ alkyl), —$O(C_{1-4}$ fluoroalkyl) or oxo.

$R^{C1}$ is either i) a ring C; or ii) is selected from hydrogen, halogen, oxo, —CN, $C_{1-6}$ aliphatic, —($C_{1-6}$ aliphatic)-$R^N$, —$OR^7$, —$OC(O)R^7$, —$O(R^7)C(O)N(R^7)_2$, —$COR^7$, —$C(O)OR^7$, —$C(O)N(R^7)_2$, —$N(R^7)C(O)R^7$, —$N(R^7)C(O)OR^7$, —$N(R^7)C(O)N(R^7)_2$, —$N(R^7)_2$, —$SR^7$, —$S(O)R^7$, —$SO_2R^7$, —$SO_2N(R^7)_2$, —$C(O)N(R^7)SO_2R^7$, —$SO_2N(R^7)COOR^7$, —$SO_2N(R^7)C(O)R^7$ or —$N(R^7)SO_2R^7$; wherein each said $C_{1-6}$ aliphatic, each $C_{1-6}$ aliphatic portion of said —($C_{1-6}$ aliphatic)-$R^N$, is optionally and independently substituted with up to 6 instances of fluoro and up to 2 instances of —CN, —$OR^8$, oxo, —$N(R^8)_2$, —$N(R^8)C(O)R^8$, —$N(R^8)C(O)OR^8$, —$N(R^8)C(O)N(R^8)_2$, —$SO_2R^8$, —$SO_2N(R^8)_2$, —$NHOR^8$, —$SO_2N(R^8)COOR^8$, —$SO_2N(R^8)C(O)R^8$, —$N(R^8)SO_2R^8$;

wherein each $R^7$ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —$NH(C_{1-4}$ alkyl), —$N(C_{1-4}$ alkyl$)_2$, —CN, —COOH, —$COO(C_{1-4}$ alkyl), —$O(C_{1-4}$ alkyl), —$O(C_{1-4}$ haloalkyl) or oxo;

each $R^8$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —$NH(C_{1-4}$ alkyl), —$N(C_{1-4}$ alkyl$)_2$, —CN, —COOH, —$COO(C_{1-4}$ alkyl), —$O(C_{1-4}$ alkyl), —$O(C_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN a $C_{1-6}$ aliphatic, —OR$^M$, —SR$^M$, —N(R$^M$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of; wherein p is 0 or an integer selected from 1, 2 or 3.

each $J^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two $J^C$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; alternatively, two instances of $R^H$ linked to the same nitrogen atom of —N(R$^H$)$_2$, together with said nitrogen atom of —N(R$^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S;

each $R^{7c}$ is independently selected from halogen, —CN, —NO$_2$, $C_{1-4}$ alkyl, $C_{1-4}$ haloalkyl, $C_{3-8}$ cycloalkyl ring, —OR$^{8b}$, —SR$^{8b}$, —N(R$^{8b}$)$_2$, —C(O)O($C_{1-4}$ alkyl), —C(O)OH, —NR(CO)CO($C_{1-4}$ alkyl) or an oxo group;

wherein each said cycloalkyl group is optionally and independently substituted with up to 3 instances of halogen;

each $R^{7d}$ is independently selected from halogen, —CN, —NO$_2$, $C_{1-4}$ alkyl, $C_{1-4}$ haloalkyl, $C_{3-8}$ cycloalkyl ring, —C(O)O($C_{1-4}$ alkyl), —C(O)OH, —OR$^{8c}$, —SR$^{8c}$, —N(R$^{8c}$)$_2$, or an oxo group; wherein each said cycloalkyl group is optionally and independently substituted with up to 3 instances of halogen;

each $R^{8b}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{8c}$ is independently selected from hydrogen, $C_{1-6}$ alkyl, $C_{1-6}$ fluoroalkyl, a $C_{3-8}$ cycloalkyl ring, a 4 to 7-membered heterocyclic ring or a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; and $R^{C2}$ is selected from hydrogen, halogen, —OH, —O($C_{1-6}$ alkyl), —O(halo$C_{1-6}$ alkyl), —O($C_{1-6}$ haloalkyl), —O(cyclopropyl), cyclopropyl, $C_{1-6}$ alkyl, $C_{1-6}$ haloalkyl and —CN;

provided that the compound is not one represented by Formula C-1 or Formula C-2 depicted below:

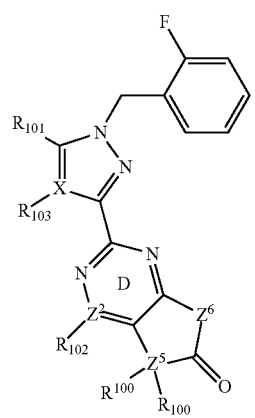

Formula C-1

-continued

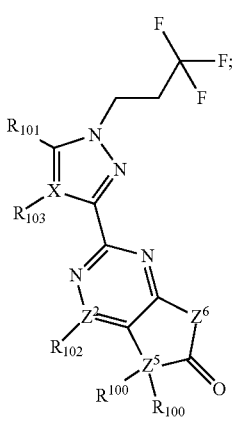

Formula C-2 wherein
$Z^2$ is selected from N or C; wherein when $Z^2$ is C, $R^{102}$ is selected from either $NH_2$, —OH, halogen or hydrogen; or, alternatively, when $Z^2$ is N, $R^{102}$ is a lone pair on N;
$Z^5$ is selected from C or N; wherein when $Z^5$ is C, each $R^{100}$ is independently selected from hydrogen, —$CH_3$, —$CF_3$, —$CONH_2$, —CONH(cyclopropyl), —COOH, —CN, —COO($C_{1-3}$ alkyl), —$NHCOOCH_3$ and

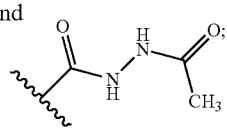

or, alternatively, when $Z^5$ is N, one of $R^{100}$ is hydrogen and the other is a lone pair on said N;
$R^{101}$ is selected from an isoxazole ring, oxo, —$OR^{104}$, —C(O)$CH_3$ and $CH_2OMe$; wherein $R^{104}$ is selected from hydrogen, methyl, ethyl and isopropyl, said methyl optionally substituted with up to 3 fluorines;
$R^{103}$ is selected from hydrogen, methyl or —CN;
$Z^6$ is selected from NH or C; said C optionally substituted by methyl and ethyl ester;
also, provided that the compound is not one represented by Formula B represented below or a pharmaceutically acceptable salt thereof, Formula B

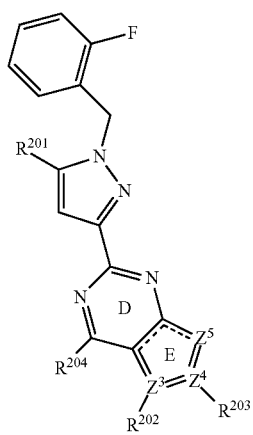

wherein ring E is a 5-membered, nitrogen containing, heteroaryl ring;

$R^{201}$ is an isoxazole, oxazole or thiazole ring;
$Z^3$ is a ring atom selected from N or C; wherein when $Z^3$ is N, $R^{202}$ is a lone pair on said N or hydrogen or Methyl; when $Z^3$ is C, $R^{202}$ is a substituent selected from hydrogen, —OH, —$NH_2$, —OCO(tert-Bu), —NHCOMe and oxo;
$Z^4$ is a ring atom selected from N or C; wherein when $Z^4$ is N, $R^{203}$ is selected from a lone pair on said N, hydrogen and Methyl; and wherein when $Z^4$ is C, $R^{203}$ is hydrogen, methyl or —CONH(tert-Bu);
$Z^5$ is a ring atom selected from N and CH;
$R^{204}$ is selected from hydrogen and —$NH_2$;
and provided the compound is not one of the compounds depicted below:

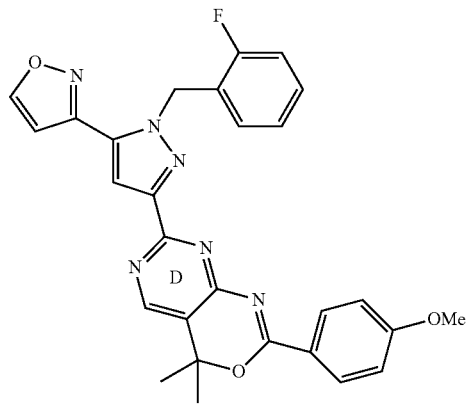

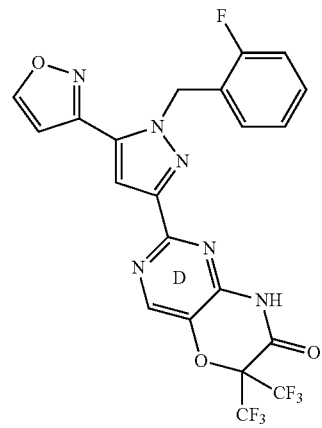

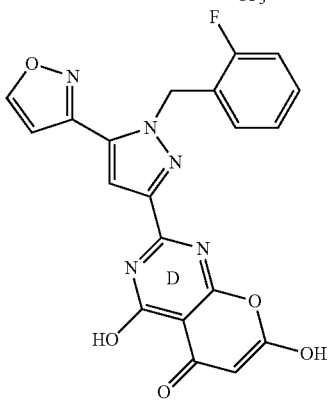

-continued

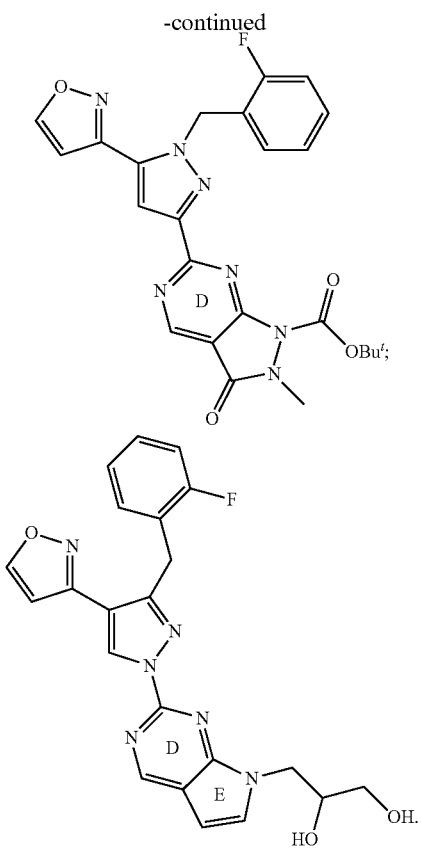

In some embodiments of the compounds of Formula I' or Formula I, the compound is one of Formula I'A or a pharmaceutically acceptable salt thereof:

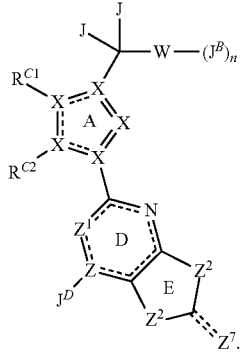

Formula I'A

In some embodiments, each instance of $Z^2$ is independently selected from N or C. In some embodiments, $Z^2$ is N and is either unsubstituted or optionally substituted with —(Y)—$R^9$. In other embodiments, $Z^2$ is C and is optionally substituted by one or two instances of —(Y)—$R^9$. In some embodiments, $Z^7$ is O and the bond between $Z^7$ and ring E is a double bond. In other embodiments, $Z^7$ is absent and the ring E carbon atom situated between the two instances of $Z^2$ is unsubstituted.

In some embodiments of the compounds of Formula I', Formula I, or Formula I'A, the compound is one of Formula I'B or a pharmaceutically acceptable salt thereof:

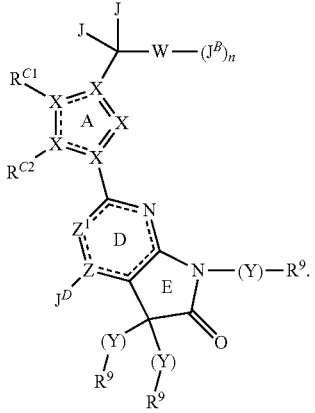

Formula I'B

In some embodiments of the compounds of Formula I', Formula I, Formula I'A, or Formula I'B, the compound is one of Formula I'C or a pharmaceutically acceptable salt thereof:

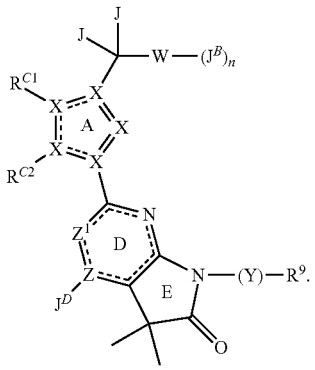

Formula I'C

In some embodiments of the compounds of Formula I', Formula I, Formula I'A, Formula I'B, or Formula I'C, the compound is one of Formula I'D or a pharmaceutically acceptable salt thereof:

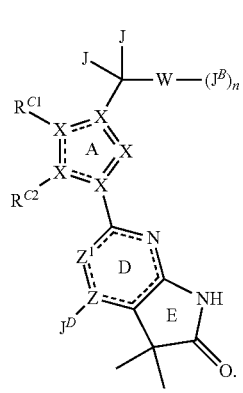

Formula I'D

In some embodiments of the compounds of Formula I', Formula I, Formula I'A, Formula I'B, Formula I'C, or Formula I'D, the compound is one of Formula IIA, Formula IIB, Formula IIC, Formula IID, Formula IIE, or Formula IIF, or a pharmaceutically acceptable salt thereof:

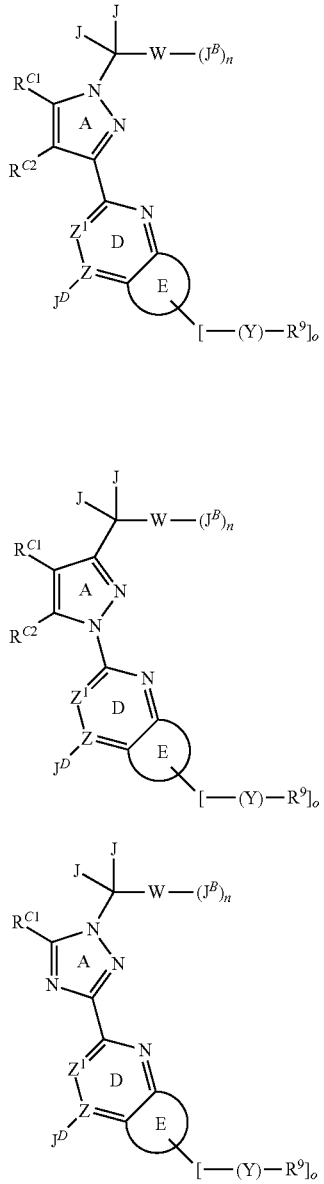

Formula IIA

Formula IIB

Formula IIC

Formula IID

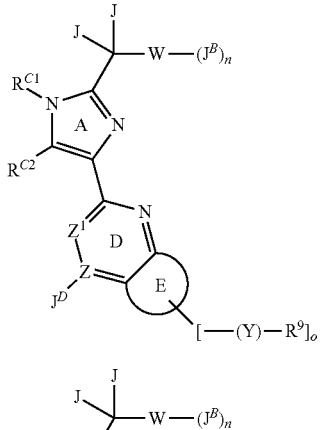

Formula IIE

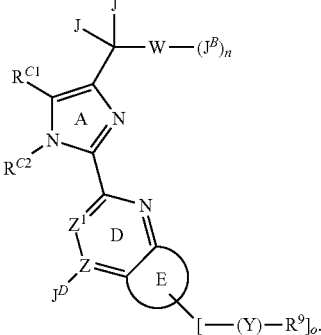

Formula IIF

In some embodiments, the compound is of Formula IIA, or a pharmaceutically acceptable salt thereof. In some embodiments, the compound is of Formula IIB, or a pharmaceutically acceptable salt thereof. In some embodiments, the compound is of Formula IIC, or a pharmaceutically acceptable salt thereof. In some embodiments, the compound is of Formula IID, or a pharmaceutically acceptable salt thereof. In some embodiments, the compound is of Formula IIE, or a pharmaceutically acceptable salt thereof. In some embodiments, the compound is of Formula IIF, or a pharmaceutically acceptable salt thereof.

In some embodiments of Formula I', Formula I, Formula I'A, Formula I'B, Formula I'C, or Formula I'D, Formula IIA, Formula IIB, Formula IIC, Formula IID, Formula IIE, or Formula IIF, $R^{C1}$ is a ring C. In other embodiments, $R^{C1}$ is not a ring C.

In some embodiments of the compounds of Formula I', Formula I, Formula I'A, Formula I'B, Formula I'C, Formula I'D, Formula IIA, Formula IIB, Formula IIC, Formula IID, Formula IIE, or Formula IIF, W is absent. In some of these embodiments, the compound is represented by Formula I-a, or a pharmaceutically acceptable salt thereof:

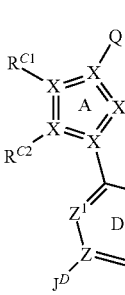

Formula I-a

In some of these embodiments, Q represents a $C_{3-8}$ alkyl group, optionally substituted with between 2 and 9 instances of fluorine; the first methylene unit of Q, which is directly attached to X of ring A, cannot be substituted by fluoro. In some of these embodiments, Q is substituted with up between 2 and 7 instances of fluorine.

In some embodiments of the compounds of Formula I', Formula I, Formula I'A, Formula I'B, Formula I'C, Formula I'D, Formula IIA, Formula IIB, Formula IIC, Formula IID, Formula IIE, or Formula IIF, the compound is represented by Formula I-c, or a pharmaceutically acceptable salt thereof:

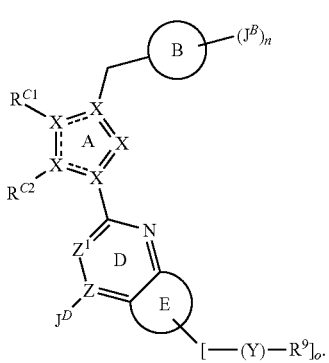

Formula I-c

In these embodiments, ring B is a phenyl, a 5 or 6-membered heteroaryl ring containing 1 or 2 ring heteroatoms selected from N, O or S, a $C_{3-7}$ cycloalkyl ring, or a 4-7-membered heterocyclic ring containing 1 to 3 ring heteroatoms selected from N, O or S. In some embodiments, ring B is phenyl or a 5 to 6-membered heteroaryl ring containing 1 or 2 ring heteroatoms selected from N, O or S. In other embodiments, ring B is a phenyl ring. In some embodiments, ring B is a phenyl ring, n is an integer selected from 1, 2 and 3 and each $J^B$ is independently selected from halogen, a $C_{1-6}$ aliphatic or —$OR^8$. In some of these embodiments, each $J^B$ is independently selected from halogen. In still other embodiments, each $J^B$ is independently selected from fluoro or chloro. In yet other embodiments, each $J^B$ is fluoro. In further embodiments, each $J^B$ is methyl or ethyl. In some embodiments, n is 1. In some of these embodiments, $J^B$ is halogen. In other embodiments, $J^B$ is fluoro or chloro. In still other embodiments, $J^B$ is fluoro. In some embodiments, at least one $J^B$ is ortho to the attachment of the methylene linker between ring B and ring A. In yet other embodiments, each of these ortho $J^B$ is independently selected from halogen. In yet further embodiments, each $J^B$ is independently selected from fluoro or chloro. In yet further embodiments, each $J^B$ is fluoro. In some embodiments, n is 1 and the $J^B$ ortho to the attachment of the methylene linker is fluoro.

In some embodiments of Formula I-c, B is a 6-membered heteroaryl ring. In some of these embodiments, ring B is a pyridyl ring. In other embodiments, ring B is a pyrimidinyl ring. In yet other embodiments, ring B is a pyridazinyl ring. In further embodiments, ring B is a pyrazinyl ring. In still further embodiments, ring B is a triazinyl ring. In some embodiments, B is a 5 or 6-membered heterocyclic ring. In other embodiments, B is a 4 to 6-membered cycloalkyl ring.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, $R^{C1}$ is not a ring. In some embodiments, $R^{C1}$ is selected from hydrogen, halogen, oxo, —CN, $C_{1-6}$ aliphatic, —$OR^7$, —$COR^7$, —$C(O)OR^7$, —$C(O)N(R^7)_2$, —$N(R^7)C(O)R^7$, —$N(R^7)_2$, —$SR^7$, —$S(O)R^7$, —$SO_2R^7$, or —$SO_2N(R^7)_2$. In some of these embodiments, the $C_{1-6}$ aliphatic is optionally and independently substituted with up to 6 instances of fluoro and up to 2 instances of $OR^8$ or oxo. In other embodiments, $R^{C1}$ is selected from hydrogen, halogen, oxo, $C_{1-3}$ alkyl, vinyl, ethynyl, —$OR^7$, —$COR^7$, —$C(O)OR^7$, —$C(O)N(R^7)_2$, —$N(R^7)C(O)R^7$, —$N(R^7)_2$, —$SR^7$, —$S(O)R^7$, —$SO_2R^7$, or $SO_2N(R^7)_2$. In some of these embodiments, the $C_{1-3}$ alkyl is optionally and independently substituted with up to 6 instances of fluoro and up to 1 instance of —OH or oxo. In further embodiments, $R^{C2}$ is hydrogen. In other embodiments, $R^{C2}$ is halogen.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, the compound is represented by Formula I-e, or a pharmaceutically acceptable salt thereof:

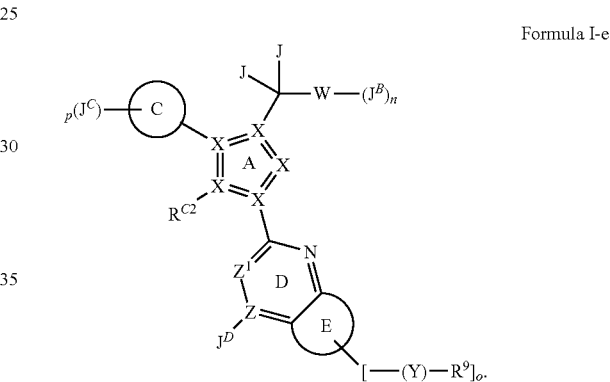

Formula I-e

In some embodiments of Formula I-e, p is 0. In other embodiments, p is an integer selected from 1 or 2. In other embodiments, p is 0 and ring C is unsubstituted. In some embodiments, ring C is a 5-membered heteroaryl ring containing up to 4 ring heteroatoms selected from N, O or S. In other embodiments, ring C is a 5-membered heteroaryl ring containing up to 3 ring heteroatoms selected from N, O or S. In still other embodiments, ring C is selected from oxazole, isoxazole, thiazole or isothiazole. In yet other embodiments, ring C is unsubstituted. In some embodiments, ring C is an isoxazole which may be substituted or unsubstituted. In other embodiments, ring C is a $C_{4-6}$ cycloalkyl ring. In other embodiments, ring C is a 4 to 6-membered heterocyclic ring containing up to 2 ring heteroatoms selected from N, O or S. In some embodiments, each $J^C$ is independently selected from halogen or a $C_{1-4}$ aliphatic optionally and independently substituted by up to 3 instances of $C_{1-4}$ alkoxy, $C_{1-4}$ fluoroalkoxy, oxo, —C(O)O($C_{1-4}$ alkyl), —C(O)OH, —OH or halogen. In other embodiments, each $J^C$ is independently selected from halogen, $C_{1-4}$ aliphatic or $C_{1-4}$ haloaliphatic.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, or Formula I-e, the compound is one of Formulae I-f or I-g, or a pharmaceutically acceptable salt thereof:

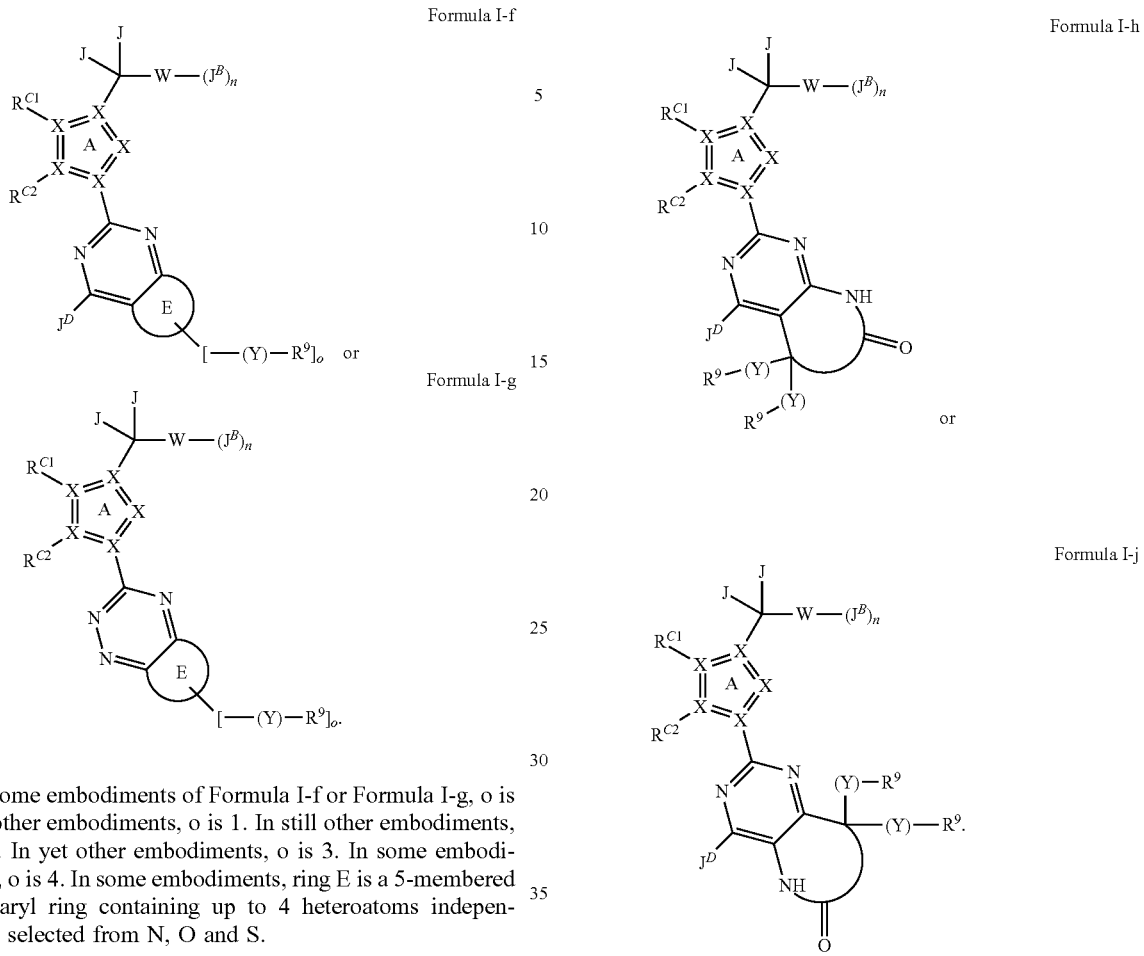

In some embodiments of Formula I-f or Formula I-g, o is 0. In other embodiments, o is 1. In still other embodiments, o is 2. In yet other embodiments, o is 3. In some embodiments, o is 4. In some embodiments, ring E is a 5-membered heteroaryl ring containing up to 4 heteroatoms independently selected from N, O and S.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, Formula I-e, Formula I-f or Formula I-g, ring E is a 5 to 7-membered heterocycle containing up to 4 heteroatoms independently selected from N, O and S. In some of these embodiments, $J^D$ is $J^A$, $-N(R^D)_2$, $-N(R^d)SO_2NHR^D$, $-N(R^d)SO_2NHCO(O)OR^D$, or $-N(R^d)SO_2NHC(O)R^D$. In other embodiments, $J^D$ is $J^A$. In still other embodiments, $J^A$ is hydrogen. In other embodiments, $J^A$ is a lone pair on nitrogen. In yet other embodiments, $J^D$ is $-N(R^D)_2$. In further embodiments, both $R^D$ moieties are hydrogen. In some embodiments, $J^D$ is $-N(R^D)_2$, and at least one instance of $R^D$ is not hydrogen. In other embodiments when $J^D$ is $-N(R^D)_2$, $R^d$ is hydrogen and $R^D$ is methyl. In yet other embodiments when $J^D$ is $-N(R^D)_2$, one $R^D$ is hydrogen and one $R^D$ is methyl. In still other embodiments, is a $C_{1-6}$ aliphatic substituted with up to 5 instances of $R^{5d}$. In some of these embodiments, $R^{5d}$ is $-OR^6$, and $R^6$ is hydrogen. In some embodiments, ring E is a 5-membered heteroaryl ring containing up to 4 heteroatoms independently selected from N, O and S.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f or Formula I-g, the compound is one of Formulae I-h or I-j, or a pharmaceutically acceptable salt thereof:

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f or Formula I-g the compound is one of Formulae I-k or I-m, or a pharmaceutically acceptable salt thereof:

-continued

Formula I-m

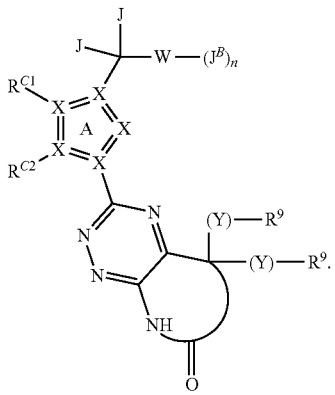

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f, Formula I-g, Formula I-k or Formula I-m, Y is present and $R^9$ is hydrogen. In other embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f, Formula I-g, Formula I-k or Formula I-m, Y is absent and $R^9$ is a 5 to 6-membered heteroaryl ring containing up to 4 heteroatoms, and is optionally substituted with up to 3 instances of $R^{11}$. In some of these embodiments, $R^9$ is $C_{1-6}$ alkyl optionally substituted with up to 3 instances of $R^{11}$. In still other embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f, Formula I-g, Formula I-k or Formula I-m, Y is absent and $R^9$ is —C(O)N($R^{10}$)$_2$, wherein $R^{10}$ is hydrogen or $C_{1-6}$ alkyl, said $C_{1-6}$ alkyl being optionally substituted with up to 3 instances of $R^{11a}$. In yet other embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, or Formula I-c, Formula I-e, Formula I-f, Formula I-g, Formula I-k or Formula I-m, Y is absent and $R^9$ is —CN. In other embodiments, Y is absent and $R^9$ is $C_{1-6}$ alkyl, optionally substituted with up to 3 instances of $R^{11}$.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, Formula I-e, Formula I-f or Formula I-g, the compound is represented by Formula I-n or Formula I-o, or a pharmaceutically acceptable salt thereof:

Formula I-n

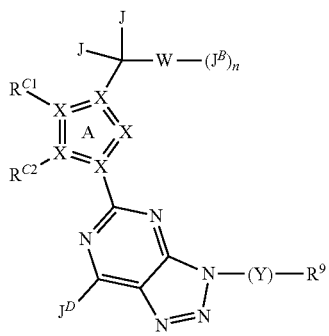

or

Formula I-o

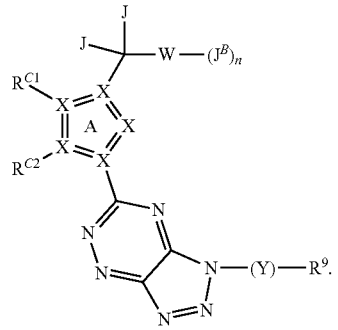

In some embodiments of Formula I-n or Formula I-o, Y is present and $R^9$ is a 5 to 6-membered heteroaryl ring containing up to 4 heteroatoms substituted with up to 3 instances of $R^{11}$. In other embodiments, $R^{11}$ is —$OR^{12}$ or $C_{1-6}$ alkyl substituted by up to 6 instances of fluoro. In some of these embodiments, $R^{12}$ is hydrogen.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, Formula I-e, Formula I-f or Formula I-g, the compound is represented by Formula I-p or Formula I-q, or a pharmaceutically acceptable salt thereof:

Formula I-p

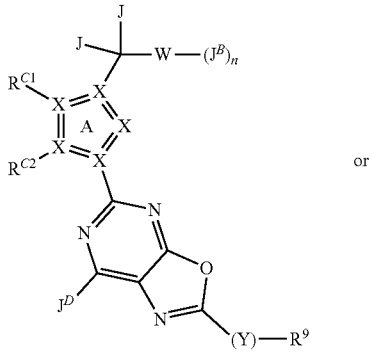

or

Formula I-q

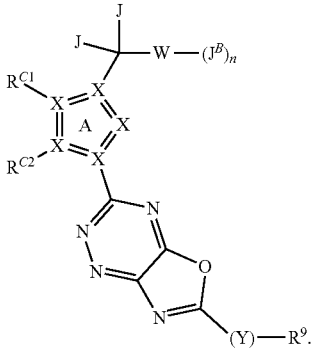

In some embodiments of Formula I-p or Formula I-q, Y is absent and $R^9$ is a $C_{3-6}$ cycloalkyl ring or a phenyl ring substituted with up to 3 instances of $R^{11}$. In other embodiments, Y is absent, $R^9$ is a $C_{3-6}$ cycloalkyl ring substituted with up to 3 instances of $R^{11}$ and $R^{11}$ is a $C_{1-6}$ alkyl optionally substituted with up to 6 instances of fluorine. In still other embodiments, Y is absent, $R^9$ is phenyl substituted with up to 3 instances of $R^{11}$ and $R^{11}$ is halogen.

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, Formula I-e, Formula I-f or Formula I-g, the compound is represented by Formula I-r or Formula I-s, or a pharmaceutically acceptable salt thereof:

Formula I-r

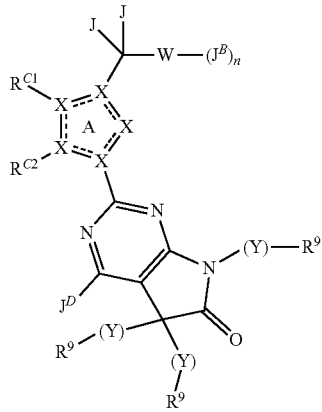

Formula I-s

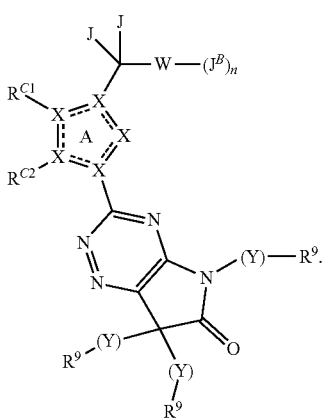

In some embodiments of Formula I', Formula I, Formula I'A, Formula I'B, Formula I'C, Formula I'D, Formula IIA, Formula IIB, Formula IIC, Formula IID, Formula IIE, Formula IIF, Formula I-a, Formula I-c, Formula I-e, Formula I-f or Formula I-g, the compound is represented by Formula I-t or Formula I-u, or a pharmaceutically acceptable salt thereof:

Formula I-t

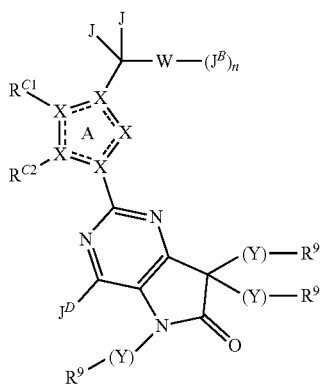

Formula I-u

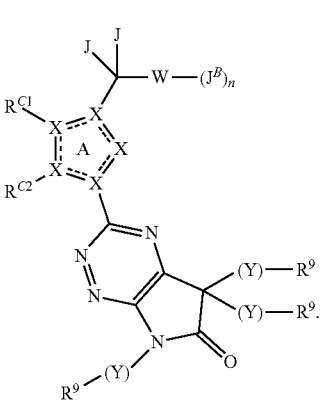

In some embodiments of Formula I-r, Formula I-s, Formula I-t or Formula I-u, the —(Y)—$R^9$ on the nitrogen atom is hydrogen. In other embodiments, at least one of the —(Y)—$R^9$ moieties on the carbon atom is methyl. In still other embodiments, both of the —(Y)—$R^9$ moieties on the carbon atom are methyl.

In some embodiments, the compound is one of Formula I" or is a pharmaceutically acceptable salt thereof:

Formula I"

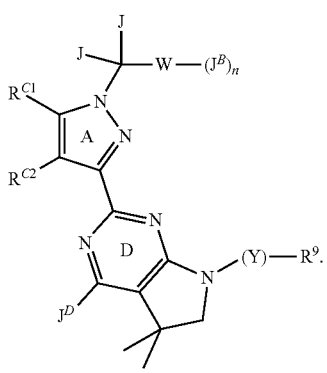

In some embodiments of Formula I", the compound is one of Formula I'" or is a pharmaceutically acceptable salt thereof:

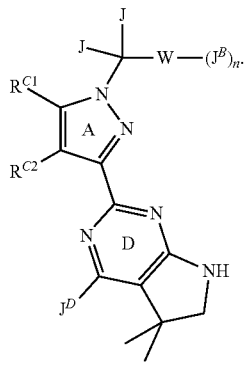
Formula I'''
In some embodiments of Formula I' or Formula I''', W is a ring B.
In some of the all the above embodiments, the compound is one selected from the Table I, below:
TABLE I
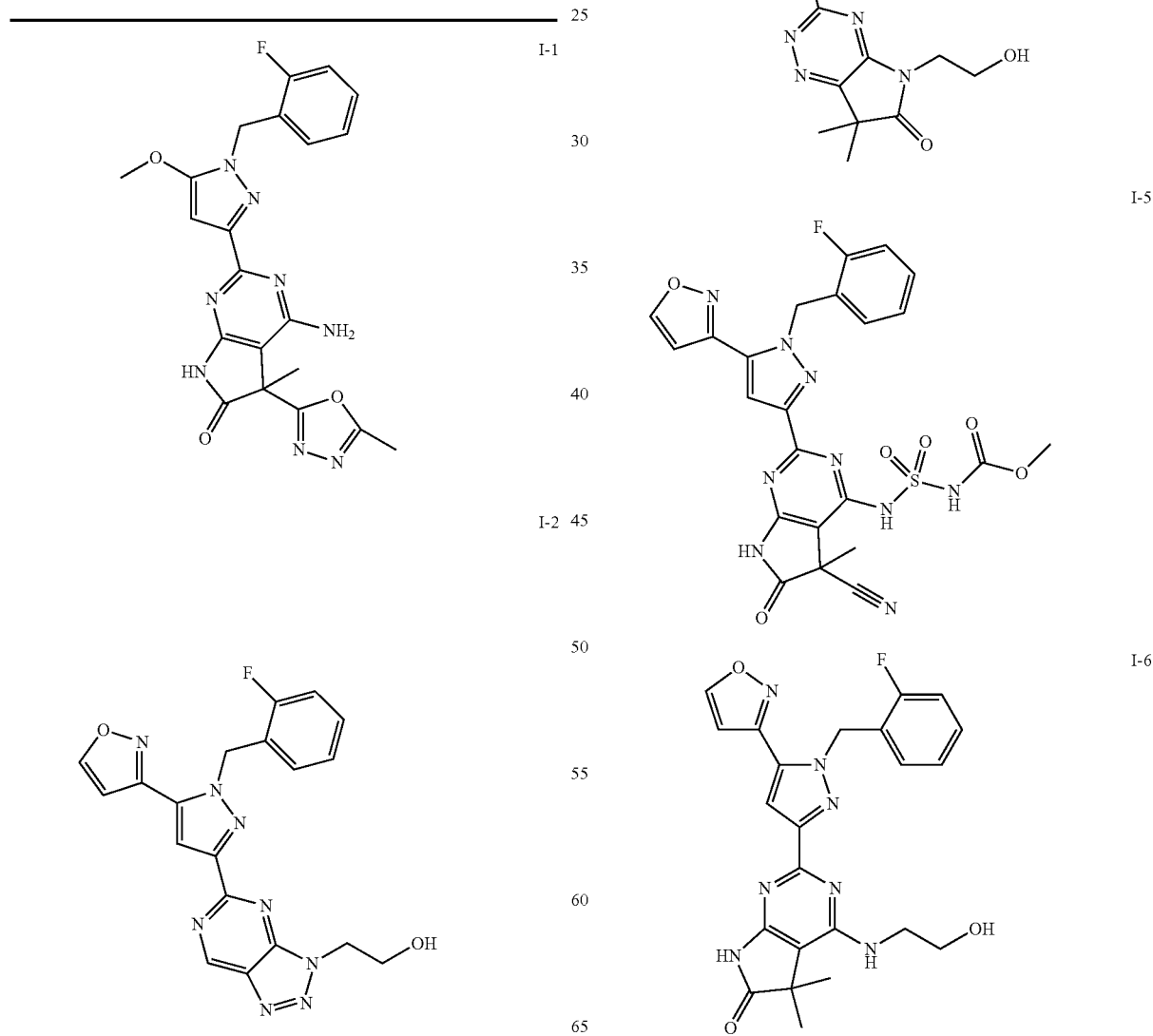
TABLE I-continued
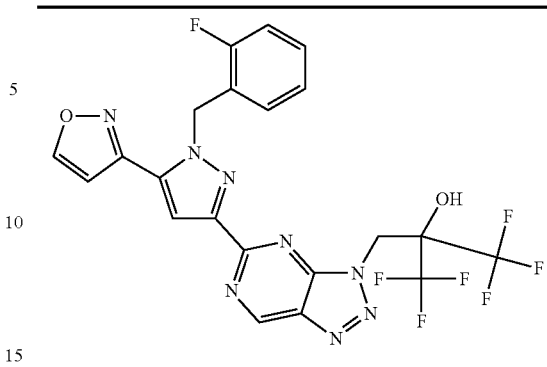

TABLE I-continued
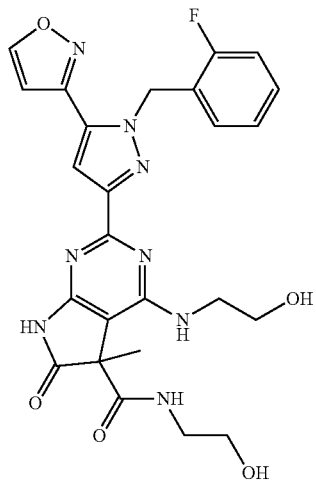 [SMILES: CC1(C(=O)NCCO)C(=O)Nc2nc(-c3cc(-c4ccon4)n(Cc4ccccc4F)n3)nc(NCCO)c21]
I-7
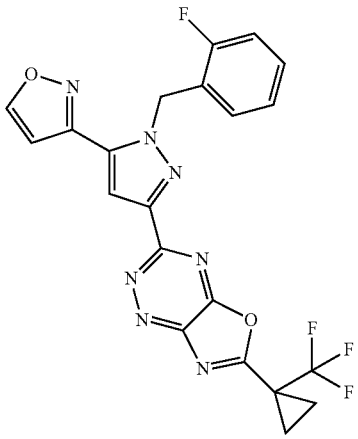 [SMILES: Fc1ccccc1Cn1nc(-c2nnc3nc(C4(C(F)(F)F)CC4)oc3n2)cc1-c1ccon1]
I-10
I-8
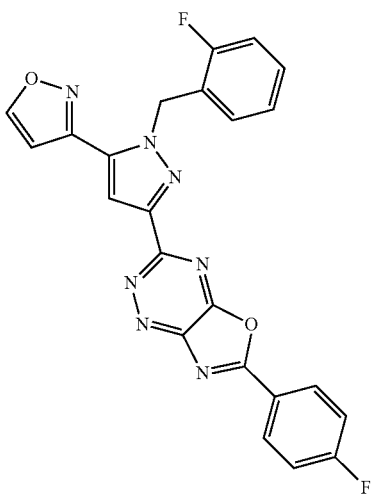 [SMILES: Fc1ccc(-c2nc3nnc(-c4cc(-c5ccon5)n(Cc5ccccc5F)n4)nc3o2)cc1]
I-11
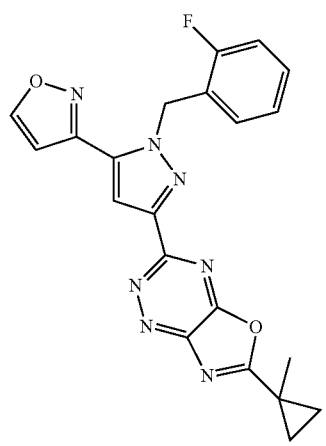
I-9
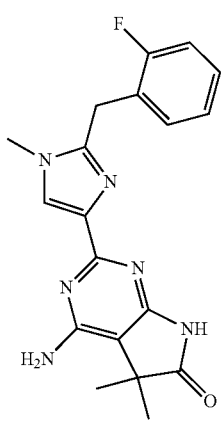 [SMILES: Cn1cc(-c2nc(N)c3c(n2)NC(=O)C3(C)C)nc1Cc1ccccc1F]
I-12

TABLE I-continued
I-13
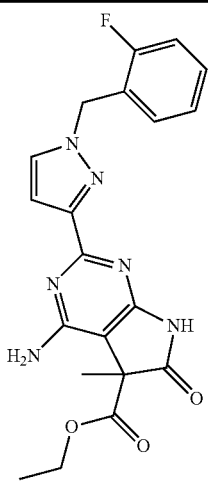
I-14
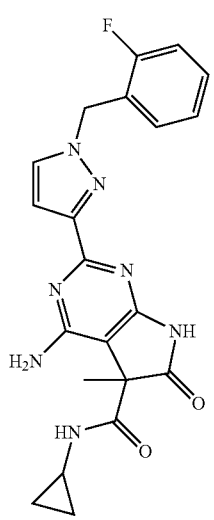 [SMILES: CC1(C(=O)NC2CC2)C(=O)Nc2nc(-c3ccn(Cc4ccccc4F)n3)nc(N)c21]
I-15
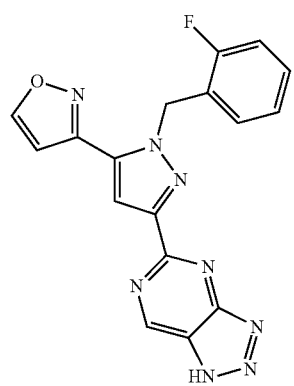 [SMILES: Fc1ccccc1Cn1nc(-c2ncc3[nH]nnc3n2)cc1-c1ccon1]
TABLE I-continued
I-16
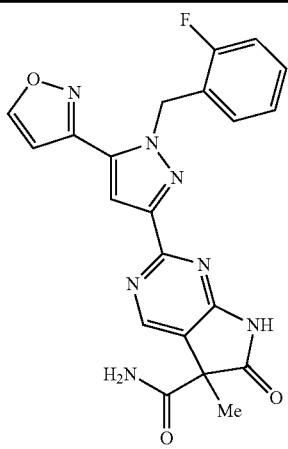
I-17
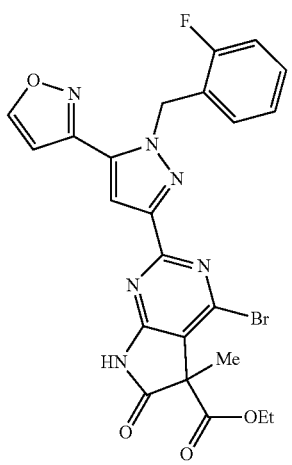 [SMILES: CCOC(=O)C1(C)C(=O)Nc2nc(-c3cc(-c4ccon4)n(Cc4ccccc4F)n3)nc(Br)c21]
I-18
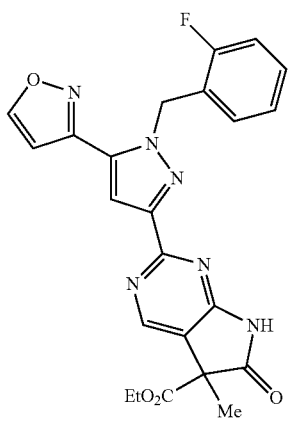 [SMILES: CCOC(=O)C1(C)C(=O)Nc2nc(-c3cc(-c4ccon4)n(Cc4ccccc4F)n3)ncc21]

TABLE I-continued
I-19
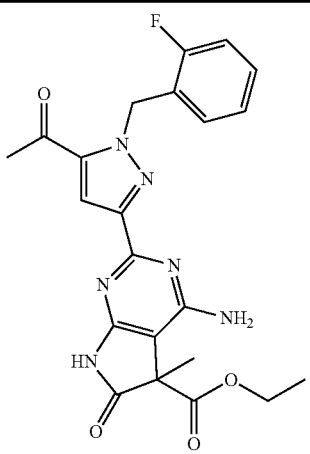
I-20
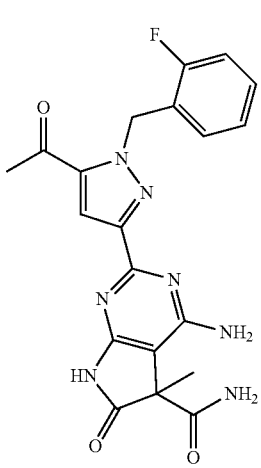 [SMILES: CC(=O)c1cc(-c2nc(N)c3c(n2)NC(=O)C3(C)C(N)=O)nn1Cc1ccccc1F]
I-21
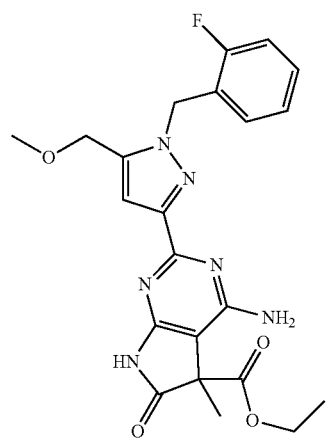 [SMILES: CCOC(=O)C1(C)C(=O)Nc2nc(-c3cc(COC)n(Cc4ccccc4F)n3)nc(N)c21]
TABLE I-continued
I-22
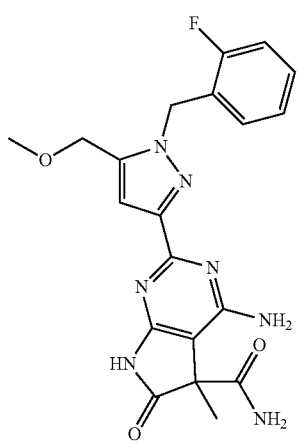 [SMILES: COCc1cc(-c2nc(N)c3c(n2)NC(=O)C3(C)C(N)=O)nn1Cc1ccccc1F]
I-23
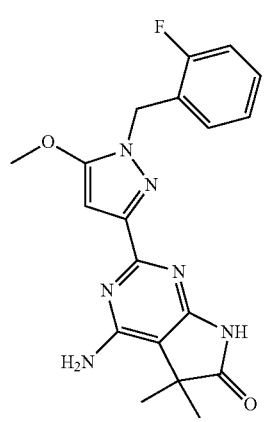 [SMILES: COc1cc(-c2nc(N)c3c(n2)NC(=O)C3(C)C)nn1Cc1ccccc1F]
I-24
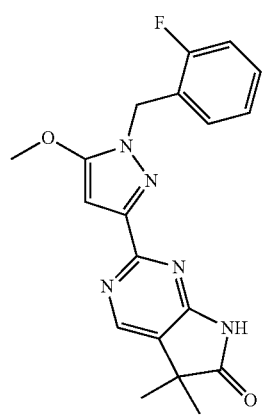 [SMILES: COc1cc(-c2ncc3c(n2)NC(=O)C3(C)C)nn1Cc1ccccc1F]

TABLE I-continued
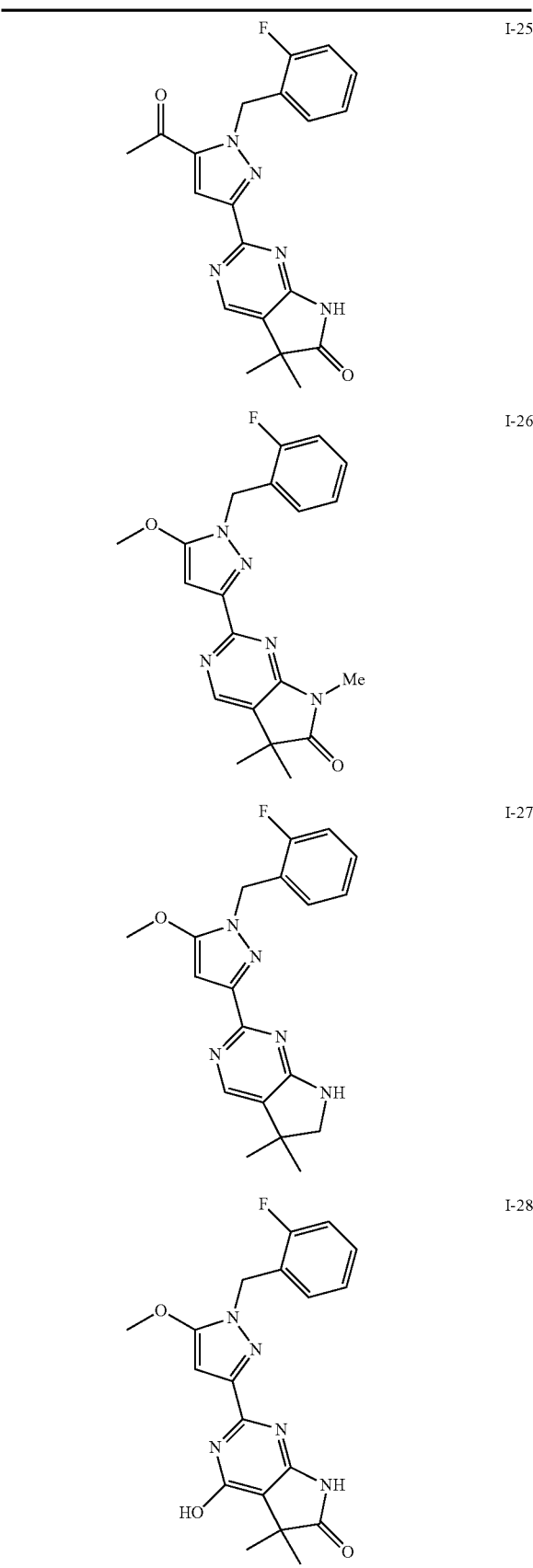
I-25
I-26
I-27
I-28
TABLE I-continued
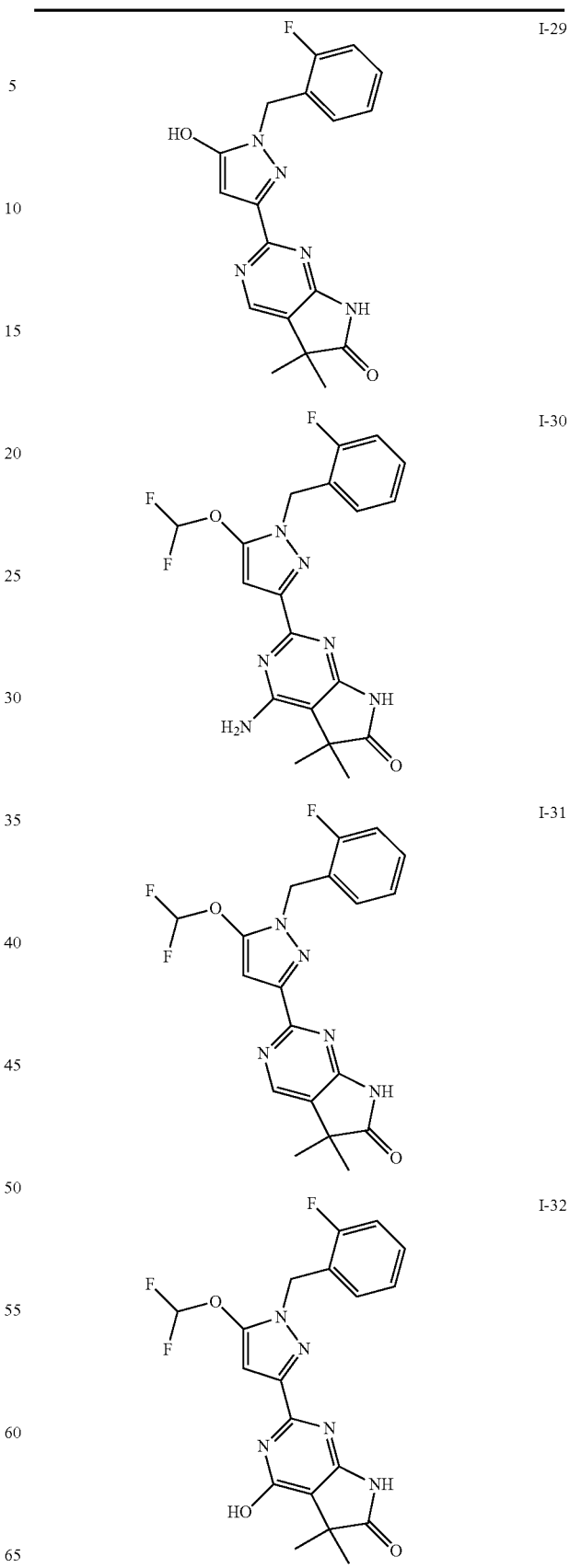
I-29
I-30
I-31
I-32

TABLE I-continued
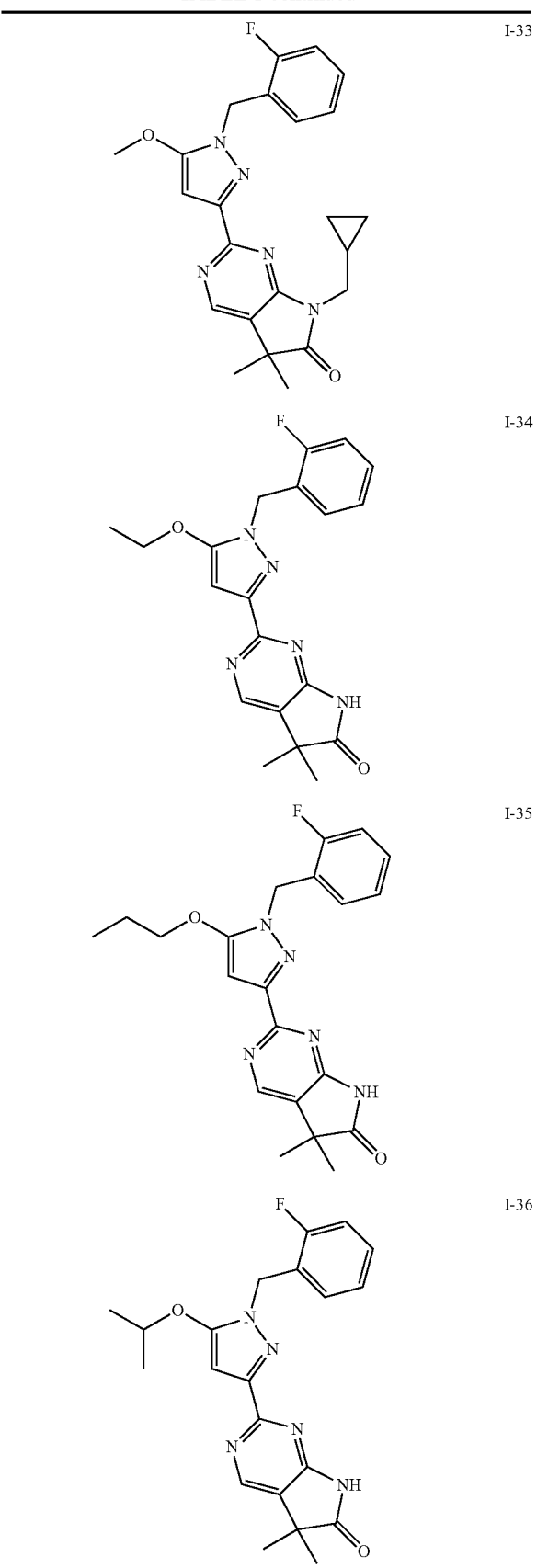

TABLE I-continued
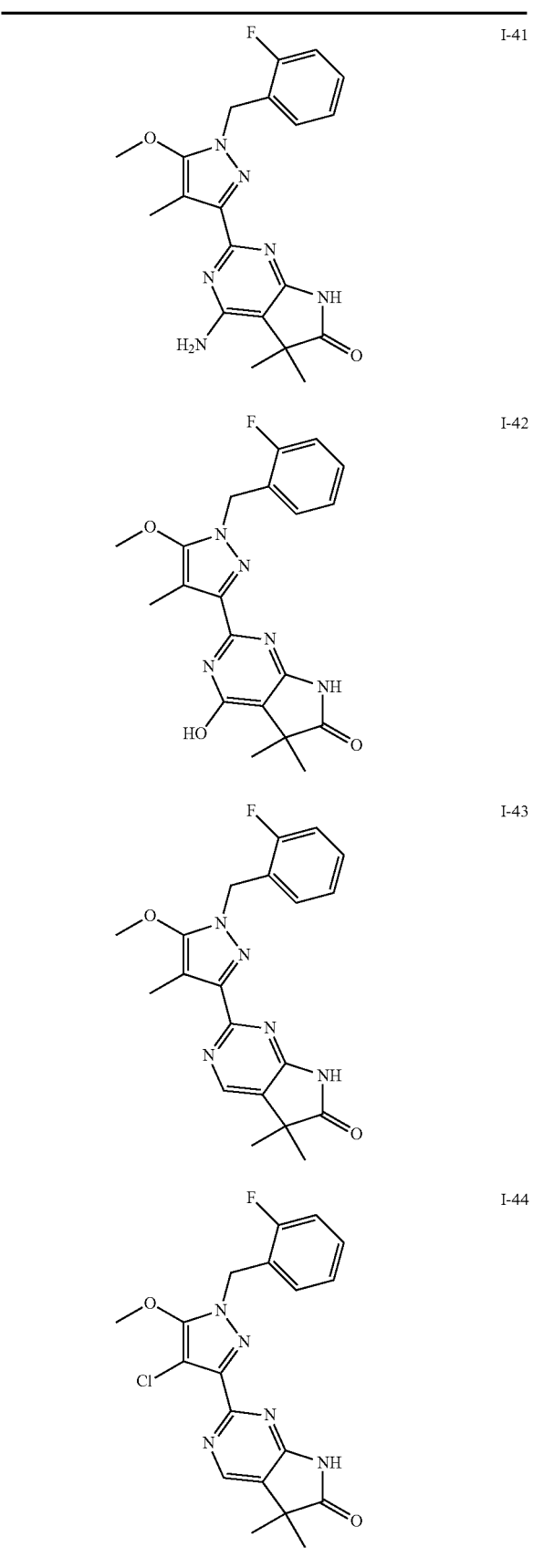
I-41
I-42
I-43
I-44
TABLE I-continued
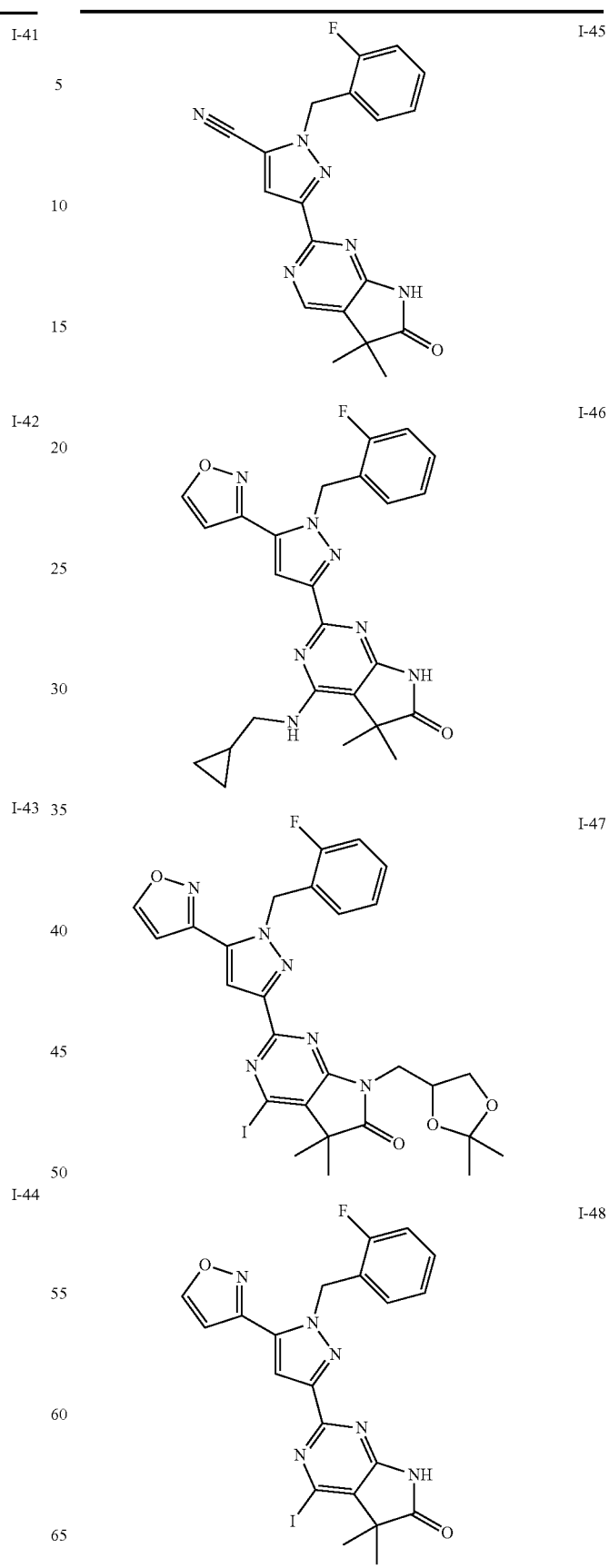
I-45
I-46
I-47
I-48

TABLE I-continued
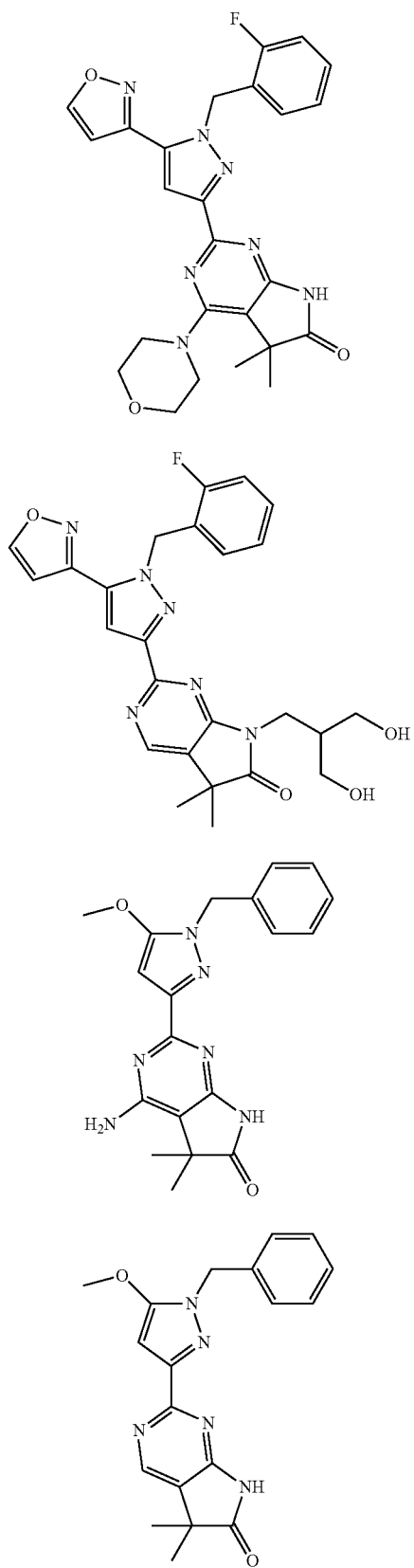
I-49
I-50
I-51
I-52
TABLE I-continued
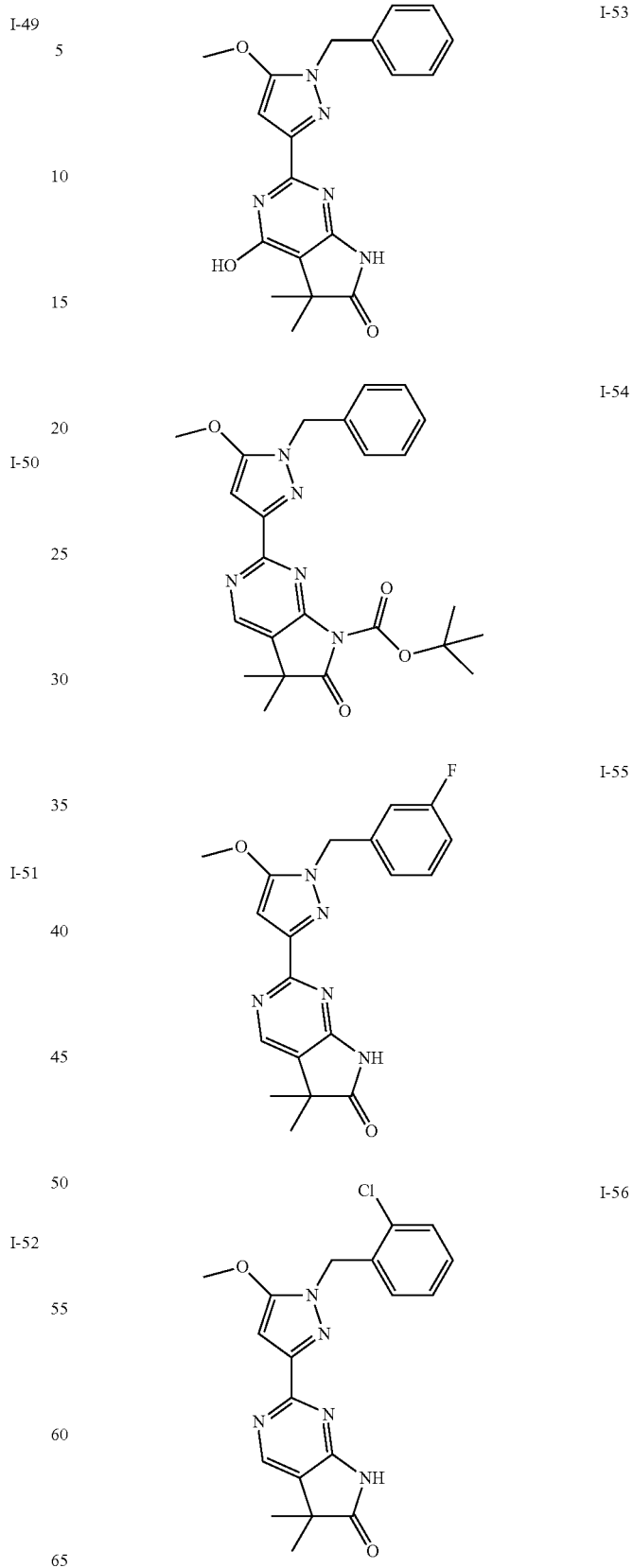
I-53
I-54
I-55
I-56

TABLE I-continued
I-57
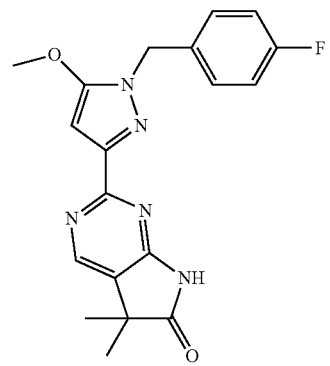 [SMILES: COc1cc(-c2ncc3c(n2)NC(=O)C3(C)C)nn1Cc1ccc(F)cc1]
I-58
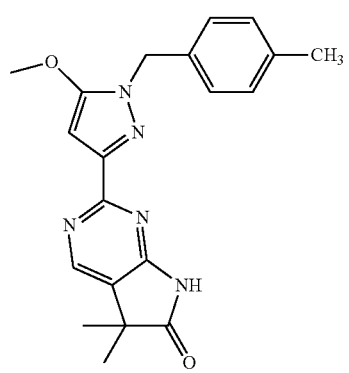
I-59
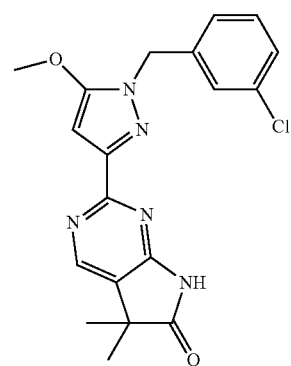 [SMILES: COc1cc(-c2ncc3c(n2)NC(=O)C3(C)C)nn1Cc1cccc(Cl)c1]
I-60
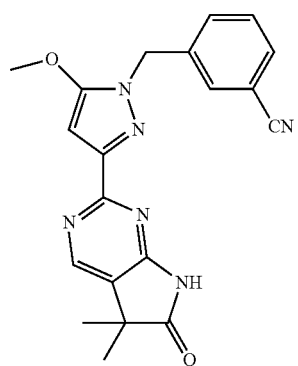 [SMILES: COc1cc(-c2ncc3c(n2)NC(=O)C3(C)C)nn1Cc1cccc(C#N)c1]
TABLE I-continued
I-61
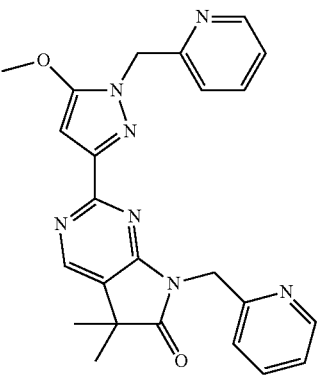 [SMILES: COc1cc(-c2ncc3c(n2)N(Cc2ccccn2)C(=O)C3(C)C)nn1Cc1ccccn1]
I-62
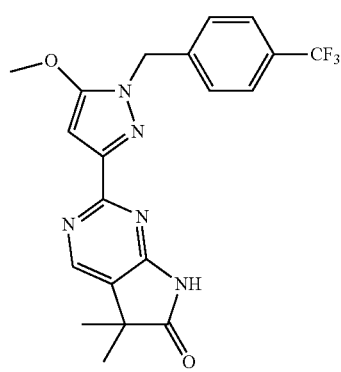 [SMILES: COc1cc(-c2ncc3c(n2)NC(=O)C3(C)C)nn1Cc1ccc(C(F)(F)F)cc1]
I-63
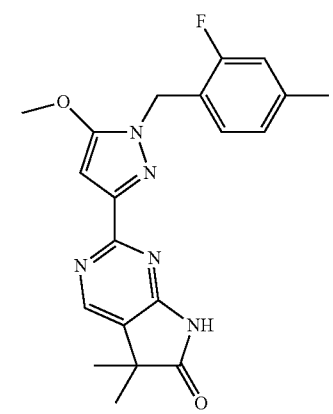
I-64
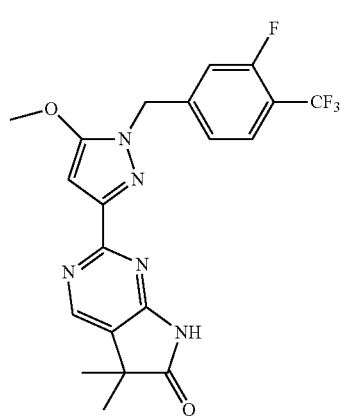 [SMILES: COc1cc(-c2ncc3c(n2)NC(=O)C3(C)C)nn1Cc1ccc(C(F)(F)F)c(F)c1]

TABLE I-continued
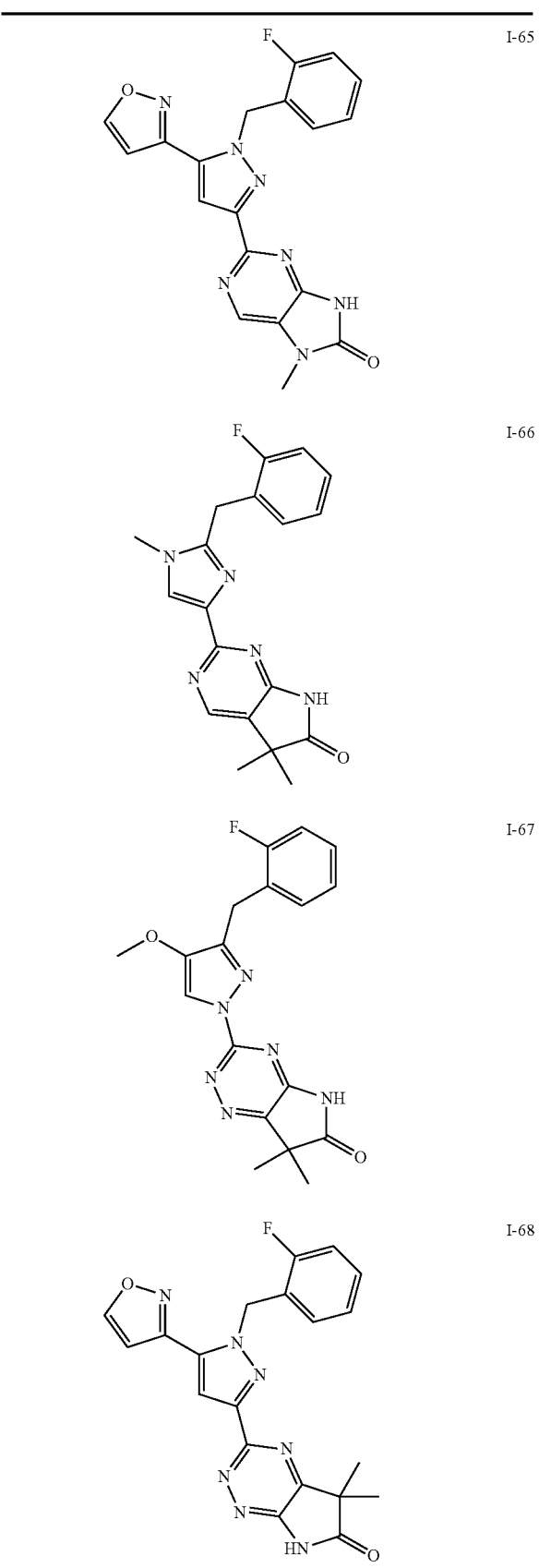
I-65
I-66
I-67
I-68
TABLE I-continued
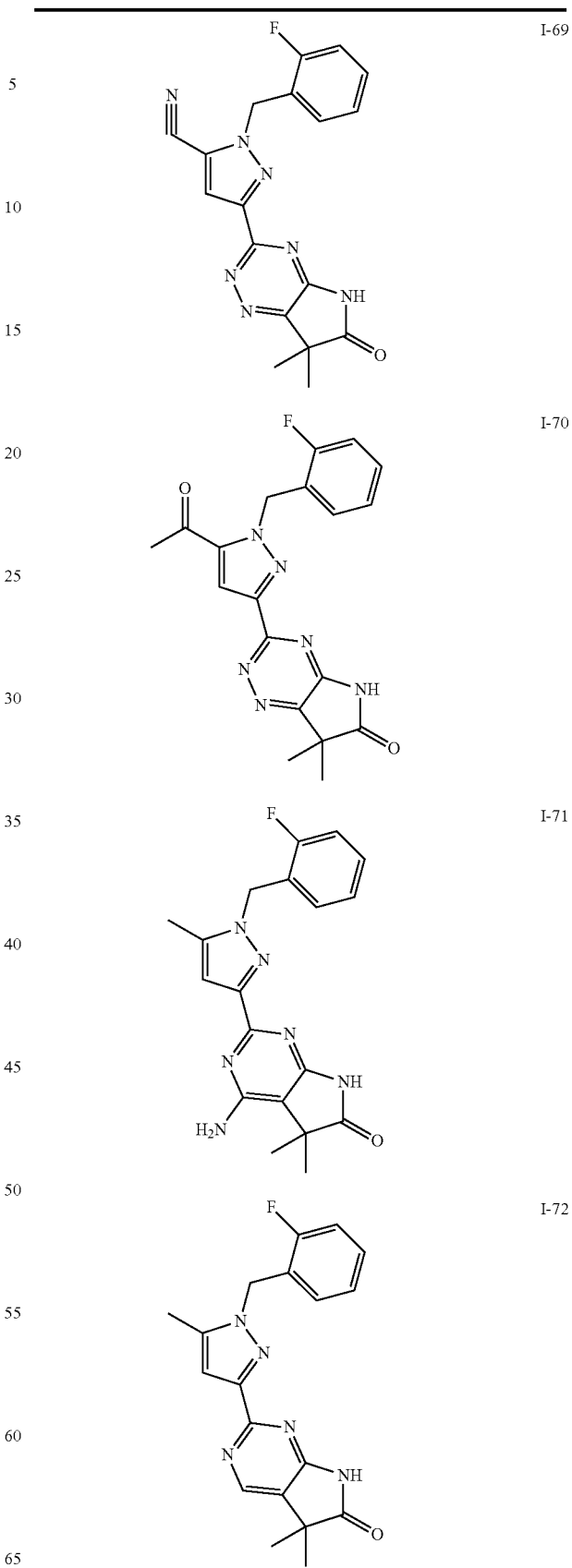
I-69
I-70
I-71
I-72

TABLE I-continued
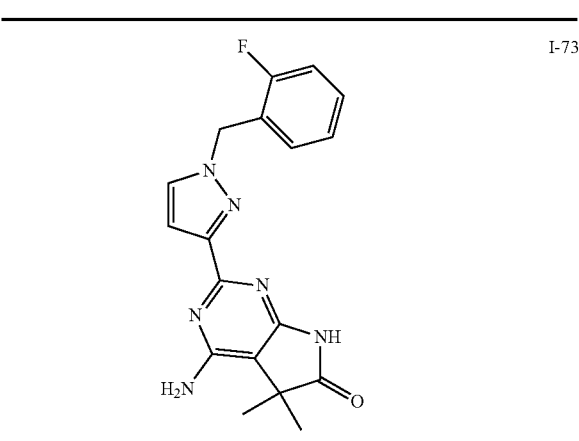
I-73
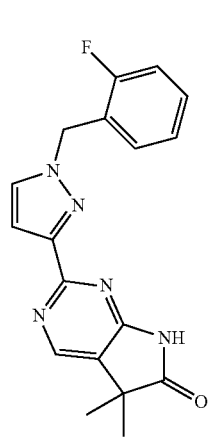 [SMILES: CC1(C)C(=O)Nc2nc(-c3ccn(Cc4ccccc4F)n3)ncc21]
I-74
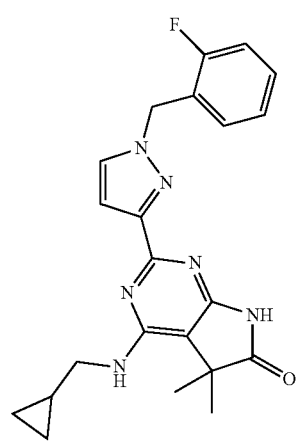 [SMILES: CC1(C)C(=O)Nc2nc(-c3ccn(Cc4ccccc4F)n3)nc(NCC3CC3)c21]
I-75
TABLE I-continued
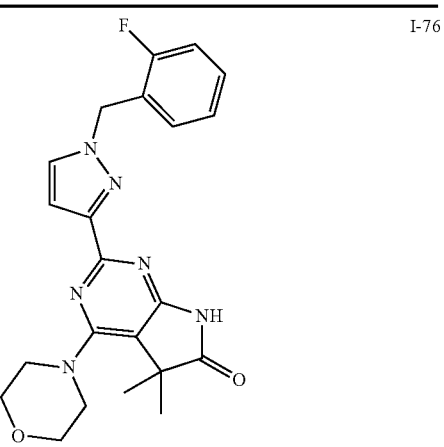
I-76
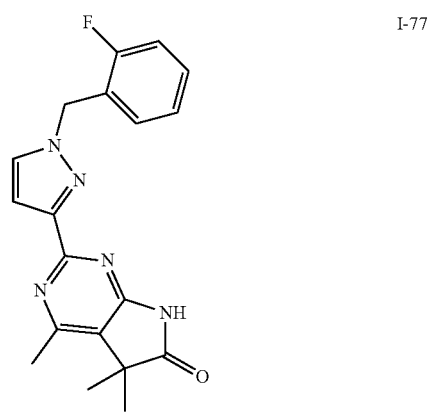
I-77
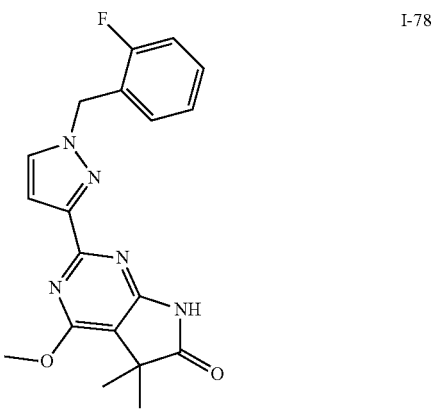
I-78
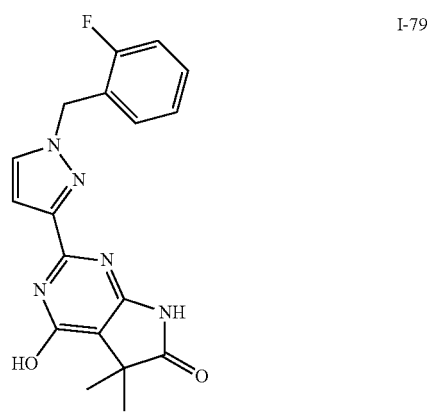
I-79

TABLE I-continued
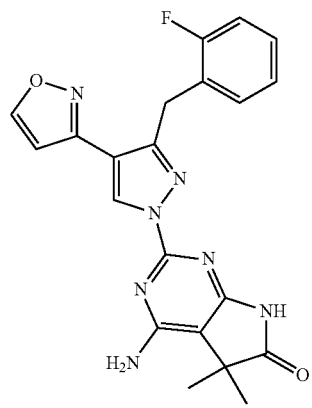 [SMILES: CC1(C)C(=O)Nc2nc(-n3cc(-c4ccon4)c(Cc4ccccc4F)n3)nc(N)c21]
I-80
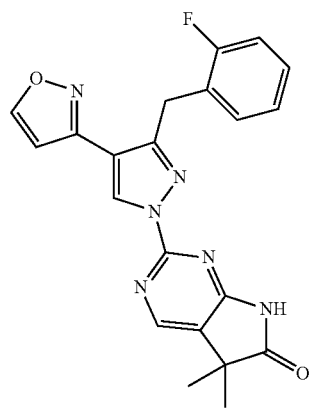 [SMILES: CC1(C)C(=O)Nc2nc(-n3cc(-c4ccon4)c(Cc4ccccc4F)n3)ncc21]
I-81
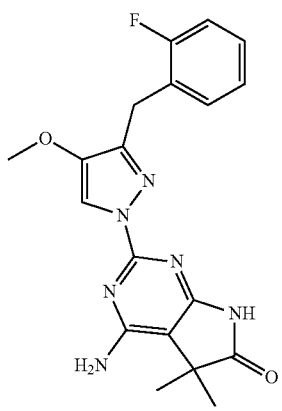 [SMILES: COc1cn(-c2nc(N)c3c(n2)NC(=O)C3(C)C)nc1Cc1ccccc1F]
I-82
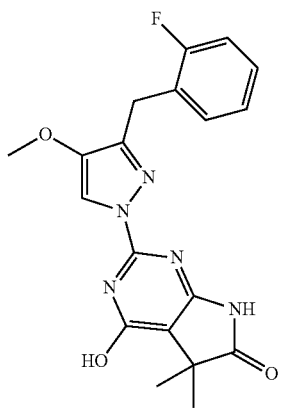 [SMILES: COc1cn(-c2nc(O)c3c(n2)NC(=O)C3(C)C)nc1Cc1ccccc1F]
I-83
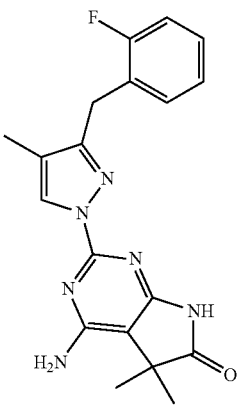 [SMILES: Cc1cn(-c2nc(N)c3c(n2)NC(=O)C3(C)C)nc1Cc1ccccc1F]
I-84
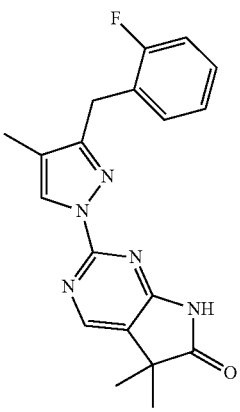 [SMILES: Cc1cn(-c2ncc3c(n2)NC(=O)C3(C)C)nc1Cc1ccccc1F]
I-85
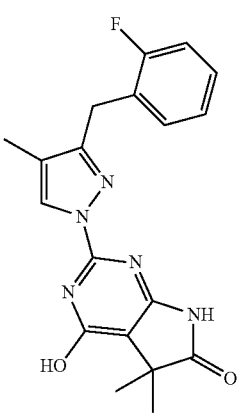 [SMILES: Cc1cn(-c2nc(O)c3c(n2)NC(=O)C3(C)C)nc1Cc1ccccc1F]
I-86
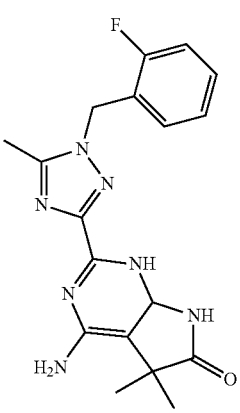 [SMILES: Cc1nc(C2=NC(N)=C3C(NC(=O)C3(C)C)N2)nn1Cc1ccccc1F]
I-87

TABLE I-continued

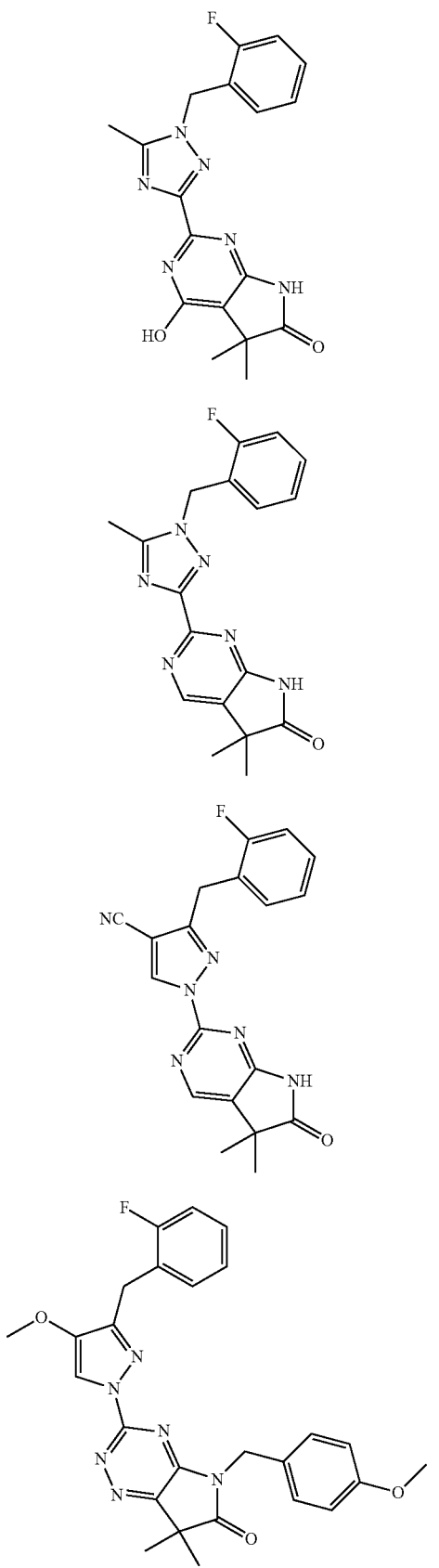

I-88

I-89

I-90

I-91

TABLE I-continued

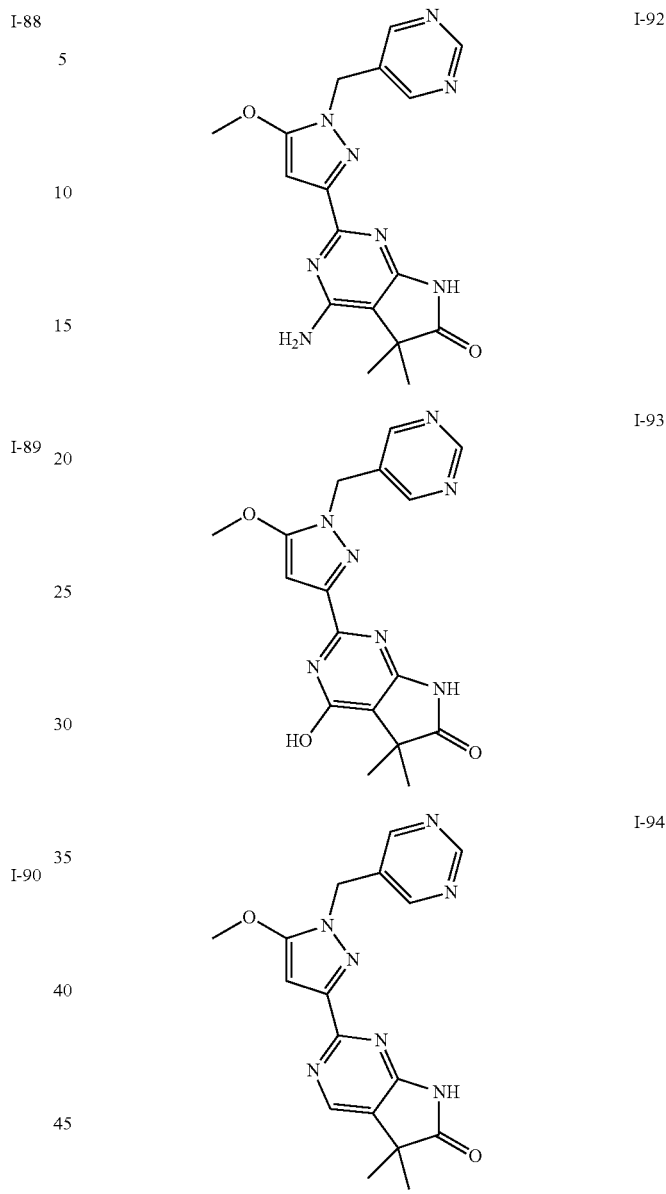

I-92

I-93

I-94

Methods of Preparing the Compounds of the Invention
General Synthetic Schemes

Compounds of the present invention embodied in Formula I', Formula I or Table I may be synthesized by those skilled in the art of synthetic organic chemistry using a variety of synthetic routes such as those depicted in, but not restricted to, the following Schemes.

As depicted in Scheme 1, pyrazole esters of general structure 4 may be synthesized by Claisen condensation of substituted hydrazines 3 with diones 2. Dione 2 may be accessed by condensation of commercially available ketone 1 and diethyl oxalate in the presence of lithium hexamethyldisilazide in ethanol (see Finn et al. *Bio. Med. Chem. Lett.* 2003, 13, 2231). If methyl ketone 1 is not commercially available, it may be synthesized by conversion of the appropriate carboxylic acid to the Weinreb amide by treatment with oxalyl chloride in the presence of catalytic N,N-dimethylformamide in a solvent such as dichloromethane, followed by treatment with N,O-dimethylhydroxylamine hydrochloride. The resulting Weinreb amide may then be alkylated using methyllithium in diethyl ether. Substituted hydrazines 3 may be synthesized by reaction of the appropriate bromide or other halide with hydrazine hydrate in a solvent such as ethanol. Alternatively, 3 may be accessed by condensation of tert-butyl carbazate with a ketone or aldehyde in THF, followed by reduction of the resulting hydrazone with palladium on activated carbon in methanol/THF, followed by carbamate removal using TFA in dichloromethane.

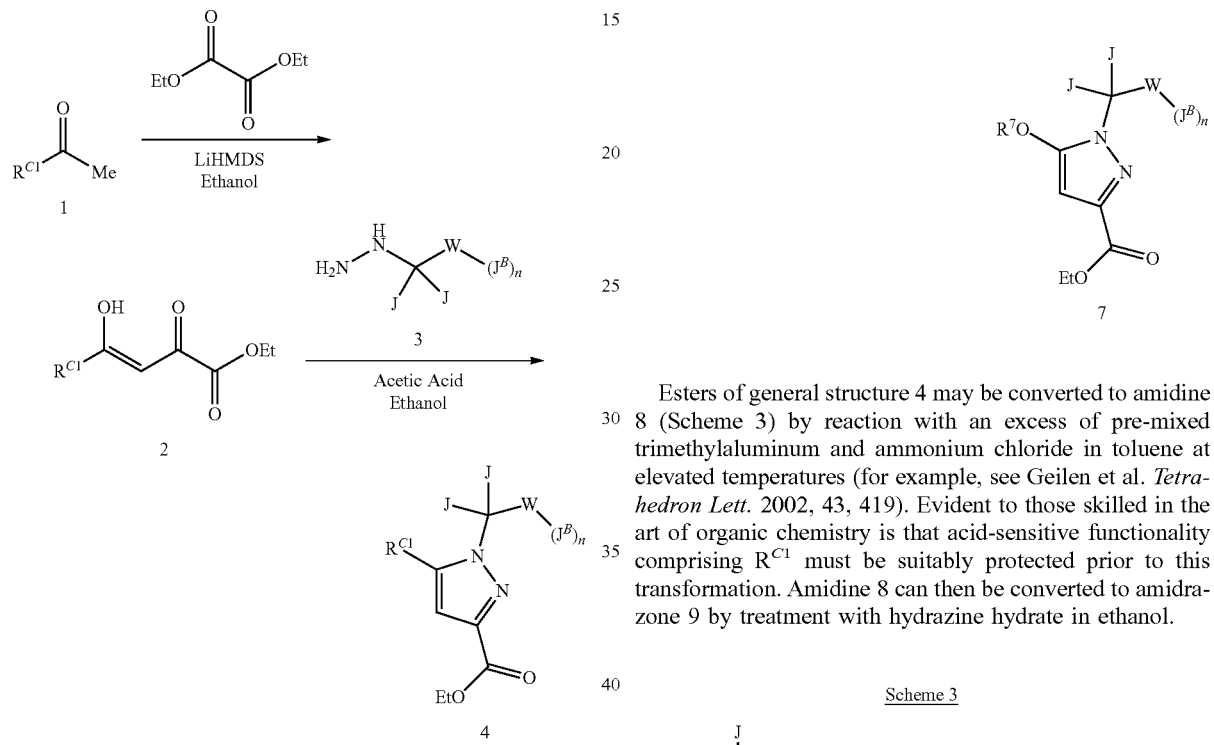

Scheme 2 illustrates the synthesis of ester pyrazole 7 when $R^{C1}$ is an alkoxy group. Refluxing hydrazine 3, commercially available diester 5, and acetic acid in ethanol leads to hydroxypyrazole 6 (see Dunn et al. WO2004/74257). Alkylation of the hydroxyl group may be accomplished using an inorganic base such as cesium carbonate or potassium carbonate along with the appropriate alkyl bromide or other halide in N,N-dimethylformamide to give alkyl ether 7.

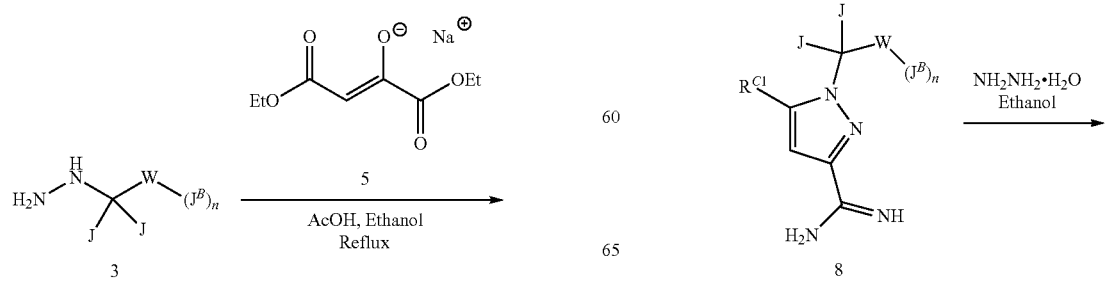

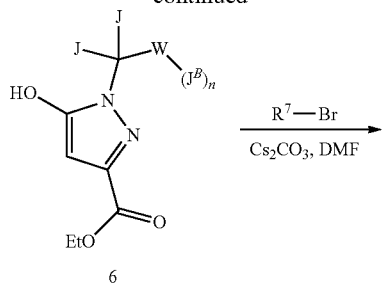

Esters of general structure 4 may be converted to amidine 8 (Scheme 3) by reaction with an excess of pre-mixed trimethylaluminum and ammonium chloride in toluene at elevated temperatures (for example, see Geilen et al. *Tetrahedron Lett.* 2002, 43, 419). Evident to those skilled in the art of organic chemistry is that acid-sensitive functionality comprising $R^{C1}$ must be suitably protected prior to this transformation. Amidine 8 can then be converted to amidrazone 9 by treatment with hydrazine hydrate in ethanol.

Scheme 3

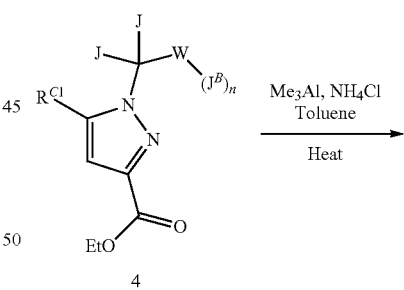

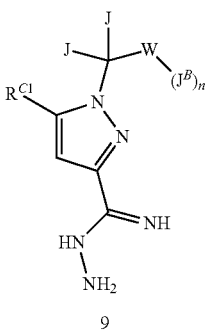

Scheme 4 illustrates a method for the synthesis of guanidine and hydrazinecarboximidamide intermediates, 19 and 20 respectively, that are useful for the synthesis of alternative pyrazole variants of Formula I compounds. Acylation of Meldrum's acid with a substituted carboxylic acid 10 using a coupling agent such as DCC followed by ethanolysis provides ketoester 11. Treatment of ketoester 11 with triethyl orthoformate or N,N-dimethylformamide dimethyl acetal affords the corresponding enolether or enamine intermediate which can then be cyclized to pyrazole 12 by reacting with hydrazine (see Okada et al. WO1993/9313099). There are other methods for constructing similarly-substituted pyrazole rings (for example, see Kelly et al. *Tetrahedron Lett.* 1999, 40, 1857). Protection of pyrazole 12 with a protecting group such as PMB followed by a three-step sequence of saponification, Curtius rearrangement (see Liu et al. *ACS Med. Chem. Lett.* 2013, 4, 259) and Sandmeyer reaction (see Atobe et al. *Bioorg. Med. Chem. Lett.* 2013, 23, 6569) affords a versatile iodopyrazole intermediate 16. As an example, transition metal-catalyzed cross-coupling reactions of iodide 16 with coupling partners such as but not limited to commercially available or literature-described boronic acids, alcohols, amines and sulfinates can be used to install a wide variety of $R^{C1}$ groups to provide substituted pyrazole 17. Alternatively, iodide intermediate 16 can be converted to the corresponding boronic acid or boronic ester via transition metal-catalyzed borylation so that additional halides and triflates can be used as coupling partners. After deprotection of the PMB group using TFA, the resultant pyrazole 18 can be converted to guanidine intermediate 19 by treatment with cyanamide under acidic conditions (see Lee et al. *Bioorg. Med. Chem. Lett.* 2000, 10, 2771) or hydrazinecarboximidamide 20 by treatment with sodium hydride/cyanogen bromide followed by hydrazine (see Kvaskoff et al. *J. Org. Chem.* 2006, 71, 4049; Bunevet et al. *Chem. Heterocyclic Compounds* 2012, 48, 1415). In addition, we have previously described a synthesis of an isoxazole-substituted pyrazole 21 or other heteroaryl-substituted pyrazoles using intermediate 13 (see Nakai et al. WO2014/047325).

Scheme 4

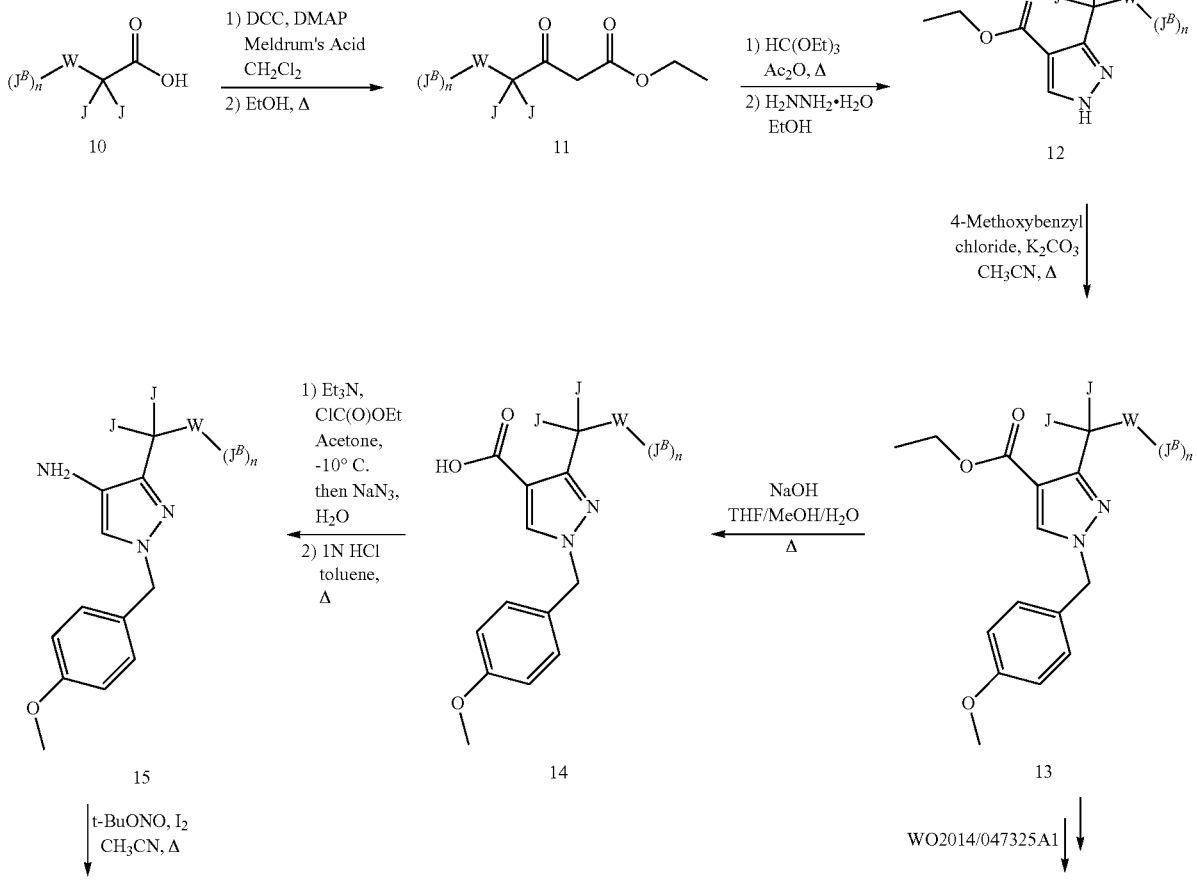

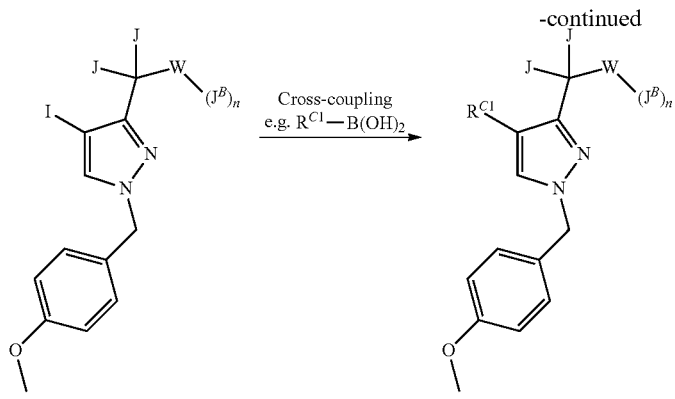

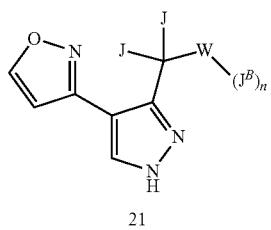

As depicted in Scheme 5, compounds of general structure 22 (for instance amidine 8 as described in Scheme 3 or guanidine 19 as described in Scheme 4) may be refluxed in ethanol with ethyl acrylate 23 in the presence of a base such as DBU to furnish 4-hydroxy-5-nitropyrimidine 24. The ethyl acrylate 23 may be obtained by stirring a neat mixture of N,N-dimethylformamide dimethyl acetal and ethyl nitroacetate at elevated temperatures (see Bekkali et al. WO2005/30213). Compound 24 can be heated with phosphorous oxychloride to give chloropyrimidine 25. Nucleophilic displacement of the chloride with commercially available or literature-described amines of general formula 26 in dioxane gives aminopyrimidines of general structure 27. 5-Nitropyrimidine 27 can be reduced to the 5-aminopyrimidine 28 using hydrogen (1 atm) in the presence of palladium on activated carbon in ethanol. Conversion of diamine 28 to the pyrimidinotriazole 29 can be effected using sodium nitrite with hydrochloric acid in ethanol and water (see Hansen et al. *Synthesis,* 2010, 689).

When ammonia is used as the nucleophile to displace the chloride of pyrimidine 25, the corresponding diaminopyrimidine intermediate 30 may be treated with an electrophile such as an alkyl halide in DMF to give substituted diaminopyrimidine 31 (see Cho et al. US2012/264727). Alternatively, substituted diaminopyrimidine 31 can be accessed by a reductive amination sequence (see Follman et al. US2014/148433). Ring closure to the isomeric pyrimidinotriazole 32 can be effected using sodium nitrite with hydrochloric acid in ethanol and water.

Scheme 5

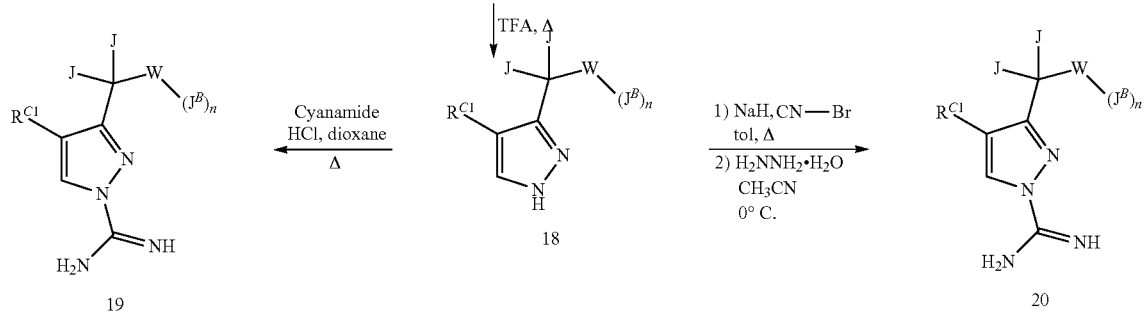

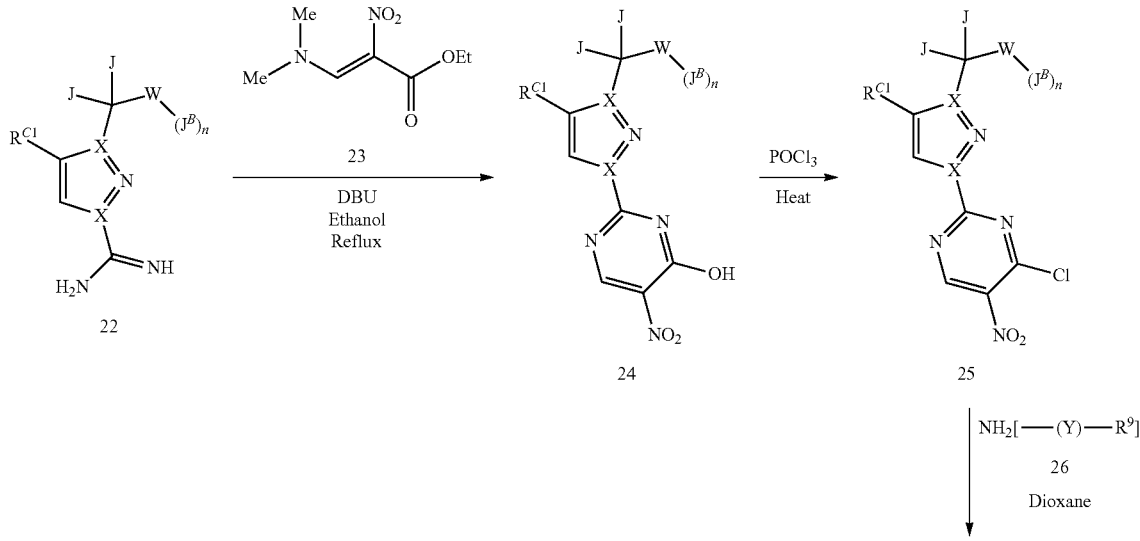

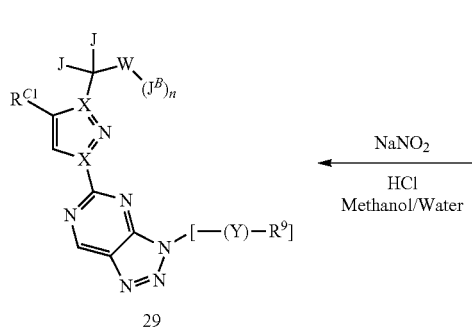
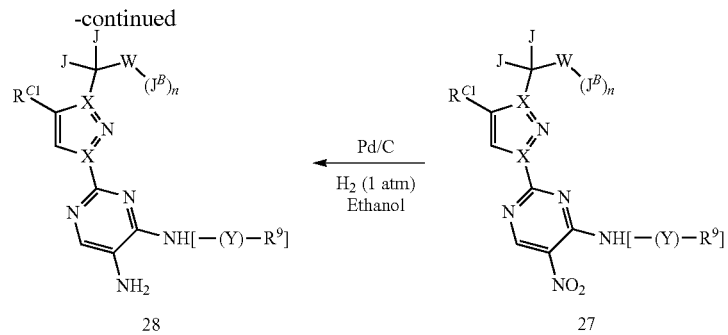
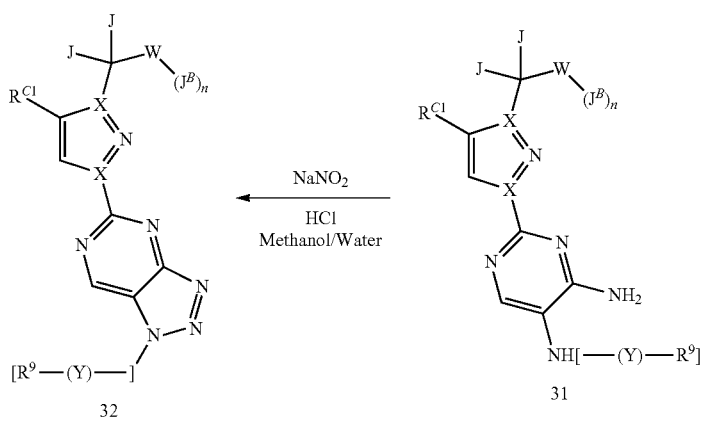
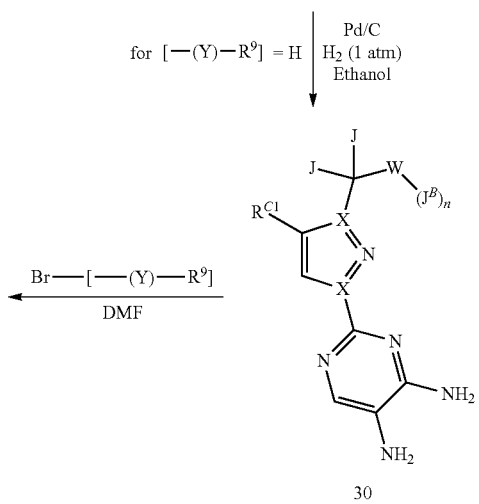

As depicted in Scheme 6, compounds of general structure 33 (for instance amidrazone 9 as described in Scheme 3 or hydrazinecarboximidamide 20 as described in Scheme 4) can be refluxed with ethyl thiooxamate in ethanol to provide aminotriazinone 34 (see Chunjian et al. WO 2010/011837). Conversion of the triazinone 34 to chlorotriazine 35 can be effected by refluxing in thionyl chloride. Compound 35 may then be converted to the diaminotriazine 36 by heating with ammonia in dioxane. Ring closed triazinotriazole 37 can be accessed using sodium nitrite in the presence of aqueous hydrochloric acid (see Tielemans et al. *J. Het. Chem.* 1987, 705). Reaction of triazinotriazole 37 using various commercially available or literature-described electrophile such as an alkyl halide in the presence of an inorganic base such as potassium carbonate in ethanol may provide a mixture of regioisomeric isomers 38a and 38b which may be readily separated by those skilled in the art of organic chemistry.

Scheme 6

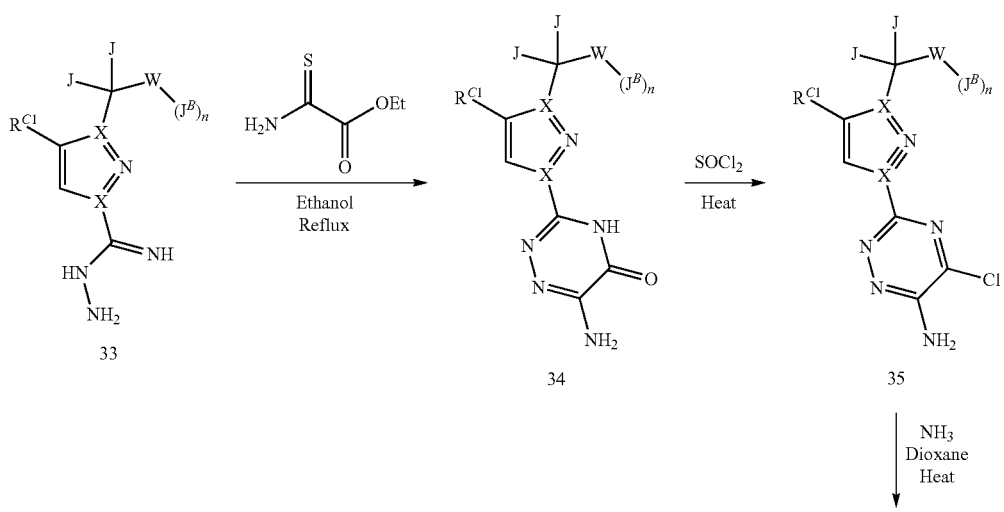

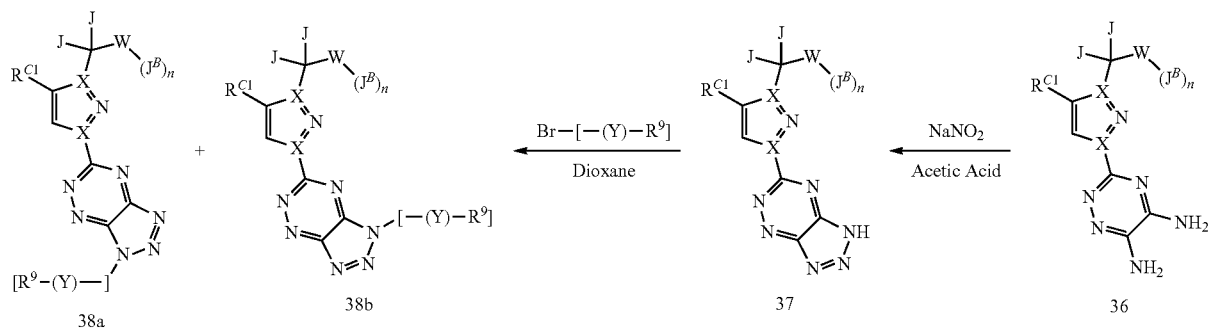

Scheme 7 illustrates a method to synthesize compounds 42 to 45 of general formula I. Following conditions detailed in our earlier work (see Kim et al. WO2013/101830 and WO2012/003405) and others (see Raghavan et al. WO2011/149921; Follmann et al. WO2013/131923 and WO2013/030288) the above described amidine 22 can be condensed with substituted dinitrile 39 in refluxing ethanol to obtain the bicyclic pyrimidine 40. The dinitrile 39 can be synthesized by procedures described in the literature. The amino group in the pyrimidine intermediate 40 can be further converted to a bromo-substituent by heating with isopropyl nitrite and copper (II) bromide in dichloroethane at 65° C. (Raghavan et al. WO2011/149921). Following a similar procedure, the amino group can also be converted to an iodo-substituent (using copper iodide). The halide group of 41 can then be functionalized using $S_NAr$ reactions with diverse nucleophiles (e.g. carbon-, amino- or hydroxyl-based nucleophiles) or transition metal catalyzed cross-coupling reactions with diverse coupling partners (e.g. boronic acids, amines, alcohols, alkynes) to give the desired compound 42. Furthermore, the annulated lactam can be substituted with a [—(Y)—$R^9$] group by treating with various electrophiles such as an alkyl halide and a base such as potassium carbonate to obtain 43.

Alternatively, the halide group of 41 can be reduced using hydrogen (1 atm) in the presence of palladium on activated carbon in ethanol to obtain pyrimidinolactam 44 (Raghavan et al. WO2011/149921). The annulated lactam can then be substituted with a [—(Y)—$R^9$] group by reacting with different electrophiles such as an alkyl halide and a base such as potassium carbonate to obtain the 45.

Scheme 7

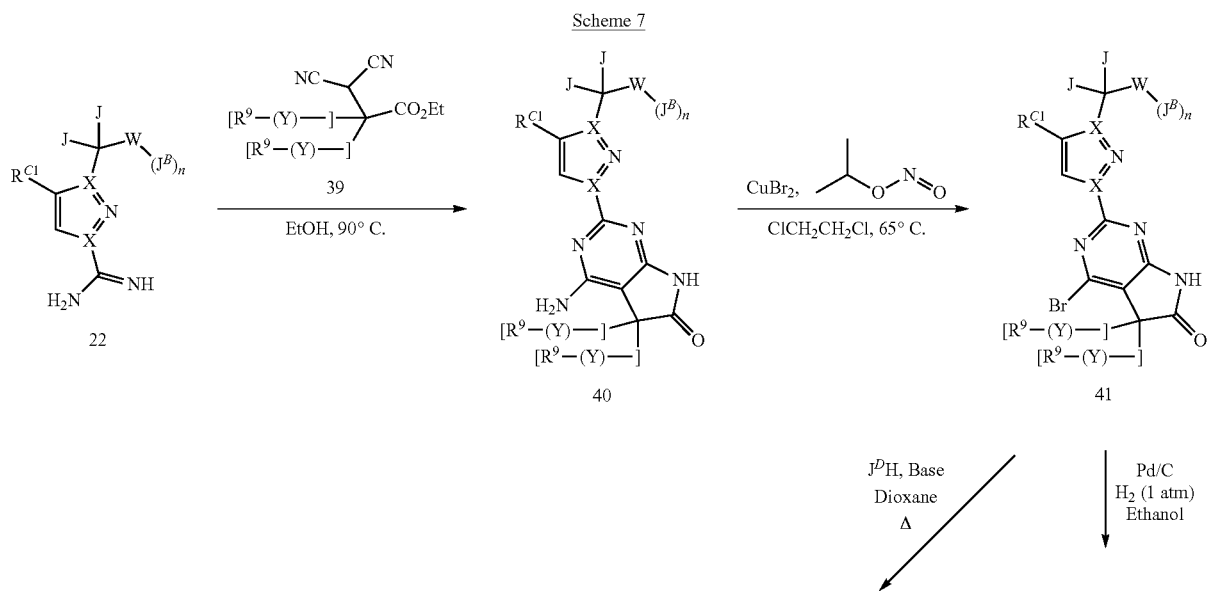

-continued

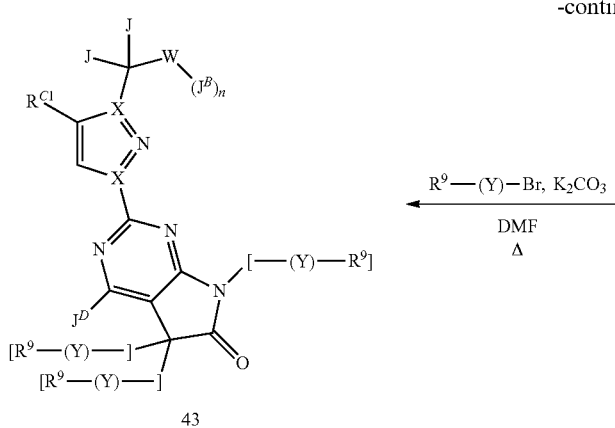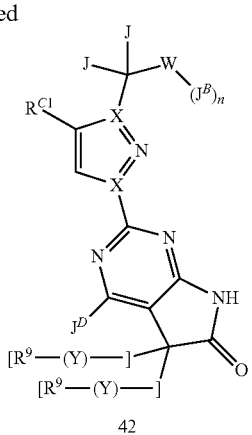

43 42

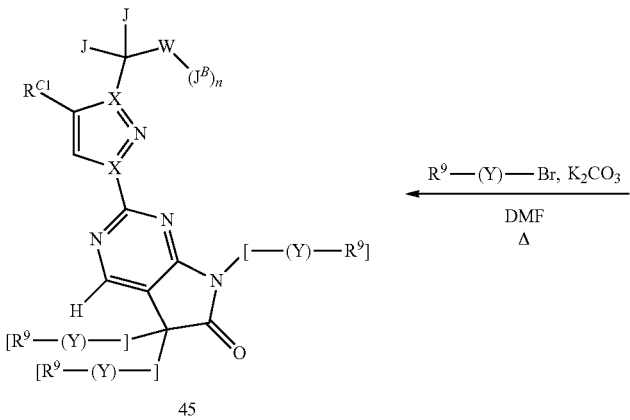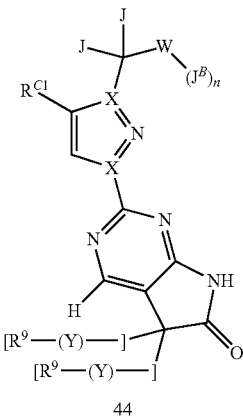

45 44

Scheme 8 described the synthesis of compounds 48 and 49 of general formula I. Chloronitropyrimidine intermediate 25 can be treated with carbon nucleophiles such as ester 46 to obtain product 47. Reduction of the nitro group in 47 under standard conditions (e.g. hydrogen and palladium on activated carbon in ethanol) will provide the corresponding aniline intermediate which will spontaneously cyclize (at ambient or elevated temperature) to yield pyrimidinolactam 48. The annulated lactam can then be substituted with a [—(Y)—R$^9$] group by reacting with different electrophiles such as an alkyl halide and a base such as potassium carbonate to obtain compound 49.

Scheme 8

-continued

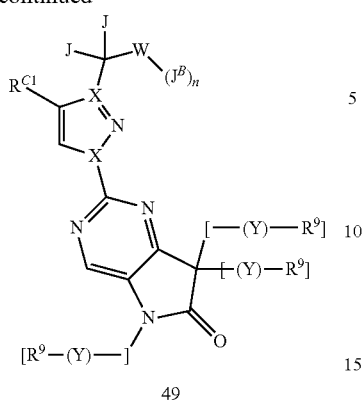

49

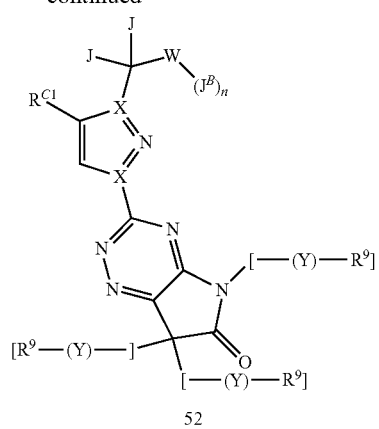

52

The procedure described for Scheme 7 can be extended to triazine-containing compound 52 as shown in Scheme 9. The intermediate 33 can be treated with keto diester 50 in refluxing ethanol to obtain the triazine 51. The keto diester can be either be sourced from commercial vendors or synthesized following literature protocols (Riahi et al. *Organic and Biomolecular Chemistry* 2009, 7, 4248). Chlorination of 51 using phosphorus oxychloride followed by substitution/cyclization with a substituted amine in methanol will lead to the desired triazinolactam 52.

Compounds 54 with the isomeric pyrazole core can also be synthesized using $S_NAr$ chemistry as described in Scheme 10. For example, 6-chloro-5,7-diazaindole 55 (obtained in 1 or 2 steps from commercially available material; see Duncan et al. WO2014/100695) can undergo a $S_NAr$ substitution reaction with pyrazole 18 to provide substituted diazaindole 56. Similarly, reaction of 6-chloro-2-oxo-4,5,7-triazaindoline 57 with pyrazole 18 will lead to the corresponding product 58 (Follmann et al. US2013/210824)

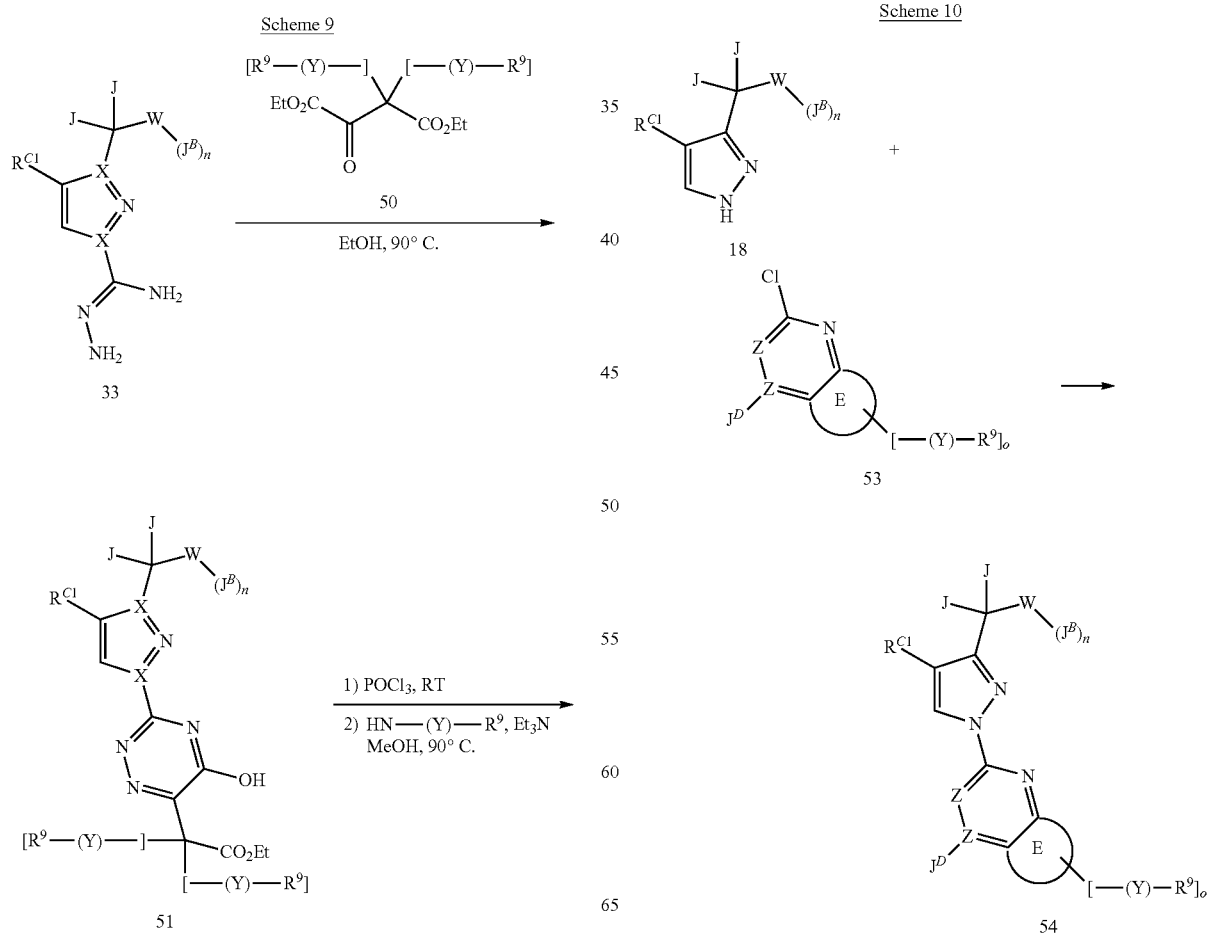

115
-continued

Example 1

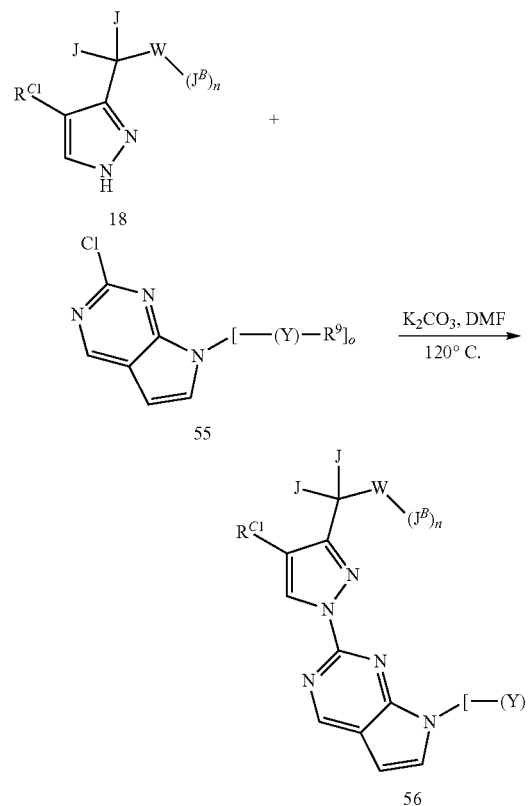

Example 2

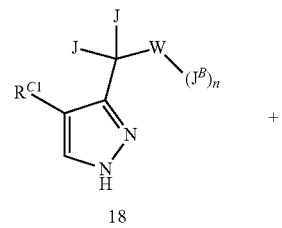

116
-continued

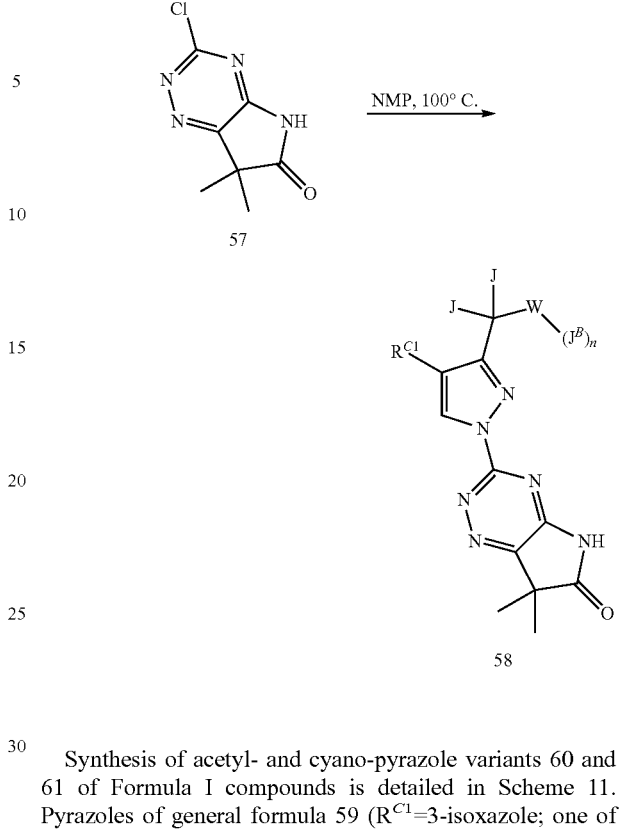

Synthesis of acetyl- and cyano-pyrazole variants 60 and 61 of Formula I compounds is detailed in Scheme 11. Pyrazoles of general formula 59 ($R^{C1}$=3-isoxazole; one of the X groups=N) can be converted to acetylpyrazole 60 by heating with sodium methoxide in MeOH in a sealed vessel at elevated temperature (e.g. 90° C.). Alternatively, pyrazoles 59 ($R^{C1}$=3-isoxazole; one of the X groups=N) can be converted to cyanopyrazole 61 by heating in DBU at elevated temperature (e.g. 125° C.) (see Kim et al. WO2013/101830). Depending on the compatibility of substituents of pyrazoles 59 with the reaction conditions, those skilled in the art may need to install protecting group(s) and/or perform these reactions at an earlier stage of the synthetic sequence.

Scheme 11

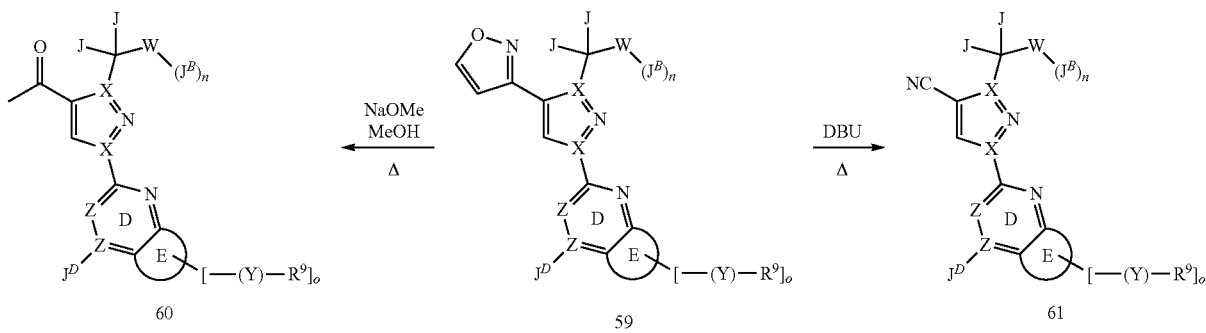

Scheme 12 details the synthesis of amidine and amidrazone intermediates 68 and 69 that are useful for the synthesis of triazole variants of Formula I compounds (see also Kim et al. WO2012/064559). Hydrazide 62, when not commercially available, can be readily synthesized by the reaction of requisite carboxylic acids or esters with hydrazine hydrate. Hydrazide 62 may be reacted with ethyl thiooxamate in the presence of ammonium chloride in refluxing ethanol to provide triazole 63. Deprotonation of the triazole with a base such as sodium hydride followed by substitution with as electrophile 64 such as an alkyl halide furnishes a regioisomeric mixture of triazoles 65a and 65b that can be separated by those skilled in the art of organic chemistry. Saponification of ester 65b followed by conversion to the corresponding nitrile provides compound 67 using previously described procedure (see Kim et al. WO 2013/101830). Nitrile 67 can be treated with sodium methoxide in methanol followed by ammonium chloride to afford triazole amidine 68. Hydrazinecarboximidamide 69 may be accessed by treatment of amidine 68 with hydrazine hydrate in ethanol.

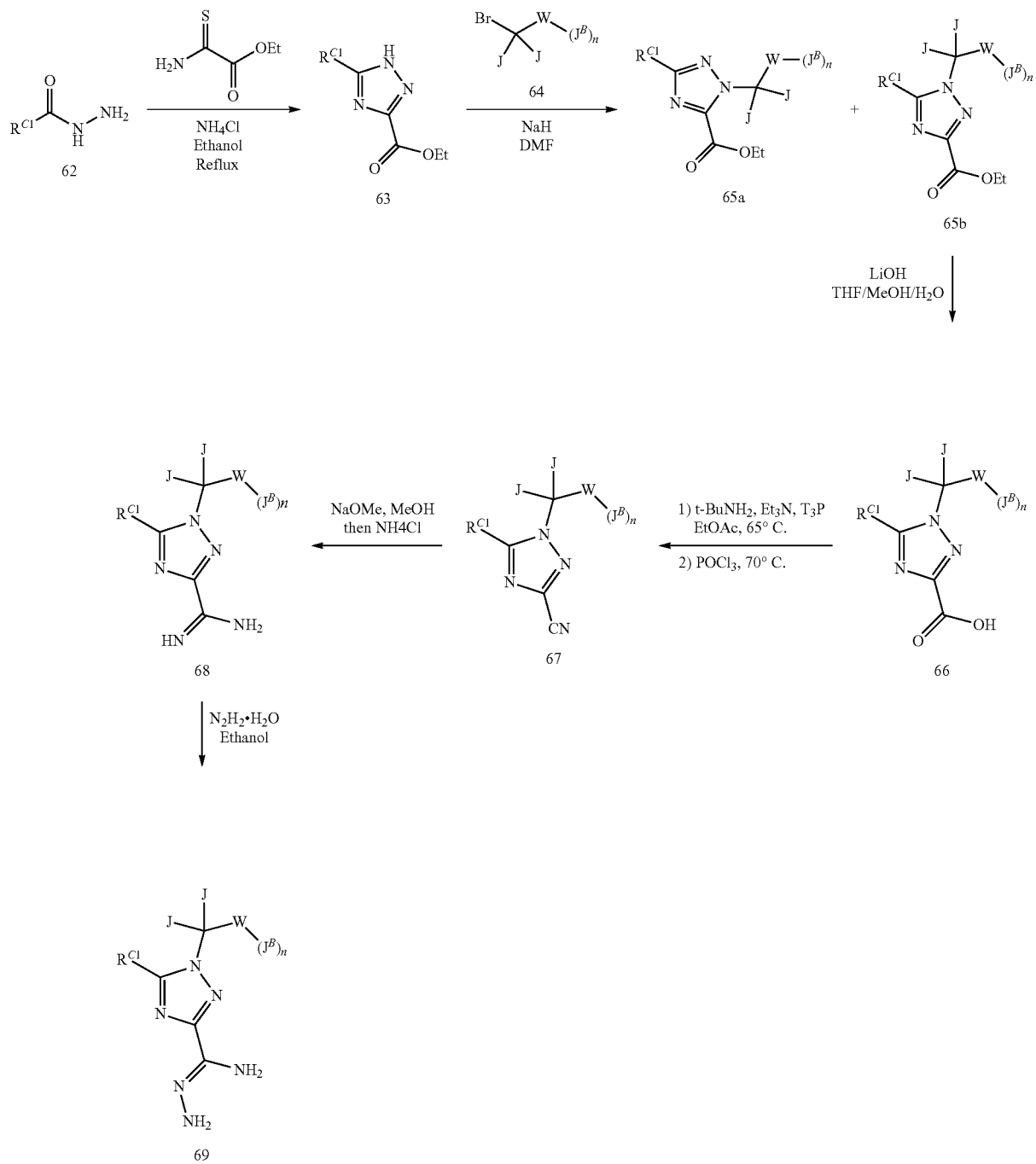

Scheme 13 describes the synthesis of imidazole ester intermediate 75 (precursor of the corresponding amidine and amidrazone intermediates, see Schemes 3 and 12) that is useful for the synthesis of imidazole variants of Formula I compounds. Conversion of nitrile 70 (either commercially available or prepared using standard nucleophilic substitution chemistry) to the corresponding imidate hydrochloride 71 can be accomplished by utilizing literature methods (see Kolb et al. US2003/0153728). Using a 2-step procedure, compound 71 can be cyclized with diamine 72a and further aromatized to imidazole 74 using an oxidant such as $MnO_2$ (see Doherty et al. US2004/0157845). The imidazole 74 can then be substituted with a $R^{C1}$ group by reacting with different electrophiles such as an alkyl halide ($S_N2$ chemistry), acyl halide or heteroaryl/aryl halide ($S_NAr$ chemistry) and a base such as sodium hydride or triethylamine to obtain compound 75. Alternatively, the $R^{C1}$ group (e.g. alkyl or aryl group) can incorporated earlier into diamine 72b to afford compound 75 directly after the cyclization/aromatization sequence.

cally acceptable salt," as used herein, refers to pharmaceutically acceptable organic or inorganic salts of a compound of Formula I', Formula I or Table I. The pharmaceutically acceptable salts of a compound of Formula I', Formula I or Table I are used in medicine. Salts that are not pharmaceutically acceptable may, however, be useful in the preparation of a compound of Formula I', Formula I or Table I or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from the compounds

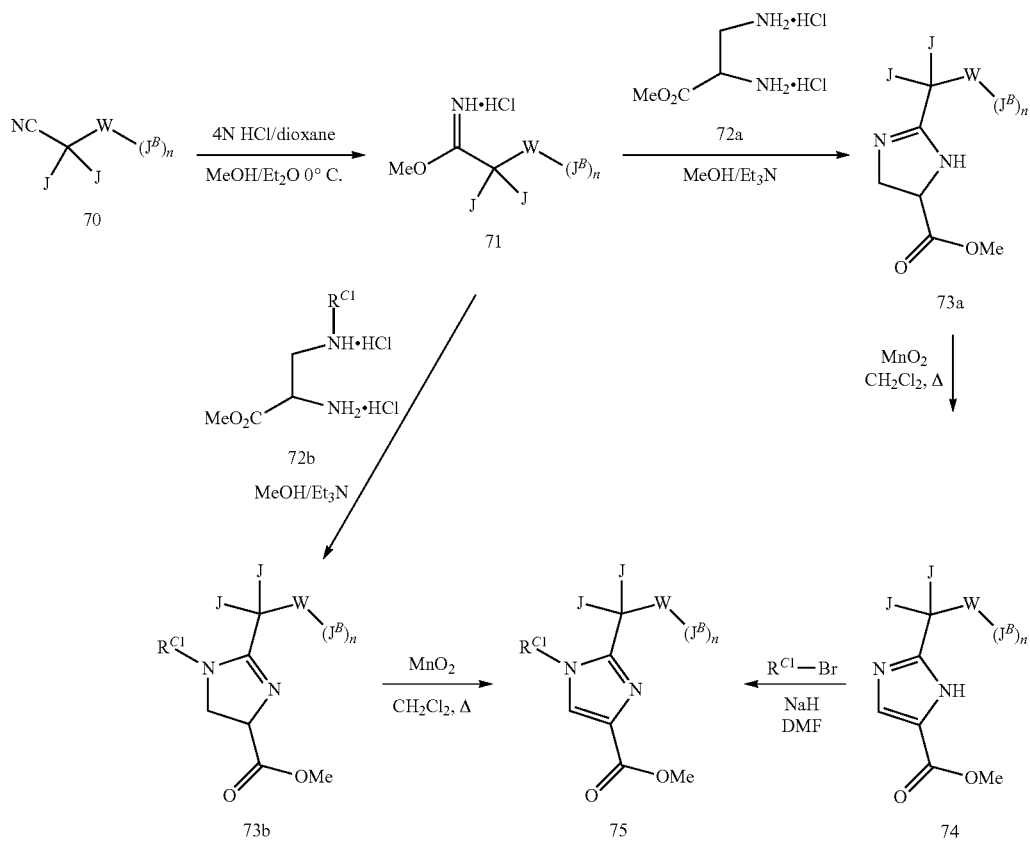

Scheme 13

Pharmaceutically Acceptable Salts of the Invention.

In a second aspect, the invention relates to a pharmaceutical composition comprising the compound of any one of the above embodiments, or a pharmaceutically acceptable salt thereof, and at least one pharmaceutically acceptable excipient.

In all instances described herein, the term "compound" also includes a pharmaceutically acceptable salt of the compound, whether or not the phrase "pharmaceutically acceptable salt" is actually used. The phrase "pharmaceutiwith inorganic acids, organic acids or bases. In some embodiments, the salts can be prepared in situ during the final isolation and purification of the compounds. In other embodiments the salts can be prepared from the free form of the compound in a separate synthetic step.

When a compound of Formula I', Formula I or Table I is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I', Formula I or Table I is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

In all instances described herein, the term "compound" also includes a pharmaceutically acceptable salt of the compound, whether or not the phrase "pharmaceutically acceptable salt" is actually used.

Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I', Formula I or Table I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I', Formula I or Table I is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I', Formula I or Table I or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I', Formula I or Table I, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I', Formula I or Table I or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I', Formula I or Table I, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I', Formula I or Table I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(–)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 Daltons, for example, the Dow Methocel™ series E5, E15LV, E50LV and K100LY) and high viscosity (MW greater than 50,000 Daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g. methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e.g., Explotab™ CLV), microcrystalline cellulose (e.g., Avicel™), microcrystalline silicified cellulose (e.g., ProSolv™) and croscarmellose sodium (e.g., Ac-Di-Sor™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. No. 6,419,952, 6,342,249, 5,324,280, 4,672,850, 4,627,850, , and 3,995, 631.

As further noted above, the agents described herein may be provided in the form of microparticulates, generally ranging in size from about 10 µm to about 2 mm (including, for example, from about 100 µm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g. orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I', Formula I or Table I that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I', Formula I or Table I in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as butylated hydroxyanisol or alpha-tocopherol.

Aqueous suspensions of a compound of Formula I', Formula I or Table I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I', Formula I or Table I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I', Formula I or Table I include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I', Formula I or Table I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or accepted in the veterinary art and are compatible with the active ingredient. These veterinary compositions may be administered parenterally, orally or by any other desired route.

Therapeutic Methods

In another aspect, the invention relates to the treatment of certain disorders by using sGC stimulators, either alone or in combination, or their pharmaceutically acceptable salts or pharmaceutical compositions comprising them, in a patient in need thereof.

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable.

Increased production of NO or increased concentration of cGMP in a tissue leads to vasodilation, inhibition of platelet aggregation and adhesion, anti-hypertensive effects, anti-remodeling effects, anti-fibrotic, anti-apoptotic effects, anti-inflammatory effects and neuronal signal transmission effects, among other effects.

In other embodiments, the compounds here disclosed are sGC stimulators that may be useful in the prevention and/or treatment of diseases and disorders characterized by undesirable reduced bioavailability of and/or sensitivity to NO in a biological system (e.g., in the human body), such as those associated with conditions of oxidative stress or nitrosative stress.

The term "cardiovascular disease" (or "cardiovascular disorder") as used herein, refers to a disease based on the abnormal symptoms of circulatory organs such as the heart, blood vessels (arteries, capillaries, and veins) or both. The term also includes any disease that affects the cardiovascular system in general, including cardiac disease, vascular diseases of the brain, vascular diseases of the kidney, liver and associated organs, or lung, and peripheral arterial disease, among others.

A "sGC-related cardiovascular disease" is one for which the NO/sGC/cGMP system is known or suspected to be involved and is a cardiovascular disease that can be treated or prevented by sGC activation/stimulation, by activation of a NO synthase, or by addition of NO or an NO-donor or an NO precursor such as L-Arginine or L-citruline, or by inhibition of a PDE (phosphodiesterase) enzyme responsible for the breakdown of cGMP, or a combination of the any of the above methods.

The term "vasodilation" as used herein, refers to the widening of blood vessels. It results from relaxation of smooth muscle cells within the vessel walls, in particular in the large veins, large arteries, and smaller arterioles. In essence, the process is the opposite of "vasoconstriction", which is the narrowing of blood vessels. When blood vessels dilate, the flow of blood is increased due to a decrease in vascular resistance. Therefore, dilation of arterial blood vessels (mainly the arterioles) decreases blood pressure. The response may be intrinsic (due to local processes in the surrounding tissue) or extrinsic (due to hormones or the nervous system). In addition, the response may be localized to a specific organ (depending on the metabolic needs of a particular tissue, as during strenuous exercise), or it may be systemic (seen throughout the entire systemic circulation).

The term "vasoconstriction" as used herein refers to the narrowing of a blood vessel due to muscle contraction. Vasoconstriction is one mechanism by which the body regulates and maintains mean arterial pressure (MAP). Generalized vasoconstriction usually results in an increase in systemic blood pressure, but it may also occur in specific tissues, causing a localized reduction in blood flow.

As used herein, the term "bronchoconstriction" is used to define the constriction of the airways in the lungs due to the tightening of surrounding smooth muscle, with consequent coughing, wheezing, and shortness of breath. The condition has a number of causes, the most common being asthma. Exercise and allergies can bring on the symptoms in an otherwise asymptomatic individual. Other conditions such as chronic obstructive pulmonary disease (COPD) can also present with bronchoconstriction.

Throughout this disclosure, the terms "hypertension", "arterial hypertension" or "high blood pressure (HBP)" are used interchangeably and refer to an extremely common and highly preventable chronic condition in which blood pressure (BP) in the arteries is higher than normal or desired. If not properly controlled, it represents a significant risk factor for several serious cardiovascular and renal conditions. Hypertension may be a primary disease, called "essential hypertension" or "idiopathic hypertension", or it may be caused by or related to other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension. Hypertension is an extremely common comorbid condition in diabetes, affecting ~20-60% of patients with diabetes, depending on obesity, ethnicity, and age. This type of hypertension is herein refered to as "diabetic hypertension". In type 2 diabetes, hypertension is often present as part of the metabolic syndrome of insulin resistance also including central obesity and dyslipidemia. In type 1 diabetes, hypertension may reflect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

The term "coronary artery disease" refers to a condition in which the blood supply to the heart muscle is partially or completely blocked (ischemia of the heart muscle or myocardium). This reduced blood supply to the myocardium may result in a number of "acute myocardial syndromes": chest pain ("angina", also called "angina pectoris", stable or unstable) and different types of heart attacks ("myocardial infarction" or MI). One common cause of coronary artery disease is "atherosclerosis" which refers to hardening of the arteries, due to fatty deposits in the artery walls which then may progress through formation of atherosclerotic plaques, to narrowing and eventually blockage of blood flow to the in the artery. This process of atherosclerosis may affect other arteries as well, not just those of the heart. A blood clot is the most common cause of the blockage of the artery, as usually the artery is already partially blocked due to atherosclerotic plaque (atheroma), the atheroma may rupture or tear, leading to the formation of a clot. Occasionally, coronary artery disease is caused by spasm of a coronary artery, which can occur spontaneously or as a result of the use of certain drugs (e.g., cocaine, nicotine). Rarely, the cause of coronary artery disease is a birth defect, a viral infection (e.g., Kawasaki disease), systemic lupus erythematosus (lupus), inflammation of the arteries (arteritis), a blood clot that travelled from a heart chamber into one of the coronary arteries or physical damage (e.g., from injury or radiation therapy).

"Unstable angina", as used herein, refers to a change in the pattern of angina symptoms including prolonged or worsening angina and new onset of severe symptoms.

MI can be classified into two types: "Non-ST-segment elevation" MI and "ST-segment elevation" MI. The complications of acute coronary syndromes depend on how much, how long, and where the coronary artery is blocked. If the blockage affects a large amount of heart muscle, the heart will not pump effectively. If the blockage shuts off blood flow to the electrical system of the heart, the heart rhythm may be affected. When a heart attack occurs, part of the myocardium dies. Dead tissue and the scar tissue that replaces it, does not contract. The scar tissue sometimes even expands or bulges when the rest of the heart tries to contract. Consequently there is less muscle to pump blood. If enough muscle dies, the heart's pumping ability may be so reduced that the heart cannot meet the body's demands for oxygen and blood. Heart failure, low blood pressure or both then develop. If more than half of the myocardium is damaged or dies, the heart generally cannot function and severe disability or death is likely.

As used herein "Heart Failure" (HF) is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neuro-hormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness; edema of the feet, ankles and legs; rapid weight gain; or chronic cough, including that producing mucus or blood. Depending on its clinical presentation, heart failure is classified as de novo, transient, acute, post-acute or chronic. Acute heart failure, i.e., the rapid or gradual onset of symptoms requiring urgent therapy, may develop de novo or as a result of chronic heart failure becoming decompensated. The term "Heart failure" is often used to mean "chronic heart failure". The terms "congestive heart failure (CHF)" or "congestive cardiac failure (CCF)" are often used interchangeably with chronic heart failure. Common causes of heart failure include coronary artery disease including a previous myocardial infarction (heart attack), high blood pressure, atrial fibrillation, valvular heart disease, and cardiomyopathy. These cause heart failure by changing either the structure or the functioning of the heart.

There are two main types of heart failure: "heart failure due to reduced ejection fraction (HFREF)", also known as "heart failure due to left ventricular systolic dysfunction" or "systolic heart failure", and "heart failure with preserved ejection fraction (HFPEF)", also known as "diastolic heart failure" or "heart failure with normal ejection fraction (HFNEF)". Ejection fraction is the proportion of blood in the heart pumped out of the heart during a single contraction. It is a percentage with normal being between 50 and 75%.

The term "acute" (as in "acute HF") is used to mean rapid onset, and "chronic" refers to long duration. Chronic heart failure is a long term situation, usually with stable treated symptomatology. "Acute decompensated" heart failure is worsening or decompensated heart failure, referring to episodes in which a person can be characterized as having a change in heart failure signs and symptoms resulting in a need for urgent therapy or hospitalization. Heart failure may also occur in situations of high output (then it is termed "high output cardiac failure") where the ventricular systolic function is normal but the heart cannot deal with an important augmentation of blood volume.

In cardiovascular physiology, the term "Ejection Fraction (EF)" is defined as the fraction of blood in the left and right ventricles that is pumped out with each heartbeat or cardiac cycle. In finite mathematics allowed by medical imaging, EF is applied to both the right ventricle, which ejects blood via the pulmonary valve into the pulmonary circulation, or the left ventricle, which ejects blood via the aortic valve into the cerebral and systemic circulation.

The term "heart failure with preserved ejection fraction (HFPEF)" is commonly understood to refer to a manifestation of signs and symptoms of heart failure with an ejection fraction greater than 55%. It is characterized by a decrease in left ventricular compliance, leading to increased pressure in the left ventricle. Increased left atrial size is often seen with HFPEF as a result of the poor left ventricular function. There is an increased risk for congestive heart failure, atrial fibrillation, and pulmonary hypertension. Risk factors are hypertension, hyperlipidemia, diabetes, smoking, and obstructive sleep apnea. In this type of heart failure, the heart muscle contracts well but the ventricle does not fill with blood well in the relaxation phase.

The term "heart failure with reduced ejection fraction (HFREF)" refers to heart failure in which the ejection fraction is less than 40%.

Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease (COPD), peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, non-voluntary loss of at least 6% of body weight over a period of six months.

The term "arrhythmias", as used herein, refers to abnormal heart rhythms that occur in more than 90% of people who have had a heart attack. Sometimes the problem is with the part of the heart that triggers the heartbeat and the heart rate may be too slow, other times the problems may cause the heart to beat too rapidly or irregularly. Sometimes the signal to beat is not conducted from one part of the heart to the other and the heartbeat may slow or stop. In addition areas of the myocardium that have not died but have poor blood flow may be irritable. This causes heart rhythm problems such as ventricular tachycardia or ventricular fibrillation. This may lead to cardiac arrest if the heart stops pumping entirely.

The "pericardium" is the sack or membrane that surrounds the heart. "Pericarditis" or inflammation of this membrane may develop as a result of a heart attack and may result in fever, pericardial effusion, inflammation of the membranes covering the lungs (pleura), pleural effusion, and joint pain. Other complications after a heart attack may include malfunction of the mitral valve, rupture of the heart muscle, a bulge in the wall of the ventricle (ventricular aneurysm), blood clots, and low blood pressure.

The term "cardiomyopathy" refers to the progressive impairment of the structure and function of the muscular walls of the heart chambers. The main types of cardiomyopathies are dilated, hypertrophic and restrictive. Cardiomyopathies often cause symptoms of heart failure, and they may also cause chest pain, fainting and sudden death.

The terms "mitral valve regurgitation", "mitral regurgitation", "mitral insufficiency" or "mitral incompetence" refer to a situation in which the mitral valve of the heart doesn't close tightly, allowing blood to flow backward in the heart. As a result, blood can't move through the heart or to the rest of the body as efficiently, resulting in fatigue or shortness of breath.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertrigliceridemia" involves elevated levels of triglycerides). "Hyperlipoproteinemia" refers to elevated levels of lipoproteins (usually LDL unless otherwise specified).

The term "steatosis" refers to the abnormal retention of lipids within a cell. It usually reflects an impairment of the normal processes of synthesis and elimination of triglycerides. Excess fat accumulates in vesicles that displace the cytoplasm of the cell. In severe cases the cell may burst. Usually steatosis is observed in the liver as it is the organ mostly associated with fat metabolism. It can also be observed in the heart, kidneys and muscle tissue.

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or the brain. PVD can result from atherosclerosis, inflammatory processes leading to stenosis, an embolism, thrombus formation or other types of occlusions. It causes either acute or chronic "ischemia (lack of blood supply)". Often PVD is a term used to refer to atherosclerotic blockages found in the lower extremity. PVD also includes a subset of diseases classified as microvascular diseases resulting from episodic narrowing of the arteries (e.g., "Raynaud's phenomenon"), or widening thereof (erythromelalgia), i.e., vascular spasms. Peripheral arterial diseases include occlusive thrombotic vasculitis, peripheral arterial occlusive disease, Raynaud's disease, and Raynaud's syndrome. Common symptoms are cold leg or feet, intermittent claudication, lower limb pain and critical limb ischemia (lower limb ulcers and necrosis). Diagnosis and treatment guidelines for peripheral arterial disease can be found in Eur. J. Vasco Endovasc. Surg, 2007, 33(1), Sl.

The term "stenosis" as used herein refers to an abnormal narrowing in a blood vessel or other tubular organ or structure. It is also sometimes called a "stricture" (as in urethral stricture). The term "coarctation" is a synonym, but is commonly used only in the context of aortic coarctation. The term "restenosis" refers to the recurrence of stenosis after a procedure.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin. The material that forms the embolism can have a number of different origins: if the material is blood the "embolus" is termed a "thrombus"; the solid material could also comprise fat, bacterial remains, infected tissue, etc.

"Ischemia" is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism). If the "ischemia" takes place in the heart muscle (or "myocardium") the ischemia is termed myocardial ischemia. Other types of ischemia are for instance cerebral ischemia, critical limb ischemia and the like.

"Reperfusion" occurs when blood supply returns to the tissue after a period of ischemia. Upon restoration of circulation to the tissue, inflammatory and oxidative stress processes may develop. One example of this chain of events is ischemia-reperfusion associated with organ transplants.

"Reperfusion injury" is the tissue damage caused when blood supply returns to the tissue after a period of ischemia and inflammation and oxidative damage ensue rather than restoration of normal function. Reperfusion of ischemic issues is often associated with microvascular injury, particularly due to the increased permeability of capillaries and arterioles that lead to an increase in diffusion and fluid filtration across the tissues. The activated endothelial cells produce more reactive oxygen species but less NO following reperfusion, and the imbalance results in an inflammatory response. White blood cells, carried to the area by the newly returned blood flow, release a host of inflammatory factors and free radicals in response to tissue damage. The restored blood flow brings with it oxygen that damages cellular proteins, DNA and plasma membranes. This process of ischemia-reperfusion is also thought to be responsible for formation and failure to heal of chronic wounds, (e.g., pressure sores or diabetic ulcers).

The term "angiopathy" as used herein is the generic term for a disease of the blood vessels (arteries, veins, and capillaries). The most common and most prevalent angiopathy is "diabetic angiopathy", a common complication of chronic diabetes. Another common type of angiopathy is "cerebral amyloid angiopathy" (CAA), also known as congophilic angiopathy, wherein amyloid deposits form in the walls of the blood vessels of the central nervous system. The term congophilic is used because the presence of the abnormal aggregations of amyloid can be demonstrated by microscopic examination of brain tissue after application of a special stain called Congo red. The amyloid material is only found in the brain and as such the disease is not related to other forms of amyloidosis.

A "stroke", or cerebrovascular accident (CVA), is the rapid loss of brain function(s) due to disturbance in the blood supply to the brain. This can be due to "ischemia" (lack of blood flow with resultant insufficient oxygen and glucose supply to the tissue) caused by blockage (thrombosis, arterial embolism, fat accumulation or a spasm), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Vascular dementia" is the 2nd most common cause of dementia among the elderly. It is more common among men and usually begins after age 70. It occurs more often in people who have vascular risk factors (e.g, hypertension, diabetes mellitus, hyperlipidemia, smoking) and in those who have had several strokes. Many people have both vascular dementia and Alzheimer disease. Vascular dementia typically occurs when multiple small cerebral infarcts (or sometimes hemorrhages) cause enough neuronal or axonal loss to impair brain function. Vascular dementias include the following types: multiple lacunar infarction (wherein small blood vessels are affected and infarcts occur deep within hemispheric white and gray matter); multi-infarct dementia (wherein medium-sized blood vessels are affected); strategic single-infarct dementia (wherein a single infarct occurs in a crucial area of the brain such as the angular gyrus or the thalamus; Binswanger dementia or subcortical arteriosclerotic encephalopathy (wherein small-vessel dementia is associated with severe, poorly controlled hypertension and systemic vascular disease and which causes diffuse and irregular loss of axons and myelin with widespread gliosis, tissue death due to an infarction, or loss of blood supply to the white matter of the brain).

The term "glioma" refers to a type of tumor that starts in the brain or spine. It is called a glioma because it arises from glial cells. The most common site of gliomas is the brain. Gliomas make up about 30% of all brain and central nervous system tumors and 80% of all malignant brain tumors.

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

In one embodiment, compounds of Formula I', Formula I or Table I that are stimulators of sGC, and their pharmaceutically acceptable salts thereof, are therefore useful in the prevention and/or treatment of the following types of cardiac, pulmonary, peripheral, hepatic, kidney, or cerebral vascular/endothelial disorders, conditions and diseases related to circulation:

disorders related to high blood pressure and decreased coronary blood flow; increased acute and chronic coronary blood pressure; arterial hypertension; vascular disorder resulting from cardiac and renal complications; vascular disorders resulting from heart disease, stroke, cerebral ischemia or renal failure; resistant hypertension; diabetic hypertension; essential hypertension; secondary hypertension; gestational hypertension; pre-eclampsia; portal hypertension; myocardial infarction;

heart failure, HFPEF, HFREF; acute and chronic HF; more specific forms of HF: acute decompensated HF, right ventricular failure, left ventricular failure, total HF, ischemic cardiomyopathy, dilatated cardiomyopathy, congenital heart defects, HF with valvular defects, mitral valve stenosis, mitral valve insufficiency, aortic valve stenosis, aortic valve insufficiency, tricuspid stenosis, tricuspic insufficiency, pulmonary valve stenosis, pulmonary valve insufficiency, combined valvular defects; diabetic heart failure; alcoholic cardiomyopathy or storage cardiomyopathies; diastolic HF, systolic HF; acute phases of an existing chronic HF (worsening HF); diastolic or systolic dysfunction; coronary insufficiency; arrhythmias; reduction of ventricular preload; cardiac hypertrophy; heart failure/cardiorenal syndrome; portal hypertension; endothelial dysfunction or injury; disturbances of atrial and ventricular rhythm and conduction disturbances: atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV junction extrasystoles, sick-sinus syndrome, syncopes, AV-node reentry tachycardia; Wolff-Parkinson-White syndrome or acute coronary syndrome; Boxer cardiomyopathy; premature ventricular contraction; cardiomyopathy; cancer-induced cardiomyopathy;

thromboembolic disorders and ischemias; myocardial ischemia; infarction; myocardial infarction; heart attack; myocardial insufficiency; endothelial dysfunction; stroke; transient ischemic attacks (TIAs); obstructive thromboanginitis; stable or unstable angina pectoris; coronary spasms or spasms of the peripheral arteries; variant angina; Prinzmetal's angina; cardiac hypertrophy; preeclampsia; thrombogenic disorders; ischemia-reperfusion damage; ischemia-reperfusion associated with organ transplant; ischemia-reperfusion associated with lung transplant, pulmonary transplant, cardiac transplant, venus graft failure; conserving blood substituents in trauma patients;

peripheral vascular disease; peripheral arterial disease; peripheral occlusive arterial disease; hypertonia; Raynaud's syndrome or phenomenon (primary and secondary); Raynaud's disease; critical limb ischemia; peripheral embolism; intermittent claudication; vaso-occlusive crisis; muscular dystrophy, Duchenne muscular dystrophy, Becker muscular dystrophy; microcirculation abnormalities; control of vascular leakage or permeability; lumbar spinal canal stenosis; occlusive thrombotic vasculitis; thrombotic vasculitis; peripheral perfusion disturbances; arterial and venous thrombosis; microalbuminuria; peripheral and autonomic neuropathies; diabetic microangiopathies;

edema; renal edema due to heart failure;

Alzheimer's disease; Parkinson's disease; vascular dementias; vascular cognitive impairment; cerebral vasospasm; congenital myasthenic syndrome; subarachnoid hemorrhage; traumatic brain injury; improving perception, capacity for concentration, capacity for learning or memory performance after cognitive disturbances such as those ocurring in mild cognitive impairment, age-related learning and memory disturbances, age-related memory loss, vascular dementia, head injury, stroke, post-stroke dementia, post-traumatic head injury, general disturbances of concentration and disturbances of concentration in children with learning and memory problems; Lewy body dementia; dementia with frontal lobe degeneration including Pick's syndrome; progressive nuclear palsy; dementia with corticobasal degeneration; Amyotropic Lateral Sclerosis (ALS); Huntington's disease; demyelination; Multiple Sclerosis; thalamic degeneration; Creutzfeldt-Jakob dementia; HIV-dementia; schizophrenia with dementia or Korsakoff psychosis; Multiple System Atrophy and other forms of Parkinsonism Plus; movement disorders; neuroprotection; anxiety, tension and depression or post-traumatic stress disorder (PTSD); bipolar disorder; schizophrenia; CNS-related sexual dysfunction and sleep disturbances; pathological eating disorders and use of luxury foods and addictive drugs; controlling cerebral perfusion; migraines; prophylaxis and control of consequences of cerebral infarction (apoplexia cerebri); prophylaxis and control of consequences of stroke, cerebral ischemias and head injury;

shock; cardiogenic shock; sepsis; septic shock; anaphylactic shock; aneurysm; control of leukocyte activation; inhibition or modulation of platelet aggregation; multiple organ dysfunction syndrome (MODS); multiple organ failure (MOF);

pulmonary/respiratory conditions: pulmonary hypertension (PH); pulmonary arterial hypertension (PAH), and associated pulmonary vascular remodeling; vascular remodeling in the form of localized thrombosis and right heart hypertrophy; pulmonary hypertonia; primary pulmonary hypertension; secondary pulmonary hypertension; familial pulmonary hypertension; sporadic pulmonary hypertension; pre-capillary pulmonary hypertension; idiopathic pulmonary hypertension; other forms of PH; PH associated with left ventricular disease, HIV, SCD, thromboembolism (CTEPH), sarcoidosis, COPD, pulmonary fibrosis, acute respiratory distress syndrome (ARDS), acute lung injury, alpha-1-antitrypsin deficiency (AATD), pulmonary emphysema, smoking-induced emphysema and cystic fibrosis (CF); thrombotic pulmonary arteriopathy; plexogenic pulmonary arteriopathy; cystic fibrosis; bronchoconstriction or pulmonary bronchoconstriction; acute respiratory distress syndrome; lung fibrosis, lung transplant; asthmatic diseases;

pulmonary hypertension associated with or related to: left ventricular dysfunction, hypoxemia, WHO groups I, II, III, IV and V hypertensions, mitral valve disease, constrictive pericarditis, aortic stenosis, cardiomyopathy, mediastinal fibrosis, pulmonary fibrosis, anomalous pulmonary venous drainage, pulmonary veno-occlusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism; pulmonary embolism due to tumor, parasites or foreign material; connective tissue disease, lupus, lupus nephritis, schistosomiasis, sarcoidosis, chronic obstructive pulmonary disease, asthma, emphysema, chronic bronchitis, pulmonary capillary hemangiomatosis, histiocytosis X, lymphangiomatosis, compressed pulmonary vessels; compressed pulmonary vessels due to adenopathy, tumor or fibrosing mediastinitis;

arterosclerotic diseases or conditions: atherosclerosis; atherosclerosis associated with endothelial injury, platelet and monocyte adhesion and aggregation, smooth muscle proliferation or migration; restenosis; restenosis developed after thrombolysis therapies, percutaneous transluminal angioplasties (PTAs), transluminal coronary angioplasties (PTCAs), heart transplant, bypass operations or inflammatory processes;

micro and macrovascular damage (vasculitis); increased levels of fibrinogen and low density DLD; increased concentration of plasminogen activator inhibitor 1 (PA-1);

metabolic syndrome; metabolic diseases or diseases associated with metabolic syndrome: obesity; excessive subcutaneous fat; excessive adiposity; diabetes; high blood pressure; lipid related disorders, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, hepatitis; preeclampsia; polycystic kidney disease progression; liver steatosis or abnormal lipid accumulation in the liver; steatosis of the heart, kidneys or muscle; alphabetalipoproteinemia; sitosterolemia; xanthomatosis; Tangier disease; hyperammonemia and related dieases; hepatic encephalopaties; other toxic encephalopaties; Reye syndrome;

sexual, gynecological and urological disorders of conditions: erectile dysfunction; impotence; premature ejaculation; female sexual dysfunction; female sexual arousal dysfunction; hypoactive sexual arousal disorder; vaginal atrophy; dyspaneuria; atrophic vaginitis; benign prostatic hyperplasia (BPH), prostatic hypertrophy, prostatic enlargement; bladder outlet obstruction; bladder pain syndrome (BPS); interstitial cystitis (IC); overactive bladder; neurogenic bladder and incontinence; diabetic nephropathy; primary and secondary dysmenhorrea; lower urinary tract syndromes (LUTS); endometriosis; pelvic pains; benign and malignant diseases of the organs of the male and female urogenital system;

chronic kidney disease; acute and chronic renal insufficiency; acute and chronic renal failure; lupus nephritis; underlying or related kidney diseases: hypoperfusion, intradialytic hypotension, obstructive uropathy, glomerulopathies, glomerulonephritis, acute glomerulonephritis, glomerulosclerosis, tubulointerstitial diseases, nephropathic diseases, primary and congenital kidney diseases, nephritis; diseases characterized by abnormally reduced creatinine and or water excretion; diseases characterized by abnormally increased blood concentrations of urea, nitrogen, potassium and/or creatinine; diseases characterized by altered activity of renal enzymes, diseases characterized by alterened activity of glutamyl synthetase; diseases characterized by altered urine osmolarity or urine volume; diseases characterized by increased microalbuminuria, diseases characterized by macroalbuminuria; diseases characterized by lesions of glomeruli and arterioles, tubular dilatation, hyperphosphatemia and/or need for dialysis; sequelae of renal insufficiency; renal-insufficiency related pulmonary enema; renal-insufficiency related to HF; renal insufficiency related to uremia or anemia; elecrolyte disturbances (herkalemia, hyponatremia); disturbances of bone and carbohydrate metabolism;

ocular diseases or disorders such as glaucoma, retinopathy and diabetic retinopathy.

The term "Inflammation" refers to the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even though the two are often correlated (the former often being a result of the latter). Inflammation can also occur in the absence of infection, although such types of inflammation are usually maladaptive (such as in atherosclerosis). Inflammation is a stereotyped response, and therefore it is considered as a mechanism of innate immunity, as compared to adaptive immunity, which is specific for each pathogen. Progressive destruction of tissue in the absence of inflammation would compromise the survival of the organism. On the other hand, chronic inflammation might lead to a host of diseases, such as hay fever, periodontitis, atherosclerosis, rheumatoid arthritis, and even cancer (e.g., gallbladder carcinoma). It is for that reason that inflammation is normally closely regulated by the body. Inflammation can be classified as either acute or chronic. "Acute inflammation" is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as "chronic inflammation", leads to a progressive shift in the type of cells present at the site of inflammation and is characterized by simultaneous destruction and healing of the tissue from the inflammatory process.

In another embodiment, compounds of Formula I', Formula I or Table I that are stimulators of sGC, and their pharmaceutically acceptable salts thereof, are therefore useful in the prevention and/or treatment of the following types of cardiac, pulmonary, peripheral, hepatic, kidney, digestive or Central Nervous System disorders, conditions and diseases which may involve inflammation or an inflammatory process:

heart muscle inflammation (myocarditis); chronic myocarditis; acute myocarditis; viral myocarditis;

vasculitis; pancreatitis; peritonitis; rheumatoid diseases;

inflammatory disease of the kidney; immunological kidney diseases: kidney transplant rejection, immune complex-induced kidney disease, nephropathy induced by toxins, constrast medium-induced nephropathy; diabetic and non-diabetic nephropathy, pyelonephritis, renal cysts, nephrosclerosis, hypertensive nephrosclerosis and nephrotic syndrome;

chronic interstitial inflammations. inflammatory bowel diseases (IBD), Crohn's, Ulcerative Colitis (UC);

inflammatory skin diseases;

inflammatory diseases of the eye, blepharitis, dry eye syndrome, and Sjögren's Syndrome; eye fibrosis.

The term "wound healing" refers to the intricate process where the skin (or another organ or tissue) repairs itself after injury. For instance, in normal skin, the epidermis (outermost layer) and dermis (inner or deeper layer) exist in a steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis (not considered a phase by some authors), (2) inflammation, (3) proliferation and (4) remodeling. Upon injury to the skin, a set of complex biochemical events takes place in a closely orchestrated cascade to repair the damage. Within the first few minutes after the injury, platelets adhere to the site of injury, become activated, and aggregate (join together), followed by activation of the coagulation cascade which forms a clot of aggregated platelets in a mesh of cross-linked fibrin protein. This clot stops active bleeding ("hemostasis"). During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction. In "angiogenesis", vascular endothelial cells form new blood vessels. In "fibroplasia" and granulation tissue formation, fibroblasts grow and form a new, provisional extracellular matrix (ECM) by excreting collagen and fibronectin. Concurrently, "re-epithelialization" of the epidermis occurs, in which epithelial cells proliferate and 'crawl' atop the wound bed, providing cover for the new tissue. During wound contraction, myofibroblasts decrease the size of the wound by gripping the wound edges and contracting using a mechanism that resembles that in smooth muscle cells. When the cells' roles are close to complete, unneeded cells undergo apoptosis. During maturation and remodeling, collagen is remodeled and realigned along tension lines, and cells that are no longer needed are removed by apoptosis. However, this process is not only complex but fragile, and is susceptible to interruption or failure leading to the formation of non-healing chronic wounds (one example includes diabetic wounds or ulcers, and, in particular, diabetic foot ulcers). Factors that contribute to non-healing chronic wounds are diabetes, venous or arterial disease, infection, and metabolic deficiencies of old age.

The terms "bone healing", or "fracture healing" refers to a proliferative physiological process in which the body facilitates the repair of a bone fracture. In the process of fracture healing, several phases of recovery facilitate the proliferation and protection of the areas surrounding fractures and dislocations. The length of the process depends on the extent of the injury, and usual margins of two to three weeks are given for the reparation of most upper bodily fractures; anywhere above four weeks given for lower bodily injury. The healing process is mainly determined by the "periosteum" (the connective tissue membrane covering the bone). The periosteum is one source of precursor cells which develop into "chondroblasts" and osteoblasts that are essential to the healing of bone. The bone marrow (when present), endosteum, small blood vessels, and fibroblasts are other sources of precursor cells.

In another embodiment, compounds of Formula I', Formula I or Table I, that are stimulators of sGC and their pharmaceutically acceptable salts thereof, are therefore useful in the treatment of the following types of diseases, disorders or conditions in which stimulation of the processes of wound or bone healing would be desirable:

wound or ulcer healing in diabetics; microvascular perfusion improvement; microvascular perfusion improvement following injury or to counteract the inflammatory response in perioperative care; anal fissures; diabetic ulcers; diabetic foot ulcers); bone healing; osteoclastic bone resorption and remodeling; and new bone formation.

The term "connective tissue" (CT) refers to a kind of animal tissue that supports, connects, or separates different types of tissues and organs of the body. It is one of the four general classes of animal tissues, the others being epithelial, muscle, and nervous tissues. Connective tissue is found everywhere, including in the central nervous system. It is located in between other tissues. All CT has three main components—ground substances, fibers and cells—and all these components are immersed in the body fluids.

The term "connective tissue disorder or condition" refers to any condition that involves abnormalities in connective tissue in one or more parts of the body. Certain disorders are characterized by over-activity of the immune system with resulting inflammation and systemic damage to the tissues, usually with replacement of normal tissue (e.g., normal tissue of a certain organ) with connective tissue. Other disorders involve biochemical abnormalities or structural defects of the connective tissue itself. Some of these disorders are inherited, and some are of unknown etiology.

When connective tissue diseases are of autoimmune origin they are classified as "rheumatic disorders", "autoimmune rheumatic disorders" or "autoimmune collagen-vascular disorders".

In an "autoimmune disorder", antibodies or other cells produced by the body attack the body's own tissues. Many autoimmune disorders affect connective tissue in a variety of organs. In autoimmune disorders, inflammation and the immune response may result in connective tissue damage, around the joints and also in other tissues, including vital organs, such as the kidneys or organs of the gastrointestinal tract. The sac that surrounds the heart (pericardium), the membrane that covers the lungs (pleura), the mediastinum (an undelineated group of structures in the thorax, surrounded by loose connective tissue, containing the heart, the great vessels of the heart, the esophagus, the trachea, the phrenic nerve, the cardiac nerve, the thoracic duct, the thymus, and the lymph nodes of the central chest) and even the brain may be affected.

The term "fibrosis" as used herein refers to the accumulation of connective tissue or fibrous tissue (scar tissue, collagen) in a certain organ or part of the body. If fibrosis arises from a single cell line it is called a "fibroma". Fibrosis occurs as the body attempts to repair and replace damaged cells, and thus can be a reactive, benign or a pathological state. Physiological fibrosis is similar to the process of scarring. A pathological state develops when the tissue in question is repeatedly and continuously damaged. A single episode of injury, even if severe, does not usually cause fibrosis. If injury is repeated or continuous (for instance as it occurs in chronic hepatitis) the body attempts to repair the damage, but the attempts result instead in excessive accumulation of scar tissue. Scar tissue starts to replace regular tissue of the organ which performs certain functions that the scar tissue is not able to perform; it can also interfere with blood flow and limit blood supply to other cells. As a result, these other functional cells start to die and more scar tissue is formed. When this occurs in the liver, blood pressure in the vein that carries blood from the intestine to the liver (portal vein) increases, giving rise to the condition known as "portal hypertension".

The term "sclerosis" refers to the hardening or stiffening of tissue or a structure or organ that would normally be flexible, usually by replacement of normal organ specific tissue with connective tissue.

There are many types of fibroses or fibrotic diseases including but not limited to pulmonary fibrosis (idiopathic pulmonary fibrosis, cystic fibrosis), fibrosis of the liver (or "cirrhosis"), endomyocardial fibrosis, old myocardial infarction, atrial fibrosis, mediastinal fibrosis, myelofibrosis (affecting the bone marrow), retroperitoneal fibrosis, progressive massive fibrosis (affects the lungs), nephrogenic fibrosis (affecting the skin), Crohn's disease, arthrofibrosis, Peyronie's disease (affecting the penis), Dupuytren's contracture (affecting the hands and fingers), some forms of adhesive capsulitis (affecting the shoulders).

There are many types of scleroses or "sclerotic diseases" including but not limited to Amyotropic Lateral Sclerosis (ALS); atherosclerosis; focal segmental glomerulosclerosis and nephrotic syndrome; hippocampal sclerosis (affecting the brain); lichen sclerosus (a disease that hardens connective tissue of the vagina and penis); liver sclerosis (chirrhosis); multiple sclerosis or focal sclerosis (diseases that affects coordination); osteosclerosis (a disease in which bone densitiy is significantly reduced); otosclerosis (disease affecting the ears); tuberous sclerosis (rare genetic disease affecting multiple systems); primary sclerosing cholanginitis (hardening of the bile duct); primary lateral sclerosis (progressive muscle weakness in the voluntary muscles); and keloids.

The term "scleroderma" or "systemic sclerosis" or "progressive systemic scleroderma" refers to a condition which involves scarring of the joints, skin and internal organs as well as blood vessel abnormalities. Systemic sclerosis can sometimes occur in limited forms, for examples sometimes affecting just the skin or mainly only certain parts of the skin or as CREST syndrome (wherein peripheral areas of the skin but not the trunk are involved). The usual initial symptom of systemic sclerosis is swelling, then thickening and tightening of the skin at the end of the fingers. "Raynaud's phenomenon", in which fingers suddenly and temporarily become very pale and tingle or become numb, painful or both, is common.

The term "polymyositis" refers to muscle inflammation. The term "dermatomyositis", refers to muscle inflammation that is accompanied by skin inflammation. The term "polychondritis" refers to cartilage inflammation.

The term "oesinophilic fasciitis" refers to a rare disorder in which oesinophilic immune cells are released and results in inflammation and hardening of the "fasciae" which is the layer of tough fibrous tissue beneath the skin, on top and between the muscles. The fasciae becomes painfully inflamed and swollen and gradually hardens in the arms and legs. As the skin of the arms and legs progressively hardens, they become difficult to move. Eventually the become stuck in unusual positions. Sometimes, if the arms are involved the person may develop carpal tunnel syndrome.

In another embodiment, specific diseases of disorders which may be treated and/or prevented by administering an sGC stimulator of Formula I', Formula I or Table I that are stimulators of sGC, and their pharmaceutically acceptable salts thereof, include but are not limited to the following type of diseases involving inflammation, autoimmunity or fibrosis (i.e., fibrotic diseases):

urogenital system disorders: diabetic nephropathy; renal fibrosis and renal failure resulting from chronic kidney diseases or insufficiency; renal fibrosis and renal failure due to accumulation/deposition and tissue injury; renal sclerosis; progressive sclerosis; glomerulonephritis; focal segmental glomerulosclerosis; nephrotic syndrome; prostate hypertrophy; kidney fibrosis; interstitial renal fibrosis;

pulmonary system disorders: pulmonary fibrosis; idiopathic pulmonary fibrosis; cystic fibrosis; progressive massive fibrosis; progressive massive fibrosis that affects the lungs);

disorders affecting the heart: endomyocardial fibrosis; old myocardial infarction; atrial fibrosis; cardiac interstitial fibrosis; cardiac remodeling and fibrosis; cardiac hypertrophy;

disorders of the liver and related organs: liver sclerosis or cirrhosis; liver cirrhosis associated with chronic liver disease; hepatic fibrosis; hepatic stellate cell activation; hepatic fibrous collagen and total collagen accumulation; liver disease of necro-inflammatory and/or of immunological origin; primary biliary cirrhosis; primary sclerosing cholanginitis; other cholestatic liver diseases: those associated with granulomatous liver diseases, liver malignancies, intrahepatic cholestasis of pregnancy, hepatitis, sepsis, drugs or toxins, graft-versus-host disease, post-liver transplantation, choledocholithiasis, bile duct tumors, pancreatic carcinoma, Mirizzi's syndrome, AIDS cholangiopathy or parasites; schistosomiasis;

digestive diseases or disorders: Crohn's disease; Ulcerative Colitis; sclerosis of the gastro-intestinal tract;

diseases of the skin or the eyes: nephrogenic fibrosis; keloids; fibrotic topical or skin disorders or conditions; dermal fibrosis; scleroderma, skin fibrosis; morphea; hypertrophic scars; naevi; proliferative vitroretinopathy; sarcoids; granulomas; eye fibrosis;

diseases affecting the nervous system: Amyotropic Lateral Sclerosis (ALS); hippocampal sclerosis, multiple sclerosis (MS); focal sclerosis; primary lateral sclerosis;

diseases of the bones; osteosclerosis;

otosclerosis; other hearing diseases or disorders; hearing impairment, partial or total hearing loss; partial or total deafness; tinnitus; noise-induced hearing loss;

other diseases involving autoimmunity, inflammation or fibrosis: scleroderma; localized scleroderma or circumscribed scleroderma; mediastinal fibrosis; fibrosis mediastinitis; myelofibrosis; retroperitoneal fibrosis; arthrofibrosis; Peyronie's disease; Dupuytren's contracture; lichen sclerosus; some forms of adhesive capsulitis; atherosclerosis; tuberous sclerosis; systemic sclerosis; polymyositis; dermatomyositis; polychondritis; oesinophilic fasciitis; Systemic Lupus Erythematosus or lupus; bone marrow fibrosis, myelofibrosis or osteomyelofibrosis; sarcoidosis; uterine fibroids; endometriosis.

In another embodiment, specific diseases of disorders which may be treated and/or prevented by administering an sGC stimulator of Formula I', Formula I or Table I that are stimulators of sGC, and their pharmaceutically acceptable salts thereof, include but are not limited to: certain types of cancers; Sickle Cell Disease; Sickle Cell Anemia; cancer metastasis; osteoporosis; gastroparesis; functional dyspepsia; diabetic complications; alopecia or hair loss; diseases associated with endothelial dysfunction; neurologic disorders associated with decreased nitric oxide production; arginosuccinic aciduria; neuromuscular diseases: Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis and spinal muscle atrophy (SMA) In some embodiments, the invention relates to a method of treating a disease, health condition or disorder in a subject, comprising administering a therapeutically effective amount of a compound of Formula I', Formula I or Table I, or a pharmaceutically acceptable salt thereof, to the subject in need of treatment, wherein the disease, health condition or disorder is selected from one of the diseases listed above.

In another embodiment, compounds of the invention can be delivered in the form of implanted devices, such as stents. A stent is a mesh 'tube' inserted into a natural passage/conduit in the body to prevent or counteract a disease-induced, localized flow constriction. The term may also refer to a tube used to temporarily hold such a natural conduit open to allow access for surgery.

A drug-eluting stent (DES) is a peripheral or coronary stent (a scaffold) placed into narrowed, diseased peripheral or coronary arteries that slowly releases a drug to block cell proliferation, usually smooth muscle cell proliferation. This prevents fibrosis that, together with clots (thrombus), could otherwise block the stented artery, a process called restenosis. The stent is usually placed within the peripheral or coronary artery by an Interventional Cardiologist or Interventional Radiologist during an angioplasty procedure. Drugs commonly used in DES in order to block cell proliferation include paclitaxel or rapamycin analogues.

In some embodiments of the invention, a sGC stimulator of the invention can be delivered by means of a drug-eluting stent coated with said sGC stimulator. A drug-eluting stent coated with a sGC stimulator of the invention may be useful in the prevention of stent restenosis and thrombosis during percutaneous coronary interventions. A drug-eluting stent coated with a sGC stimulator of the invention may be able to prevent smooth cell proliferation as well as to assist re-vascularization and re-generation of the endothelial tissue of the artery in which the stent is inserted.

An alternative to percutaneous coronary intervention for the treatment of intractable angina due to coronary artery occlusive disease is the procedure named Coronary Artery Bypass Grafting (CABG). CABG provides only palliation of an ongoing process that is further complicated by the rapid development of graft atherosclerosis. The saphenous vein graft is the most commonly used conduit in CABG surgery. The long-term clinical success of venous CABG is hampered for three main reasons: accelerated graft atherosclerosis, incomplete endothelialization and thrombosis.

In some embodiments, a sGC stimulator of the invention can be used for the prevention of saphenous graft failure during CABG. Compounds of the invention may assist the process of endothelialization and help prevent thrombosis. In this indication, the sGC stimulator is delivered locally in the form of a gel.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I', Formula I or Table I, or a pharmaceutically acceptable salt thereof, to the subject in need of the treatment. Alternatively, the invention provides the use of a compound of Formula I', Formula I or Table I, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I', Formula I or Table I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernable symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g., a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I', Formula I or Table I or a pharmaceutically acceptable salt thereof and a second amount of an additional suitable therapeutic agent.

In one embodiment of this invention, a compound of Formula I', Formula I or Table I and the additional therapeutic agent are each administered in an effective amount (i.e., each in an amount which would be therapeutically effective if administered alone). In another embodiment, the compound of Formula I', Formula I or Table I and the additional therapeutic agent are each administered in an amount which alone does not provide a therapeutic effect (a sub-therapeutic dose). In yet another embodiment, the compound of Formula I', Formula I or Table I can be administered in an effective amount, while the additional therapeutic agent is administered in a sub-therapeutic dose. In still another embodiment, the compound of Formula I', Formula I or Table I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Formula I', Formula I or Table I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I', Formula I or Table I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatratee®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CINOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405, 919, 5,650,442, 5,700,830, 5,632,981, 6,290,981, 5,691, 423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-yl-amide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P1487);

(6) NO independent heme-independent sGC activators, including, but not limited to: BAY 58-2667 (see patent publication DE19943635)

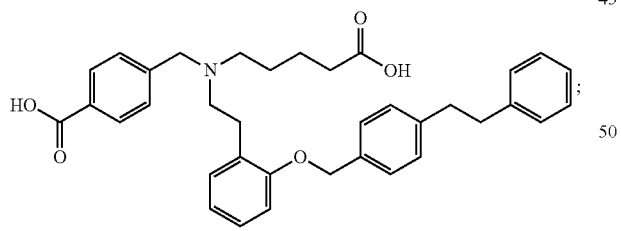

HMR-1766 (ataciguat sodium, see patent publication WO2000002851)

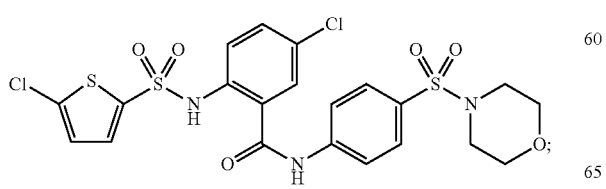

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

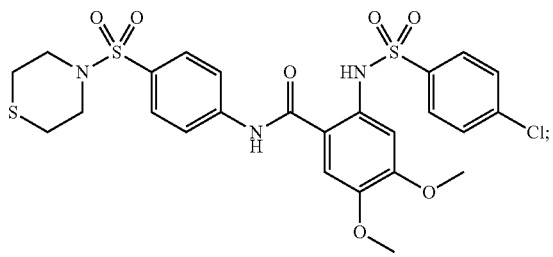 [SMILES: COc1cc(NS(=O)(=O)c2ccc(Cl)cc2)c(C(=O)Nc2ccc(S(=O)(=O)N3CCSCC3)cc2)cc1OC]

and HMR-1069 (Sanofi-Aventis).

(7) Heme-dependent sGC stimulators including, but not limited to:

YC-1 (see patent publications EP667345 and DE19744026)

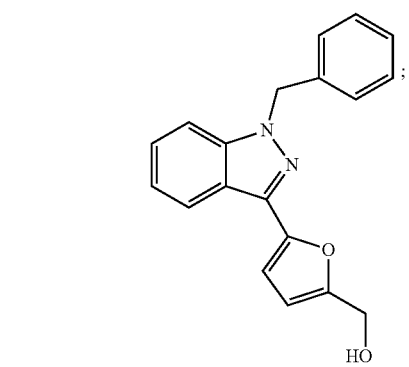 [SMILES: OCc1ccc(-c2nn(Cc3ccccc3)c3ccccc23)o1]

Riociguat (BAY 63-2521, Adempas, commercial product, described in DE19834044)

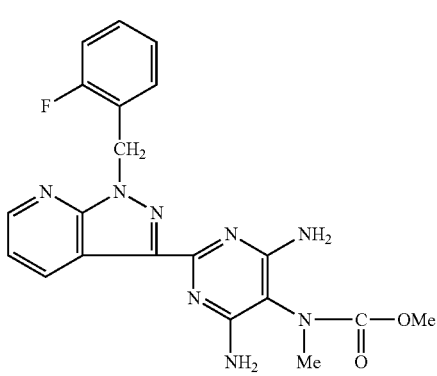 [SMILES: COC(=O)N(C)c1c(N)nc(-c2nn(Cc3ccccc3F)c3ncccc23)nc1N]

157
Neliciguat (BAY 60-4552, described in WO 2003095451)
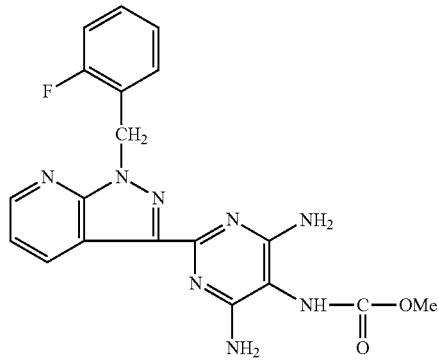 [SMILES: COC(=O)Nc1c(N)nc(-c2nn(Cc3ccccc3F)c3ncccc23)nc1N]
Vericiguat (BAY 1021189, clinical backup to Riociguat), BAY 41-2272 (described in DE19834047 and DE19942809)
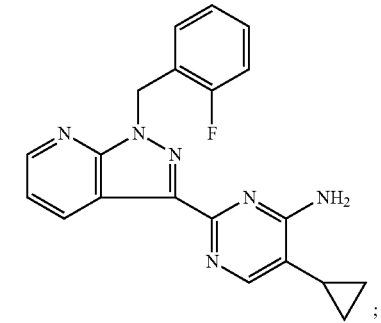 [SMILES: Nc1nc(-c2nn(Cc3ccccc3F)c3ncccc23)ncc1C1CC1]
BAY 41-8543 (described in DE19834044)
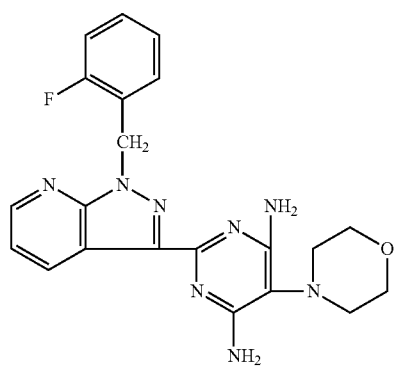 [SMILES: Nc1nc(-c2nn(Cc3ccccc3F)c3ncccc23)nc(N)c1N1CCOCC1]
158
Etriciguat (described in WO 2003086407)
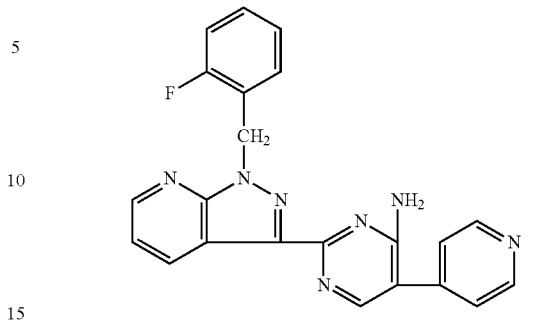
CFM-1571 (see patent publication WO2000027394)
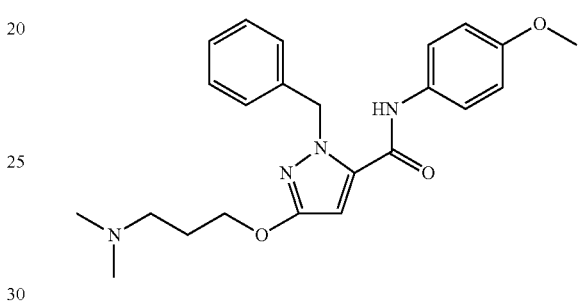
A-344905, its acrylamide analogue A-350619 and the aminopyrimidine analogue A-778935.
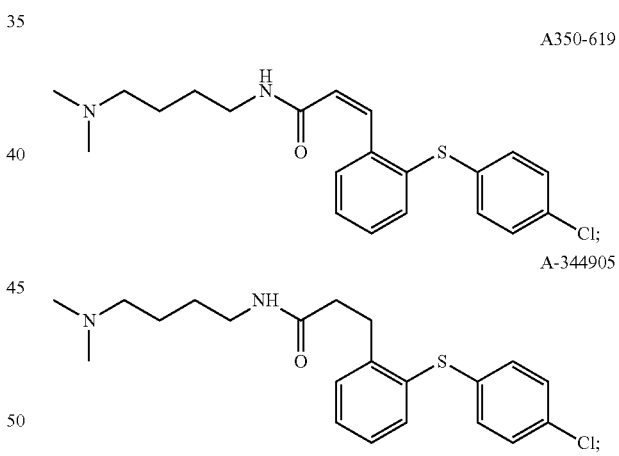
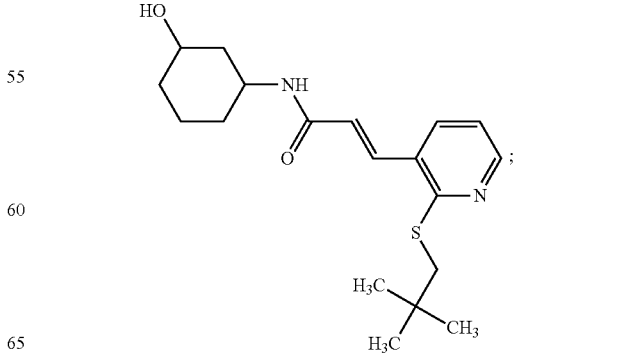

Compounds disclosed in one of publications: US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds disclosed in Tetrahedron Letters (2003), 44(48): 8661-8663.

(8) Compounds that inhibit the degradation of cGMP, such as:

PDE5 inhibitors, such as, for example, Sildenafil (Viagra®) and other related agents such as Avanafil, Lodenafil, Mirodenafil, Sildenafil citrate (Revatio®), Tadalafil (Cialis® or Adcirca®), Vardenafil (Levitra®) and Udenafil; Alprostadil; and Dipyridamole; PF-00489791

PDE9 inhibitors, such as, for example, PF-04447943;

(9) Calcium channel blockers such as:

Dihydropyridine calcium channel blockers: Amlodipine (Norvasc), Aranidipine (Sapresta), Azelnidipine (Calblock), Bamidipine (HypoCa), Benidipine (Coniel), Cilnidipine (Atelec, Cinalong, Siscard), Clevidipine (Cleviprex), Diltiazem, Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);

Phenylalkylamine calcium channel blockers: Verapamil (Calan, Isoptin)

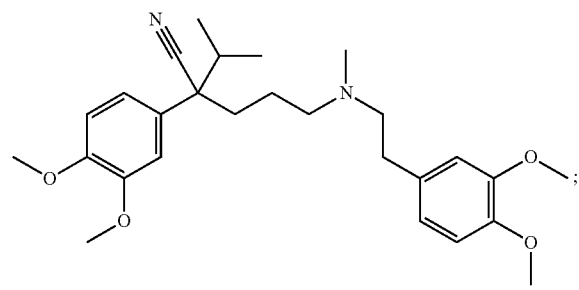

Gallopamil (Procorum, D600);
Benzothiazepines: Diltiazem (Cardizem);

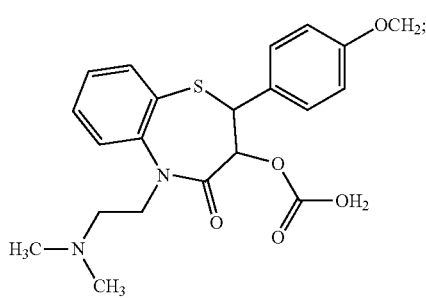

Nonselective calcium channel inhibitors such as: mibefradil, bepridil and fluspirilene, fendiline;

(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;

(11) Prostacyclin derivatives or analogues: for instance prostacyclin (prostaglandin $I_2$), Epoprostenol (synthetic prostacyclin, marketed as Flolan®); Treprostinil (Remodulin®), Iloprost (Ilomedin®), Iloprost (marketed as Ventavis®); oral and inhaled forms of Remodulin® that are under development; Beraprost, an oral prostanoid available in Japan and South Korea;

(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fibric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;

(13) Anticoagulants, such as the following types:

Coumarines (Vitamin K antagonists): Warfarin® (Coumadin) mostly used in the US and UK; Acenocoumarol® and Phenprocoumon®, mainly used in other countries; Phenindione®;

Heparin and derivative substances such as: Heparin; low molecular weight heparin, Fondaparinux and Idraparinux;

Direct thrombin inhibitors such as: Argatroban, Lepirudin, Bivalirudin and Dabigatran; Ximelagatran (Exanta®), not approved in the US;

Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:

Sulfhydryl-containing agents such as Captopril (trade name Capoten®), the first ACE inhibitor and Zofenopril;

Dicarboxylate-containing agents such as Enalapril (Vasotec/Renitec®); Ramipril (Altace/Tritace/Ramace/Ramiwin®); Quinapril (Accupril®), Perindopril (Coversyl/Aceon®); Lisinopril (Lisodur/Lopril/Novatec/Prinivil/Zestrile®) and Benazepril (Lotensin®);

Phosphonate-containing agents such as: Fosinopril;

Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;

Other ACE inhibitors such as Alacepril, Delapril, Cilazapril, Imidapril, Trandolapril, Temocapril, Moexipril, Spirapril,

(16) Supplemental oxygen therapy;

(17) Beta blockers, such as the following types:

Non-selective agents: Alprenolol®, Bucindolol®, Carteolol®, Carvedilol® (has additional α-blocking activity); Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;

$\beta_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;

$\beta_2$-Selective agents: Butaxamine® (weak α-adrenergic agonist activity);

(18) Antiarrhythmic agents such as the following types:
Type I (sodium channel blockers): Quinidine, Lidocaine, Phenytoin, Propafenone
Type III (potassium channel blockers): Amiodarone, Dofetilide, Sotalol
Type V: Adenosine, Digoxin

(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide (20a) Direct-acting vasodilators such as Hydralazine hydrochloride, Diazoxide, Sodium nitroprusside, Cadralazine; other vasodilators such as Isosorbide dinitrate and Isosorbide 5-mononitrate;

(20b) Exogenous vasodilators such as:
Adenocard®, an adenosine agonist, primarily used as an anti-arrhythmic;
Alpha blockers (which block the vasoconstricting effect of adrenaline):
Alpha-1-adrenoceptor antagonists such as Prazosin, Indoramin, Urapidil, Bunazosin, Terazosin, Doxazosin
Atrial natriuretic peptide (ANP);
Ethanol;
Histamine-inducers, which complement proteins C3a, C4a and C5a work by triggering histamine release from mast cells and basophil granulocytes;
Tetrahydrocannabinol (THC), major active chemical in marijuana which has minor vasodilatory effects;
Papaverine, an alkaloid found in the opium poppy *Papaver somniferum*; b

(21) Bronchodilators: there are two major types of bronchodilator, $\beta_2$ agonists and anticholinergics, exemplified below:
$\beta_2$ agonists: Salbutamol® or albuterol (common brand name: Ventolin) and Terbutaline® are short acting $\beta_2$ agonists for rapid relief of COPD symptoms. Long acting $\beta_2$ agonists (LABAs) such as Salmeterol® and Formoterol®;
anticholinergics: Ipratropium® is the most widely prescribed short acting anticholinergic drug. Tiotropium® is the most commonly prescribed long-acting anticholinergic drug in COPD;
Theophylline®, a bronchodilator and phosphodiesterase inhibitor;

(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide

(23) Dietary supplements such as, for example: omega-3 oils; folid acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporin A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex@), rofecoxib (Vioxx®), valdecoxib, etoricoxib, parecoxib and lumiracoxib;

(opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), α-glucosidase inhibitors (such as Acarbose, Epalrestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromium picolinate (optionally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VS01; cytokine targeted therapies in development for the treatment of diabetes such as Anakinra, Canakinumab, Diacerein, Gevokizumab, LY-2189102, MABP-1, GIT-027; drugs in development for the treatment of diabetes:

| Drugs in development for the treatment of diabetes | | | |
|---|---|---|---|
| Dapagliflozin | AstraZeneca/ Bristol-Myers Squibb | SGLT-2 Inhibitors | Recommended Approval |
| Alogliptin benzoate/metformin hydrochloride | Takeda | Insulin Sensitizers/ Dipeptidyl Peptidase IV (CD26; DPP-IV; DP-IV) Inhibitors | Pre-Registered |
| Anagliptin | Kowa/Sanwa | Dipeptidyl Peptidase IV (CD26; DPP-IV; DP-IV) Inhibitors | Pre-Registered |
| Insulin degludec | Novo Nordisk | | Pre-Registered |
| Insulin degludec/insulin aspart | Novo Nordisk | | Pre-Registered |
| Insulin human (rDNA origin) inhalation powder | MannKind | | Pre-Registered |
| Lixisenatide | Sanofi | Insulin Secretagogues/GLP-1 Receptor Agonists | Pre-Registered |
| Recombinant human insulin | Biodel | | Pre-Registered |
| Teneligliptin | Mitsubishi Tanabe Pharma | Dipeptidyl Peptidase IV (CD26; DPP-IV; DP-IV) Inhibitors | Pre-Registered |
| AVE-0277 | Andromeda Biotech/ Teva | | Phase III |
| Albiglutide | GlaxoSmithKline | GLP-1 Receptor Agonists | Phase III |
| Aleglitazar | Roche | PPARalpha Agonists/ PPARgamma Agonists | Phase III |
| Atorvastatin calcium/glimepiride | GlaxoSmithKline | K(ATP) Channel Blockers/Dipeptidyl Peptidase IV (CD26; DPP-IV; DP-IV) Inhibitors/HMG-CoA Reductase Inhibitors/ TNFSF6 Expression Inhibitors | Phase III |
| BYK-324677 | Nycomed | | Phase III |
| Balaglitazone | Dr. Reddy's Laboratories | Insulin Sensitizers/ PPARgamma Partial Agonists | Phase III |
| CSG-452 | Chugai Pharmaceutical | SGLT-2 Inhibitors | Phase III |
| Canagliflozin | Johnson & Johnson/ Mitsubishi Tanabe Pharma | SGLT-2 Inhibitors | Phase III |
| Canagliflozin/metformin hydrochloride | Johnson & Johnson | SGLT-2 Inhibitors/ Insulin Sensitizers | Phase III |
| Dapagliflozin/Metformin hydrochloride | AstraZeneca/ Bristol-Myers Squibb | SGLT-2 Inhibitors/ Insulin Sensitizers | Phase III |
| Dulaglutide | Lilly | Insulin Secretagogues/GLP-1 Receptor Agonists | Phase III |
| Empagliflozin | Boehringer Ingelheim/ Lilly | SGLT-2 Inhibitors | Phase III |
| Empagliflozin/linagliptin | Boehringer Ingelheim/ Lilly | SGLT-2 Inhibitors/ Dipeptidyl Peptidase IV (CD26; DPP-IV; DP-IV) Inhibitors | Phase III |
| Gemigliptin | LG Life Sciences | Dipeptidyl Peptidase IV (CD26; DPP-IV; DP-IV) Inhibitors | Phase III |
| Hepatic-directed vesicle insulin | Diasome Pharmaceuticals | | Phase III |
| Human isophane insulin | Wockhardt | | Phase III |
| IN-105 | Biocon | | Phase III |

-continued

| Drugs in development for the treatment of diabetes | | | |
|---|---|---|---|
| Insulin degludec/liraglutide | Novo Nordisk | Insulin Secretagogues/GLP-1 Receptor Agonists | Phase III |
| Insulin glargine | Sanofi | | Phase III |
| Ipragliflozin L-proline | Astellas Pharma/ Kotobuki | SGLT-2 Inhibitors | Phase III |
| LY-2605541 | Lilly | | Phase III |
| LY-2963016 | Lilly | | Phase III |
| Lixisenatide/Insulin glargine | Sanofi | Insulin Secretagogues/GLP-1 Receptor Agonists | Phase III |
| Lobeglitazone sulfate | Chong Kun Dang Pharm (CKD Pharm) | PPARalpha Agonists/ PPARgamma Agonists/ Insulin Sensitizers | Phase III |
| Luseogliflozin | Taisho | SGLT-2 Inhibitors | Phase III |
| Otelixizumab | Tolerx | Anti-CD3 | Phase III |
| Ranolazine | Gilead | Sodium Channel Blockers | Phase III |
| Recombinant human insulin | National Institute of Health Sciences | | Phase III |
| Sitagliptin phosphate monohydrate/pioglitazone hydrochloride | Merck & Co. | PPARgamma Agonists/ Insulin Sensitizers/ Dipeptidyl Peptidase IV (CD26; DPP-IV; DP-IV) Inhibitors | Phase III |
| Sitagliptin/atorvastatin calcium | Merck & Co. | Dipeptidyl Peptidase IV (CD26; DPP-IV; DP-IV) Inhibitors/ HMG-CoA Reductase Inhibitors/TNFSF6 Expression Inhibitors | Phase III |
| TAK-875 | Takeda | Free Fatty Acid Receptor 1 (FFAR1; GPR40) Agonists/ Insulin Secretagogues | Phase III |
| TT-401 | 7TM Pharma | Cannabinoid CB1 Antagonists | Phase I |
| TT-401 | Transition Therapeutics | | Phase I |
| ZYH-2 | Cadila Healthcare (d/b/a Zydus Cadila) | PPARalpha Ligands/ PPARgamma Ligands | Phase I |
| ZYO-1 | Cadila Healthcare (d/b/a Zydus Cadila) | Cannabinoid CB1 Antagonists | Phase I |
| 701645 | Cellonis Biotechnologies | | Phase I |
| 701499 | Cellonis Biotechnologies | | Phase I |
| 743300 | University of California, San Francisco | | Phase I |
| 448661 | University of Pittsburgh | | Phase I |
| AD-1 | National Institute Pharma Res Dev | | Clinical |
| Colesevelam hydrochloride | Daiichi Sankyo | Bile Acid Sequestrants | Clinical |
| DBPR-108 | National Health Research Institutes/ ScinoPharm | | IND Filed |
| Nodlin | Biolaxy | | IND Filed |
| PSN-491 | Prosidion | Glucose-Dependent Insulinotropic Receptor (GDIR, GPR119) Agonists/ Dipeptidyl Peptidase IV (CD26; DPP-IV; DP-IV) Inhibitors | IND Filed |
| Tolimidone | Melior Discovery | Lyn Kinase Activators | IND Filed |
| ZYD-1 | Cadila Healthcare (d/b/a Zydus Cadila) | GLP-1 Receptor Agonists | IND Filed |
| ZYOG-1 | Cadila Healthcare (d/b/a Zydus Cadila) | GLP-1 Receptor Agonists | IND Filed |

(30) HDL cholesterol-increasing agents such as Anacetrapib, MK-524A, CER-001, DRL-17822, Dalcetrapib, JTT-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2 ®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;

(33) Renin inhibitors such as Aliskiren hemifumirate;

(34) Centrally acting alpha-2-adrenoceptor agonists such as Methyldopa, Clonidine, Guanfacine;

(35) Adrenergic neuron blockers such as Guanethidine, Guanadrel;

(36) Imidazoline I-1 receptor agonists such as Rimenidine dihydrogen phosphate and Moxonidine hydrochloride hydrate;

(37) Aldosterone antagonists such as Spironolactone and Eplerenone

(38) Potassium channel activators such as Pinacidil

(39) Dopamine D1 agonists such as Fenoldopam mesilate; Other dopamine agonists such as Ibopamine, Dopexamine and Docarpamine;

(40) 5-HT2 antagonists such as Ketanserin;

(41) Drugs that are currently being developed for the treatment of arterial hypertension:

| Drugs in development for the treatment of hypertension | | | |
|---|---|---|---|
| Azilsartan | Takeda | Angiotensin AT1 Antagonists/ Angiotensin AT2 Antagonists/Insulin Sensitizers | Registered |
| Amlodipine besylate/irbesartan | Dainippon Sumitomo Pharma | Angiotensin AT1 Antagonists/Calcium Channel Blockers | Pre-Registered |
| Azilsartan/amlodipine besilate | Takeda | Angiotensin AT1 Antagonists/Insulin Sensitizers/Calcium Channel Blockers | Phase III |
| Cilnidipine/valsartan | Ajinomoto/ Mochida | Angiotensin AT1 Antagonists/Calcium Channel Blockers | Phase III |
| Fimasartan | Boryung | Angiotensin AT1 Antagonists | Phase III |
| Irbesartan/atorvastatin | Hanmi | Angiotensin AT1 Antagonists/Dipeptidyl Peptidase IV (CD26; DPP-IV; DP-IV) Inhibitors/HMG-CoA Reductase Inhibitors/ TNFSF6 Expression Inhibitors | Phase III |
| Irbesartan/trichlormethiazide | Shionogi | Angiotensin AT1 Antagonists | Phase III |
| Losartan potassium/hydrochlorothiazide/amlodipine besylate | Merck & Co. | Angiotensin AT1 Antagonists/Calcium Channel Blockers | Phase III |
| Pratosartan | Boryung | Angiotensin AT1 Antagonists | Phase III |
| ACT-280778 | Actelion | | Phase II |
| Amiloride hydrochloride/spironolactone | Hemodynamic Therapeutics | Mineralocorticoid Receptor (MR) Antagonists/Na+/H+ Exchanger (NHE) Inhibitors/Epithelial Sodium Channels (ENaC) Blockers/ K(V)1.5 Channel Blockers/K(V)4.3 Channel Blockers | Phase II |
| Angiotensin vaccine/CoVaccine HT | BTG | | Phase II |
| CYT006-AngQb | Cytos Biotechnology | Anti-Angiotensin II | Phase II |

| Drugs in development for the treatment of hypertension | | | |
|---|---|---|---|
| Cholecalciferol | Emory University | | Phase II |
| Cobiprostone | Sucampo Pharmaceuticals | ClC-2 Channel Activators | Phase II |
| INT-001 | IntelGenx | | Phase II |
| LCZ-696 | Novartis | Angiotensin AT1 Antagonists/Neprilysin (Enkephalinase, Neutral Endopeptidase, NEP) Inhibitors | Phase II |
| LFF-269 | Novartis | | Phase II |
| Octreotide acetate | Chiasma | Growth Hormone Release Inhibitors/ Somatostatin Agonists | Phase II |
| PL-3994 | Palatin Technologies | Atrial Natriuretic Peptide A (NPR1; Guanylate Cyclase A) Receptor Agonists | Phase II |
| Rostafuroxine | Sigma-Tau | | Phase II |
| SLx-2101 | NT Life Sciences | Phosphodiesterase V (PDE5A) Inhibitors | Phase II |
| TBC-3711 | Encysive Pharmaceuticals | Endothelin ETA Receptor Antagonists | Phase II |
| Udenafil | Dong-A/Falk Pharma | Phosphodiesterase V (PDE5A) Inhibitors | Phase II |
| Atorvastatin calcium/losartan potassium | HanAll BioPharma | Angiotensin AT1 Antagonists/Dipeptidyl Peptidase IV (CD26; DPP-IV; DP-IV) Inhibitors/HMG-CoA Reductase Inhibitors/ TNFSF6 Expression Inhibitors | Phase I |
| BIA-5-1058 | BIAL | Dopamine beta-monooxygenase Inhibitors | Phase I |
| CS-3150 | Daiichi Sankyo | | Phase I |
| DSP-9599 | Dainippon Sumitomo Pharma | Renin Inhibitors | Phase I |
| MK-1597 | Actelion/Merck & Co. | Renin Inhibitors | Phase I |
| MK-4618 | Merck & Co. | | Phase I |
| MK-5478 | Merck & Co. | | Phase I |
| MK-7145 | Merck & Co. | | Phase I |
| MK-8266 | Merck & Co. | | Phase I |
| MK-8457 | Merck & Co. | | Phase I |
| MP-157 | Mitsubishi Tanabe Pharma | Angiotensin AT2 Agonists | Phase I |
| MT-3995 | Mitsubishi Tanabe Pharma | Mineralocorticoid Receptor (MR) Antagonists | Phase I |
| Mirodenafil hydrochloride | SK Chemicals | Phosphodiesterase V (PDE5A) Inhibitors | Phase I |
| NV-04 | Novogen | Antioxidants | Phase I |
| Nifedipine/Candesartan cilexetil | Bayer | Angiotensin AT1 Antagonists/Calcium Channel Blockers/ Antioxidants | Phase I |
| QGC-001 | Quantum Genomics | Glutamyl Aminopeptidase (Aminopeptidase A) Inhibitors | Phase I |
| RDX-5791 | Ardelyx | Na+/H+ Exchanger type 3 (NHE-3) Inhibitors | Phase I |
| TAK-272 | Takeda | Renin Inhibitors | Phase I |
| TAK-591 | Takeda | Angiotensin AT2 Antagonists | Phase I |
| VTP-27999 | Vitae Pharmaceuticals | Renin Inhibitors | Phase I |
| Vasomera | PhaseBio | VPAC2 (VIP2) Agonists | Phase I |

(42) Vasopressin antagonists such as Tolvaptan;
(43) Calcium channel sensitizers such as Levosimendan or activators such as Nicorandil;
(44) PDE-3 inhibitors such as Amrinone, Milrinone, Enoximone, Vesnarinone, Pimobendan, Olprinone;
(45) Adenylate cyclase activators such as Colforsin dapropate hydrochloride;
(46) Positive inotropic agents such as Digoxin and Metildigoxin; metabolic cardiotonic agents such as Ubidecarenone; brain naturetic peptides such as Nesiritide;

(47) Drugs that are currently in development for the treatment of heart failure:

| Drugs in development for the treatment of heart failure | | | |
|---|---|---|---|
| Bucindolol hydrochloride | ARCA | beta-Adrenoceptor Antagonists | Pre-Registered |
| Aliskiren hemifumarate | Novartis | Renin Inhibitors | Phase III |
| Ferric carboxymaltose | Vifor | | Phase III |
| LCZ-696 | Novartis | Angiotensin AT1 Antagonists/Neprilysin (Enkephalinase, Neutral Endopeptidase, NEP) Inhibitors | Phase III |
| Neuregulin-1 | Zensun | | Phase III |
| Olmesartan medoxomil | Tohoku University | Angiotensin AT1 Antagonists | Phase III |
| C3BS-CQR-1 | Cardio3 BioSciences | | Phase II/III |
| MyoCell | Bioheart | | Phase II/III |
| Serelaxin | Novartis | | Phase II/III |
| AAV1/SERCA2a | AmpliPhi Biosciences/ Celladon/Mount Sinai School of Medicine | | Phase II |
| Albiglutide | GlaxoSmithKline | GLP-1 Receptor Agonists | Phase II |
| Allogeneic mesenchymal precursor cells | Mesoblast | | Phase II |
| AlsterMACS | Miltenyi Biotec | | Phase II |
| BAY-94-8862 | Bayer | Mineralocorticoid Receptor (MR) Antagonists | Phase II |
| COR-1 | Corimmun | | Phase II |
| CXL-1020 | Cardioxyl Pharmaceuticals | Nitric Oxide Donors | Phase II |
| Cenderitide | Nile Therapeutics | Guanylate Cyclase Activators | Phase II |
| Endometrial regenerative cells | ERCell/Medistem | | Phase II |
| JNJ-39588146 | Johnson & Johnson | | Phase II |
| Omecamtiv mecarbil | Amgen/ Cytokinetics | Cardiac Myosin Activators | Phase II |
| PL-3994 | Palatin Technologies | Atrial Natriuretic Peptide A (NPR1; Guanylate Cyclase A) Receptor Agonists | Phase II |
| Remestemcel-L | Osiris | | Phase II |
| TRV-120027 | Trevena | Angiotensin AT1 Receptor Ligands | Phase II |
| Urocortin 2 | Neurocrine Biosciences | CRF2 Agonists | Phase II |
| AAV6-CMV-SERCA2a | Imperial College | | Phase I/II |
| Anakinra | National Institutes of Health (NIH) | IL-1 Receptor Antagonists | Phase I/II |
| LipiCell | Bioheart/Institute de Medicina Regenerativa | | Phase I/II |
| ALD-201 | Cytomedix/Texas Heart Institute | | Phase I |
| BAY-1021189/Vericiguat | Bayer | | Phase I I |
| BAY-1067197 | Bayer | Adenine Receptor Agonists | Phase I |
| BAY-86-8050 | Bayer | Drugs Acting on Vasopressin (AVP) Receptors | Phase I |
| BIA-5-1058 | BIAL | Dopamine beta-monooxygenase Inhibitors | Phase I |
| CSCs | University of Louisville | | Phase I |
| Calcitonin gene related peptide | VasoGenix | | Phase I |
| JVS-100 | Juventas Therapeutics | | Phase I |
| MyoCell SDF-1 | Bioheart | | Phase I |
| Myoblast | Advanced Cell Technology (ACT) | | Phase I |
| RO-1160367 | Serodus | 5-HT4 Antagonists | Phase I |
| Recombinant human glial growth factor 2 | Acorda/Vanderbilt University | | Phase I |

| Drugs in development for the treatment of heart failure | | |
|---|---|---|
| [18F]LMI-1195 | Lantheus Medical Imaging | Phase I |
| 677950 | Kyoto Prefectural University of Medicine | Phase I |

(48) Drugs currently in development for the treatment of pulmonary hypertension:

| Drugs in development for the treatment of pulmonary hypertension | | | |
|---|---|---|---|
| Imatinib mesylate | Novartis | Breast Cancer-Resistant Protein (BCRP; ABCG2) Inhibitors/Abl Kinase Inhibitors/Angiogenesis Inhibitors/Bcr-Abl Kinase Inhibitors/CSF1R (c-FMS) Inhibitors/KIT (C-KIT) Inhibitors/Apoptosis Inducers/PDGFRalpha Inhibitors/PDGFRbeta Inhibitors/Inhibitors of Signal Transduction Pathways | Pre-Registered |
| Treprostinil diethanolamine | United Therapeutics | Prostacyclin Analogs | Pre-Registered |
| GSK-1325760A | GlaxoSmithKline | | Phase III |
| Macitentan | Actelion | Endothelin ETA Receptor Antagonists/Endothelin ETB Receptor Antagonists | Phase III |
| Riociguat/Adempas | Bayer | Guanylate Cyclase Activators | Approved 2013 |
| Selexipag | Actelion/Nippon Shinyaku | Prostanoid IP Agonists | Phase III |
| Udenafil | Dong-A | Phosphodiesterase V (PDE5A) Inhibitors | Phase III |
| L-Citrulline | Nat Heart, Lung, and Blood Institute/Vanderbilt University | | Phase II/III |
| BQ-123 | Brigham & Women's Hospital | Endothelin ETA Receptor Antagonists | Phase II |
| Cicletanine | Gilead | | Phase II |
| Fasudil hydrochloride | Asahi Kasei | Rho Kinase Inhibitors/Calcium Sensitizers | Phase II |
| Nilotinib hydrochloride monohydrate | Novartis | Bcr-Abl Kinase Inhibitors/Apoptosis Inducers/Inhibitors of Signal Transduction Pathways | Phase II |
| PRX-08066 | Clinical Data | 5-HT2B Antagonists | Phase II |
| Terguride | ErgoNex Pharma | 5-HT2A Antagonists/5-HT2B Antagonists/Dopamine Autoreceptor Agonists/Dopamine D2 Receptor Partial Agonists/Prolactin Secretion Inhibitors | Phase II |
| Tezosentan disodium | Actelion | Endothelin ETA Receptor Antagonists/Endothelin ETB Receptor Antagonists | Phase II |
| Anakinra | Virginia Commonwealth University (VCU) | IL-1 Receptor Antagonists | Phase I/II |
| Simvastatin | Imperial College | HDL-Cholesterol Increasing Agents/HMG-CoA Reductase Inhibitors | Phase I/II |
| 99mTC-PulmoBind | Montreal Heart Institute (MHI) | | Phase I |
| APD-811 | Arena | Prostanoid IP Agonists | Phase I |
| Sorafenib | Bayer | Raf kinase B Inhibitors/Raf kinase C Inhibitors/Angiogenesis Inhibitors/Flt3 (FLK2/STK1) Inhibitors/VEGFR-1 (Flt-1) Inhibitors/KIT (C-KIT) Inhibitors/VEGFR-2 (FLK-1/KDR) Inhibitors/VEGFR-3 (FLT4) Inhibitors/PDGFRbeta Inhibitors/RET Inhibitors/Inhibitors of Signal Transduction Pathways | Phase I |
| Triplelastat | Proteo Biotech | Elastase Inhibitors | Phase I |

(49) Drugs in current development for the treatment of female sexual dysfunction:

| Drugs in active development for the treatment of female sexual dysfunction | | | |
|---|---|---|---|
| Alprostadil | Apricus Biosciences/ VIVUS | | Phase III |
| Prasterone | EndoCeutics/ Monash University | HSD11B1 Expression Inhibitors | Phase III |
| Testosterone transdermal gel | BioSante | Androgen Receptor Agonists | Phase III |
| Bremelanotide | Palatin Technologies | Melanocortin MC3 Receptor Agonists/Melanocortin MC4 Receptor Agonists | Phase II |
| Pill-Plus | Pantarhei Bioscience | | Phase II |
| Testosterone MDTS | Acrux | Androgen Receptor Agonists | Phase II |
| Estradiol/testosterone | BioSante | Estrogen Receptor (ER) Agonists/Androgen Receptor Agonists | Phase I |
| LGD-2941 | Ligand | Selective Androgen Receptor Modulators (SARM) | Phase I |
| Lidocaine/heparin | Urigen | | Phase I |
| OnabotulinumtoxinA | Allergan | | Phase I |

(50) Drugs used for the treatment of erectile dysfunction such as Alprostadil, Aviptadil, Phentolamine mesilate, Weige, Alprostadil;

(51) Drugs currently in development for the treatment of male sexual dysfunction:

| Drugs in active development for the treatment of erectile dysfunction | | | |
|---|---|---|---|
| Fluvastatin sodium | Novartis | Apoptosis Inducers/HMG-CoA Reductase Inhibitors | Phase III |
| Lodenafil carbonate | Cristalia | Phosphodiesterase V (PDE5A) Inhibitors | Phase III |
| EFLA-400 | Chonbuk National University Hospital | | Phase II/III |
| Apomorphine hydrochloride | Vectura | Dopamine D2 Agonists | Phase II |
| LY-900010 | Lilly | Phosphodiesterase V (PDE5A) Inhibitors/Selective Androgen Receptor Modulators (SARM) | Phase II |
| Nitroglycerin | Futura Medical | | Phase II |
| RX-10100 | Rexahn | Drugs Acting on Dopaminergic Transmission/Drugs Acting on Serotonergic Transmission | Phase II |
| YHD-1023 | Yuhan | | Phase II |
| INT-007 | IntelGenx | | Phase I |
| LY-2452473 | Lilly | Selective Androgen Receptor Modulators (SARM) | Phase I |
| hMaxi-K | Albert Einstein College of Medicine/Ion Channel Innovations/Mount Sinai School of Medicine | | Phase I |
| KH-204 | KMSI | | Clinical |

(51) Drugs in development for the treatment of sleep apnea:

| Drugs in development for the treatment of sleep apnea | | | |
|---|---|---|---|
| CX-1739 | Cortex | AMPA Receptor Modulators | Phase II |
| Phentermine/ topiramate | VIVUS | AMPA Antagonists/Kainate Antagonists/Sodium Channel Blockers/Carbonic Anhydrase Type II Inhibitors | Phase II |
| AVE-0118 | Sanofi | Potassium Channel Blockers | Phase I |
| Suvorexant | Merck & Co. | Orexin Receptor Antagonists | Phase I |

(52) Drugs currently in development for the treatment of metabolic syndrome:

| Antihyperlipidemic drugs under active development for the treatment of patients with metabolic syndrome | | | |
|---|---|---|---|
| GFT-505 | Genfit | PPARalpha Agonists/ PPARdelta Agonists | Phase II |
| MBX-8025 | Metabolex | PPARdelta Agonists | Phase II |
| Pitavastatin calcium | Kowa | APOA1 Expression Enhancers/ HMG-CoA Reductase Inhibitors/SPP1 (Osteopontin) Expression Inhibitors | Phase I |

(53) Antiobesity drugs:

| Drugs marketed for the treatment of obesity | | | |
|---|---|---|---|
| Methamphetamine hydrochloride (Desoxyn) | Abbott | Noradrenergic, alpha- and beta-adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |
| Orlistat (Xenical) | Roche | Pancreatic lipase inhibitor | 1998 (New Zealand) |

(54) Drugs used for the treatment of Alzheimer's disease: e.g., cholinesterase inhibitors prescribed for mild to moderate Alzheimer's disease, including Razadyne® (galantamine), Exelon® (rivastigmine), and Aricept® (donepezil), Cognex® (tacrine); Namendat (memantine), an N-methyl D-aspartate (NMDA) antagonist, and Aricept®, prescribed to treat moderate to severe Alzheimer's disease; vitamin E (an anti-oxidant).

(55) Antidepressants: tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®); SNRIs (e.g., venlafaxine and reboxetine); dopaminergic antidepressants (e.g., bupropion and aminceptine).

(56) Neuroprotective agents: e.g., memantine, L-dopa, bromocriptine, pergolide, talipexol, pramipexol, cabergoline, neuroprotective agents currently under investigation including anti-apoptotic drugs (CEP 1347 and CTCT346), lazaroids, bioenergetics, antiglutamatergic agents and dopamine receptors. Other clinically evaluated neuroprotective agents are, e.g., the monoamine oxidase B inhibitors selegiline and rasagiline, dopamine agonists, and the complex I mitochondrial fortifier coenzyme Q10.

(57) Antipsychotic medications: e.g., ziprasidone (Geodon™), risperidone (Risperdal™), and olanzapine (Zyprexa™)

(58) NEP inhibitors such as Sacubitril, Omapatrilat.

(59) Methylene Blue (MB).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

General Synthetic Schemes

Compounds of the present invention embodied in Formula I', Formula I or Table I may be synthesized by those skilled in the art of synthetic organic chemistry using a variety of synthetic routes such as those depicted in, but not restricted to, the following Schemes.

As depicted in Scheme 1, pyrazole esters of general structure 4 may be synthesized by Claisen condensation of substituted hydrazines 3 with diones 2. Dione 2 may be accessed by condensation of commercially available ketone 1 and diethyl oxalate in the presence of lithium hexamethyldisilazide in ethanol (see Finn et al. *Bio. Med. Chem. Lett.* 2003, 13, 2231). If methyl ketone 1 is not commercially available, it may be synthesized by conversion of the appropriate carboxylic acid to the Weinreb amide by treatment with oxalyl chloride in the presence of catalytic N,N-dimethylformamide in a solvent such as dichloromethane, followed by treatment with N,O-dimethylhydroxylamine hydrochloride. The resulting Weinreb amide may then be alkylated using methyllithium in diethyl ether. Substituted hydrazines 3 may be synthesized by reaction of the appropriate bromide or other halide with hydrazine hydrate in a solvent such as ethanol. Alternatively, 3 may be accessed by condensation of tert-butyl carbazate with a ketone or aldehyde in THF, followed by reduction of the resulting hydrazone with palladium on activated carbon in methanol/THF, followed by carbamate removal using TFA in dichloromethane.

Scheme 1

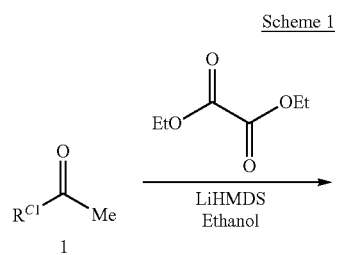

-continued

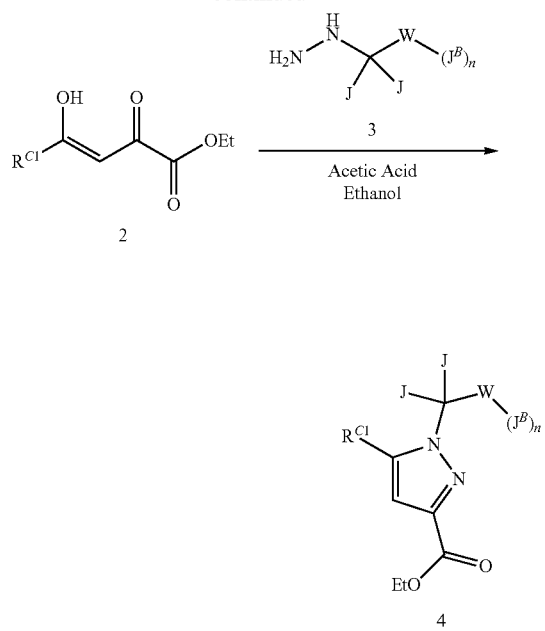

Scheme 2 illustrates the synthesis of ester pyrazole 7 when $R^{C1}$ is an alkoxy group. Refluxing hydrazine 3, commercially available diester 5, and acetic acid in ethanol leads to hydroxypyrazole 6 (see Dunn et al. WO2004/74257). Alkylation of the hydroxyl group may be accomplished using an inorganic base such as cesium carbonate or potassium carbonate along with the appropriate alkyl bromide or other halide in N,N-dimethylformamide to give alkyl ether 7.

Scheme 2

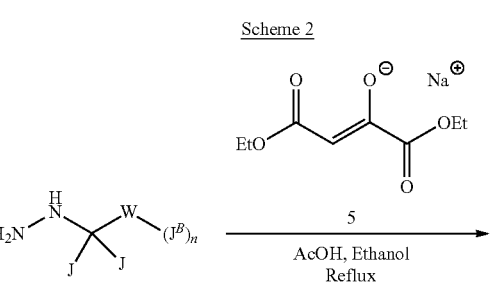

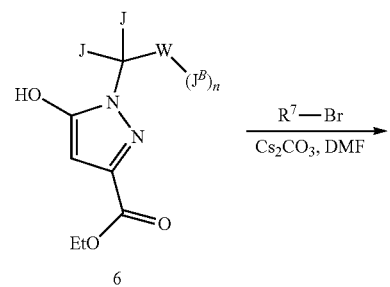

-continued

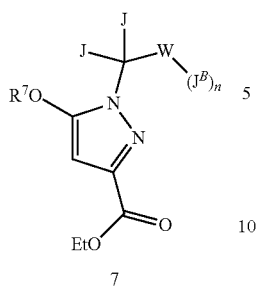

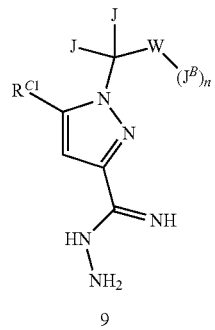

Esters of general structure 4 may be converted to amidine 8 (Scheme 3) by reaction with an excess of pre-mixed trimethylaluminum and ammonium chloride in toluene at elevated temperatures (for example, see Geilen et al. *Tetrahedron Lett.* 2002, 43, 419). Evident to those skilled in the art of organic chemistry is that acid-sensitive functionality comprising $R^{C1}$ must be suitably protected prior to this transformation. Amidine 8 can then be converted to amidrazone 9 by treatment with hydrazine hydrate in ethanol.

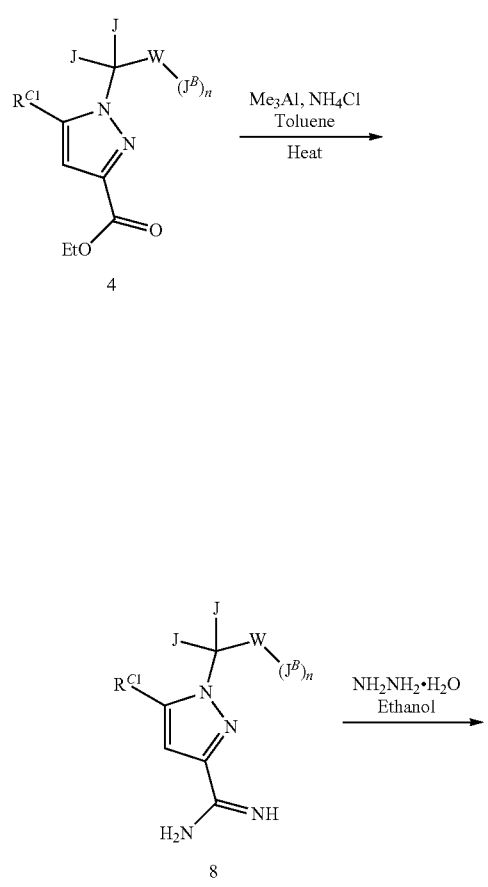

Scheme 4 illustrates a method for the synthesis of guanidine and hydrazinecarboximidamide intermediates, 19 and 20 respectively, that are useful for the synthesis of alternative pyrazole variants of Formula I compounds. Acylation of Meldrum's acid with a substituted carboxylic acid 10 using a coupling agent such as DCC followed by ethanolysis provides ketoester 11. Treatment of ketoester 11 with triethyl orthoformate or N,N-dimethylformamide dimethyl acetal affords the corresponding enolether or enamine intermediate which can then be cyclized to pyrazole 12 by reacting with hydrazine (see Okada et al. WO1993/9313099). There are other methods for constructing similarly-substituted pyrazole rings (for example, see Kelly et al. *Tetrahedron Lett.* 1999, 40, 1857). Protection of pyrazole 12 with a protecting group such as PMB followed by a three-step sequence of saponification, Curtius rearrangement (see Liu et al. *ACS Med Chem. Lett.* 2013, 4, 259) and Sandmeyer reaction (see Atobe et al. *Bioorg. Med. Chem. Lett.* 2013, 23, 6569) affords a versatile iodopyrazole intermediate 16. As an example, transition metal-catalyzed cross-coupling reactions of iodide 16 with coupling partners such as but not limited to commercially available or literature-described boronic acids, alcohols, amines and sulfinates can be used to install a wide variety of $R^{C1}$ groups to provide substituted pyrazole 17. Alternatively, iodide intermediate 16 can be converted to the corresponding boronic acid or boronic ester via transition metal-catalyzed borylation so that additional halides and triflates can be used as coupling partners. After deprotection of the PMB group using TFA, the resultant pyrazole 18 can be converted to guanidine intermediate 19 by treatment with cyanamide under acidic conditions (see Lee et al. *Bioorg. Med. Chem. Lett.* 2000, 10, 2771) or hydrazinecarboximidamide 20 by treatment with sodium hydride/cyanogen bromide followed by hydrazine (see Kvaskoff et al. *J. Org. Chem.* 2006, 71, 4049; Bunevet et al. *Chem. Heterocyclic Compounds* 2012, 48, 1415). In addition, we have previously described a synthesis of an isoxazole-substituted pyrazole 21 or other heteroaryl-substituted pyrazoles using intermediate 13 (see Nakai et al. WO2014/047325).

Scheme 4
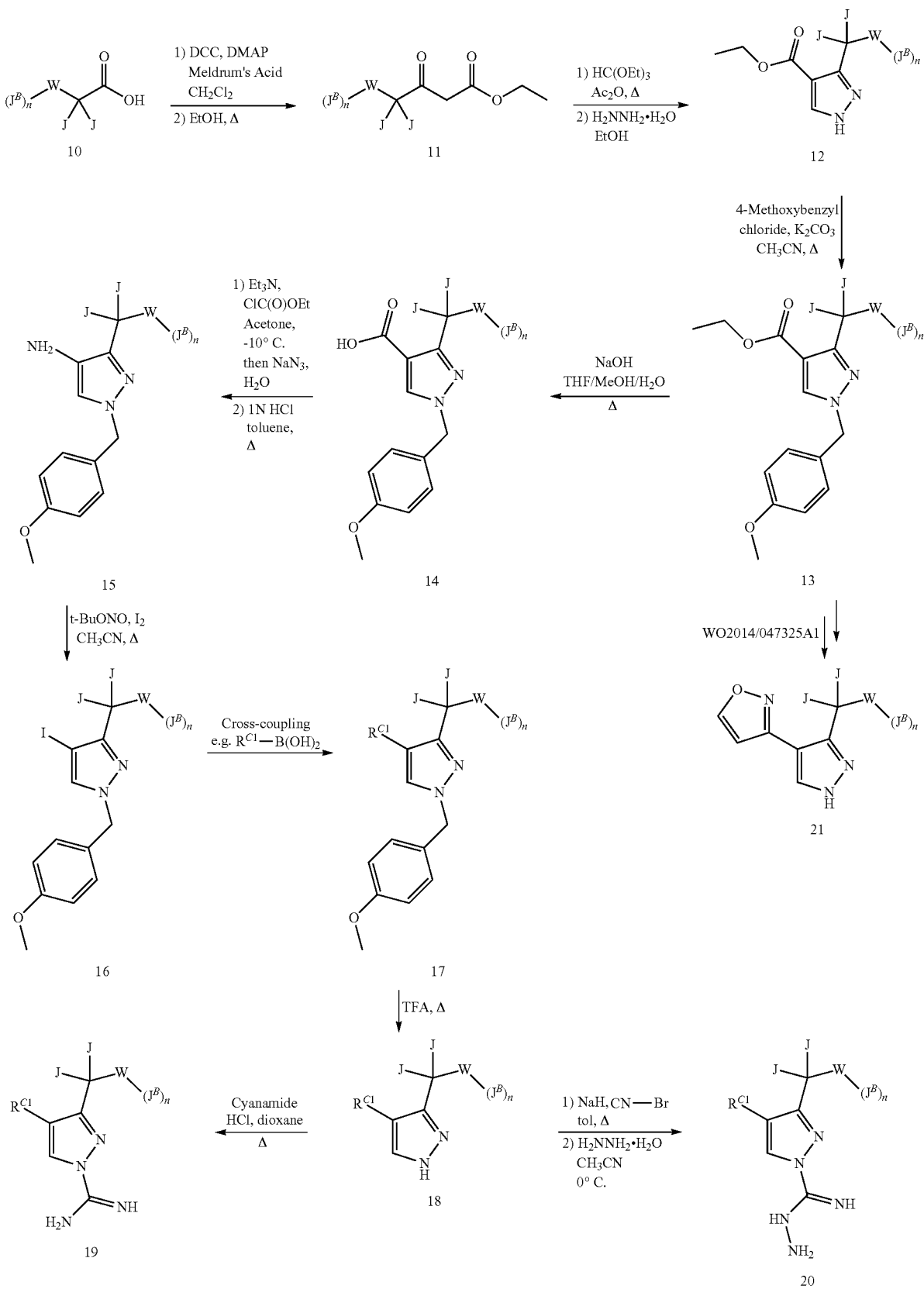

As depicted in Scheme 5, compounds of general structure 22 (for instance amidine 8 as described in Scheme 3 or guanidine 19 as described in Scheme 4) may be refluxed in ethanol with ethyl acrylate 23 in the presence of a base such as DBU to furnish 4-hydroxy-5-nitropyrimidine 24. The ethyl acrylate 23 may be obtained by stirring a neat mixture of N,N-dimethylformamide dimethyl acetal and ethyl nitroacetate at elevated temperatures (see Bekkali et al. WO2005/30213). Compound 24 can be heated with phosphorous oxychloride to give chloropyrimidine 25. Nucleophilic displacement of the chloride with commercially available or literature-described amines of general formula 26 in dioxane gives aminopyrimidines of general structure 27. 5-Nitropyrimidine 27 can be reduced to the 5-aminopyrimidine 28 using hydrogen (1 atm) in the presence of palladium on activated carbon in ethanol. Conversion of diamine 28 to the pyrimidinotriazole 29 can be effected using sodium nitrite with hydrochloric acid in ethanol and water (see Hansen et al. *Synthesis,* 2010, 689).

When ammonia is used as the nucleophile to displace the chloride of pyrimidine 25, the corresponding diaminopyrimidine intermediate 30 may be treated with an electrophile such as an alkyl halide in DMF to give substituted diaminopyrimidine 31 (see Cho et al. US2012/264727). Alternatively, substituted diaminopyrimidine 31 can be accessed by a reductive amination sequence (see Follman et al. US2014/148433). Ring closure to the isomeric pyrimidinotriazole 32 can be performed using sodium nitrite with hydrochloric acid in ethanol and water.

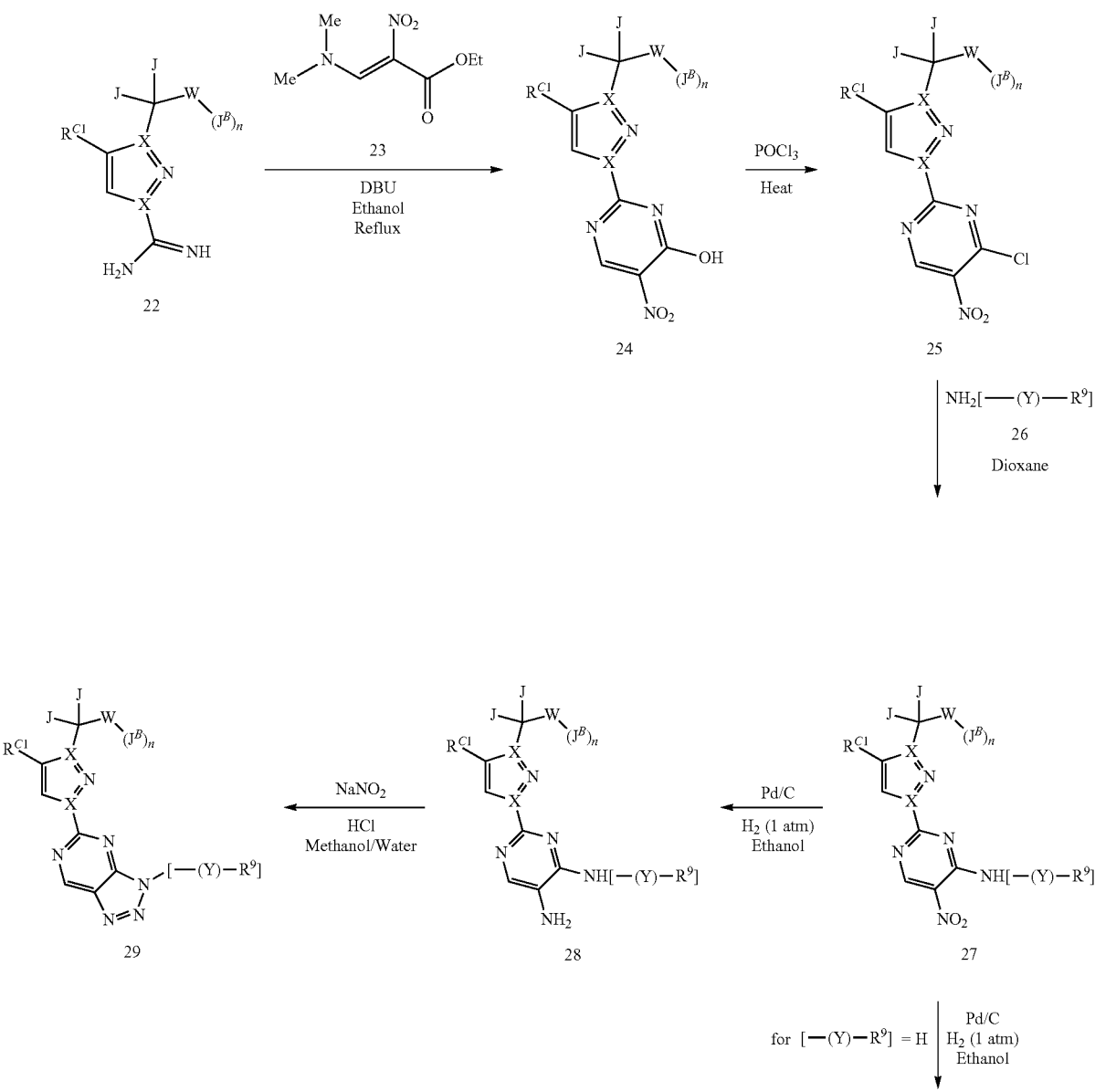

Scheme 5

-continued

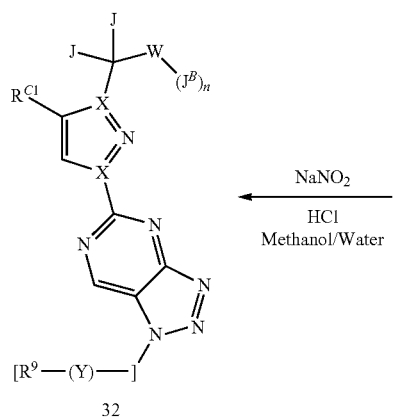

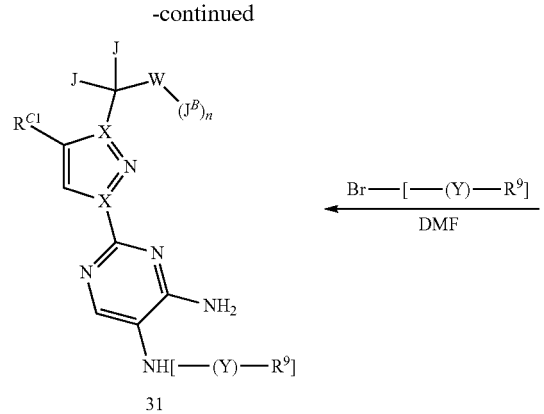

As depicted in Scheme 6, compounds of general structure 33 (for instance amidrazone 9 as described in Scheme 3 or hydrazinecarboximidamide 20 as described in Scheme 4) can be refluxed with ethyl thiooxamate in ethanol to provide aminotriazinone 34 (see Chunjian et al. WO 2010/011837). Conversion of the triazinone 34 to chlorotriazine 35 can be effected by refluxing in thionyl chloride. Compound 35 may then be converted to the diaminotriazine 36 by heating with ammonia in dioxane. Ring closed triazinotriazole 37 can be accessed using sodium nitrite in the presence of aqueous hydrochloric acid (see Tielemans et al. *J. Het. Chem.* 1987, 705). Reaction of triazinotriazole 37 using various commercially available or literature-described electrophile such as an alkyl halide in the presence of an inorganic base such as potassium carbonate in ethanol may provide a mixture of regioisomeric isomers 38a and 38b which may be readily separated by those skilled in the art of organic chemistry.

Scheme 6

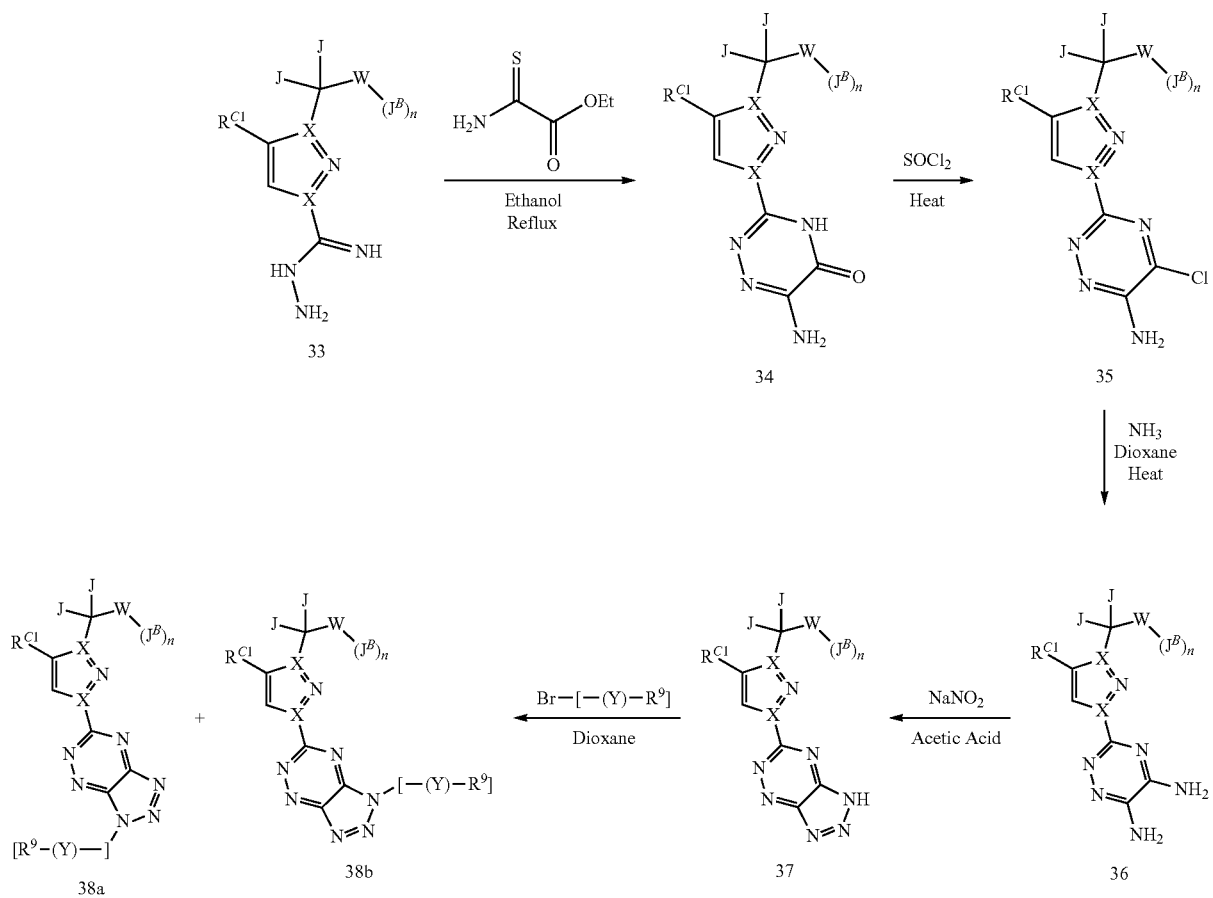

Scheme 7 illustrates a method to synthesize compounds 42 to 45 of general formula I. Following conditions detailed in our earlier work (see Kim et al. WO2013/101830 and WO2012/003405) and others (see Raghavan et al. WO2011/149921; Follmann et al. WO2013/131923 and WO2013/030288) the above described amidine 22 can be condensed with substituted dinitrile 39 in refluxing ethanol to obtain the bicyclic pyrimidine 40. The dinitrile 39 can be synthesized by procedures described in the literature. The amino group in the pyrimidine intermediate 40 can be further converted to a bromo-substituent by heating with isopropyl nitrite and copper (II) bromide in dichloroethane at 65° C. (Raghavan et al. WO2011/149921). Following a similar procedure, the amino group can also be converted to an iodo-substituent (using copper iodide). The halide group of 41 can then be functionalized using $S_NAr$ reactions with diverse nucleophiles (e.g. carbon-, amino- or hydroxyl-based nucleophiles) or transition metal catalyzed cross-coupling reactions with diverse coupling partners (e.g. boronic acids, amines, alcohols, alkynes) to give the desired compound 42. Furthermore, the annulated lactam can be substituted with a [—(Y)—R$^9$] group by treating with various electrophiles such as an alkyl halide and a base such as potassium carbonate to obtain 43.

Alternatively, the halide group of 41 can be reduced using hydrogen (1 atm) in the presence of palladium on activated carbon in ethanol to obtain pyrimidinolactam 44 (Raghavan et al. WO2011/149921). The annulated lactam can then be substituted with a [—(Y)—R$^9$] group by reacting with different electrophiles such as an alkyl halide and a base such as potassium carbonate to obtain the 45.

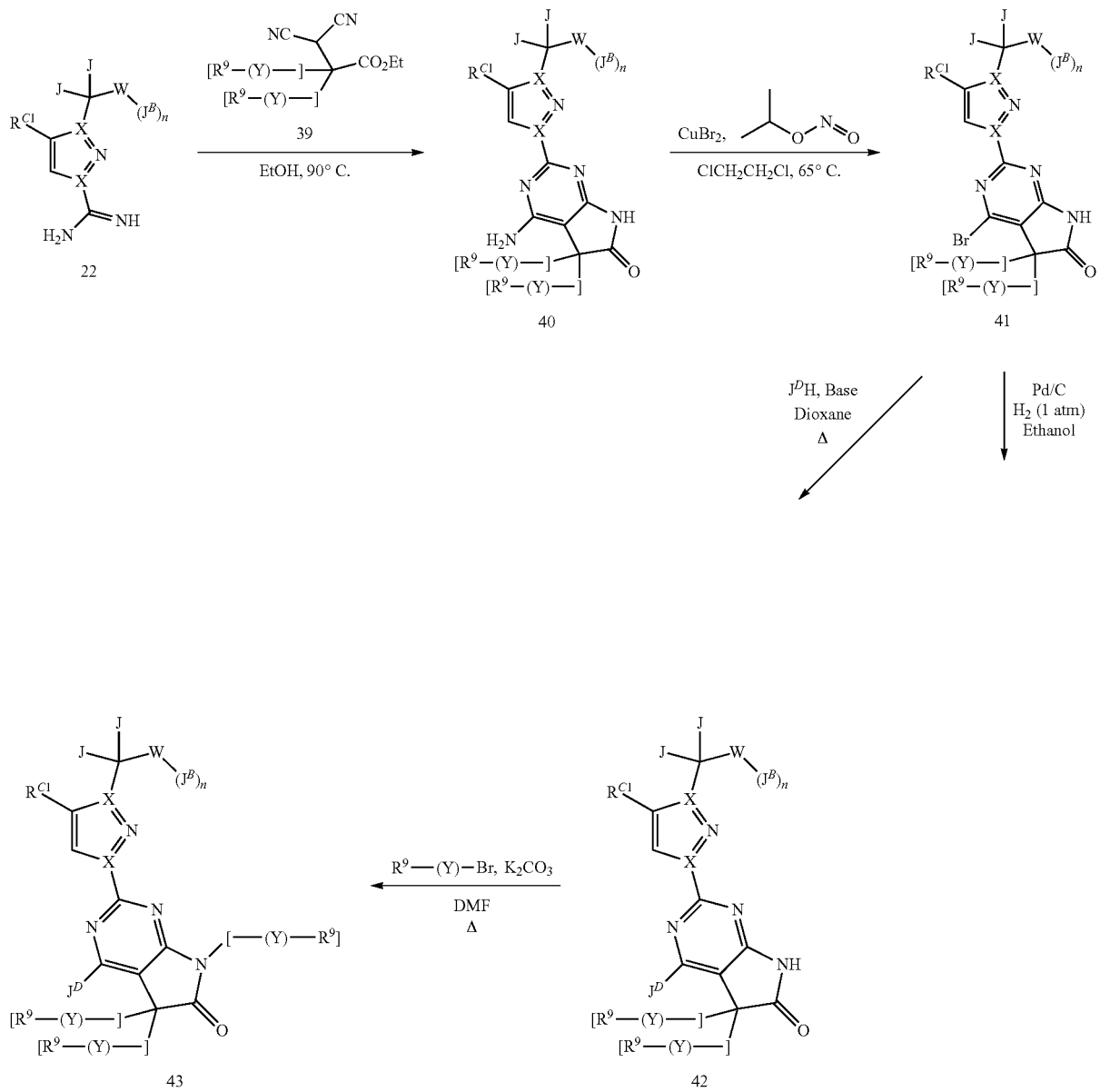

Scheme 7

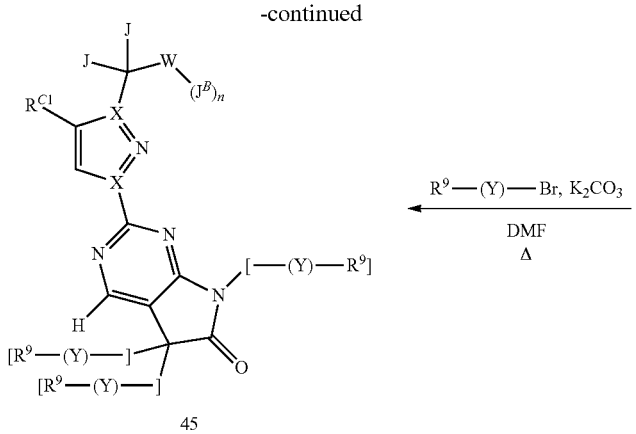
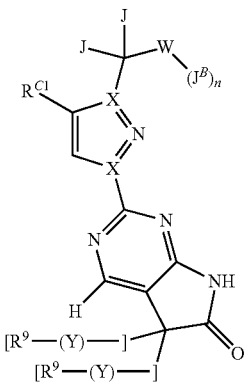

Scheme 8 described the synthesis of compounds 48 and 49 of general formula I. Chloronitropyrimidine intermediate 25 can be treated with carbon nucleophiles such as ester 46 to obtain product 47. Reduction of the nitro group in 47 under standard conditions (e.g. hydrogen and palladium on activated carbon in ethanol) will provide the corresponding aniline intermediate which will spontaneously cyclize (at ambient or elevated temperature) to yield pyrimidinolactam 48. The annulated lactam can then be substituted with a [—(Y)—$R^9$] group by reacting with different electrophiles such as an alkyl halide and a base such as potassium carbonate to obtain compound 49.

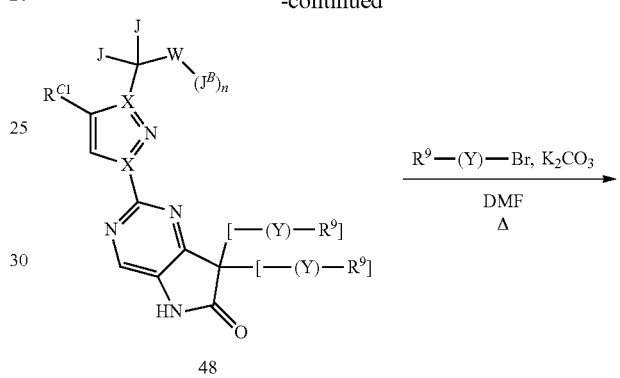

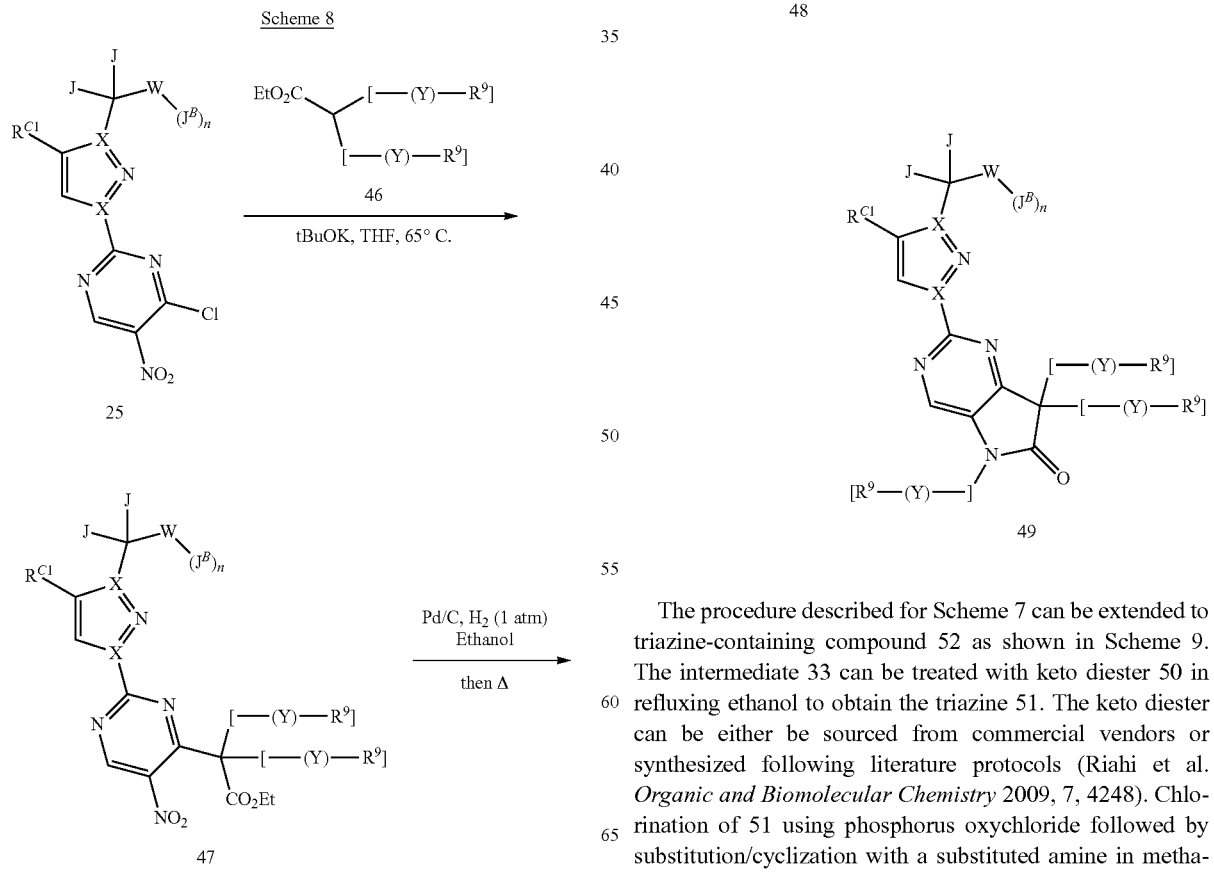

The procedure described for Scheme 7 can be extended to triazine-containing compound 52 as shown in Scheme 9. The intermediate 33 can be treated with keto diester 50 in refluxing ethanol to obtain the triazine 51. The keto diester can be either be sourced from commercial vendors or synthesized following literature protocols (Riahi et al. *Organic and Biomolecular Chemistry* 2009, 7, 4248). Chlorination of 51 using phosphorus oxychloride followed by substitution/cyclization with a substituted amine in methanol will lead to the desired triazinolactam 52.

Scheme 9

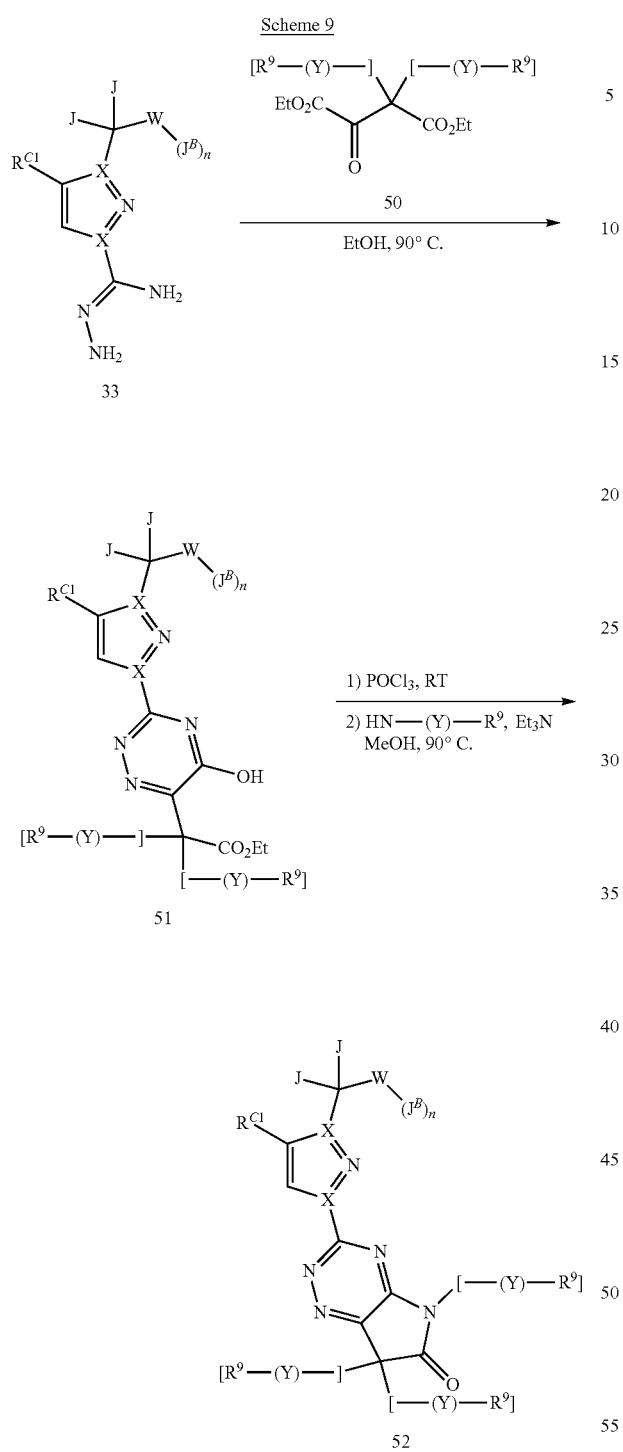

Scheme 10

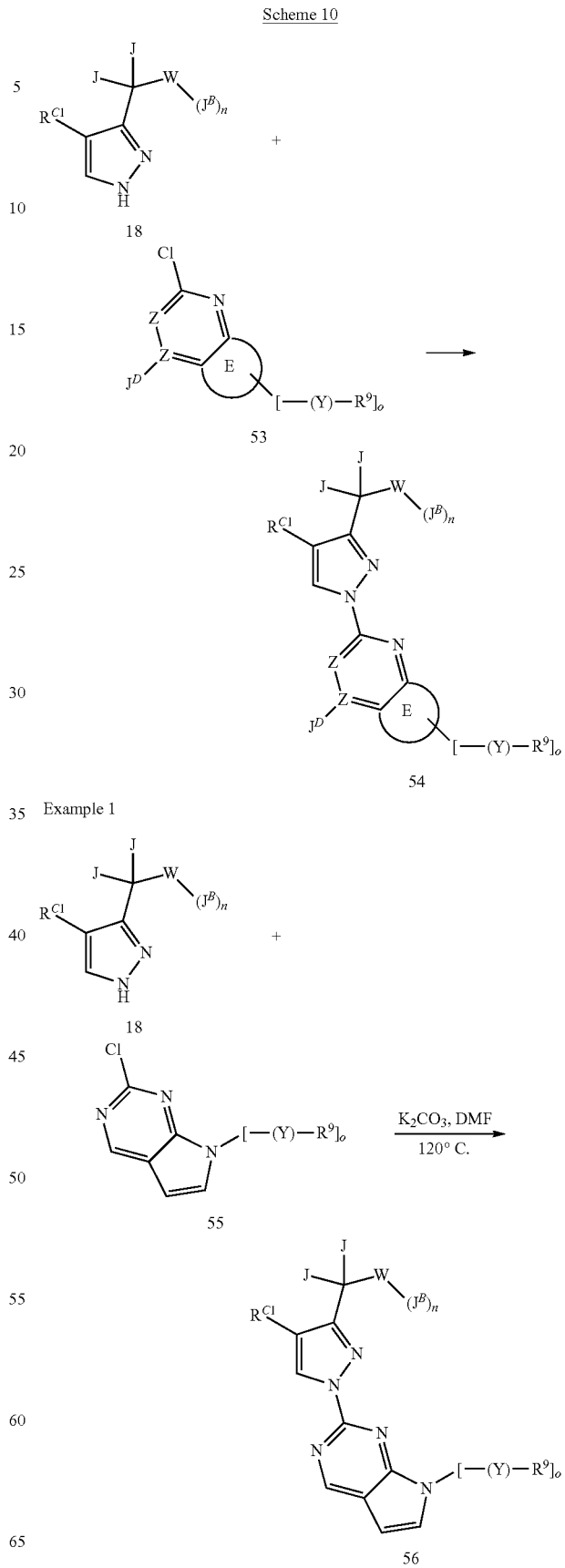

Example 1

Compounds 54 with the isomeric pyrazole core can also be synthesized using $S_NAr$ chemistry as described in Scheme 10. For example, 6-chloro-5,7-diazaindole 55 (obtained in 1 or 2 steps from commercially available material; see Duncan et al. WO2014/100695) can undergo a $S_NAr$ substitution reaction with pyrazole 18 to provide substituted diazaindole 56. Similarly, reaction of 6-chloro-2-oxo-4,5,7-triazaindoline 57 with pyrazole 18 will lead to the corresponding product 58 (Follmann et al. US2013/210824)

Example 2

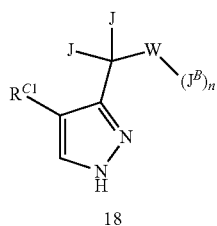

18

+

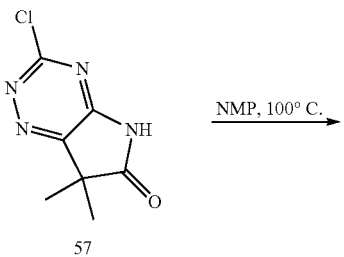

57

NMP, 100° C. →

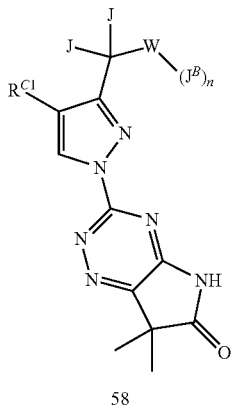

58

Synthesis of acetyl- and cyano-pyrazole variants 60 and 61 of Formula I compounds is detailed in Scheme 11. Pyrazoles of general formula 59 ($R^{C1}$=3-isoxazole; one of the X groups=N) can be converted to acetylpyrazole 60 by heating with sodium methoxide in MeOH in a sealed vessel at elevated temperature (e.g. 90° C.). Alternatively, pyrazoles 59 ($R^{C1}$=3-isoxazole; one of the X groups=N) can be converted to cyanopyrazole 61 by heating in DBU at elevated temperature (e.g. 125° C.) (see Kim et al. WO2013/101830). Depending on the compatibility of substituents of pyrazoles 59 with the reaction conditions, those skilled in the art may need to install protecting group(s) and/or perform these reactions at an earlier stage of the synthetic sequence.

Scheme 11

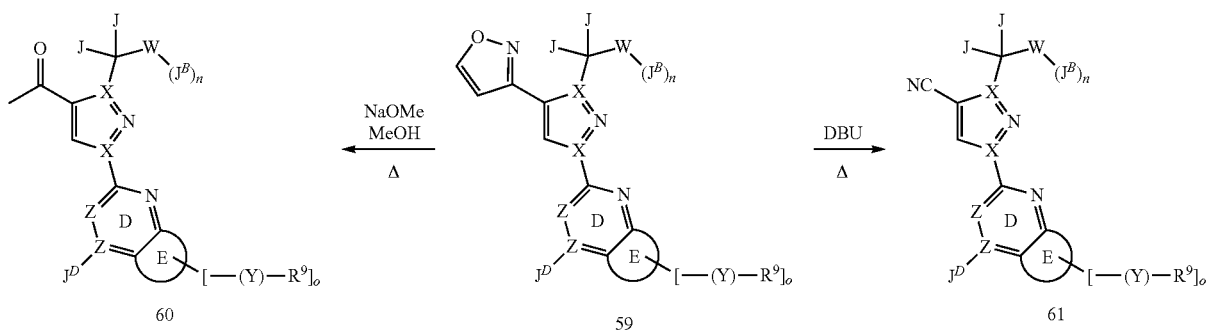

Scheme 12 details the synthesis of amidine and amidrazone intermediates 68 and 69 that are useful for the synthesis of triazole variants of Formula I compounds (see also Kim et al. WO2012/064559). Hydrazide 62, when not commercially available, can be readily synthesized by the reaction of requisite carboxylic acids or esters with hydrazine hydrate. Hydrazide 62 may be reacted with ethyl thiooxamate in the presence of ammonium chloride in refluxing ethanol to provide triazole 63. Deprotonation of the triazole with a base such as sodium hydride followed by substitution with as electrophile 64 such as an alkyl halide furnishes a regioisomeric mixture of triazoles 65a and 65b that can be separated by those skilled in the art of organic chemistry. Saponification of ester 65b followed by conversion to the corresponding nitrile provides compound 67 using previously described procedure (see Kim et al. WO 2013/101830). Nitrile 67 can be treated with sodium methoxide in methanol followed by ammonium chloride to afford triazole amidine 68. Hydrazinecarboximidamide 69 may be accessed by treatment of amidine 68 with hydrazine hydrate in ethanol.

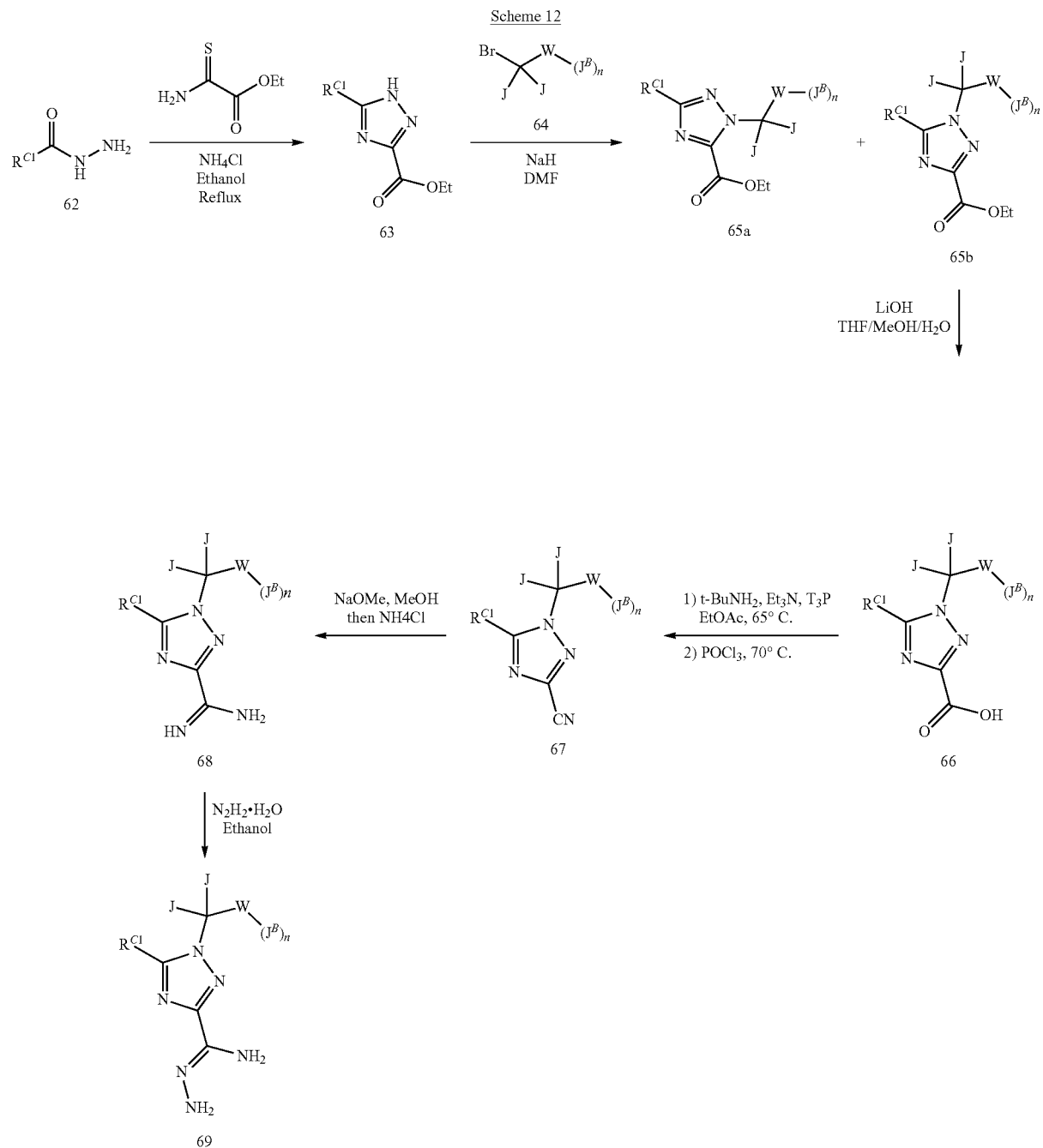

Scheme 12

Scheme 13 describes the synthesis of imidazole ester intermediate 75 (precursor of the corresponding amidine and amidrazone intermediates, see Schemes 3 and 12) that is useful for the synthesis of imidazole variants of Formula I compounds. Conversion of nitrile 70 (either commercially available or prepared using standard nucleophilic substitution chemistry) to the corresponding imidate hydrochloride 71 can be accomplished by utilizing literature methods (see Kolb et al. US2003/0153728). Using a 2-step procedure, compound 71 can be cyclized with diamine 72a and further aromatized to imidazole 74 using an oxidant such as $MnO_2$ (see Doherty et al. US2004/0157845). The imidazole 74 can then be substituted with a $R^{C1}$ group by reacting with different electrophiles such as an alkyl halide ($S_N2$ chemistry), acyl halide or heteroaryl/aryl halide ($S_NAr$ chemistry) and a base such as sodium hydride or triethylamine to obtain compound 75. Alternatively, the $R^{C1}$ group (e.g. alkyl or aryl group) can incorporated earlier into diamine 72b to afford compound 75 directly after the cyclization/aromatization sequence.

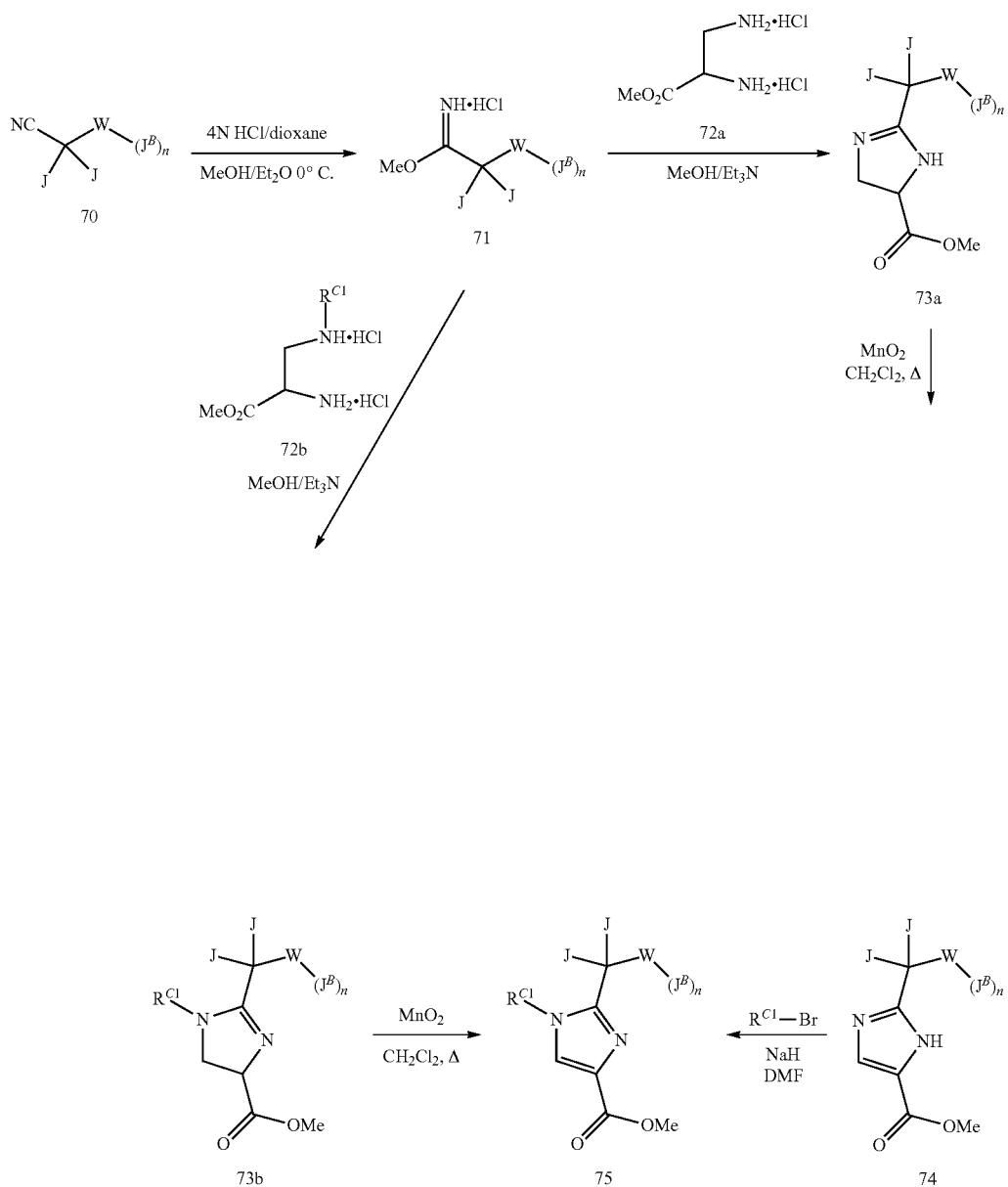

Scheme 13

General Procedure A

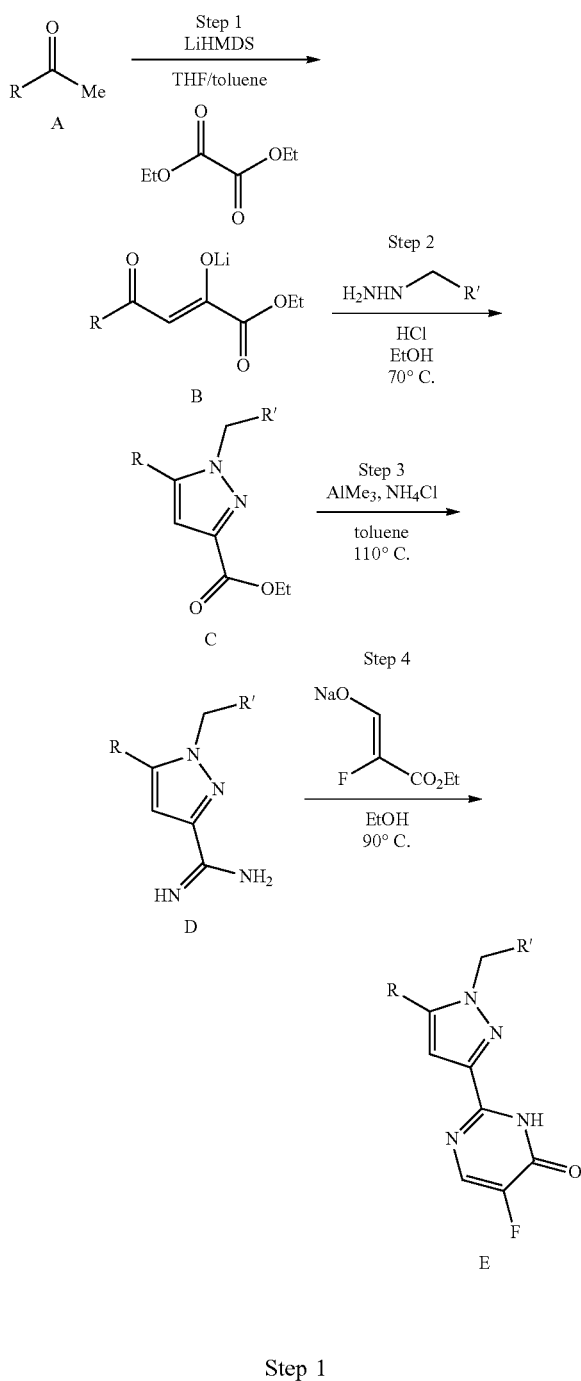

Step 1

Dione Enolate Formation:

To a solution of ketone A in THF cooled to −78° C., LiHMDS (e.g., 0.9 equiv, 1.0 M in toluene) was added dropwise via syringe. The reaction was allowed to warm to 0° C., then charged with diethyl oxalate (1.2 equiv). At this time, the reaction was warmed to room temperature and stirred at that temperature until judged complete (e.g., using either TLC or LC/MS analysis). Once the reaction was complete (reaction time was typically 45 minutes), the product dione enolate B was used "as-is" in Step 2, i.e., the cyclization step, without any further purification.

Step 2

Pyrazole Formation:

Dione enolate B was diluted with ethanol and consecutively charged with HCl (e.g., 3 equiv, 1.25 M solution in ethanol) and arylhydrazine hydrate (e.g., 1.15 equiv). The reaction mixture was heated to 70° C. and stirred at this temperature until cyclization was deemed complete (e.g., by LC/MS analysis, typically 30 minutes). Once complete, the reaction mixture was treated carefully with solid sodium bicarbonate (e.g., 4 equiv) and diluted with dichloromethane and water. Layers were separated, and aqueous layer was further diluted with water before extraction with dichloromethane (3×). The combined organics were washed with brine, dried over $MgSO_4$, filtered, and concentrated in vacuo. The resulting pyrazole C was then purified by SiO2 chromatography using an appropriate gradient of EtOAc in hexanes.

Step 3

Amidine Formation:

To a suspension of NH4Cl (e.g., 5 equiv) in toluene cooled to 0° C. was added $AlMe_3$ (e.g., 5 equiv, 2.0M solution in toluene) dropwise via syringe. The reaction was allowed to warm to room temperature, and stirred at this temperature until no more bubbling was observed. Pyrazole C was added in 1 portion to the reaction mixture, heated to 110° C., and stirred at this temperature until judged complete (e.g., using either TLC or LC/MS analysis). Once complete, the reaction was cooled, treated with excess methanol, and stirred vigorously for 1 hour at room temperature. The thick slurry was filtered, and the resulting solid cake was washed with methanol. The filtrate was concentrated in vacuo, and the resulting solids were re-suspended in an ethyl acetate: isopropyl alcohol=5:1 solvent mixture. The reaction was further treated with saturated sodium carbonate solution, and stirred for 10 minutes before the layers are separated. The aqueous layer was extracted with the ethyl acetate:isopropyl alcohol=5:1 solvent mixture (3×), and the combined organics were washed with brine. The organics were further dried over MgSO4, filtered, and the solvent removed in vacuo. The product amidine D was used as-is in subsequent steps without further purification.

Step 4

Pyrimidone Formation:

Amidine D was suspended in ethanol, and stirred vigorously at 23° C. to encourage full solvation. The reaction was further treated with sodium 3-ethoxy-2-fluoro-3-oxoprop-1-en-1-olate (e.g., 3 equiv.), and the flask was equipped with a reflux condenser. The reaction was placed into a pre-heated oil bath maintained at 90° C. and stirred until full consumption of starting material was observed on the LC/MS (reaction times were typically 1 h). The contents were cooled to 23° C., and the reaction mixture acidified with HCl (e.g., 3 equiv., 1.25M solution in EtOH). The mixture was stirred for 30 minutes, and the majority of the solvent was removed in vacuo. Contents were re-suspended in ether and water (1:1 mixture), and the resulting slurry was stirred for 20 min. The suspension was vacuum filtered, and the solid cake was rinsed with additional water and ether and dried on high vacuum overnight. The resulting pyrimidone E was used as-is in subsequent steps without further purification.

Compound I-1

The title compound was synthesized in 7 steps, and the first three steps follow general procedure A described above.

Step 1: Synthesis of ethyl 1-(2-fluorobenzyl)-5-hydroxy-1H-pyrazole-3-carboxylate

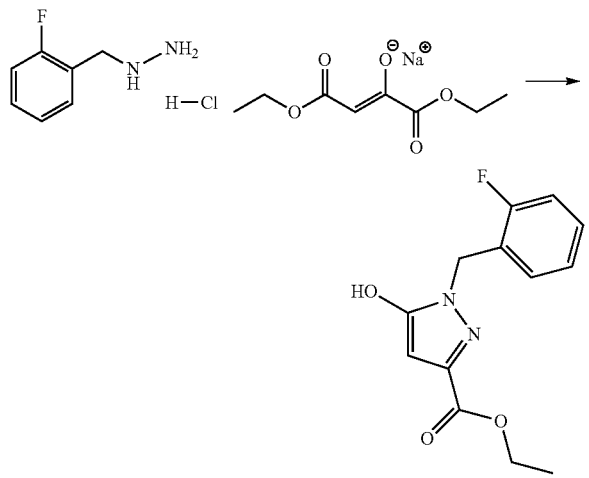

A mixture containing acetic acid (15 equiv.) and diethyl oxalacetate sodium salt (1 equiv.) in benzene was stirred at 25° C. for 30 min. To this mixture was added (2-fluorobenzyl)hydrazine hydrochloride (2 equiv.). The resulting mixture was heated to 100° C. for 2 h. The mixture was cooled to 23° C. and concentrated under vacuum. The precipitate formed was collected by filtration. The solid was dissolved in ethyl acetate and washed with 1N HCl solution (×3). The organic layer was dried, filtered, and evaporated to give a solid containing the desired product. The solid was rinsed with a minimal amount of a methanol-diethyl ether mixture, dried under vacuum to deliver the desired intermediate, ethyl 1-(2-fluorobenzyl)-5-hydroxy-1H-pyrazole-3-carboxylate (11.8 g, 71% yield) as a cream colored solid. $^1$H NMR (500 MHz, CD$_3$OD) δ ppm 7.24-7.41 (m, 1H), 7.09-7.16 (m, 2H), 7.02-7.07 (m, 1H), 5.95 (s, 1H), 5.29 (s, 2H), 4.33 (q, 2H), 1.36 (t, 3H).

Step 2: Synthesis of ethyl 1-(2-fluorobenzyl)-5-methoxy-1H-pyrazole-3-carboxylate

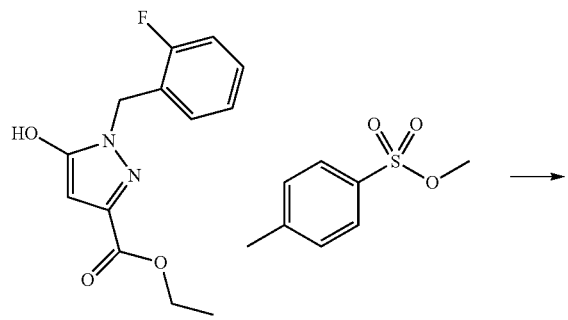

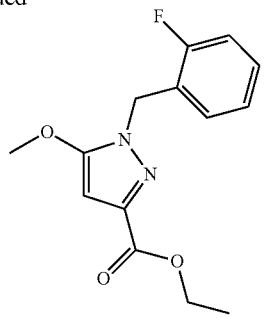

A mixture of potassium carbonate (2.5 equiv.), methyl ester of p-toluenesulfonic acid (1.1 equiv.) and ethyl 1-(2-fluorobenzyl)-5-hydroxy-1H-pyrazole-3-carboxylate (1 equiv.) in DMF was stirred at 23° C. for 24 h. The mixture was diluted with ethyl acetate and washed with water. The organic layer was dried, filtered and evaporated to give an oil. The oil was purified by silica gel chromatography (0 to 100% ethyl acetate in hexanes) to deliver the desired intermediate, ethyl 1-(2-fluorobenzyl)-5-methoxy-1H-pyrazole-3-carboxylate (2.8 g, 88% yield) as a clear oil.
$^2$H NMR (500 MHz, CDCl$_3$) δ ppm 7.22-7.29 (m, 1H), 7.03-7.10 (m, 2H), 6.98 (td, 1H), 6.12 (s, 1H), 5.33 (s, 2H), 4.36-4.45 (m, 2H), 3.88-3.92 (m, 3H), 1.36-1.44 (m, 3H).

Step 3: Synthesis of 1-(2-fluorobenzyl)-5-methoxy-1H-pyrazole-3-carboximidamide (Intermediate-4)

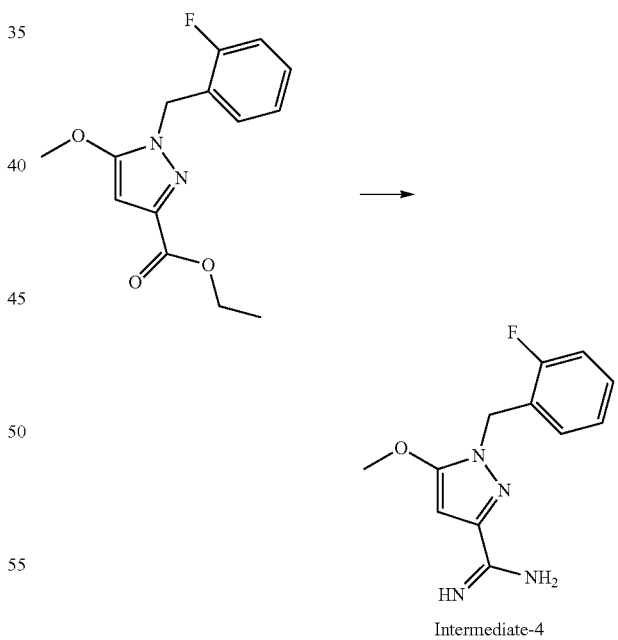

Intermediate-4

To a cold suspension of ammonium chloride (5.3 equiv.) in toluene at 0° C. was added, slowly, a 2.0 M solution of triemthylaluminum in toluene (5.3 equiv.). The mixture was removed from the ice bath and stirred at 23° C. until the bubbling ceased. To this mixture was added a solution of ethyl 1-(2-fluorobenzyl)-5-methoxy-1H-pyrazole-3-carboxylate (1 equiv.) in toluene. The mixture was heated to 90° C. for 24 h. The mixture was cooled to 23° C. and quenched with methanol (5.3 equiv.). The white precipitate was removed by filtration. The filtrate was washed with water, dried, and concentrated under vacuum to deliver the desired intermediate, 1-(2-fluorobenzyl)-5-methoxy-1H-pyrazole-3-carboximidamide (110 mg, 5% yield) as a white solid. $^1$H NMR (500 MHz, CD$_3$OD) δ ppm 7.25-7.35 (m, 1H), 7.02-7.24 (m, 3H), 6.17-6.22 (m, 1H), 5.22-5.28 (m, 2H), 4.92 (s, 3H)

Step 4: Synthesis of Intermediate-1

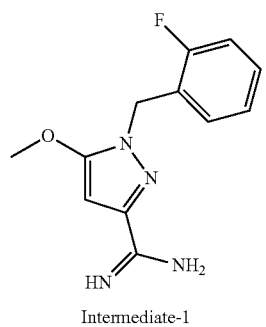

Intermediate-1

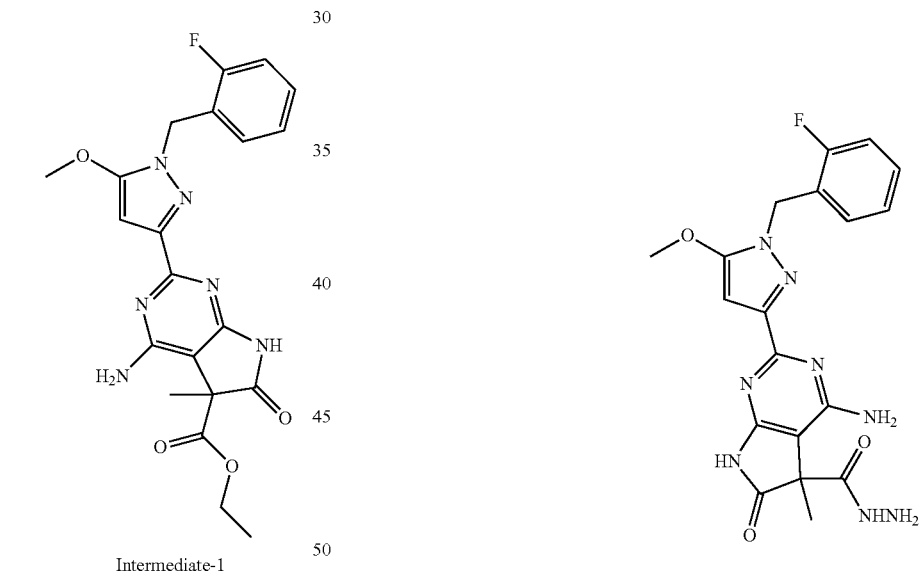

Intermediate-1

A mixture containing diethyl 2-(dicyanomethyl)-2-methylmalonate (1.5 equiv.), potassium hydrogencarbonate (2 equiv.) and 1-(2-fluorobenzyl)-5-methoxy-1H-pyrazole-3-carboximidamide (Intermediate-4, 1 equiv.) in tert-butanol was heated to 85° C. for 1 h. The mixture was diluted in ethyl acetate and washed with water. The organic layer was dried, filtered and evaporated to give an oil that was purified via silica gel chromatography (0 to 100% ethyl acetate in hexanes) to deliver the desired compound (125 mg, 53% yield) as a white solid. $^1$H NMR (500 MHz, DMSO-d$_6$) δ ppm 7.31-7.39 (m, 1H), 7.19-7.24 (m, 1H), 7.17 (td, 1H), 7.07 (td, 1H), 6.17 (s, 1H), 5.22 (s, 2H), 4.05-4.15 (m, 2H), 3.93 (s, 3H), 1.57 (s, 3H), 1.10 (t, 3H).

Step 5: Synthesis of 4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide

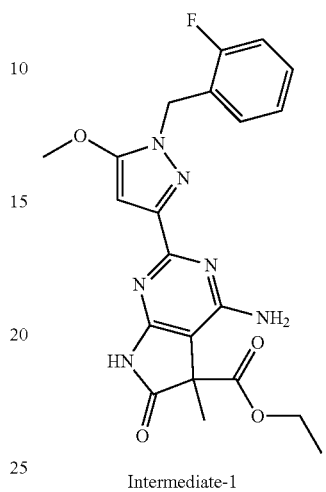

Intermediate-1

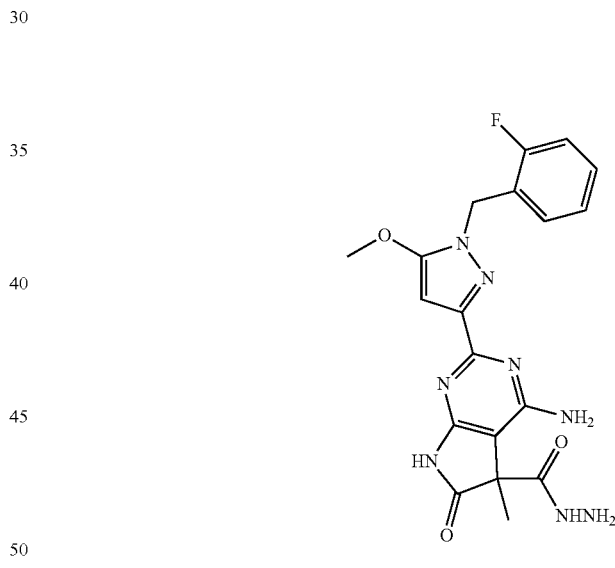

A mixture containing water (11 equiv.), anhydrous hydrazine (325 equiv.), and Intermediate-1 (1 equiv.) in methanol was heated to 50° C. for 4 h. The mixture was concentrated under vacuum. An excess hydrazine was removed using methanol and benzene as azeotropes. The resulting solid was dried under vacuum for an additional 24 h to deliver the desired intermediate, 4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide (1.0 g, quantitative yield) as a white solid.

$^1$H NMR (500 MHz, DMSO-d$_6$) δ ppm 7.32-7.38 (m, 1H), 7.19-7.24 (m, 1H), 7.16 (t, 1H), 7.04-7.10 (m, 1H), 6.14-6.18 (m, 1H), 5.22 (s, 2H), 3.92 (s, 3H), 1.53 (s, 3H).

Step 6: Synthesis of N-acetyl-4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide

Step 7: Synthesis of Compound I-I

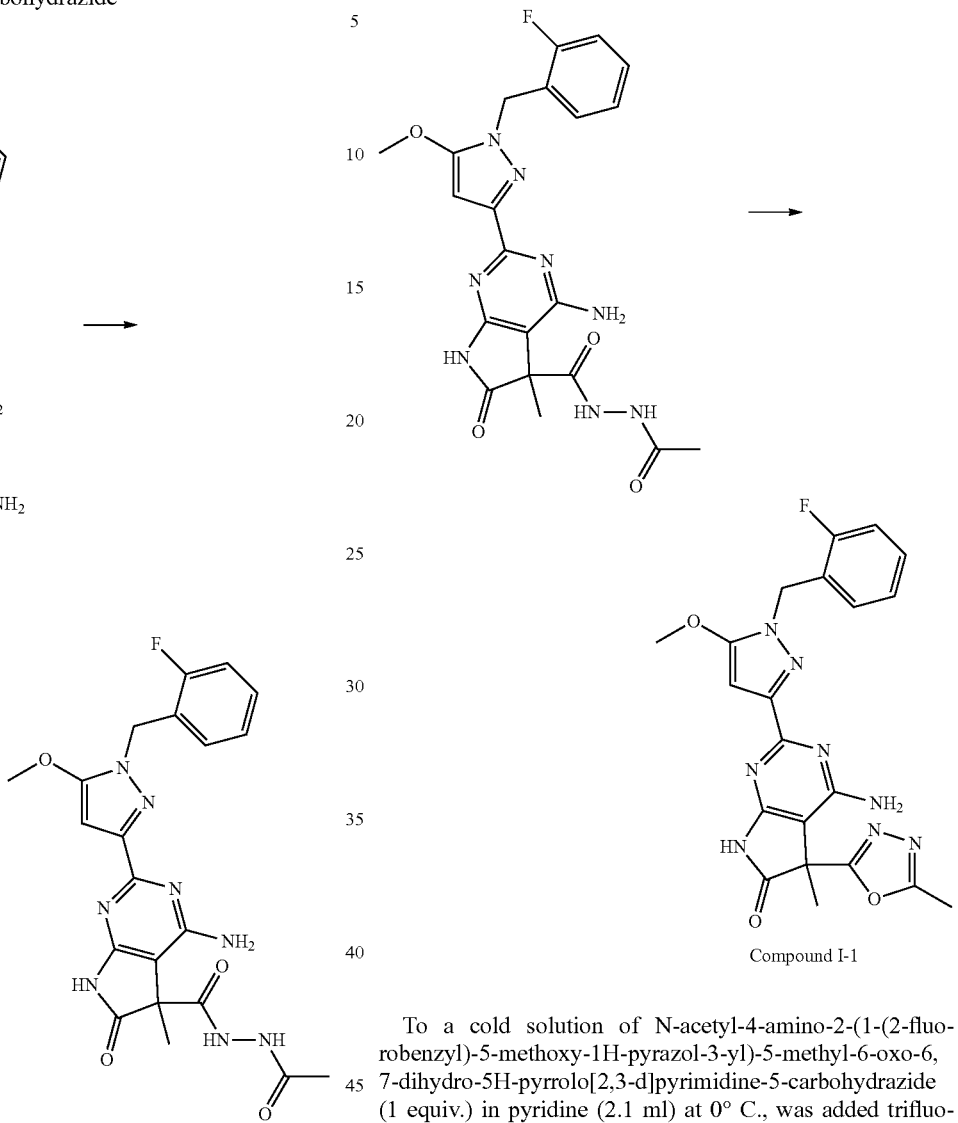

Compound I-1

To a mixture of potassium carbonate (5 equiv.) and 4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide (1 equiv.) in a 1:1 mixture of THF and water was added acetyl chloride (5 equiv.). The mixture was stirred at 23° C. for 1 h. The mixture was diluted in ethyl acetate and washed with sodium bicarbonate. The organic layer was dried, filtered and evaporated to give a crude oil. The oil was purified via silica gel chromatography (0 to 40% methanol in dichloromethane) to deliver the desired intermediate, N-acetyl-4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide (200 mg, 33% yield) as a white solid.

$^1$H NMR (500 MHz, DMSO-$d_6$) δ ppm 7.30-7.39 (m, 1H), 7.19-7.26 (m, 1H), 7.16 (t, 1H), 7.04-7.10 (m, 1H), 6.12-6.19 (m, 1H), 5.22 (s, 2H), 3.93 (s, 3H), 2.50 (s, 3H), 1.53 (d, 3H).

To a cold solution of N-acetyl-4-amino-2-(1-(2-fluorobenzyl)-5-methoxy-1H-pyrazol-3-yl)-5-methyl-6-oxo-6,7-dihydro-5H-pyrrolo[2,3-d]pyrimidine-5-carbohydrazide (1 equiv.) in pyridine (2.1 ml) at 0° C., was added trifluoromethanesulfonic anhydride (3 equiv.). The mixture was stirred at rt for 24 h. The mixture was diluted in ethyl acetate and washed, in sequence, with 1N HCl, followed by saturated sodium bicarbonate. The organic layer was dried, filtered and evaporated to give a crude oil. The oil was purified by column chromatography (0 to 100% ethyl acetate in hexanes) to give 4-amino-2-(1-(2-fluorobenzyl)-5-methoxy-1H-pyrazol-3-yl)-5-methyl-5-(5-methyl-1,3,4-oxadiazol-2-yl)-5H-pyrrolo[2,3-d]pyrimidin-6(7H)-one (16 mg, 9% yield) as a light orange solid.

$^1$H NMR (500 MHz, CD$_3$OD) δ ppm 7.27-7.34 (m, 2H), 7.08-7.15 (m, 2H), 6.98-7.05 (m, 1H), 5.32 (s, 2H), 3.96-3.99 (m, 3H), 2.52-2.55 (m, 3H), 1.92 (s, 3H).

Synthesis of Intermediate-2

A suspension of 5-fluoro-2-(1-(2-fluorobenzyl)-5-(isoxazol-3-yl)-1H-pyrazol-3-yl)-pyrimidin-4-ol (Intermediate-3; generated via general procedure A described above, using 1-(isoxazol-3-yl)ethanone in step 1 and 2-fluorobenzylhydrazine in step 2, 11.5 g, 32.4 mmol, 1 equiv.) in phosphoryl trichloride (60.3 mL, 647 mmol, 20 equiv.) was heated at 60° C. for 3 h. The solution was cooled to 23° C., and poured portionwise over the course of 15 min into ice water (800 mL) with stirring. After completion of addition, contents were stirred for an additional 15 min, and diluted with dichloromethane (500 mL). The layers were separated and the aqueous layer was extracted with dichloromethane (2×200 mL). The organics were dried over magnesium sulfate, filtered, and the solvent was removed in vacuo to yield Intermediate-2 (12.5 g, 103% yield) as a tan solid.

$^1$H NMR (500 MHz, DMSO-d$_6$) δ 9.11 (d, 1H), 9.04 (s, 1H), 7.71-7.68 (m, 1H), 7.37-7.30 (m, 2H), 7.25-7.20 (m, 1H), 7.12 (t, 1H), 6.92 (td, 1H), 5.95 (s, 2H).

Compound I-2

This compound was synthesized in 4 steps:

Step 1: Preparation of Intermediate-9

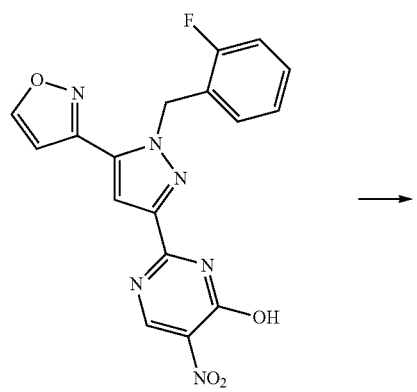

2-(1-(2-fluorobenzyl)-5-(isoxazol-3-yl)-1H-pyrazol-3-yl)-5-nitropyrimidin-4-ol (this starting material was described in a previously published patent application WO2012/3405, 25 mg, 1 equiv.) was treated with POCl$_3$ (457 µl, 75 equiv.) and stirred at reflux for 1.5 h. Contents were concentrated in vacuo, and residue was azeotroped with toluene (×2). The resulting crude material was used in the next step without additional purification.

Step 2: Preparation of Intermediate-6

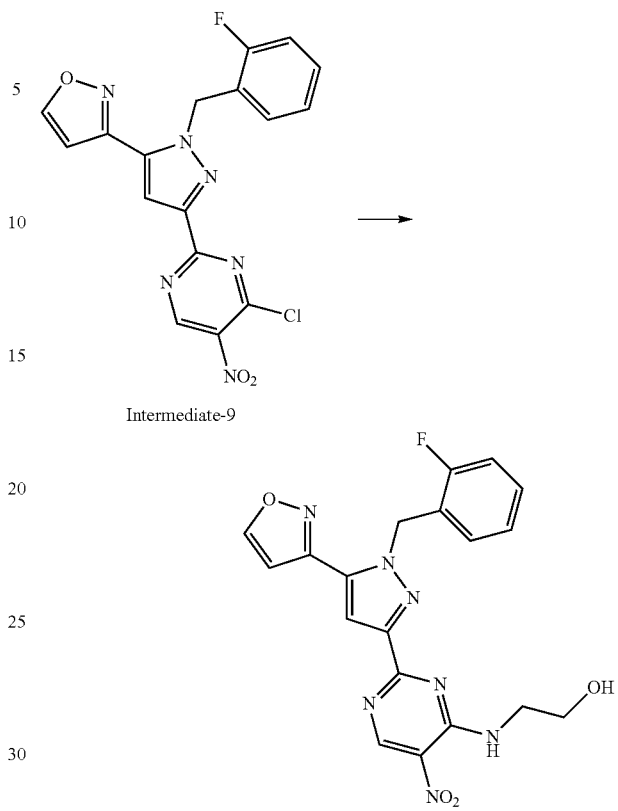

To a solution of Intermediate-9 generated in Step 1 (1.0 equiv.) in anhydrous dioxane was added 2-aminoethanol (4.0 equiv.). The reaction mixture became an orange suspension. After 20 h, water was added and the solid was filtered and dried in vacuo to deliver the desired Intermediate-6 (160 mg, 89% yield) as a yellowish tan solid.

$^1$H-NMR (500 MHz, DMSO-d$_6$) δ ppm 9.19 (s, 1H), 9.12 (d, 1H), 8.83 (t, 1H), 7.73 (s, 1H), 7.34 (m, 1H), 7.28 (d, 1H), 7.23 (m, 1H), 7.11 (app. t, 1H), 6.87 (app. t, 1H), 5.95 (s, 2H), 4.96 (t, 1H), 3.80 (dt, 2H), 3.67 (dt, 2H).

Step 3: Synthesis of 2-((5-amino-2-(1-(2-fluorobenzyl)-5(isoxazol-3-yl)-1H-pyrazol-3-yl)pyrimidin-4-yl)amino) ethanol (Intermediate-28)

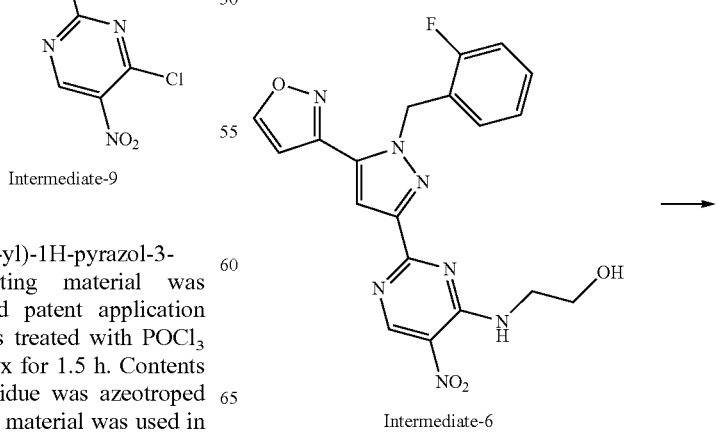

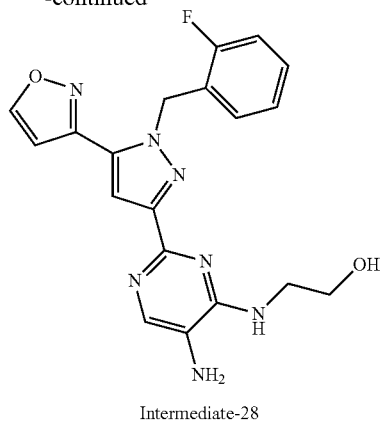

Intermediate-28

A suspension of Intermediate-6 in MeOH/ethyl acetate (1:1) under a nitrogen atmosphere was treated with 10% palladium on carbon (0.2 equiv.). Hydrogen was introduced (using a balloon) and the resultant mixture was stirred for 1 h 40 min. The reaction vessel was then flushed with nitrogen and the contents were filtered through Celite. The solvent was removed in vacuo to deliver the desired intermediate, 2-((5-amino-2-(1-(2-fluorobenzyl)-5-(isoxazol-3-yl)-1H-pyrazol-3-yl)pyrimidin-4-yl)amino)ethanol, which was used in the next step without further manipulation.

Step 4: Synthesis of Compound I-2

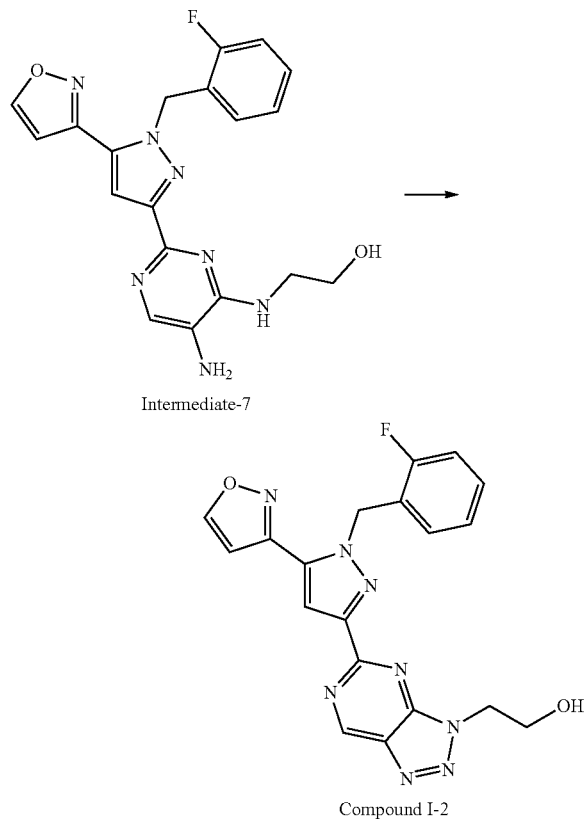

Intermediate-7

Compound I-2

An orange solution of 2-((5-amino-2-(1-(2-fluorobenzyl)-5-(isoxazol-3-yl)-1H-pyrazol-3-yl)pyrimidin-4-yl)amino) ethanol (Intermediate-28, 1.0 equiv.) in acetic acid was treated with sodium nitrite (1.2 equiv.). The reaction mixture became an olive green color solution instantaneously. After 30 min, water was added and the contents were neutralized to pH 6 by addition of saturated sodium bicarbonate solution and extracted with dichloromethane. The organic phases were dried over sodium sulfate, filtered and the solvent was removed in vacuo. The crude material was purified via silica gel chromatography utilizing 0-10% acetonitrile-methanol (7:1) in dichloromethane to deliver the desired compound (30 mg, 53% yield over 2 steps) as a white solid.

$^1$H-NMR (500 MHz, DMSO-$d_6$) δ ppm 9.81 (s, 1H), 9.12 (d, 1H), 7.85 (s, 1H), 7.35 (d, 1H), 7.34 (m, 1H), 7.24 (m, 1H), 7.12 (app. t, 1H), 6.88 (app. t, 1H), 6.00 (s, 2H), 5.01 (t, 1H), 4.79 (t, 2H), 4.01 (dt, 2H).

General Procedure B

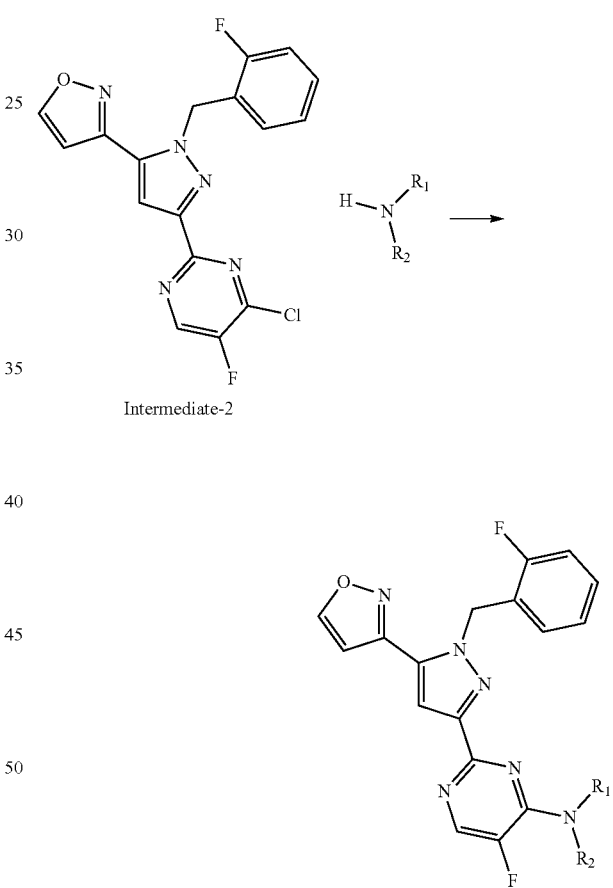

Intermediate-2

A solution of amino nucleophile (3 equiv.), triethylamine (10 equiv.), and Intermediate-2 (1 equiv.) was stirred in dioxane (or alternative solvent, e.g., THF) and water (2:1 ratio) at 90° C. until complete consumption of starting material was observed by LC/MS. The solution was diluted with aqueous 1N hydrochloric acid and dichloromethane. The layers were then separated and the aqueous layer was extracted with dichloromethane. The organics were combined, dried over magnesium sulfate, filtered, and the solvent was removed in vacuo. Purification yielded the desired product.

Compound I-3

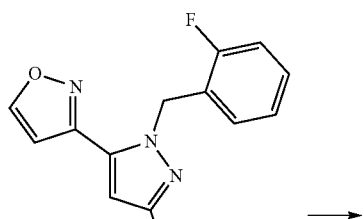

Intermediate-9

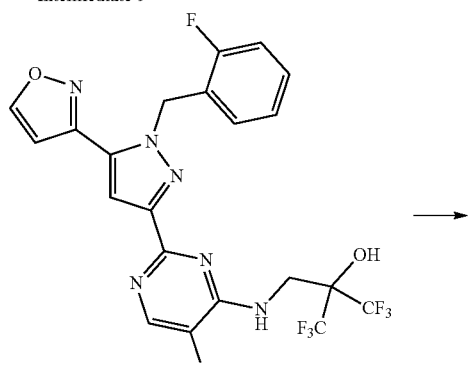

Intermediate-10

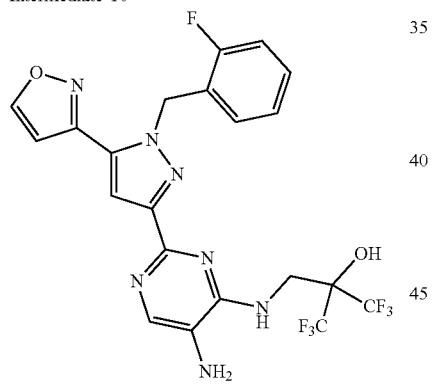

Intermediate-11

The title compound was synthesized in 3 steps:

Step 1: Preparation of Intermediate-10

Following general procedure B, Intermediate-9 (prepared as shown above in the preparation of Compound I-2) was used in place of Intermediate-2, 2-(aminomethyl)-1,1,1,3,3,3-hexafluoropropan-2-ol (1.5 equiv.) was the amine reactant, 3 equivalents of triethylamine was used, and contents were heated at 30° C. for 1 h as a solution in dioxane:water (3:1). The reaction was cooled and diluted with ethyl acetate. The organic layer was washed with water (2×) and brine, then dried over sodium sulfate, filtered, and concentrated in vacuo. The crude material was purified via silica gel chromatography utilizing a 0-100% ethyl acetate/hexanes gradient to deliver the desired intermediate (77 mg, 73% yield) as a white solid.

$^1$H-NMR (400 MHz, CDCl$_3$) δ ppm 9.36 (s, 1H), 8.59 (m, 1H), 8.55 (d, 1H), 7.64 (br s, 1H), 7.42 (s, 1H), 7.28 (m, 1H), 7.08 (m, 1H), 7.06 (m, 1H), 6.64 (d, 1H), 5.98 (s, 2H), 4.27, (d, 2H).

Step 2: Synthesis of Intermediate-11

A solution of Intermediate-10 (1 equiv.) in methanol at 23° C. was treated with 10% palladium on carbon (0.2 equiv.), then placed under an atmosphere of H$_2$ delivered via a balloon filled with hydrogen attached to a needle. The mixture was stirred for 1 h under positive H$_2$ pressure, and filtered through celite. The filter cake was rinsed with methanol, and the combined washes were concentrated in vacuo. The resulting crude residue was purified via silica gel chromatography utilizing a ethyl acetate in hexanes gradient to deliver the desired compound (53 mg, 66% yield) as a white solid. $^1$H-NMR (400 MHz, CDCl$_3$) δ ppm 9.39 (s, 1H), 7.92 (br s, 1H), 7.19 (m, 1H), 7.13 (m, 2H), 7.98 (m, 1H), 6.92 (m, 2H), 6.52 (s, 1H), 5.85 (s, 2H), 4.01, (s, 2H).

Step 3: Preparation of Compound I-3

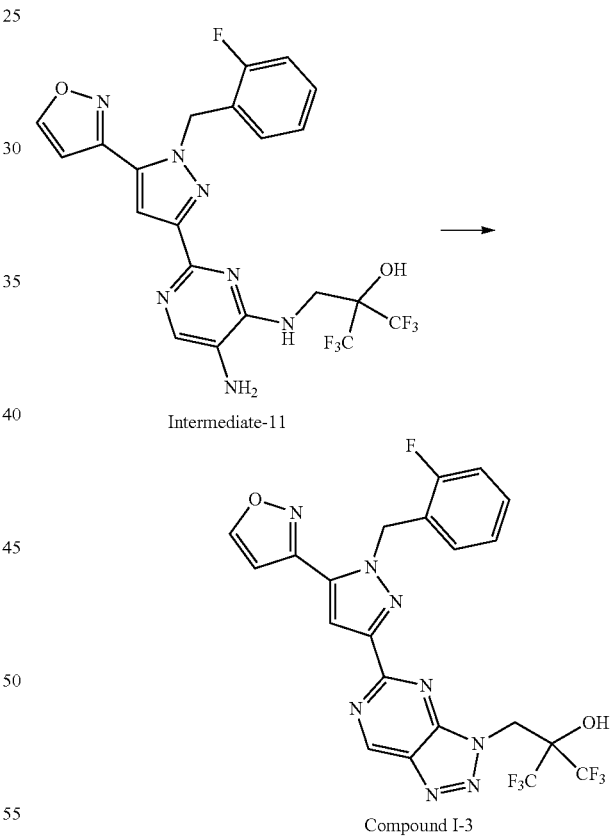

Intermediate-11

Compound I-3

A solution of Intermediate-11 (1.0 equiv.) in acetic acid was treated with sodium nitrite (1.2 equiv.). The reaction mixture became an olive green color solution instantaneously. After 4 min, water was added and the contents were neutralized to pH 6 by addition of saturated sodium bicarbonate solution and extracted with dichloromethane. The organic phases were dried over sodium sulfate, filtered and the solvent was removed in vacuo to deliver the desired compound (8.3 mg, 95% yield) as a tan solid. $^1$H-NMR (500 MHz, CDCl$_3$) δ ppm 9.68 (s, 1H), 8.53 (d, 1H), 7.60-7.40

(br. s, 1H), 7.51 (s, 1H), 7.25 (m, 1H), 7.09-6.97 (m, 3H), 6.67 (d, 1H), 6.03 (s, 2H), 5.37 (s, 2H).

Compound I-4

The title compound was synthesized in 3 steps:

Step 1: Synthesis of 1-(2-fluorobenzyl)-5-(isoxazol-3-yl)-1H-pyrazole-3-carboximidhydrazide

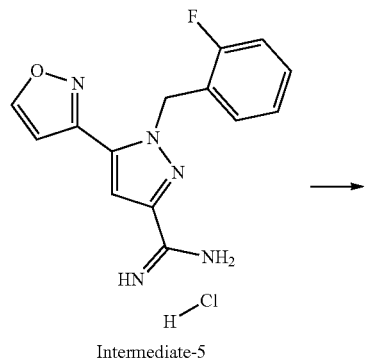

Intermediate-5

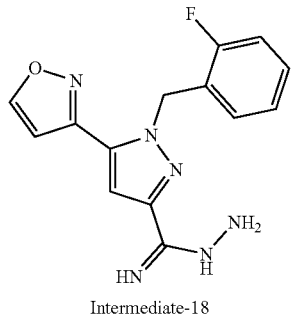

Intermediate-18

To a suspension of 1-(2-fluorobenzyl)-5-(isoxazol-3-yl)-1H-pyrazole-3-carboximidamide hydrochloride (Intermediate-5, generated in step 3 of general procedure A, by using 1-(isoxazol-3-yl)ethanone in step 1 and 2-fluorobenzylhydrazine in step 2, 1 equiv.) in ethanol was added triethylamine (4 equiv.). To this mixture was added hydrazine monohydrate (1 equiv.). The mixture was stirred at 23° C. for 24 h and concentrated in vacuo. The resulting residue was diluted with ethyl acetate and washed with brine. The organic layer was dried, filtered and evaporated to deliver the desired intermediate, 1-(2-fluorobenzyl)-5-(isoxazol-3-yl)-1H-pyrazole-3-carboximidhydrazide (461 mg, 99% yield) as a light yellow solid. $^1$H NMR (500 MHz, CD$_3$OD) δ ppm 8.75 (d, 1H), 7.18-7.40 (m, 1H), 6.97-7.15 (m, 3H), 6.79-6.92 (m, 2H), 5.82-5.97 (m, 2H).

Step 2: Synthesis of ethyl 2-(3-(1-(2-fluorobenzyl)-5-(isoxazol-3-yl)-1H-pyrazol-3-yl)-5-hydroxyl-1,2,4-triazin-6-yl)-2-methylpropanoate (Intermediate-17)

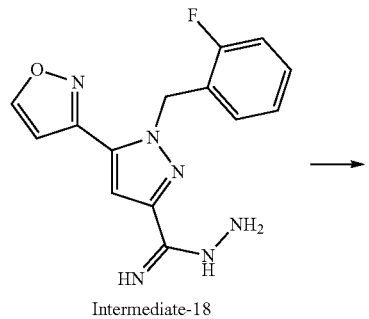

Intermediate-18

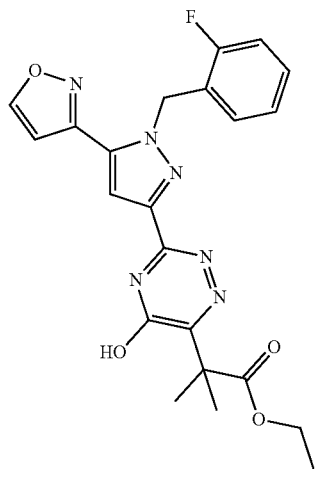

Intermediate-17

A mixture containing 1-(2-fluorobenzyl)-5-(isoxazol-3-yl)-1H-pyrazole-3-carbohydrazonamide (Intermediate-18, 1 equiv.), potassium bicarbonate (1.2 equiv.), and diethyl 2,2-dimethyl-3-oxosuccinate (1.2 equiv.) in ethanol was heated at 80° C. for 24 h and concentrated in vacuo. The resulting residue was diluted in ethyl acetate and washed with brine. The organic layer was dried, filtered and evaporated to give a crude oil. The oil was purified by column chromatography to deliver the desired intermediate, ethyl 2-(3-(1-(2-fluorobenzyl)-5-(isoxazol-3-yl)-1H-pyrazol-3-yl)-5-hydroxy-1,2,4-triazin-6-yl)-2-methylpropanoate (400 mg, 34% yield) as a light yellow solid. $^1$H NMR (500 MHz, CD$_3$OD) δ ppm 8.80 (d, 1H), 8.77 (d, 1H), 7.53 (s, 1H), 7.36 (s, 1H), 7.26-7.33 (m, 3H), 6.03 (s, 2H), 4.11-4.17 (m, 2H), 1.53 (s, 6H), 1.22-1.27 (m, 3H).

Step 3: Synthesis of Compound I-4

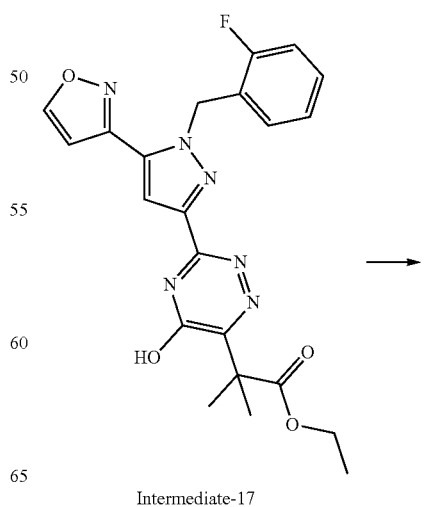

Intermediate-17

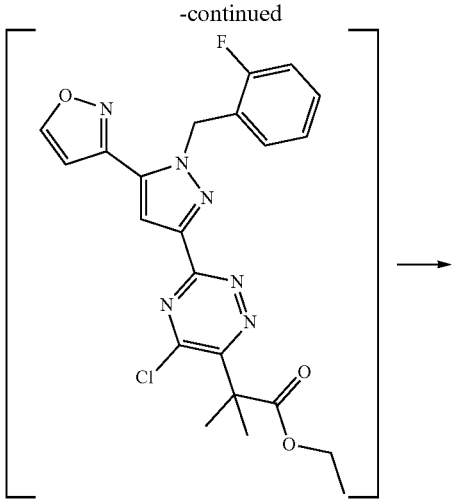

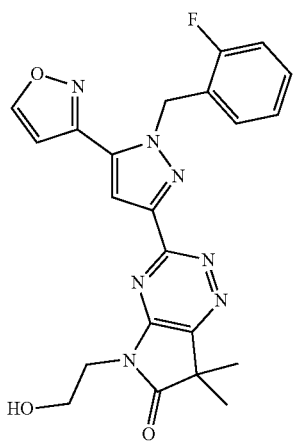

Compound I-4

A mixture containing ethyl 2-(3-(1-(2-fluorobenzyl)-5-(isoxazol-3-yl)-1H-pyrazol-3-yl)-5-hydroxy-1,2,4-triazin-6-yl)-2-methylpropanoate (Intermediate-17, 1 equiv.) and phosphorus oxychloride (10 equiv.) was stirred at 23° C. for 2 h. The mixture was concentrated in vacuo. The resulting residue was dissolved in 1,4-dioxane, and to this solution was added 2-aminoethanol (1.1 equiv.), triethylamine (1.1 equiv.), and methanol (0.5 ml). The mixture was heated to 90° C. for 1 h. The resulting precipitate was separated from the solution, and the solution was concentrated in vacuo. The resulting residue was diluted in dicholoromethane and washed with brine. The organic layer was dried, filtered and evaporated to give a crude oil. Purification of the oil via silica gel chromatography delivered the desired compound (8.6 mg, 10% yield) as a white solid.

$^1$H NMR (500 MHz, CD$_3$OD) δ ppm 8.79 (d, 1H), 7.65 (s, 1H), 7.29 (d, 1H), 7.08-7.15 (m, 1H), 7.04 (t, 1H), 6.95 (d, 1H), 6.85 (t, 1H), 6.02 (s, 2H), 4.02-4.06 (m, 2H), 3.89 (t, 2H), 1.56 (s, 6H).

Compound I-5
This compound was prepared in 4 steps:

Step 1: Synthesis of diethyl 2-(dicyanomethyl)-2-methylmalonate

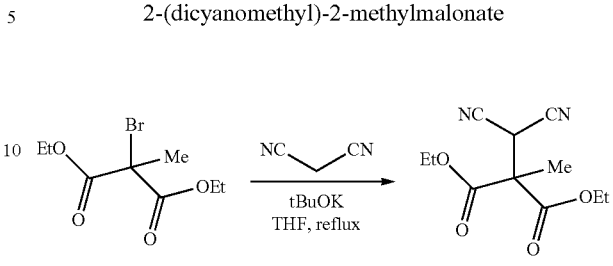

A mixture of diethyl 2-bromo-2-methylmalonate (1 equiv.), malononitrile (1 equiv.) and potassium t-butoxide (1 equiv.) in THF was heated to reflux for 15 h. The mixture was diluted with ethyl acetate and saturated aqueous ammonium chloride solution and the phases were separated. The aqueous phase was extracted twice with ethyl acetate. The combined organic phase was washed with brine, dried over anhydrous sodium sulfate, filtered and concentrated to give an oil. The oil was purified by silica gel chromatography (10-15% ethyl acetate in hexane gradient) to give diethyl 2-(dicyanomethyl)-2-methylmalonate (5.76 g, 32% yield) as a colorless oil.

$^1$H NMR (500 MHz, CDCl$_3$) δ ppm 4.53 (s, 1H), 4.27-4.39 (m, 4H), 1.81 (s, 3H), 1.33 (t, 6H).

Step 2: Synthesis of Intermediate-12

Intermediate-12

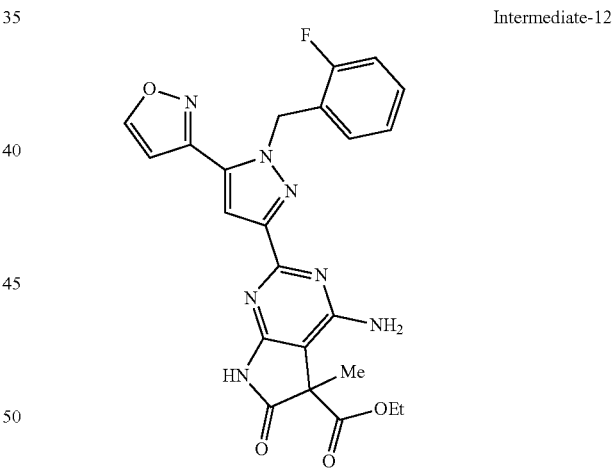

A mixture of 1-(2-fluorobenzyl)-5-(isoxazol-3-yl)-1H-pyrazole-3-carboximidamide hydrochloride (Intermediate-5, 1 equiv.), diethyl 2-(dicyanomethyl)-2-methylmalonate (1.15 equiv.) and potassium bicarbonate (2 equiv.) in t-BuOH was heated to reflux for 5 h. After cooling, the reaction mixture was added with water and stirred for 30 min. The precipitate was filtered, washed with a minimum amount of water and diethyl ether and dried overnight under high vacuum to give the title compound (385 mg, 52% yield) as a white solid.

$^1$H NMR (500 MHz, DMSO-d$_6$) δ ppm 11.30 (s, 1H), 9.10 (d, 1H), 7.38 (s, 1H), 7.29-7.36 (m, 1H), 7.18-7.26 (m, 2H), 7.08-7.14 (m, 1H), 6.81-6.90 (m, 1H), 6.65 (br. s., 2H), 5.88 (s, 2H), 4.04-4.16 (m, 2H), 1.59 (s, 3H), 1.11 (t, 3H).

Step 3: Synthesis of Intermediate-13

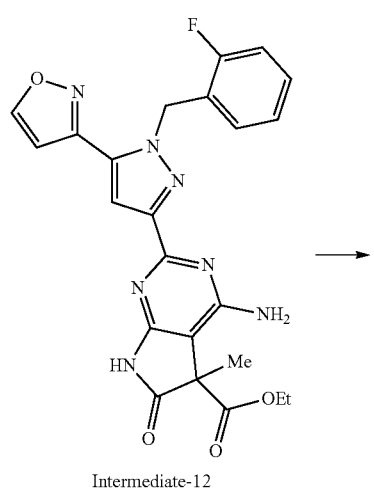

Intermediate-12

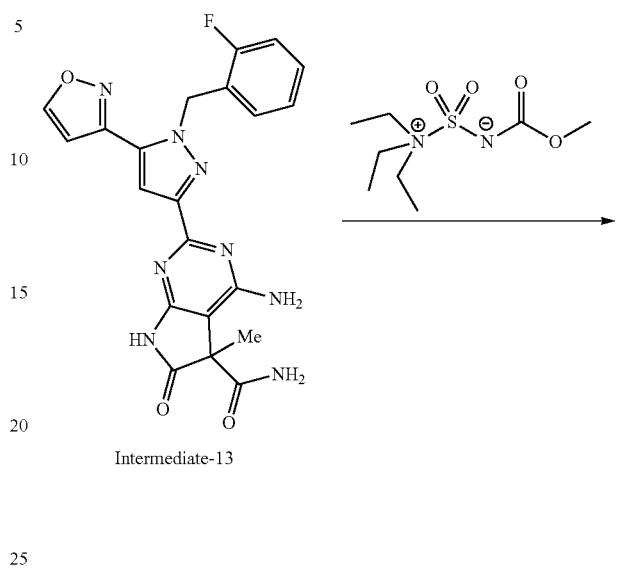

Intermediate-13

Ammonia (7.0 M in MeOH) (200 equiv.) was added to Intermediate-12 (1 equiv.). The reaction mixture was heated at 50° C. for 16 h. The resultant solution was then concentrated in vacuo, and the residue was purified via reverse phase HPLC (5-60% acetonitrile in water with 1% TFA) to deliver the desired compound (24 mg, 63% yield) as a white solid.

$^1$H NMR (400 MHz, DMSO-$d_6$) δ ppm 11.35 (br. s., 1H), 9.08-9.13 (m, 1H), 7.47 (s, 1H), 7.43 (s, 1H), 7.28-7.38 (m, 1H), 7.23-7.27 (m, 1H), 7.17-7.23 (m, 2H), 7.06-7.14 (m, 1H), 6.77-7.00 (m, 3H), 5.91 (s, 2H), 1.56 (s, 3H).

Step 4: Preparation of Compound I-5

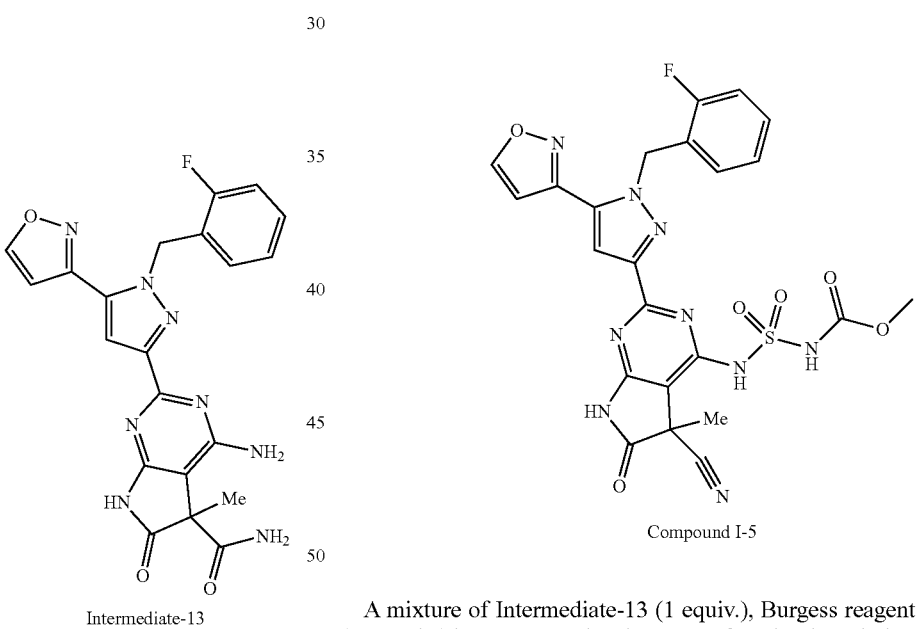

Compound I-5

A mixture of Intermediate-13 (1 equiv.), Burgess reagent (3.5 equiv.) in THF was stirred at 23° C. for 3 h. The solution was diluted with water and dichloromethane. Phases were separated and the aqueous phase was extracted twice with dichloromethane. The combined organic phase was dried over anhydrous magnesium sulfate, filtered and concentrated. The crude solid was then purified by reverse phase HPLC (C18 column, 20% to 60% acetonitrile in water with 0.1% TFA over 20 mins) to deliver the desired compound (10 mg, 9% yield) as a pale yellow solid.

$^1$H NMR (500 MHz, DMSO-$d_6$) δ ppm 13.08 (br. s., 1H), 12.52 (br. s., 1H), 11.57 (br. s., 1H), 9.16 (d, 1H), 7.73 (br. s., 1H), 7.31-7.39 (m, 2H), 7.19-7.26 (m, 1H), 7.12 (t, 1H), 6.94-7.03 (m, 1H), 5.96 (br. s., 2H), 3.54 (br. s., 3H), 1.76 (br. s., 3H).

Compound I-6

The title compound was prepared in 2 steps:

Step 1: Synthesis of Intermediate-15

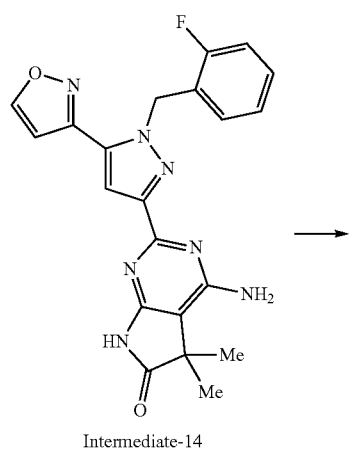

Intermediate-14

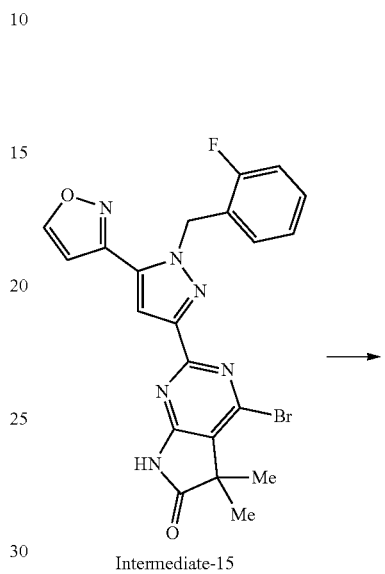

Intermediate-15

A mixture of Intermediate-14 (Described in a previous patent application publication WO2013/101830) (1 equiv.), isopropyl nitrite (1.5 equiv.) and copper(II) bromide (1.2 equiv.) in dichloroethane was heated at 65° C. in a sealed vial for 2 h. Reaction mixture was then diluted with water and dichloromethane. Phases were separated and the aqueous phase was extracted with ethyl acetate (2×). The combined organic phase was dried over anhydrous magnesium sulfate, filtered and concentrated. The residue was purified via silica gel chromatography (5% to 50% ethyl acetate in hexane over 30 mins) to deliver the desired intermediate, 4-bromo-2-(1-(2-fluorobenzyl)-5-(isoxazol-3-yl)-1H-pyrazol-3-yl)-5,5-dimethyl-5H-pyrrolo[2,3-d]pyrimidin-6(7H)-one (0.85 g, 37% yield) as a yellow solid.

$^1$H NMR (500 MHz, DMSO-d$_6$) δ 11.87 (s, 1H), 9.10 (d, 1H), 7.60 (s, 1H), 7.30-7.37 (m, 2H), 7.20-7.25 (m, 1H), 7.11 (t, 1H), 6.87 (t, 1H), 5.95 (s, 2H), 1.41 (s, 6H).

Step 2: Synthesis of Compound I-6

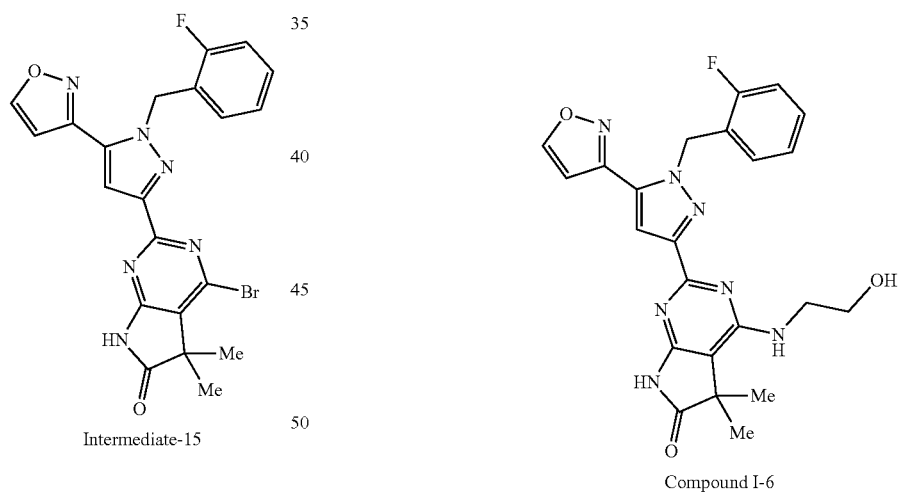

Intermediate-15

Compound I-6

A mixture of Intermediate-15 (1 equiv.) and ethanolamine (5 equiv.) in THF was sealed in a microwave tube and subjected to microwave irradiation at 150° C. for 1 h. Volatiles were removed under a stream of nitrogen, and the crude residue was purified via reverse phase HPLC (C18 column, 5% to 95% acetonitrile in water with 0.1% TFA over 20 mins) to deliver the desired compound (61 mg, 79% yield) as a white solid.

$^1$H NMR (500 MHz, DMSO-d$_6$) δ ppm 10.96 (s, 1H), 9.10 (d, 1H), 7.44 (s, 1H), 7.28-7.36 (m, 1H), 7.22 (s, 2H), 7.10 (t, 1H), 6.84 (t, 1H), 6.56 (br. s., 1H), 5.88 (s, 2H), 3.59 (m, 4H), 1.34 (s, 6H).

Compound I-7

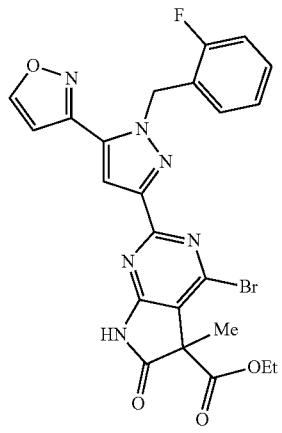

Compound I-17

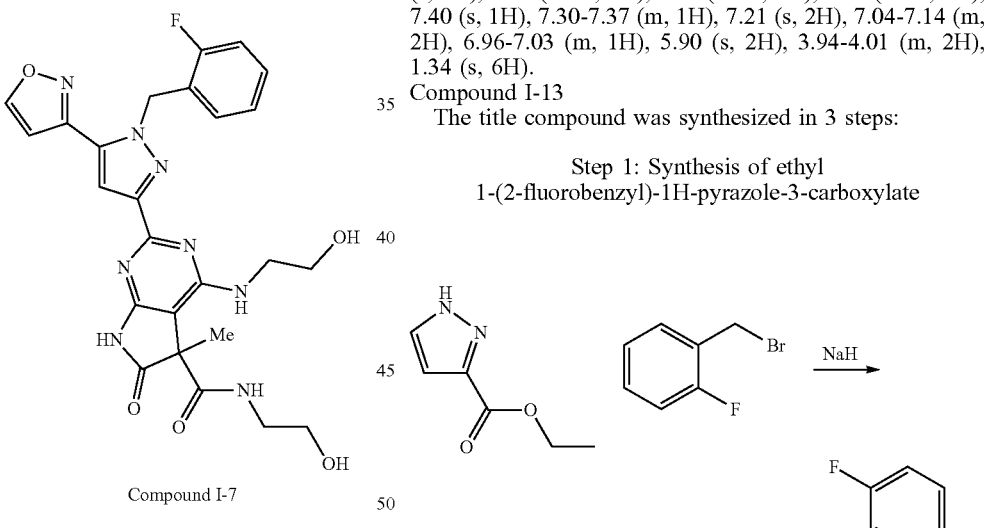

Compound I-7

A mixture of Compound I-17 (1 equiv., this was prepared from amino Intermediate-12, using a procedure analogous to that used for converting Intermediate-14 to Intermediate-15, as described below), ethanolamine (6 equiv.), and DIPEA (4 equiv.) in NMP was heated at 65° C. for 15 h. Volatiles were removed under a stream of nitrogen, and the crude residue was purified via reverse phase HPLC (C18 column, 5% to 95% acetonitrile in water with 0.1% TFA over 20 mins) to deliver the desired compound (56 mg, 51% yield) as a pale yellow solid.

$^1$H NMR (500 MHz, DMSO-d$_6$) δ ppm 11.33-11.37 (m, 1H), 9.10 (s, 1H), 7.68 (t, 1H), 7.48 (s, 1H), 7.33 (q, 1H), 7.18-7.27 (m, 2H), 7.06-7.13 (m, 2H), 6.80-6.88 (m, 1H), 5.90 (s, 2H), 3.52-3.66 (m, 4H), 3.36-3.43 (m, 2H), 3.09-3.24 (m, 2H), 2.54 (s, 2H), 1.57 (s, 3H).

Compound I-8

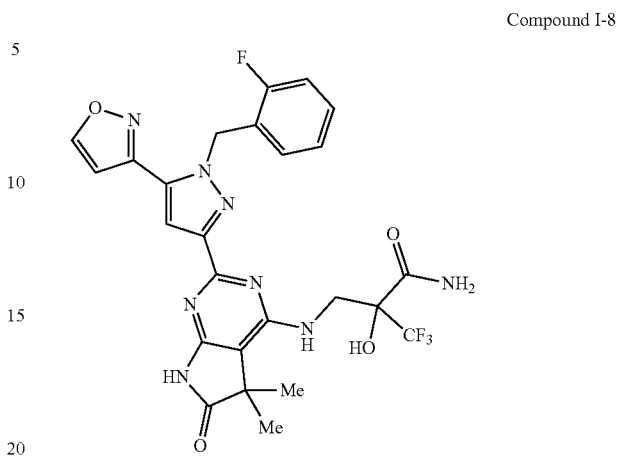

Compound I-8

A mixture of Intermediate-15 (1 equiv.), 2-(aminomethyl)-3,3,3-trifluoro-2-hydroxypropanamide (3 equiv.) and triethyl amine (5 equiv.) in water and dioxane (1:2) was heated at 100° C. for 3 h. Volatiles were removed under a stream of nitrogen, and the crude residue was purified via reverse phase HPLC (C18 column, 5% to 95% acetonitrile in water with 0.1% TFA over 20 mins) to deliver the desired compound (13 mg, 44% yield) as a white solid.

$^1$H NMR (500 MHz, DMSO-d$_6$) δ ppm 11.22 (s, 1H), 9.12 (s, 1H), 8.61 (br. s., 1H), 7.75 (br. s., 1H), 7.69 (br. s., 1H), 7.40 (s, 1H), 7.30-7.37 (m, 1H), 7.21 (s, 2H), 7.04-7.14 (m, 2H), 6.96-7.03 (m, 1H), 5.90 (s, 2H), 3.94-4.01 (m, 2H), 1.34 (s, 6H).

Compound I-13

The title compound was synthesized in 3 steps:

Step 1: Synthesis of ethyl 1-(2-fluorobenzyl)-1H-pyrazole-3-carboxylate

To a cold solution of ethyl 1H-pyrazole-3-carboxylate (1 equiv.) in THF at 0° C., was added sodium hydride [60 wt % disperion on mineral oil] (1 equiv.). The mixture was stirred at 0° C. for 15 min. To this mixture, was added 2-fluorobenzyl bromide (1 equiv.). The mixture was stirred at rt for 2 h. The mixture was diluted in ethyl acetate (100 ml) and washed with water (50 ml). The organic layer was dried, filtered and evaporated to give an oil. The oil was purified by column chromatography (0 to 30% ethyl acetate in hexanes) to give ethyl 1-(2-fluorobenzyl)-1H-pyrazole-3-carboxylate (1.5 g, 85% yield) as a clear oil.

¹H NMR (500 MHz, CHLOROFORM-d) δ ppm 7.44 (d, 1H) 7.33-7.39 (m, 1H) 7.19-7.26 (m, 1H) 7.08-7.18 (m, 2H) 6.85 (d, 1H) 5.48 (s, 2H) 4.43 (q, 2H) 1.42 (t, 3H)

Step 2: Synthesis of 1-(2-fluorobenzyl)-1H-pyrazole-3-carboximidamide (Intermediate-26)

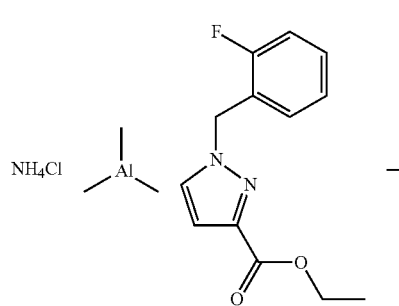

In a 250 ml round bottom flask equipped with a reflux condenser, a suspension of ammonium chloride (5.3 equiv.) in toluene was cooled to 0° C. To this mixture, was added triemthylaluminum [2M solution in toluene] (5.3 equiv.). The mixture was allowed to warm to rt and stirred at rt until the bubbling ceased. To this mixture, was added ethyl 1-(2-fluorobenzyl)-1H-pyrazole-3-carboxylate (1 equiv.). The mixture was heated to reflux for 24 h. The mixture was cooled 0° C. and quenched with methanol (5.3 equiv.). The mixture was stirred until it formed a slurry and it was left standing at rt over the weekend. The slurry mixture was filtered through a bucnher funnel. The solid was rinsed with a minimal amount of methanol. The filtrate was diluted in ethyl acetate (100 ml) and washed with 10% potassium carbonate solution (50 ml). The organic layer was dried, filtered and evaporated to give 1-(2-fluorobenzyl)-1H-pyrazole-3-carboximidamide (56 mg, 4% yield) as a clear oil.

¹H NMR (500 MHz, METHANOL-d₄) δ ppm 7.70 (d, 1H) 7.30-7.38 (m, 2H) 7.19-7.25 (m, 1H) 7.09-7.17 (m, 1H) 6.75-6.81 (m, 1H) 5.39-5.48 (m, 2H).

Step 3: Synthesis of ethyl 4-amino-2-(1-(2-fluorobenzyl)-1H-pyrazol-3-yl)-5-methyl-6-oxo-6,7-dihydro-5H-pyrrolo[2,3-d]pyrimidine-5-carboxylate

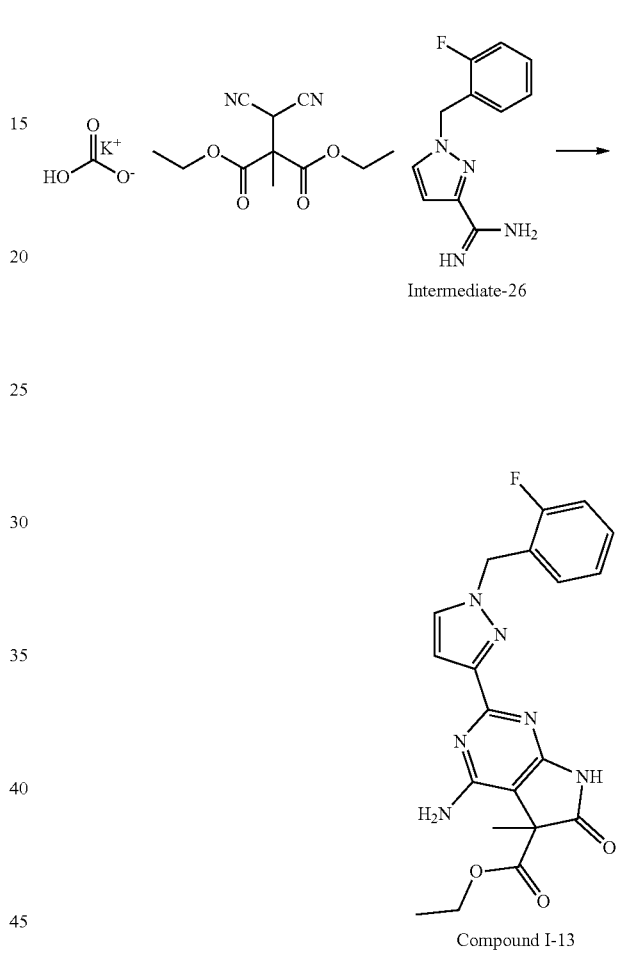

Compound I-13

A mixture of potassium hydrogencarbonate (2 equiv.), diethyl 2-(dicyanomethyl)-2-methylmalonate (1.2 equiv.) and 1-(2-fluorobenzyl)-1H-pyrazole-3-carboximidamide (Intermediate-26, 1 equiv.) in tert-butanol was heated to 83° C. for 3 h. The mixture was cooled to rt and diluted with ethyl acetate (100 ml). The organic layer was washed with brine (50 ml), dried, filtered and concentrated under vacuum to give a crude solid. The solid was purified by column chromatography (0 to 100% ethyl acetate in hexanes) to give ethyl 4-amino-2-(1-(2-fluorobenzyl)-1H-pyrazol-3-yl)-5-methyl-6-oxo-6,7-dihydro-5H-pyrrolo[2,3-d]pyrimidine-5-carboxylate (68 mg, 65% yield) as a white solid.

¹H NMR (500 MHz, METHANOL-d₄) δ ppm 7.69 (d, 1H) 7.31-7.39 (m, 1H) 7.19-7.23 (m, 1H) 7.09-7.18 (m, 2H) 6.94 (d, 1H) 5.46-5.52 (m, 2H) 4.15-4.24 (m, 2H) 1.66-1.70 (m, 3H) 1.20 (t, 3H).

Compound I-14

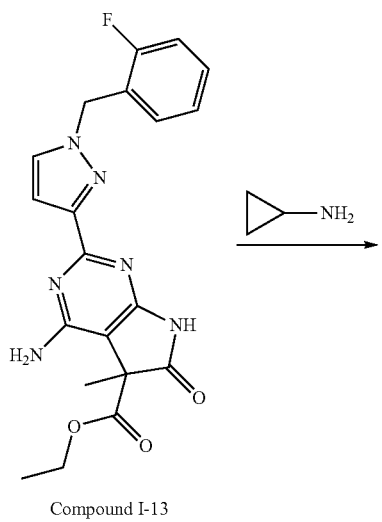

Compound I-13

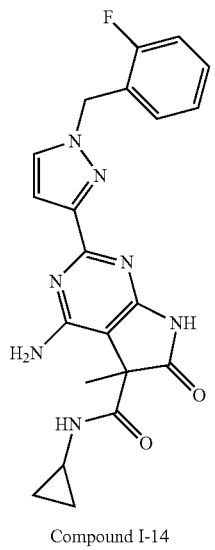

Compound I-14

A mixture of cyclopropanamine (130 equiv.) and ethyl 4-amino-2-(1-(2-fluorobenzyl)-1H-pyrazol-3-yl)-5-methyl-6-oxo-6,7-dihydro-5H-pyrrolo[2,3-d]pyrimidine-5-carboxylate (Compound I-13, 1 equiv.) in MeOH was heated to 50° C. for 24 h. The mixture was concentrated under vacuum to give 4-amino-N-cyclopropyl-2-(1-(2-fluorobenzyl)-1H-pyrazol-3-yl)-5-methyl-6-oxo-6,7-dihydro-5H-pyrrolo[2,3-d]pyrimidine-5-carboxamide (22 mg, 69% yield) as a white solid.

¹H NMR (500 MHz, METHANOL-d₄) δ ppm 7.69 (d, 1H) 7.32-7.39 (m, 1H) 7.19-7.25 (m, 1H) 7.10-7.17 (m, 2H) 6.94 (d, 1H) 5.49 (s, 2H) 2.68 (tt, 1H) 1.65-1.69 (m, 3H) 0.70-0.75 (m, 2H) 0.50-0.55 (m, 2H).

Compound I-9

This compound was prepared in two steps:

Step 1: Preparation of Intermediate-16

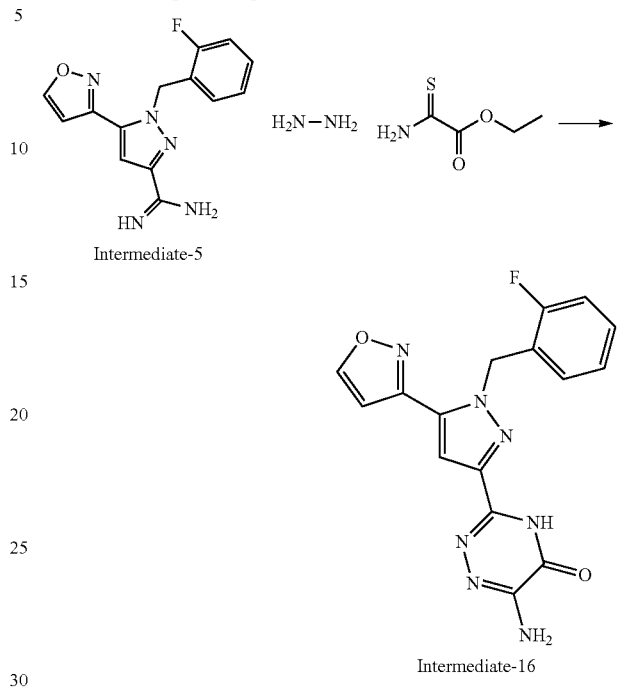

To a suspension of 1-(2-fluorobenzyl)-5-(isoxazol-3-yl)-1H-pyrazole-3-carboximidamide (Intermediate-5, 1 equiv., generated in step 3 of general procedure A, by using 1-(isoxazol-3-yl)ethanone in step 1 and 2-fluorobenzylhydrazine in step 2, 1 equiv) in EtOH, was added hydrazine monohydrate (1.2 equiv.). The mixture was stirred at rt for 1 h. To this mixture, was added ethyl 2-amino-2-thioxoacetate (5 equiv). The mixture was stirred at rt for 3 days. The precipitate formed was filtered and collected. It was suspended in ethanol (20 ml) and heated to 60° C. The suspension was collected and dried under vacuum to give 6-amino-3-(1-(2-fluorobenzyl)-5-(isoxazol-3-yl)-1H-pyrazol-3-yl)-1,2,4-triazin-5(4H)-one (976 mg, 79% yield) as a light yellow solid.

¹H NMR (400 MHz, DMSO-d₆) δ ppm 9.08-9.14 (m, 1H) 7.57-7.60 (m, 1H) 7.30-7.38 (m, 1H) 7.19-7.28 (m, 2H) 7.12 (t, 1H) 6.88 (t, 1H) 5.93 (s, 2H).

Step 2: Preparation of Compound I-9

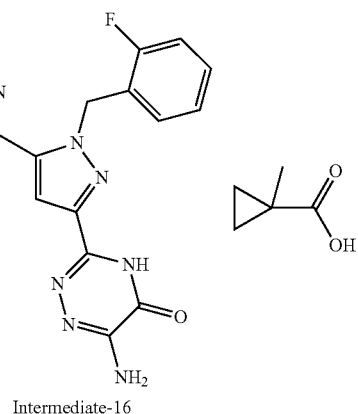

Intermediate-16

-continued

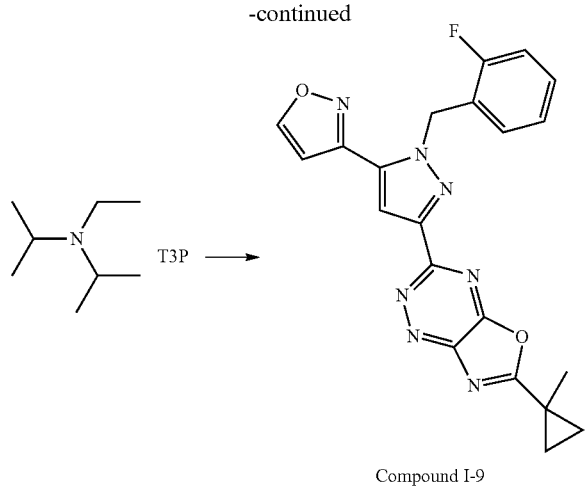

Compound I-9

To mixture of Intermediate-16 (1 equiv.), 1-methylcyclopropanecarboxylic acid (3 equiv.) and Hunig's base (10 equiv.) in NMP, was added T3P (7 equiv.). The mixture was stirred at rt for 5 h. The mixture was quenched with water and extracted with ethyl acetate (100 ml). The organic layer was dried, filtered and evaporated to give an oil. The oil was purified by column chromatography (0 to 80% ethyl acetate in hexanes) to give 3-(1-(2-fluorobenzyl)-5-(isoxazol-3-yl)-1H-pyrazol-3-yl)-6-(1-methylcyclopropyl)oxazolo[5,4-e][1,2,4]triazine (10 mg, 8% yield) as a yellow solid.
$^1$H NMR (400 MHz, DMSO-d$_6$) δ ppm 9.14 (d, 1H) 7.86 (d, 1H) 7.30-7.40 (m, 2H) 7.21-7.27 (m, 1H) 7.14 (t, 1H) 6.99 (t, 1H) 5.97 (s, 2H) 1.61 (s, 3H) 1.58 (d, 2H) 1.31-1.36 (m, 2H).
Compound I-10

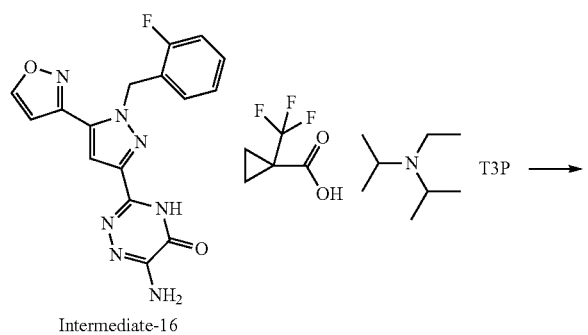

Compound I-10

To a mixture of 6-amino-3-(1-(2-fluorobenzyl)-5-(isoxazol-3-yl)-1H-pyrazol-3-yl)-1,2,4-triazin-5(2H)-one (Intermediate-16, 1 equiv.), 1-(trifluoromethyl)cyclopropanecarboxylic acid (2 equiv.) and N-ethyl-N-isopropylpropan-2-amine (10 equiv.) in NMP, was added T3P (4 equiv.). The mixture was stirred at rt for 3 days. It was taken up in ethyl acetate (100 ml) and washed with water (50 ml×2). The organic layer was dried, filtered and evaporated to give an oil. Purification of the oil by column chromatography (0 to 80% ethyl acetate in hexanes) and recrystallization from a minimal amount methanol and diethyl ether gave 3-(1-(2-fluorobenzyl)-5-(isoxazol-3-yl)-1H-pyrazol-3-yl)-6-(1-(trifluoromethyl)cyclopropyl)oxazolo[5,4-e][1,2,4]triazine (55 mg, 28% yield) as a cream colored solid.
$^1$H NMR (400 MHz, DMSO-d$_6$) δ ppm 9.12-9.18 (m, 1H) 7.90 (s, 1H) 7.32-7.40 (m, 2H) 7.20-7.28 (m, 1H) 7.14 (t, 1H) 7.01 (t, 1H) 5.98 (s, 2H) 1.90-2.01 (m, 4H)
Compound I-11

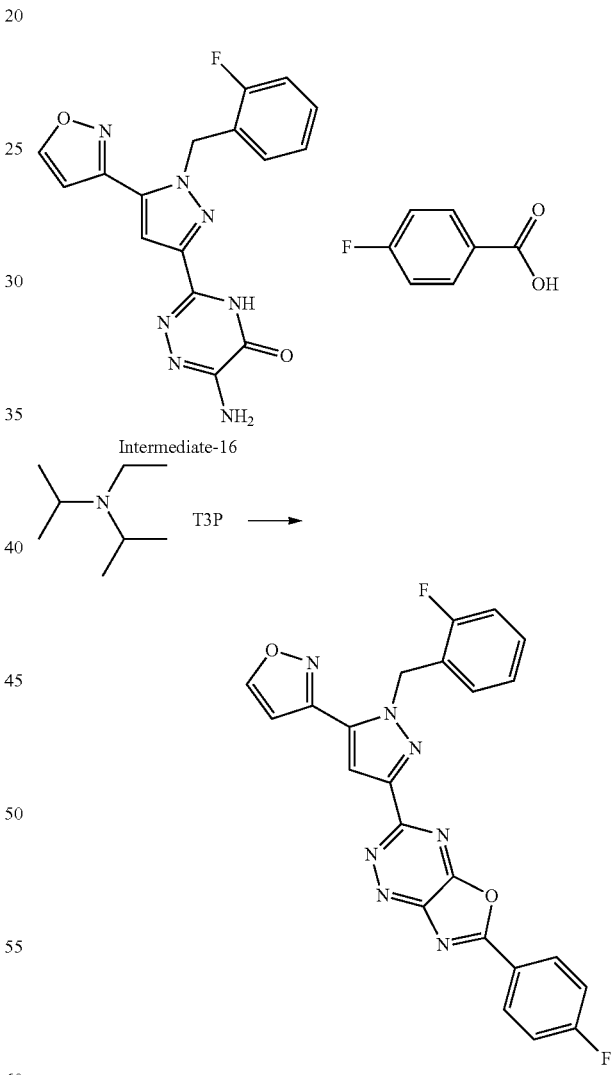

Compound I-11

To a mixture of Intermediate-16 (1 equiv.), 4-fluorobenzoic acid (2 equiv.) and Hunig's base (6 equiv.) in NMP, was added, over the course of 30 min., T3P (5 equiv.). The solution became clear and it was stirred at rt for 24 h. The mixture was diluted in ethyl acetate (200 ml) and washed with water (50 ml×4). The organic layer was dried, filtered and evaporated to give solid. The solid was rinsed with a minimal amount of methanol, collected by filtration and dried under vacuum to give 3-(1-(2-fluorobenzyl)-5-(isoxazol-3-yl)-1H-pyrazol-3-yl)-6-(4-fluorophenyl)oxazolo[5,4-e][1,2,4]triazine (132 mg, 41% yield) as a light yellow solid.

$^1$H NMR (400 MHz, DMSO-d$_6$) δ ppm 9.09-9.14 (m, 1H) 8.41 (dd, 2H) 7.90 (d, 1H) 7.57 (t, 2H) 7.30-7.37 (m, 2H) 7.18-7.25 (m, 1H) 7.11 (t, 1H) 6.96 (t, 1H) 5.97 (s, 2H).

Compound I-15

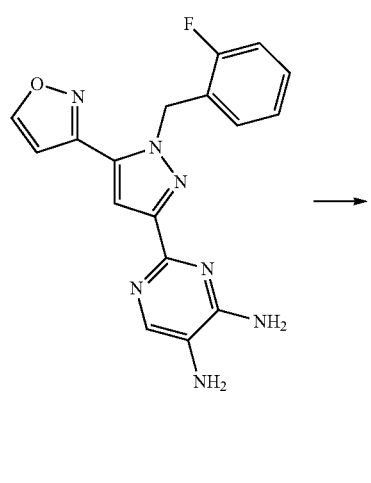

Compound I-15

A yellow solution of 2-(1-(2-fluorobenzyl)-5-(isoxazol-3-yl)-1H-pyrazol-3-yl) pyrimidine-4,5-diamine (described in previous patent application publications WO2012/3405, and WO2013/101830) (1.0 equiv.) in acetic acid was treated with sodium nitrite (1.2 equiv.). The reaction mixture became a white suspension instantaneously. After 25 min, water was added and the resulting precipitate was filtered and dried in vacuo to deliver the desired compound (23 mg, 81% yield) as a white solid.

$^1$H-NMR (500 MHz, DMSO-d$_6$) δ ppm 9.78 (s, 1H), 9.13 (d, 1H), 7.80 (s, 1H), 7.35 (m, 1H), 7.34 (d, 1H), 7.24 (m, 1H), 7.13 (app. t, 1H), 6.98 (app. t, 1H), 5.97 (s, 2H). The exchangeable NH proton was not observed.

Compound I-21

The title compound was synthesized in 5 steps:

Step 1: Synthesis of 3-(ethoxycarbonyl)-1-(2-fluorobenzyl)-1H-pyrazole-5-carboxylic acid

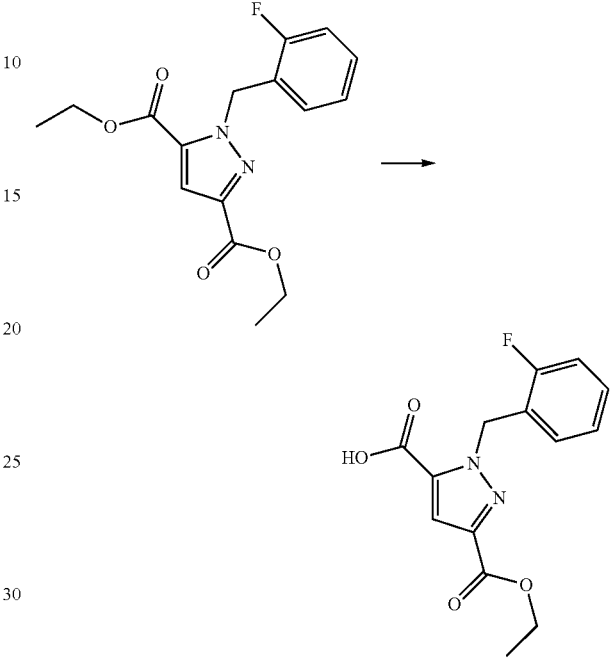

To a suspension of diethyl 1-(2-fluorobenzyl)-1H-pyrazole-3,5-dicarboxylate (previously described in the literature) (1 equiv.) in ethanol was added potassium hydroxide slowly over the course of 1.5 h, as not all of the starting material fully went into solution. After stirring for 15 h at 23° C., LCMS indicated starting material still present. Added additional 20 mol % of potassium hydroxide, continued to stir at 23° C. for 1.5 h, then added additional 30 mol % and stirred for another 2 h. The solution was poured into saturated NH4Cl solution and extracted with dichloromethane (6×). The combined organics were dried over magnesium sulfate, filtered, and the solvent was removed in vacuo to deliver the desired intermediate 3-(ethoxycarbonyl)-1-(2-fluorobenzyl)-1H-pyrazole-5-carboxylic acid (2.98 g, 108% yield) as a white solid. The crude material was carried on to the next step without further purification.

Step 2: Synthesis of 1-(2-fluorobenzyl)-5-(hydroxymethyl)-1H-pyrazole-3-carboxylic acid

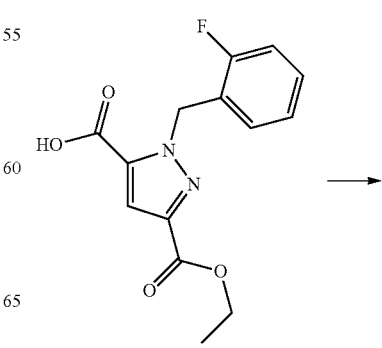

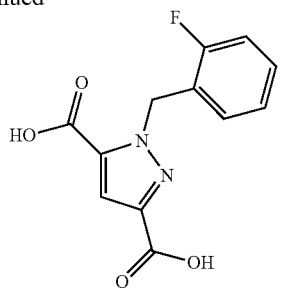

To a solution of 3-(ethoxycarbonyl)-1-(2-fluorobenzyl)-1H-pyrazole-5-carboxylic acid (1 equiv.) in THF at 0° C. was added 10M borane-methyl sulfide complex (3 equiv.) dropwise. After gas evolution had ceased (15 min), the solution was slowly warmed to 23° C. and then stirred at 65° C. for 4 h. The reaction was cooled to 23° C. and quenched with 1N HCl (aq) and stirred for 1 h. The mixture was diluted with ethyl acetate and washed with water. The organic layer was dried, filtered and evaporated to give the desired intermediate 1-(2-fluorobenzyl)-5-(hydroxymethyl)-1H-pyrazole-3-carboxylic acid (0.59 g, 74% yield) as a colorless oil.

$^{1}$H-NMR (500 MHz, DMSO-d$_6$) δ ppm 12.67 (m, 1H), 7.37 (m, 1H), 7.24 (m, 1H), 7.16 (m, 1H), 7.03 (m, 1H), 6.65 (m, 1H), 5.46 (s, 2H), 4.52 (m, 2H).

Step 3: Synthesis of methyl 1-(2-fluorobenzyl)-5-(methoxymethyl)-1H-pyrazole-3-carboxylate

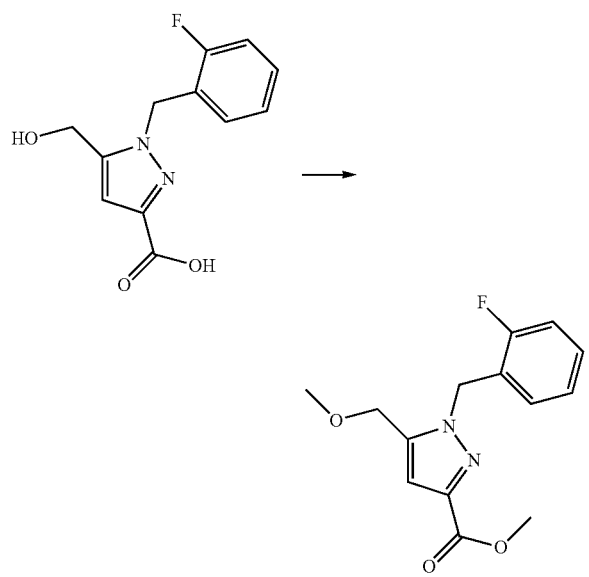

To a solution of 1-(2-fluorobenzyl)-5-(hydroxymethyl)-1H-pyrazole-3-carboxylic acid (1 equiv.) in DMF was added sodium hydride (2.1 equiv.) at 0° C. The solution was stirred for 30 min at 0° C. and for 30 min at 23° C. To the solution was added methyl iodide (4.2 equiv.) and stirred for 18 h. The mixture was diluted with ethyl acetate and washed with water. The organic layer was dried, filtered and evaporated to give a crude oil which was purified via silica gel chromatography to deliver the desired intermediate methyl 1-(2-fluorobenzyl)-5-(methoxymethyl)-1H-pyrazole-3-carboxylate (260 mg, 42% yield) as a clear colorless oil.

$^{1}$H-NMR (500 MHz, DMSO-d$_6$) δ ppm 7.34 (m, 1H), 7.22 (m, 1H), 7.13 (m, 1H), 6.90 (m, 2H), 5.76 (m, 2H), 4.37 (s, 2H), 3.81 (m, 3H), 3.25 (s, 3H).

Step 4: Synthesis of 1-(2-fluorobenzyl)-5-(methoxymethyl)-1H-pyrazole-3-carboximidamide

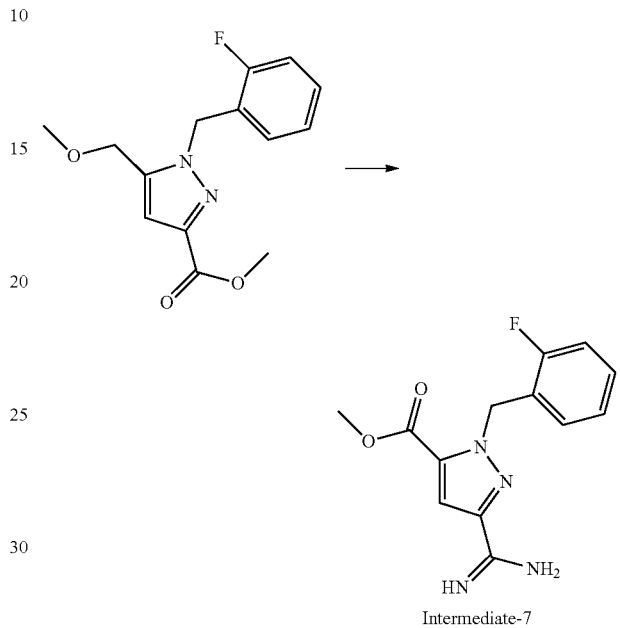

Intermediate-7

To a suspension of ammonia hydrochloride (5.3 equiv.) in toluene at 0° C., was added a solution of trimethylaluminum 2M in toluene (5.3 equiv.). The mixture was removed from the ice bath and stirred at 23° C. until bubbling ceased. To this mixture was added a solution of methyl 1-(2-fluorobenzyl)-5-(methoxymethyl)-1H-pyrazole-3-carboxylate (1 equiv.) in toluene and stirred at 80° C. for 24 h. The mixture was cooled in an ice bath and quenched slowly with methanol and the resulting white precipitate was removed by filtration on celite pad. The filtrate was concentrated and dried under vacuum to deliver the desired intermediate 1-(2-fluorobenzyl)-5-(methoxymethyl)-1H-pyrazole-3-carboximidamide (258 mg, 100% yield) as an off-white solid.

$^{1}$H-NMR (500 MHz, DMSO-d$_6$) δ ppm 7.29 (m, 6H), 6.85 (m, 1H), 5.55 (s, 2H), 4.36 (s, 2H), 3.34 (s, 1H), 3.26 (s, 3H).

Step 5: Synthesis of Compound I-21

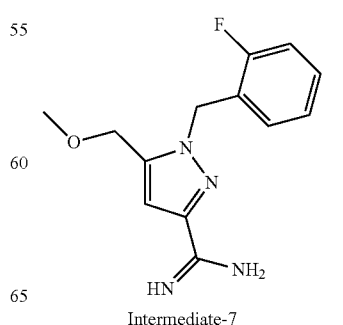

Intermediate-7

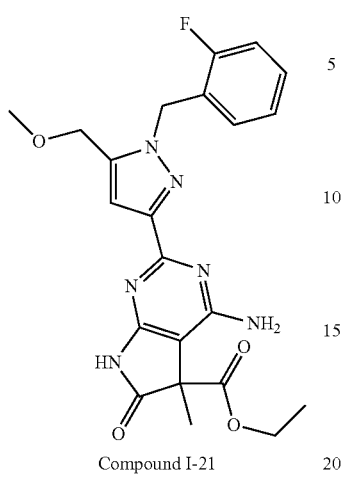

Compound I-21

A mixture containing 1-(2-fluorobenzyl)-5-(methoxymethyl)-1H-pyrazole-3-carboximidamide (1 equiv.), diethyl 2-(dicyanomethyl)-2-methylmalonate (Intermediate-7, 1.5 equiv.), and potassium hydrogencarbonate (2 equiv.) in tert-butanol was heated at 85° C. for 5 h. The mixture was cooled, diluted with ethyl acetate, and washed with water. The organic layer was dried, filtered and evaporated to give a crude oil which was purified via silica gel chromatography to deliver the desired compound (2.4 mg, 3% yield) as an off white solid.

$^1$H-NMR (500 MHz, DMSO-d$_6$) δ ppm 11.32 (m, 1H), 7.29 (m, 1H), 7.17 (m, 1H), 7.08 (m, 1H), 6.88 (m, 1H), 6.83 (s, 1H), 6.69 (m, 2H), 6.11 (m, 2H), 4.34 (s, 2H), 4.10 (m, 2H), 3.25 (s, 3H), 1.59 (m, 3H), 1.10 (t, 3H).

Compound I-22

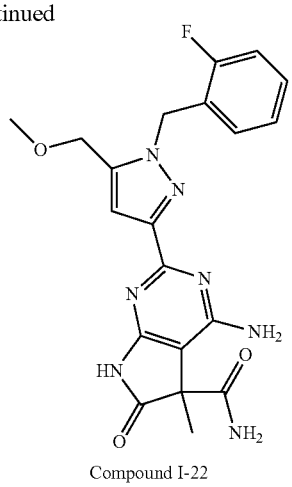

Compound I-22

A solution of Compound I-21 (1 equiv.) in 7N ammonia in methanol (excess) was stirred at 23° C. for 18 h. The solvent was removed in vacuo to deliver the desired compound (4.6 mg, 96% yield) as an off white solid.

$^1$H-NMR (500 MHz, CD$_3$OD) δ 7.24 (m, 1H), 7.04 (m, 3H), 6.80 (t, 1H), 6.15 (s, 2H), 4.47 (s, 2H), 3.39 (s, 3H), 1.69 (s, 3H).

Compound I-18

This compound was prepared in two steps:

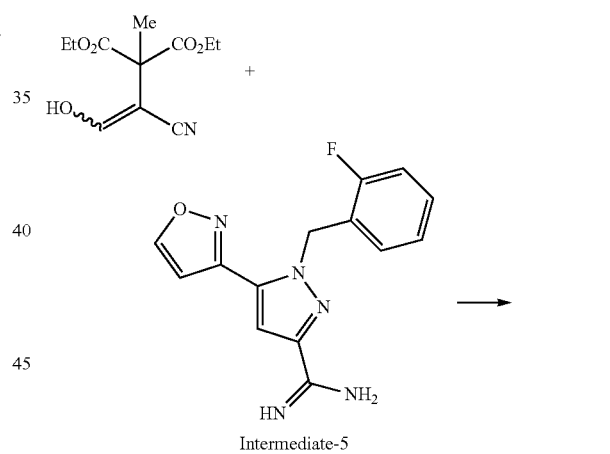

Intermediate-5

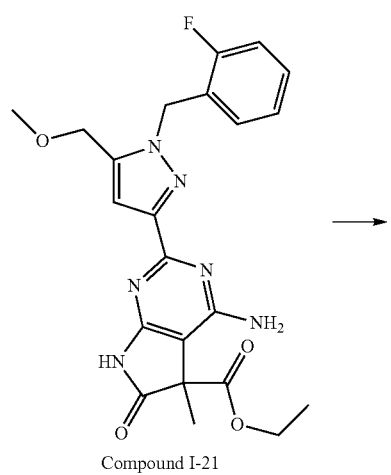

Compound I-21

→

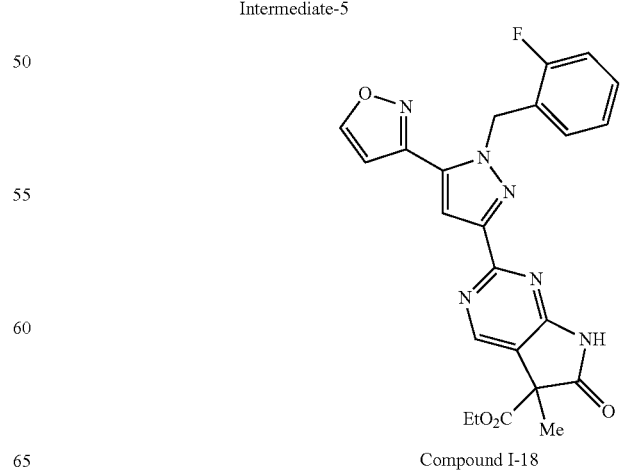

Compound I-18

237

Step 1

To a suspension of potassium tert-butoxide (2.2 equiv.) in tetrahydrofuran at 23° C. was added dropwise over 5 min ethyl formate (3.35 equiv.) and diethyl 2-(cyanomethyl)-2-methylmalonate (1 equiv.) in tetrahydrofuan. After stirring for 3 h, the solution was poured into ice water and ethyl acetate (1:1). The layers were separated and the aqueous layer was treated with aqueous 1N hydrochloric acid until pH 4. The aqueous solution was then extracted with ethyl acetate (4×), the organics were dried over magnesium sulfate, filtered, and the solvent was removed in vacuo to give the desired intermediate, diethyl 2-(1-cyano-2-hydroxyvinyl)-2-methylmalonate.

Step 2

Diethyl 2-(1-cyano-2-hydroxyvinyl)-2-methylmalonate (2 equiv.) was combined with 1-(2-fluorobenzyl)-5-(isoxazol-3-yl)-1H-pyrazole-3-carboximidamide (Intermediate-5, 1 equiv.) and heated as a neat mixture at 80° C. for 60 h. The resulting purple oil was placed under vacuum to remove volatiles. The crude reaction mixture was combined with the crude product from a previous reaction, and purification via silica gel chromatography (methanol in dichloromethane) gave impure product. Repurification (15-70% ethyl acetate in hexanes) delivered the desired compound (11 mg, 4% combined yield) as a white film. $^1$H-NMR (500 MHz, CDCl$_3$) δ ppm 8.88 (br s, 1H), 8.48 (m, 2H), 7.57 (s, 1H), 7.23-7.19 (m, 1H), 7.05-7.02 (m, 1H), 6.97 (t, 1H), 6.87-6.84 (m, 1H), 6.64 (m, 1H), 6.06 (s, 2H), 4.28-4.16 (m, 2H), 1.80 (s, 3H), 1.22 (t, 3H).

Compound I-16

238

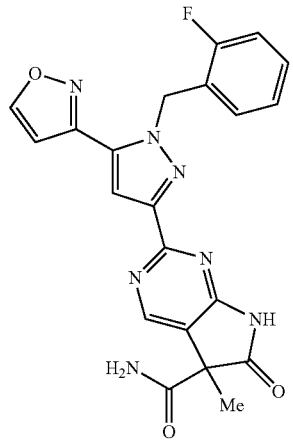

Compound I-16

A suspension of Compound I-18 (1 equiv.) in a methanolic 7 N solution of ammonia (large excess) was stirred at room temperature for 72 h. The solvent was removed in vacuo. Purification via silica gel chromatography (ethyl acetate), delivered the desired compound (1.9 mg, 29% yield) as a solid.

$^1$H-NMR (500 MHz, CD$_3$OD) δ ppm 8.80 (m, 1H), 8.60 (s, 1H), 7.55 (s, 1H), 7.32-7.28 (m, 1H), 7.14-7.10 (m, 1H), 7.07-7.04 (m, 1H), 6.92-6.87 (m, 2H), 6.00 (s, 2H), 1.78 (s, 3H).

Compound I-17

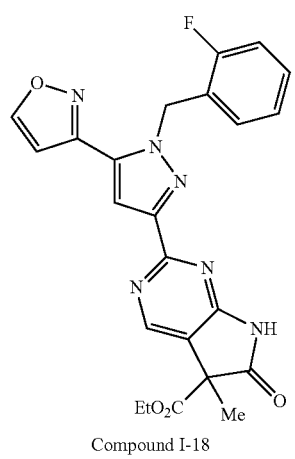

Compound I-18

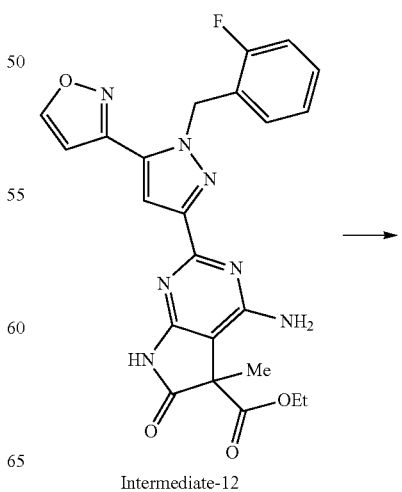

Intermediate-12

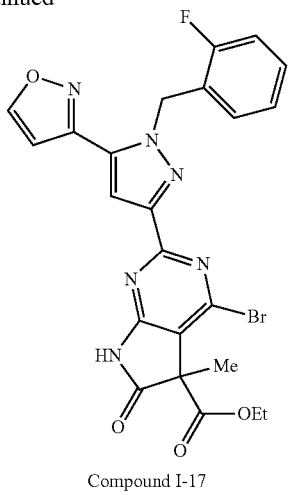

Compound I-17

A mixture of Intermediate-12 (1 equiv.), isopropyl nitrite (1.5 equiv.) and copper(II) bromide (1.2 equiv.) in dichloroethane was heated at 65° C. in a sealed vial for 2 h. Reaction mixture was then diluted with water and dichloromethane. Phases were separated and the aqueous phase was extracted with ethyl acetate (3×). The combined organic phase was dried over anhydrous magnesium sulfate, filtered and concentrated. The residue was purified via silica gel chromatography (30% to 100% ethyl acetate in hexane over 50 mins) to deliver the desired compound (0.67 g, 59% yield) as a greenish blue solid.

$^1$H NMR (500 MHz, DMSO-$d_6$) δ ppm 12.34 (br. s., 1H), 9.11 (s, 1H), 7.63 (s, 1H), 7.31-7.38 (m, 2H), 7.23 (t, 1H), 7.12 (t, 1H), 6.90 (t, 1H), 5.96 (s, 2H), 4.15-4.24 (m, 1H), 4.06-4.14 (m, 1H), 1.66 (s, 3H), 1.07-1.14 (m, 3H).

Compound I-19

The title compound was synthesized in 3 steps:

Step 1: Synthesis of ethyl 5-acetyl-1-(2-fluorobenzyl)-1H-pyrazole-3-carboxylate

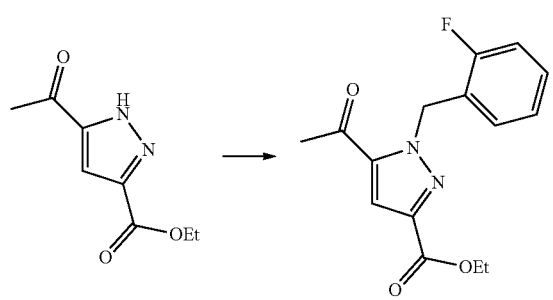 [SMILES: CCOC(=O)c1cc(C(C)=O)[nH]n1 ; CCOC(=O)c1cc(C(C)=O)n(Cc2ccccc2F)n1]

To a solution of ethyl 5-acetyl-1H-pyrazole-3-carboxylate (prepared according to literature methods) (1 equiv.) and cesium carbonate (1.3 equiv.) in DMF was added 1-(bromomethyl)-2-fluorobenzene (1.3 equiv.) and stirred at 23° C. for 3 h. The reaction was quenched and neutralized to pH 7 with 1 N HCl solution, extracted with ethyl acetate, and concentrated in vacuo. The residue was purified via silica gel chromatography to deliver the desired intermediate, ethyl 5-acetyl-1-(2-fluorobenzyl)-1H-pyrazole-3-carboxylate (45 mg, 13%) as a tan solid.

$^1$H NMR (500 MHz, CDCl$_3$) δ ppm 7.39-7.45 (m, 1H), 7.19-7.26 (m, 1H), 7.07 (d, 1H), 7.01 (t, 1H), 6.81 (t, 1H), 5.92 (s, 2H), 4.40-4.49 (m, 2H), 2.53 (s, 3H), 1.41-1.45 (m, 3H).

Step 2: Synthesis of 5-acetyl-1-(2-fluorobenzyl)-1H-pyrazole-3-carboximidamide

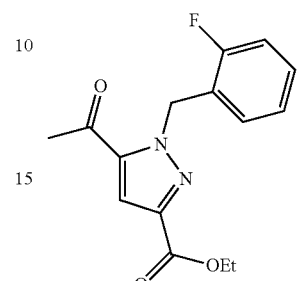

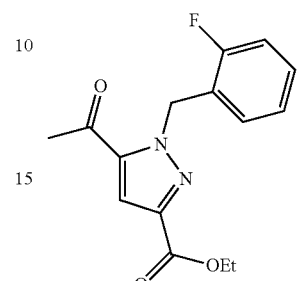

Intermediate-27

To a cooled suspension of ammonia hydrochloride (8 equiv.) in toluene at 0° C. was added trimethylaluminum (7.9 equiv.) dropwise via syringe. The reaction was then allowed to warm to 23° C., and stirred until no more bubbling was observed. Into this clear solution was added ethyl 5-acetyl-1-(2-fluorobenzyl)-1H-pyrazole-3-carboxylate (1 equiv.) in one portion and heated at 100° C. for 18 h. The contents were cooled to 0° C. and the reaction carefully quenched with MeOH (250 equiv.). The reaction was warmed to 23° C. and stirred vigorously for 1 h. The mixture was then filtered, and the solids were rinsed with methanol. The filtrate was concentrated in vacuo, and the residue was taken up in 10% methanol in dichloromethane solution. Significant precipitate forms. The mixture was filtered, and the solids were dried to deliver the desired intermediate, 5-acetyl-1-(2-fluorobenzyl)-1H-pyrazole-3-carboximidamide as a brown solid. The impure material was carried forward as is.

Step 3: Synthesis of Compound I-19

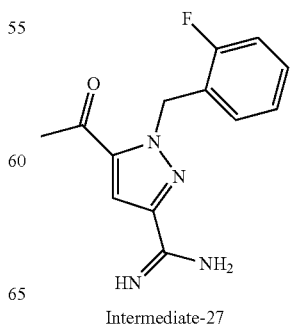

Intermediate-27

Compound I-19

A mixture of 5-acetyl-1-(2-fluorobenzyl)-1H-pyrazole-3-carboximidamide (Intermediate-27, 1 equiv.), diethyl 2-(dicyanomethyl)-2-methylmalonate (8 equiv.) and potassium bicarbonate (18 equiv.) in t-BuOH was heated at 85° C. for 6 h. The reaction mixture was filtered, concentrated and purified via reverse phase HPLC to deliver the desired compound (10 mg, 20% yield, TFA salt) as a white solid.

$^1$H NMR (500 MHz, DMSO-d$_6$) δ ppm 11.23-11.41 (m, 1H, from TFA) 7.55 (s, 1H) 7.29-7.39 (m, 1H) 7.18-7.26 (m, 1H) 7.04-7.17 (m, 2H) 6.84 (t, 1H) 6.71 (br. s., 2H) 5.82 (s, 2H) 4.06-4.13 (m, 2H) 2.56 (s, 3H) 1.59 (s, 3H) 1.08-1.13 (m, 3H)

Compound I-20

A mixture of Compound I-19 (1 equiv.) and 7M ammonia in MeOH (a large excess) was stirred at 23° C. for 15 h. The reaction mixture was concentrated in vacuo to deliver the desired compound (4.4 mg, 82% yield) as a white solid.

$^1$H NMR (500 MHz, CD$_3$OD) δ ppm 7.70 (s, 1H), 7.22-7.33 (m, 1H), 7.02-7.15 (m, 2H), 6.80 (t, 1H), 5.87-5.92 (m, 2H), 2.52-2.59 (m, 3H), 1.70-1.74 (m, 3H). NH and NH$_2$ protons exchanged.

Compound I-23

The title compound was prepared in 2 steps:

Step 1: Synthesis of methyl 3,3-dicyano-2,2-dimethylpropanoate

A mixture of methyl 2-bromo-2-methylpropanoate (1 equiv.), malononitrile (1 equiv.) and potassium t-butoxide (1 equiv.) in THF was heated to 50° C. for 15 h. The mixture was diluted with diethyl ether and 1 N HCl solution. Phases were separated and the aqueous phase was extracted twice with diethyl ether. The combined organic phase was washed with brine, dried over anhydrous sodium sulfate, filtered and concentrated. The residue was purified by silica gel chromatography (120 g, 5% to 30% ethyl acetate in hexane over 30 mins and then 30% to 50% ethyl acetate in hexane over 10 mins) to give methyl 3,3-dicyano-2,2-dimethylpropanoate (20 g, 64% yield) as a colorless oil.

$^1$H NMR (500 MHz, DMSO-d$_6$) δ ppm 5.26 (s, 1H) 3.74 (s, 3H) 1.40 (s, 6H).

Step 2: Synthesis of Compound I-23

A mixture of 1-(2-fluorobenzyl)-5-methoxy-1H-pyrazole-3-carboximidamide (Intermediate-4, 1 equiv.), methyl 3,3-dicyano-2,2-dimethylpropanoate (1.5 equiv.) and potassium bicarbonate (1.5 equiv.) in t-butanol was heated to reflux overnight. After cooling, the reaction mixture was added with water and stirred for 30 min. The precipitate was filtered, washed with a minimum amount of water and diethyl ether and then dried overnight under high vacuum to give Compound I-23 (3.7 g, 69% yield) as a white solid.

$^1$H NMR (500 MHz, DMSO-$d_6$) δ ppm 10.84 (s, 1H) 7.32-7.38 (m, 1H) 7.21 (t, 1H) 7.16 (t, 1H) 7.07 (t, 1H) 6.58 (br s, 2H) 6.15 (s, 1H) 5.21 (s, 2H) 3.92 (s, 3H) 2.48-2.52 (m, 3H) 1.31 (s, 6H). m/z=383.0 (M+H).

Compound I-24

The title compound was prepared in 2 steps:

Step 1: Synthesis of 4-bromo-2-(1-(2-fluorobenzyl)-5-methoxy-1H-pyrazol-3-yl)-5,5-dimethyl-5H-pyrrolo[2,3-d]pyrimidin-6(7H)-one (Intermediate-8)

Step 2: Synthesis of Compound I-24

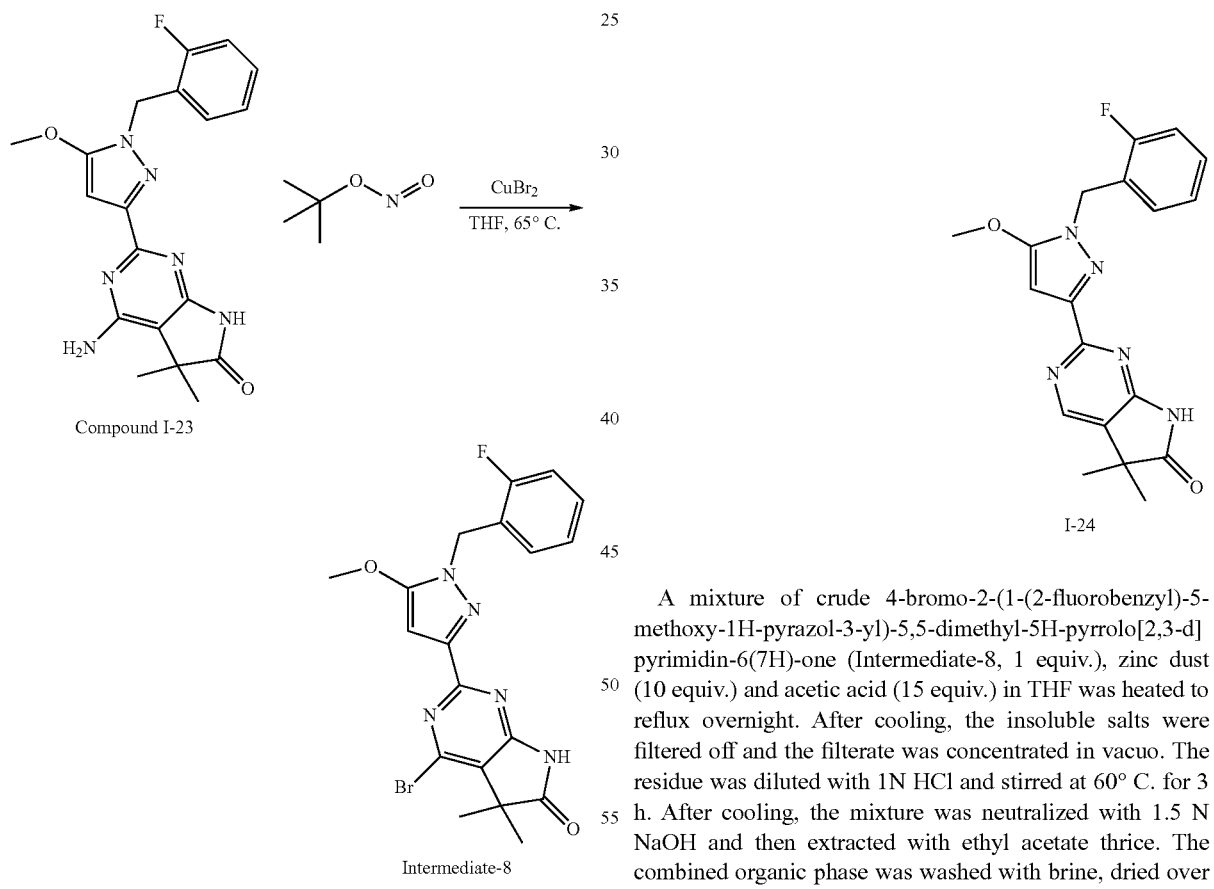

A mixture of Compound I-23 (1 equiv.), tert-butyl nitrite (1.5 equiv.) and copper(II) bromide (1.2 equiv.) in THF was heated to reflux overnight. After cooling, the insoluble salts were filtered off and washed with DCM. The filtrate was partitioned with water and the separated aqueous phase was back extracted with DCM twice. The combined organic phase was concentrated to give a crude residue that was carried forward to the next step without any purification.

A mixture of crude 4-bromo-2-(1-(2-fluorobenzyl)-5-methoxy-1H-pyrazol-3-yl)-5,5-dimethyl-5H-pyrrolo[2,3-d]pyrimidin-6(7H)-one (Intermediate-8, 1 equiv.), zinc dust (10 equiv.) and acetic acid (15 equiv.) in THF was heated to reflux overnight. After cooling, the insoluble salts were filtered off and the filterate was concentrated in vacuo. The residue was diluted with 1N HCl and stirred at 60° C. for 3 h. After cooling, the mixture was neutralized with 1.5 N NaOH and then extracted with ethyl acetate thrice. The combined organic phase was washed with brine, dried over anhydrous sodium sulfate, filtered and concentrated. The crude material was then purified by reverse phase HPLC (C18 column, 5% to 95% acetonitrile in water with 0.1% TFA over 20 mins) to obtain Compound I-24 (0.76 g, 79% yield) as a white solid.

$^1$H NMR (500 MHz, DMSO-$d_6$) δ ppm 11.43 (s, 1H) 8.47 (s, 1H) 7.33-7.39 (m, 1H) 7.15-7.25 (m, 2H) 7.10 (td, 1H) 6.31 (s, 1H) 5.24 (s, 2H) 3.95 (s, 3H) 1.34 (s, 6H). m/z=368.1 (M+H).

Compound I-25

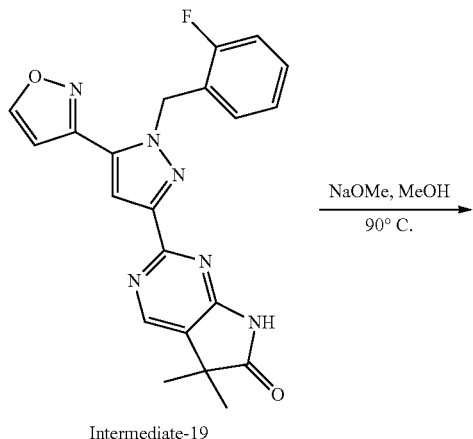

Intermediate-19

Compound I-26

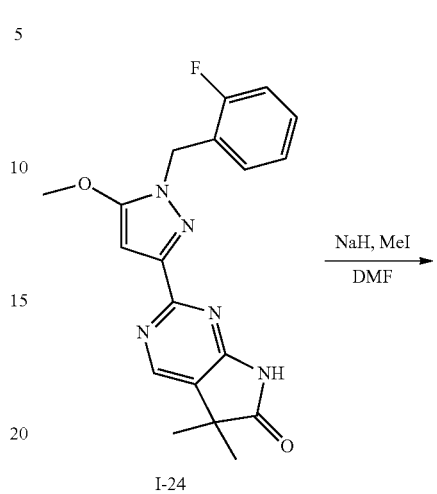

I-24

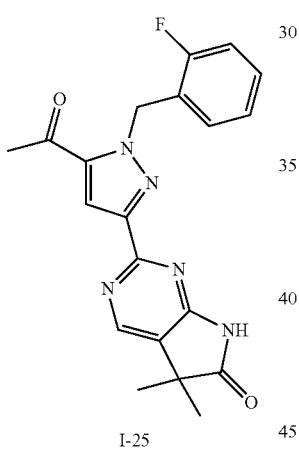

I-25

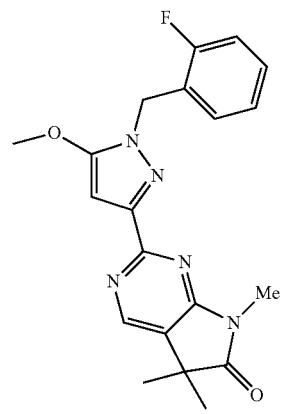

I-26

A mixture of 2-(1-(2-fluorobenzyl)-5-(isoxazol-3-yl)-1H-pyrazol-3-yl)-5,5-dimethyl-5H-pyrrolo[2,3-d]pyrimidin-6(7H)-one (Intermediate 1-19, 1 equiv., the synthesis of which was described in patent application publication WO2013101830) and sodium methoxide (0.5 N in methanol) (2.5 equiv.) was heated to reflux overnight. After cooling, the volatiles were removed by vacuum and the residue was diluted with water, acidified to pH 2 with 3 N HCl and extracted with DCM three times. The combined organic phase was concentrated and purified by reverse phase HPLC (C18 column, 5% to 95% acetonitrile in water with 0.1% formic acid over 20 mins) to obtain Compound I-25 (113 mg, 48% yield) as a white solid.

$^1$H NMR (500 MHz, DMSO-d$_6$) δ ppm 11.55 (br s, 1H) 8.55 (s, 1H) 7.74 (s, 1H) 7.30-7.37 (m, 1H) 7.20-7.26 (m, 1H) 7.09-7.14 (m, 1H) 6.88 (t, 1H) 5.84 (s, 2H) 2.58 (s, 3H) 1.36 (s, 6H). m/z=380.2 (M+H).

A mixture of Compound I-24 (1 equiv.) and sodium hydride (3 equiv.) in DMF was stirred at room temperature for 1 h. The mixture was then added with iodo methane (4 equiv.) and stirred at room temperature overnight, after which it was diluted with water and ethyl acetate. Phases were separated and the aqueous phase was extracted twice with ethyl acetate. The combined organic phase was washed with brine, dried over anhydrous magnesium sulfate, filtered and concentrated. The crude material was purified by reverse phase HPLC (C18 column, 5% to 95% acetonitrile in water with 0.1% formic acid over 20 mins) to obtain Compound I-26 (112 mg, 63% yield) as a white solid. $^1$H NMR (500 MHz, DMSO-d$_6$) δ ppm 8.52 (s, 1H) 7.33-7.38 (m, 1H) 7.23 (t, 1H) 7.17 (t, 1H) 7.03 (t, 1H) 6.43 (s, 1H) 5.29 (s, 2H) 3.96 (s, 3H) 3.18 (s, 3H) 1.37 (s, 6H). m/z=382.2 (M+H).

Compound I-27

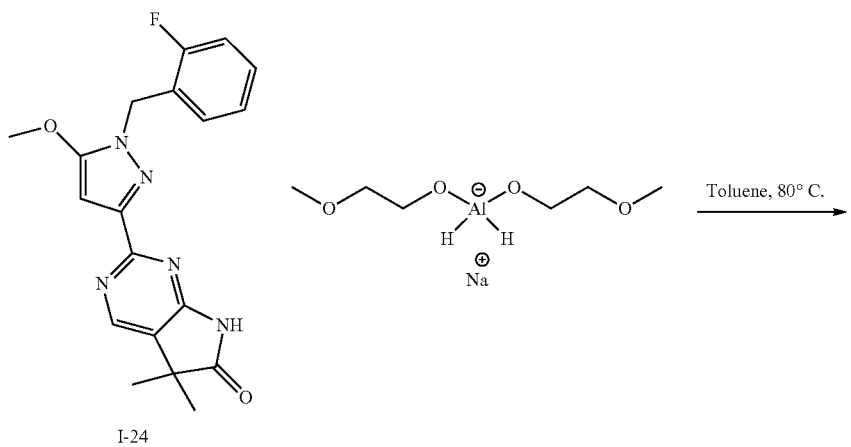

A mixture of Compound I-24 (1 equiv.) and Red-Al® (6 equiv.) in toluene was stirred at 80° C. for 2 h. The mixture was cooled to 0° C., quenched with 1N NaOH solution, and diluted with water and ethyl acetate. Phases were separated and the aqueous phase was extracted twice with ethyl acetate. The combined organic phase was washed with brine, dried over anhydrous sodium sulfate, filtered and concentrated. The crude material was purified by reverse phase HPLC (C18 column, 5% to 95% acetonitrile in water with 0.1% formic acid over 20 mins) to obtain Compound I-27 (26 mg, 45% yield) as a white solid.

$^1$H NMR (500 MHz, METHANOL-$d_4$) δ ppm 7.77 (s, 1H) 7.25-7.41 (m, 1H) 7.07-7.21 (m, 3H) 6.44 (s, 1H) 5.36 (s, 2H) 4.02 (s, 3H) 3.66 (s, 2H) 1.43 (s, 6H). m/z=353.8 (M+H).

Compound I-28

-continued

An ice cold solution of Compound I-23 (1 equiv.) in TFA was added with water (27 equiv.) followed by sodium nitrite (1.5 equiv.) at which point gas evolution was observed. The reaction mixture was continued to stir at 0° C. for 20 mins, after which it was quenched by addition of water. The resultant precipitate was filtered, washed with water and dried in vacuo to obtain Compound I-28 (227 mg, 91% yield) as a pale yellow solid.

$^1$H NMR (500 MHz, DMSO-$d_6$) δ ppm 11.99 (br s, 1H) 10.99 (s, 1H) 7.34-7.40 (m, 1H) 7.16-7.25 (m, 3H) 6.40 (s, 1H) 5.27 (s, 2H) 3.94 (s, 3H) 1.28 (s, 6H). m/z=384.1 (M+H).

Compound I-29

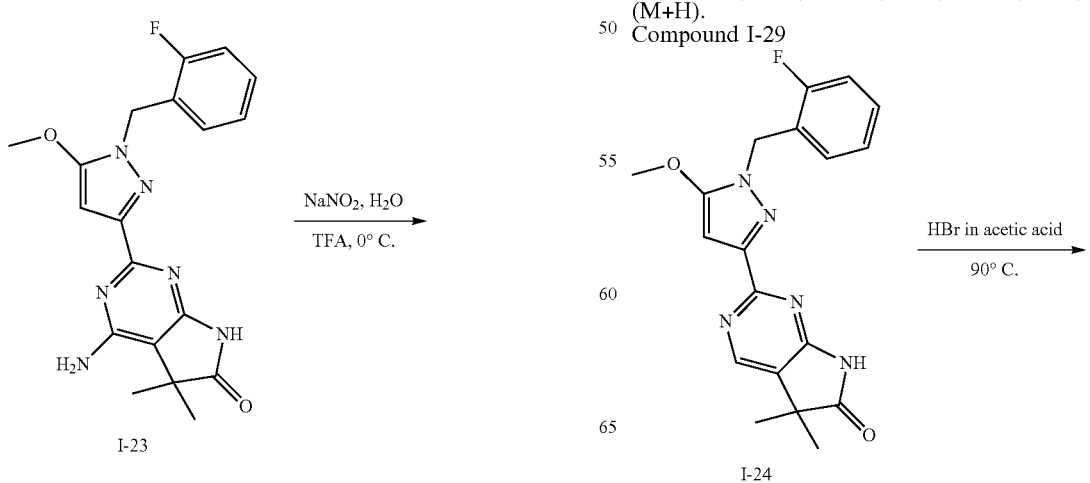

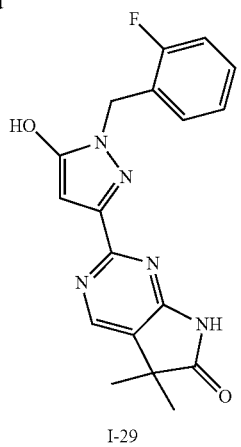

I-29

A mixture of Compound I-24 (1 equiv.) and hydrogen bromide (33% wt in acetic acid) (81 equiv.) was stirred at 90° C. for 8 h. After cooling, the mixture was diluted with ethyl acetate and saturated aqueous solution of sodium bicarbonate. Layers were separated and the aqueous phase was extracted with ethyl acetate thrice. The combined organic phase was washed with brine, dried over anhydrous sodium sulfate, filtered and concentrated. The crude material was purified by reverse phase HPLC (C18 column, 5% to 95% acetonitrile in water with 0.1% formic acid over 20 mins) to obtain Compound I-29 (114 mg, 79% yield) as a white solid.

$^1$H NMR (500 MHz, DMSO-d$_6$) δ ppm 11.71 (br s, 1H) 8.47-8.52 (m, 1H) 7.36 (q, 1H) 7.20-7.25 (m, 1H) 7.17 (t, 1H) 7.07-7.12 (m, 1H) 6.01-6.06 (m, 1H) 5.24 (br s, 2H) 1.34 (s, 6H). m/z=354.1 (M+H).

Compound I-30

The title compound was prepared in 3 steps:

Step 1: Synthesis of ethyl 5-(difluoromethoxy)-1-(2-fluorobenzyl)-1H-pyrazole-3-carboxylate

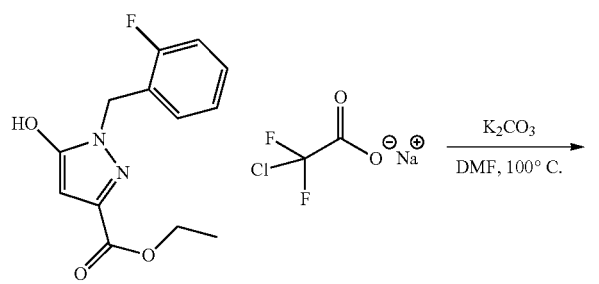

A mixture of potassium carbonate (1.1 equiv.), sodium 2-chloro-2,2-difluoroacetate (1.4 equiv.) and ethyl 1-(2-fluorobenzyl)-5-hydroxy-1H-pyrazole-3-carboxylate (1 equiv.) [Step 1 of the synthesis of Intermediate-4) in DMF was stirred at 100° C. overnight. After cooling, the mixture was diluted with ethyl acetate. The organic phase was washed with water three times, dried over anhydrous magnesium sulfate, filtered and concentrated. The residue was purified by silica gel chromatography (120 g ISCO, 0% to 50% ethyl acetate in hexane over 30 mins) to give ethyl 5-(difluoromethoxy)-1-(2-fluorobenzyl)-1H-pyrazole-3-carboxylate (1.34 g, 56% yield) as a yellow oil.

$^1$H NMR (500 MHz, DMSO-d$_6$) δ ppm 7.37 (s, 2H) 7.17-7.26 (m, 3H) 6.52 (s, 1H) 5.37 (s, 2H) 4.26 (q, 2H) 1.27 (t, 3H). m/z=314.9 (M+H).

Step 2: Synthesis of 5-(difluoromethoxy)-1-(2-fluorobenzyl)-1H-pyrazole-3-carboximidamide

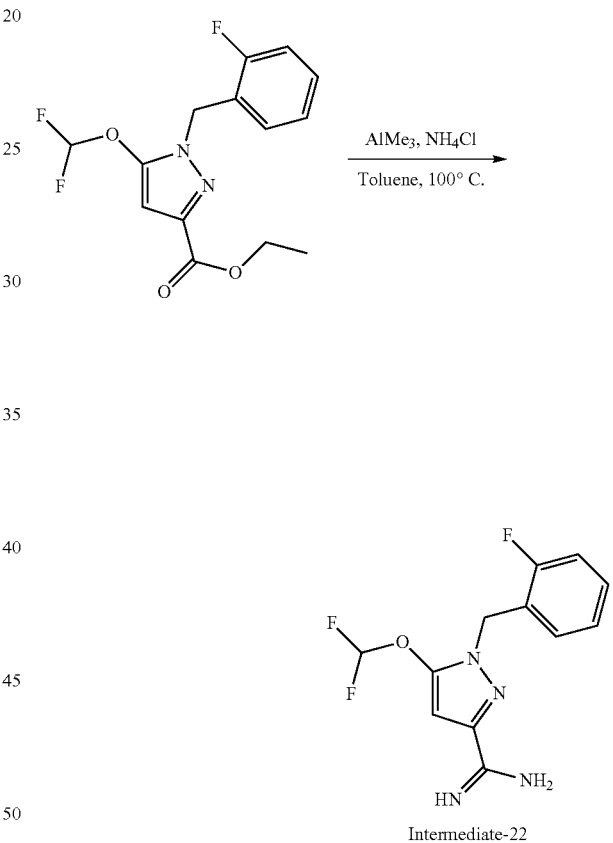

Intermediate-22

To a suspension of ammonium chloride (5.5 equiv.) in toluene at 0° C., was added, slowly, a 2.0 M solution of triethylaluminum in toluene. The mixture was removed from the ice bath and stirred at room temperature until the bubbling ceased. To this mixture, was added a solution of ethyl 5-(difluoromethoxy)-1-(2-fluorobenzyl)-1H-pyrazole-3-carboxylate (1 equiv.) in toluene. The mixture was stirred at 100° C. overnight. The reaction mixture was then cooled to 0° C., carefully added with methanol (10 ml) and stirred for 3 h at room temperature. The white precipitate was filtered off and washed with methanol. The filterate was brought to dryness to give 5-(difluoromethoxy)-1-(2-fluorobenzyl)-1H-pyrazole-3-carboximidamide (1.1 g, 92% yield) as a pale yellow solid. m/z=285.1 (M+H).

Step 3: Synthesis of Compound I-30

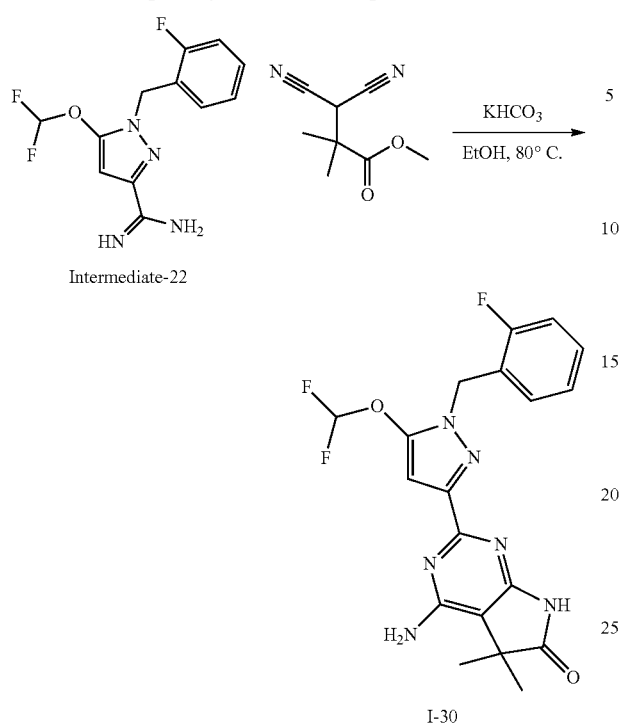

A mixture of 5-(difluoromethoxy)-1-(2-fluorobenzyl)-1H-pyrazole-3-carboximidamide (Intermediate-22, 1 equiv.), methyl 3,3-dicyano-2,2-dimethylpropanoate (2.4 equiv.) and potassium bicarbonate (3.6 equiv.) in ethanol was heated to reflux overnight. After cooling, the reaction mixture was added with water and stirred for 30 min. The precipitate was filtered, washed with a minimum amount of water and diethyl ether and then dried overnight under high vacuum to give Compound I-30 (1.3 g, 77% yield) as a pale cream colored solid.

$^1$H NMR (500 MHz, DMSO-$d_6$) δ ppm 10.88 (s, 1H) 7.34-7.42 (m, 2H) 7.15-7.26 (m, 3H) 6.64 (br s, 2H) 6.46 (s, 1H) 5.32 (s, 2H) 1.31 (s, 6H). m/z=419.1 (M+H).

Compound I-31

The title compound was prepared in 2 steps:

Step 1: Synthesis of 4-bromo-2-(5-(difluoromethoxy)-1-(2-fluorobenzyl)-1H-pyrazol-3-yl)-5,5-dimethyl-5H-pyrrolo[2,3-d]pyrimidin-6(7H)-one

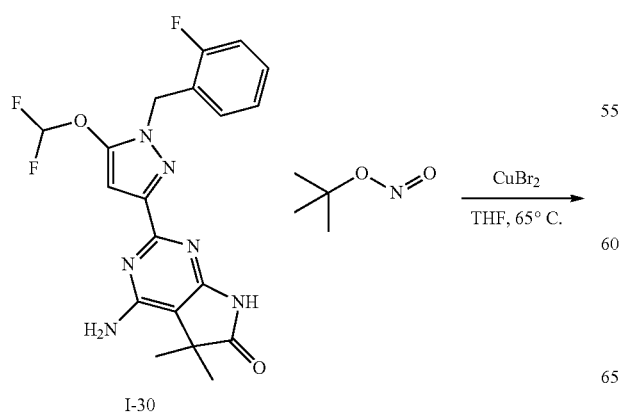

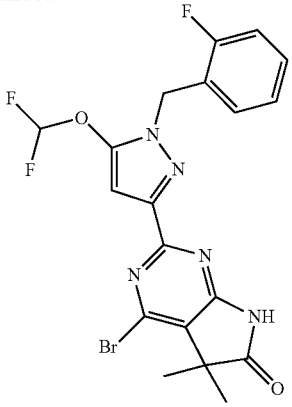

A mixture of Compound I-30 (1 equiv.), tert-butyl nitrite (1.5 equiv.) and copper (II) bromide (1.2 equiv.) in THF was heated to reflux overnight. After cooling, the insoluble salts were filtered off and washed with DCM. The filterate was partitioned with water and the separated aqueous phase was back extracted with DCM (twice). The combined organic phase was concentrated to give a crude residue that was carried forward to the next step without any purification.

Step 2: Synthesis of Compound I-31

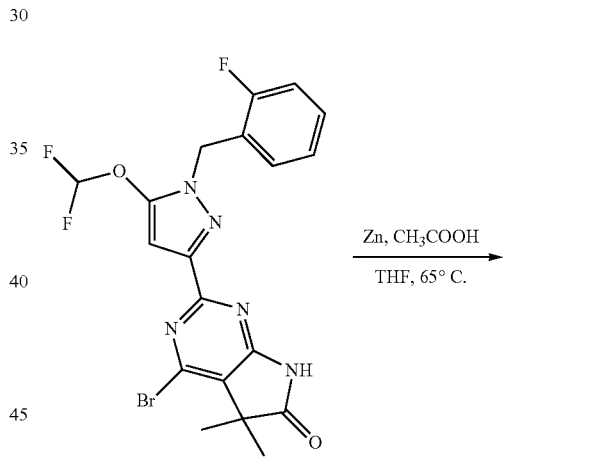

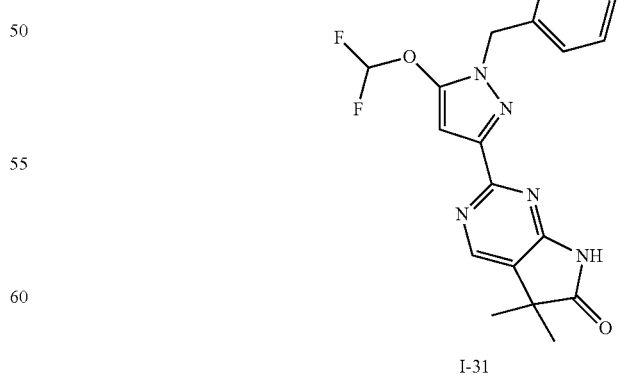

A mixture of 4-bromo-2-(5-(difluoromethoxy)-1-(2-fluorobenzyl)-1H-pyrazol-3-yl)-5,5-dimethyl-5H-pyrrolo[2,3-d]pyrimidin-6(7H)-one (1 equiv.), zinc dust (10 equiv.) and acetic acid (15 equiv.) in THF was heated to reflux overnight. After cooling, the insoluble salts were filtered off and the filterate was concentrated in vacuo. The residue was diluted with 1N HCl and stirred at 60° C. for 3 h. After cooling, the mixture was neutralized with 1 N NaOH and then extracted with ethyl acetate thrice. The combined organic phase was washed with brine, dried over anhydrous sodium sulfate, filtered and concentrated. The crude material was then purified by reverse phase HPLC (C18 column, 5% to 95% acetonitrile in water with 0.1% TFA over 20 mins) to obtain Compound I-31 (0.55 g, 51% yield) as a white solid.

$^1$H NMR (500 MHz, DMSO-$d_6$) δ ppm 11.48 (s, 1H) 8.49 (s, 1H) 7.36-7.42 (m, 2H) 7.18-7.27 (m, 3H) 6.61 (s, 1H) 5.36 (s, 2H) 1.34 (s, 6H). m/z=404.1 (M+H).

Compound I-32

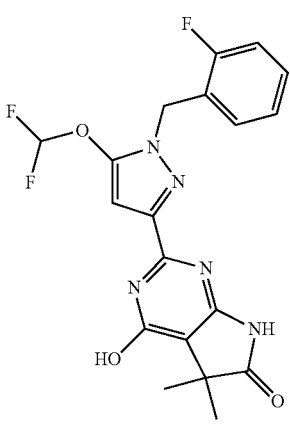

I-32

The aqueous phase from the above experiment (step 2 of Compound I-31) was acidified to pH 2 with 6 N HCl and left standing overnight. The resultant precipitate was filtered, washed with water and dried in vacuo to obtain Compound I-32 (30 mg, 3% yield) as a white solid.

$^1$H NMR (500 MHz, DMSO-$d_6$) δ ppm 12.22 (br s, 1H) 11.00 (br s, 1H) 7.36-7.43 (m, 2H) 7.19-7.33 (m, 3H) 6.74 (br s, 1H) 5.38 (s, 2H) 1.29 (s, 6H). m/z=420.2 (M+H).

Compound I-33

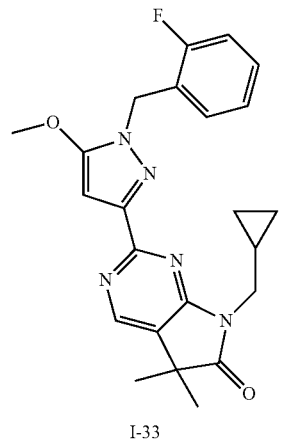

I-33

A mixture of Compound I-24 (1 equiv.) and sodium hydride (1.68 equiv.) in DMF was stirred at room temperature for 1 h. The mixture was then added with cyclopropyl methyl bromide (3 equiv.) and stirred at 50° C. for 2 h, after which it was diluted with water and ethyl acetate. Phases were separated and the aqueous phase was extracted twice with ethyl acetate. The combined organic phase was washed with brine, dried over anhydrous sodium sulfate, filtered and concentrated. The crude material was purified by reverse phase HPLC (C18 column, 5% to 95% acetonitrile in water with 0.1% TFA over 20 mins) to obtain Compound I-33 (38 mg, 59% yield) as a white solid.

$^1$H NMR (500 MHz, DMSO-$d_6$) δ ppm 8.54 (s, 1H) 7.36 (q, 1H) 7.23 (t, 1H) 7.16 (t, 1H) 7.04 (t, 1H) 6.40 (s, 1H) 5.29 (s, 2H) 3.96 (s, 3H) 3.60 (d, 2H) 1.38 (s, 6H) 1.15-1.25 (m, 1H) 0.41-0.51 (m, 2H) 0.34-0.40 (m, 2H). m/z=422.2 (M+H).

Compound I-34

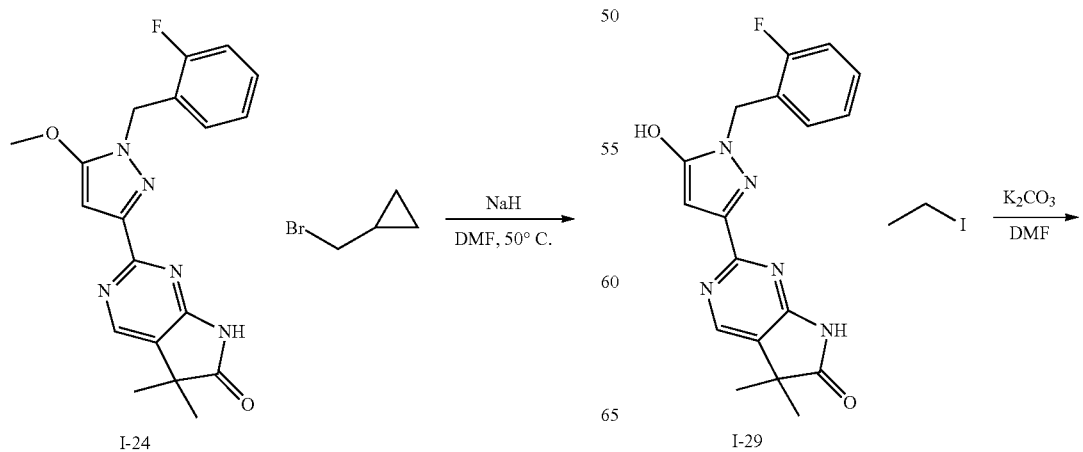

255
-continued

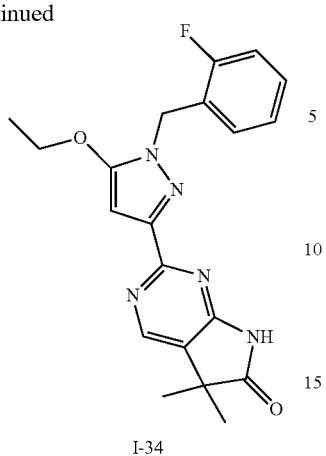

I-34

256
-continued

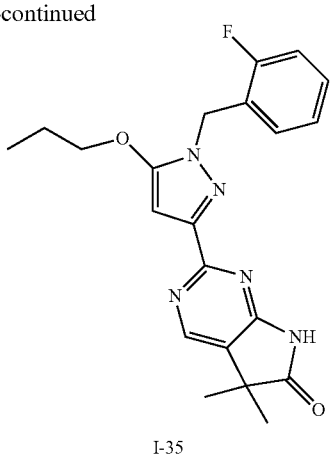

I-35

A mixture of potassium carbonate (1.2 equiv.), iodo ethane (1 equiv.) and Compound I-29 (1 equiv.) in DMF was stirred at room temperature 3 h. The mixture was quenched with saturated aqueous ammonium chloride, and diluted with water and ethyl acetate. Phases were separated and aqueous phase was extracted with ethyl acetate twice. The combined organic phase was washed with water, brine, dried over anhydrous magnesium sulfate, filtered and concentrated. The crude material was purified by reverse phase HPLC (C18 column, 5% to 95% acetonitrile in water with 0.1% TFA over 20 mins) to obtain Compound I-34 (11 mg, 68% yield) as a white solid.

$^1$H NMR (500 MHz, DMSO-$d_6$) δ ppm 11.48 (s, 1H) 8.47 (s, 1H) 7.33-7.39 (m, 1H) 7.10-7.24 (m, 3H) 6.30 (s, 1H) 5.24 (s, 2H) 4.19-4.25 (m, 2H) 1.29-1.37 (m, 9H). m/z=382.2 (M+H).

Compound I-35

A mixture of potassium carbonate (1.2 equiv.), 1-iodo propane (1 equiv.) and Compound I-29 (1 equiv.) in DMF was stirred at room temperature overnight. The mixture was quenched with saturated aqueous ammonium chloride, diluted with water and ethyl acetate. Phases were separated and aqueous phase was extracted with ethyl acetate twice. The combined organic phase was washed with water, brine, dried over anhydrous magnesium sulfate, filtered and concentrated. The crude material was purified by reverse phase HPLC (C18 column, 5% to 95% acetonitrile in water with 0.1% TFA over 20 mins) to obtain Compound I-35 (6.3 mg, 38% yield) as a yellow solid.

$^1$H NMR (500 MHz, DMSO-$d_6$) δ ppm 11.51 (s, 1H) 8.48 (s, 1H) 7.32-7.39 (m, 1H) 7.10-7.24 (m, 3H) 6.29 (s, 1H) 5.26 (s, 2H) 4.12 (t, 2H) 1.68-1.76 (m, 2H) 1.34 (s, 6H) 0.93 (t, 3H). m/z=396.2 (M+H).

Compound I-36

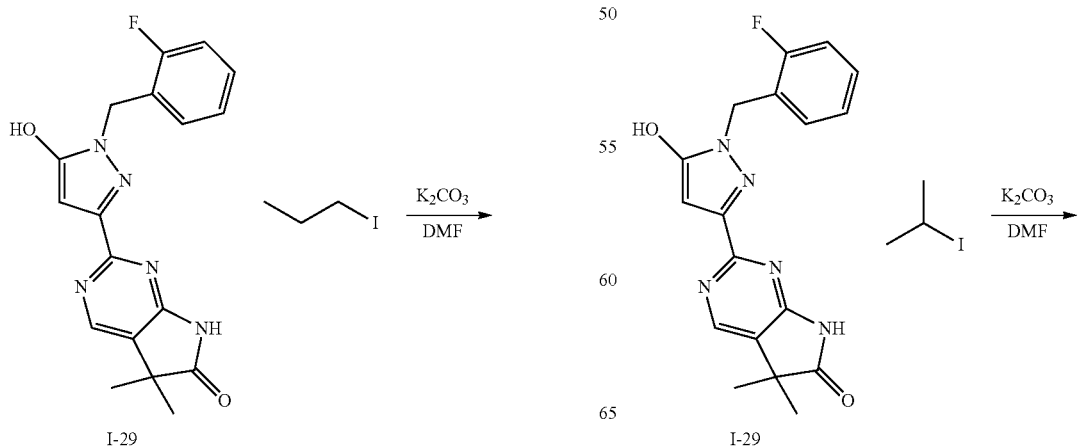

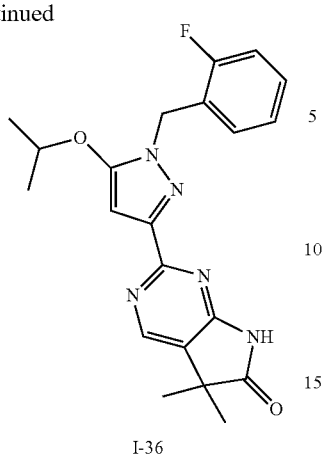

I-36

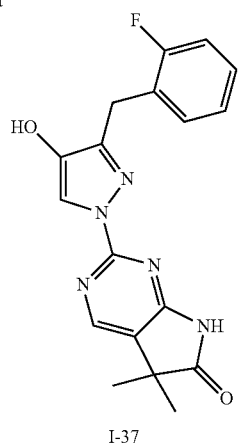

I-37

A mixture of potassium carbonate (1.2 equiv.), 2-iodo propane (1 equiv.) and Compound I-29 (1 equiv.) in DMF was stirred at room temperature overnight. The mixture was quenched with saturated aqueous ammonium chloride, diluted with water and ethyl acetate. Phases were separated and aqueous phase was extracted with ethyl acetate twice. The combined organic phase was washed with water, brine, dried over anhydrous magnesium sulfate, filtered and concentrated. The crude material was purified by reverse phase HPLC (C18 column, 5% to 95% acetonitrile in water with 0.1% TFA over 20 mins) to obtain Compound I-36 (5.8 mg, 35% yield) as a white solid.

$^1$H NMR (500 MHz, DMSO-$d_6$) δ ppm 11.54 (br s, 1H) 8.48 (s, 1H) 7.30-7.42 (m, 1H) 7.11-7.24 (m, 3H) 6.30 (s, 1H) 5.23 (s, 2H) 4.60 (dquin, 1H) 1.34 (s, 6H) 1.30 (s, 3H) 1.28 (s, 3H). m/z=396.2 (M+H).

Compound I-37

A mixture of Compound I-38 (1 equiv.) and hydrogen bromide (33% wt in acetic acid) (100 equiv.) was stirred at 90° C. for 48 h. After cooling, the mixture was diluted with ethyl acetate and saturated aqueous solution of sodium bicarbonate. Layers were separated and the aqueous phase was extracted twice with ethyl acetate. The combined organic phase was washed with brine, dried over anhydrous magnesium sulfate, filtered and concentrated. The crude material was purified by reverse phase HPLC (C18 column, 5% to 95% acetonitrile in water with 0.1% formic acid over 20 mins) to obtain Compound I-37 (25 mg, 21% yield) as a white solid.

$^1$H NMR (500 MHz, METHANOL-$d_4$) δ ppm 8.53 (s, 1H) 8.29 (s, 1H) 8.03 (s, 1H) 7.17-7.28 (m, 2H) 7.01-7.09 (m, 2H) 4.06 (s, 2H) 1.43 (s, 6H). m/z=354.1 (M+H).

Compound I-39

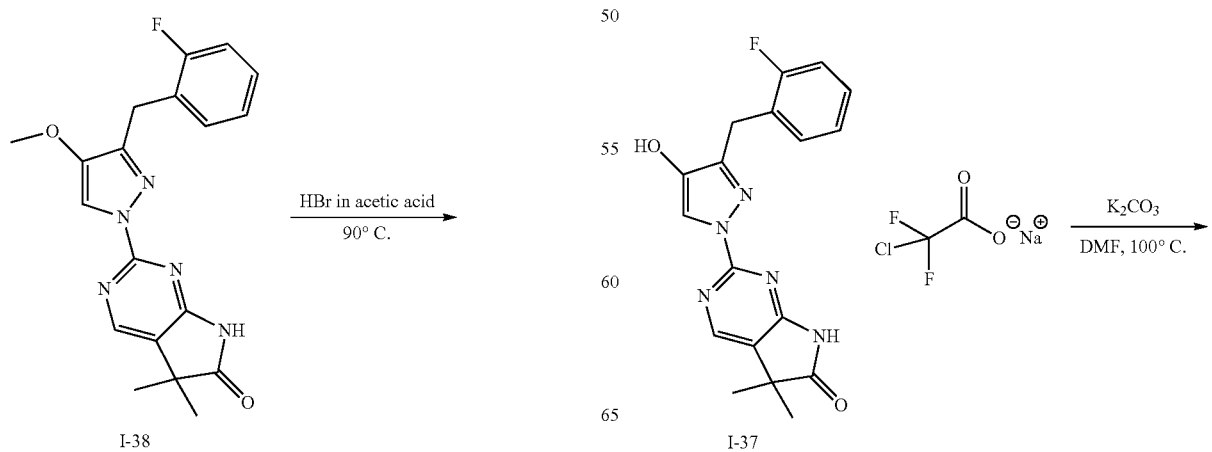

259
-continued

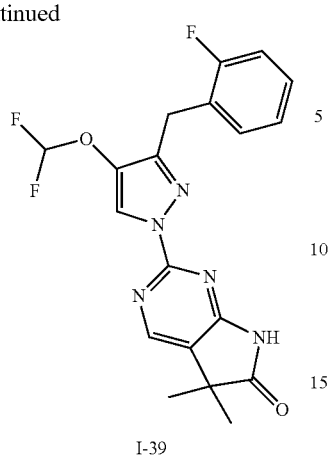
I-39

A mixture of potassium carbonate (1.1 equiv.), sodium 2-chloro-2,2-difluoroacetate (1.4 equiv.) and Compound I-37 (1 equiv.) in DMF was stirred at 100° C. overnight. After cooling, the mixture was diluted with water and ethyl acetate. Phases were separated and aqueous phase was extracted with ethyl acetate twice. The combined organic phase was washed with water, brine, dried over anhydrous magnesium sulfate, filtered and concentrated. The crude material was purified by reverse phase HPLC (C18 column, 5% to 95% acetonitrile in water with 0.1% TFA over 20 mins) to obtain Compound I-39 (2 mg, 7% yield) as a white solid.

$^1$H NMR (500 MHz, METHANOL-$d_4$) δ ppm 8.53 (s, 2H) 8.51 (s, 1H) 8.35 (s, 1H) 7.21-7.30 (m, 2H) 7.04-7.12 (m, 2H) 4.10 (s, 2H) 1.45 (s, 6H). m/z=396.2 (M+H).

Compound I-40

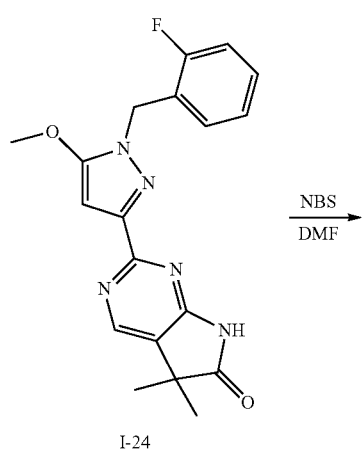
I-24

→ NBS / DMF

260
-continued

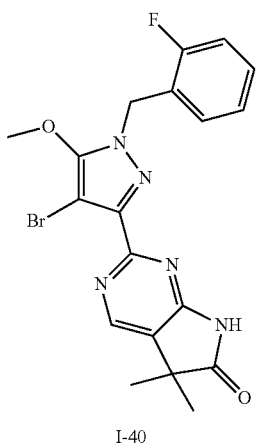
I-40

A mixture of Compound I-24 (1 equiv.) and N-bromosuccinimide (1.5 equiv.) in DMF was stirred at room temperature overnight. The mixture was diluted with water and ethyl acetate. Phases were separated and the aqueous phase was extracted twice with ethyl acetate. The combined organic phase was washed with brine, dried over anhydrous magnesium sulfate, filtered and concentrated. The crude material was purified by silica gel chromatography (24 g ISCO, 30% to 100% ethyl acetate in hexane over 30 mins) to obtain Compound I-40 (33 mg, 49% yield) as a yellowish orange solid.

$^1$H NMR (500 MHz, DMSO-$d_6$) δ ppm 11.52 (s, 1H) 8.54 (s, 1H) 7.35-7.43 (m, 1H) 7.17-7.28 (m, 3H) 5.34 (s, 2H) 4.01 (s, 3H) 1.34 (s, 6H). m/z=446.1 and 448.1 (M+H).

Compound I-41

The title compound was prepared in 4 steps:

Step 1: Synthesis of ethyl 1-(2-fluorobenzyl)-5-hydroxy-4-methyl-1H-pyrazole-3-carboxylate

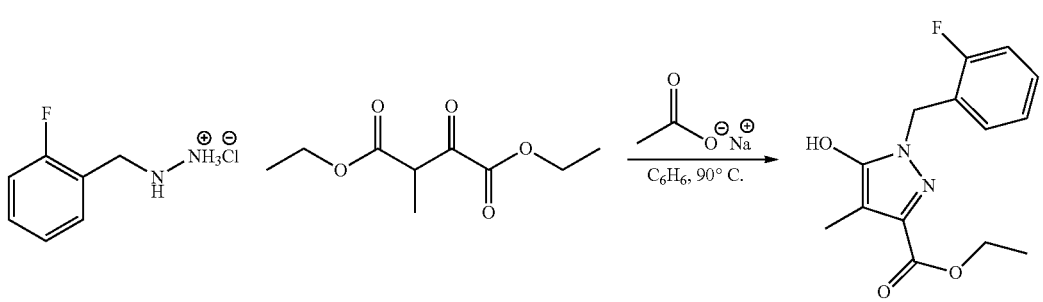

A mixture containing (2-fluorobenzyl) hydrazine hydrochloride (1 equiv.), diethyl 2-methyl-3-oxosuccinate (1 equiv.) and sodium acetate (1 equiv.) in benzene was stirred at 90° C. overnight. After cooling, the mixture was diluted with ethyl acetate and water. Phases were separated and the organic phase was washed with water, dried over anhydrous magnesium sulfate, filtered and concentrated. The crude material was purified by silica gel chromatography (80 g ISCO, 30% to 100% ethyl acetate in hexane over 35 mins) to give ethyl 1-(2-fluorobenzyl)-5-hydroxy-4-methyl-1H-pyrazole-3-carboxylate (2.9 g, 49% yield) as an offwhite solid.

$^1$H NMR (500 MHz, DMSO-$d_6$) δ ppm 10.73 (s, 1H) 7.35 (q, 1H) 7.21 (t, 1H) 7.16 (t, 1H) 7.01 (t, 1H) 5.22 (s, 2H) 4.20 (q, 2H) 2.05 (s, 3H) 1.25 (t, 3H). m/z=279.1 (M+H).

Step 2: Synthesis of ethyl 1-(2-fluorobenzyl)-5-methoxy-4-methyl-1H-pyrazole-3-carboxylate

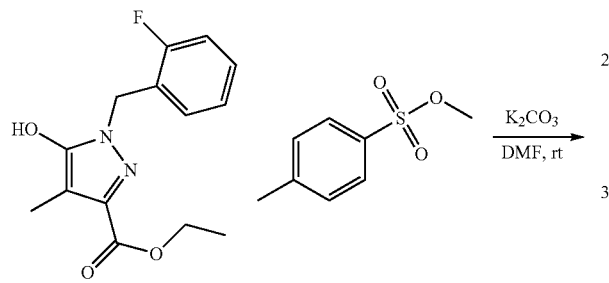

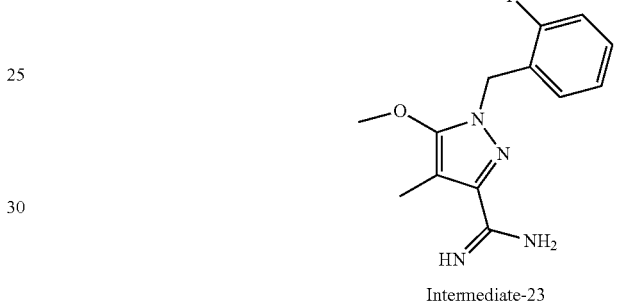

A mixture of potassium carbonate (4 equiv.), methyl ester of p-toluenesulfonic acid (1.5 equiv.) and ethyl 1-(2-fluorobenzyl)-5-hydroxy-4-methyl-1H-pyrazole-3-carboxylate (1 equiv.) in DMF was stirred at room temperature for 24 h. The mixture was diluted with ethyl acetate and washed with water twice. The organic phase was then washed with brine, dried over anhydrous magnesium sulfate, filtered and concentrated. The crude material was purified by silica gel chromatography (80 g ISCO, 0% to 30% ethyl acetate in hexane over 35 mins) to give ethyl 1-(2-fluorobenzyl)-5-methoxy-4-methyl-1H-pyrazole-3-carboxylate (1.1 g, 88% yield) as a colorless viscous oil.

$^1$H NMR (500 MHz, DMSO-$d_6$) δ ppm 7.35-7.40 (m, 1H) 7.23 (t, 1H) 7.18 (t, 1H) 7.09 (td, 1H) 5.27 (s, 2H) 4.23 (q, 2H) 3.85 (s, 3H) 2.15 (s, 3H) 1.26 (t, 3H). m/z=293.1 (M+H).

Step 3: Synthesis of 1-(2-fluorobenzyl)-5-methoxy-4-methyl-1H-pyrazole-3-carboximidamide

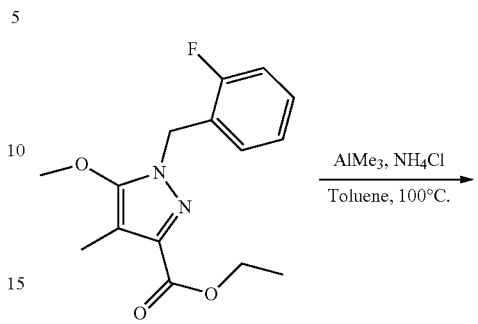

Intermediate-23

To a suspension of ammonium chloride (5.5 equiv.) in toluene at 0° C., was added, slowly, a 2.0 M solution of triethylaluminum in toluene. The mixture was removed from the ice bath and stirred at room temperature until the bubbling ceased. To this mixture, was added a solution of ethyl 1-(2-fluorobenzyl)-5-methoxy-4-methyl-1H-pyrazole-3-carboxylate (1 equiv.) in toluene. The mixture was stirred at 100° C. overnight. The reaction mixture was then cooled to 0° C., carefully added with methanol (10 ml) and stirred for overnight at room temperature. The white precipitate was filtered off and washed with methanol. The filterate was brought to dryness to give 1-(2-fluorobenzyl)-5-methoxy-4-methyl-1H-pyrazole-3-carboximidamide (1.6 g, 177% yield) as a pale yellow solid. m/z=263.1 (M+H).

Step 4: Synthesis of Compound I-41

Intermediate-23

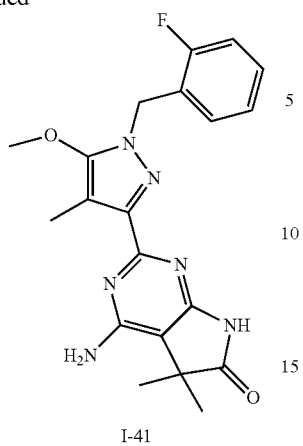

I-41

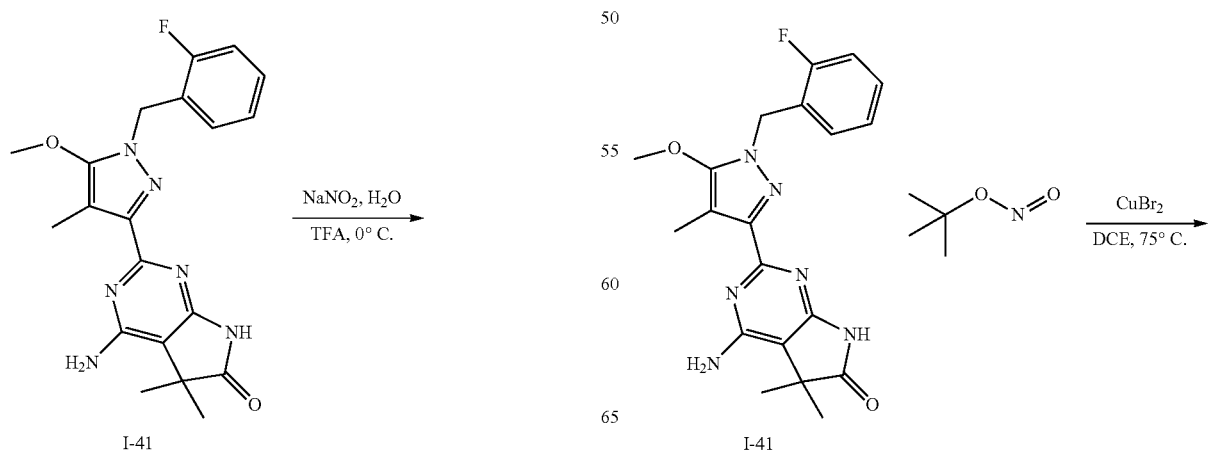

I-42

A mixture of 1-(2-fluorobenzyl)-5-methoxy-4-methyl-1H-pyrazole-3-carboximidamide (Intermediate-23, 1 equiv.), methyl 3,3-dicyano-2,2-dimethylpropanoate (3 equiv.) and potassium bicarbonate (3 equiv.) in t-butanol and ethanol (1.5:1) was heated to reflux for 24 h. After cooling, the mixture was concentrated to dryness and the residue was diluted with water and DCM. Layers were separated and the aqueous phase was extracted with DCM twice. The combined organic phase was then dried over anhydrous magnesium sulfate, filtered and concentrated. The crude material was purified by silica gel chromatography (40 g ISCO, 5% to 50% ethyl acetate in hexane over 30 mins) to give Compound I-41. A small portion of the material was further purified by reverse phase HPLC (C18 column, 5% to 95% acetonitrile in water with 0.1% formic acid over 20 mins) to obtain Compound I-41 (82 mg, 52% yield) as a white solid.

$^1$H NMR (500 MHz, DMSO-$d_6$) δ ppm 11.23 (br s, 1H) 7.30-7.44 (m, 1H) 7.21-7.27 (m, 1H) 7.18 (t, 1H) 7.07 (t, 1H) 5.29 (s, 2H) 3.88 (s, 3H) 2.30 (s, 3H) 1.34 (s, 6H). m/z=397.2 (M+H).

Compound I-42

An ice cold solution of Compound I-41 (1 equiv.) in TFA was added with water (27 equiv.) followed by sodium nitrite (1.5 equiv.) at which point gas evolution was observed. The reaction mixture was continued to stir at 0° C. for 20 mins, after which it was quenched by addition of water. The resultant precipitate was filtered, washed with water and dried in vacuo to obtain Compound I-42 (40 mg, 78% yield) as a white solid.

$^1$H NMR (500 MHz, DMSO-$d_6$) δ ppm 11.63 (s, 1H) 10.96 (s, 1H) 7.34-7.41 (m, 1H) 7.16-7.30 (m, 3H) 5.29 (s, 2H) 3.88 (s, 3H) 2.25 (s, 3H) 1.29 (s, 6H). m/z=398.1 (M+H).

Compound I-43

The title compound was prepared in 2 steps:

Step 1: Synthesis of 4-bromo-2-(1-(2-fluorobenzyl)-5-methoxy-4-methyl-1H-pyrazol-3-yl)-5,5-dimethyl-5H-pyrrolo[2,3-d]pyrimidin-6(7H)-one -continued

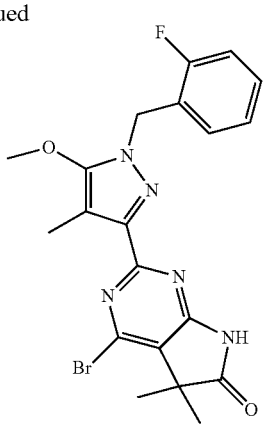

A mixture of Compound I-41 (1 equiv.), tert-butyl nitrite (1.5 equiv.) and copper (II) bromide (1.2 equiv.) in dichloroethane was heated to reflux overnight. After cooling, the insoluble salts were filtered off and washed with DCM. The filtrate was partitioned with water and the separated organic phase was washed with saturated aqueous sodium bicarbonate solution thrice, then washed with brine, dried over anhydrous magnesium sulfate, filtered and concentrated. The crude material was carried forward to the next step without any purification.

Step 2: Synthesis of Compound I-43

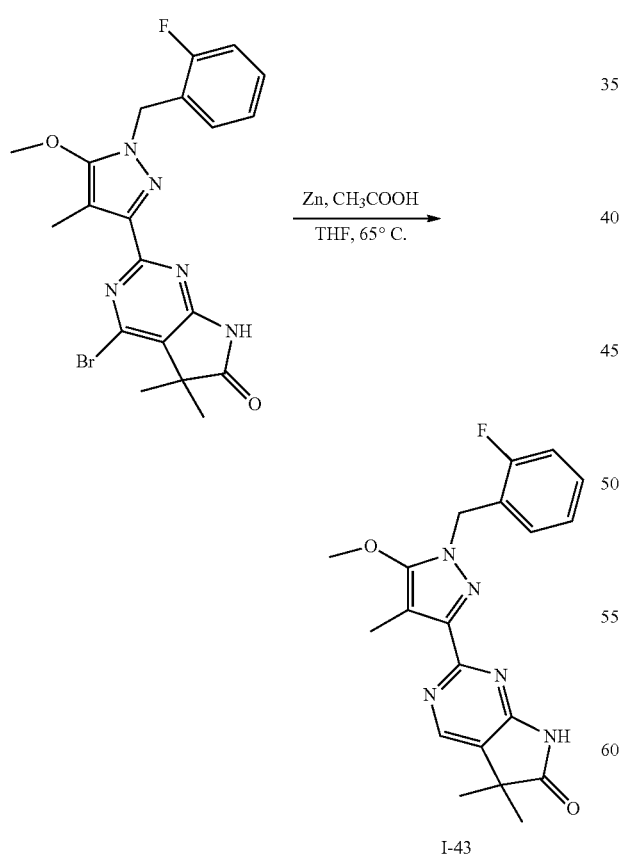

I-43

A mixture of crude 4-bromo-2-(1-(2-fluorobenzyl)-5-methoxy-4-methyl-1H-pyrazol-3-yl)-5,5-dimethyl-5H-pyrrolo[2,3-d]pyrimidin-6(7H)-one (1 equiv.), zinc dust (10 equiv.) and acetic acid (15 equiv.) in THF was heated to reflux overnight. After cooling, the insoluble salts were filtered off and the filterate was concentrated in vacuo. The residue was diluted with ethyl acetate and washed with saturated aqueous sodium bicarbonate solution twice followed by brine, then dried over anhydrous sodium sulfate, filtered and concentrated. The crude material was then purified by reverse phase HPLC (C18 column, 5% to 95% acetonitrile in water with 0.1% formic acid over 20 mins) to obtain Compound I-43. For further purification, a small portion of the material was diluted with 1N HCl and stirred at 60° C. for 3 h. After cooling, the mixture was diluted with DCM and saturated aqueous sodium bicarbonate solution. Phases were separated and the organic layer was washed with saturated aqueous sodium bicarbonate solution again, dried over anhydrous magnesium sulfate, filtered and concentrated. The residue was then dissolved in 1:1 water/acetonitrile mixture with 0.1% TFA and then lyophilized to obtain Compound I-43 (53 mg, 39% yield) as a white solid.

$^1$H NMR (500 MHz, DMSO-$d_6$) δ ppm 11.64 (br s, 1H) 8.53 (s, 1H) 7.37 (q, 1H) 7.23 (t, 1H) 7.18 (t, 1H) 7.06-7.15 (m, 1H) 5.29 (s, 2H) 3.89 (s, 3H) 2.30 (s, 3H) 1.35 (s, 6H). m/z=382.2 (M+H).

Compound I-44

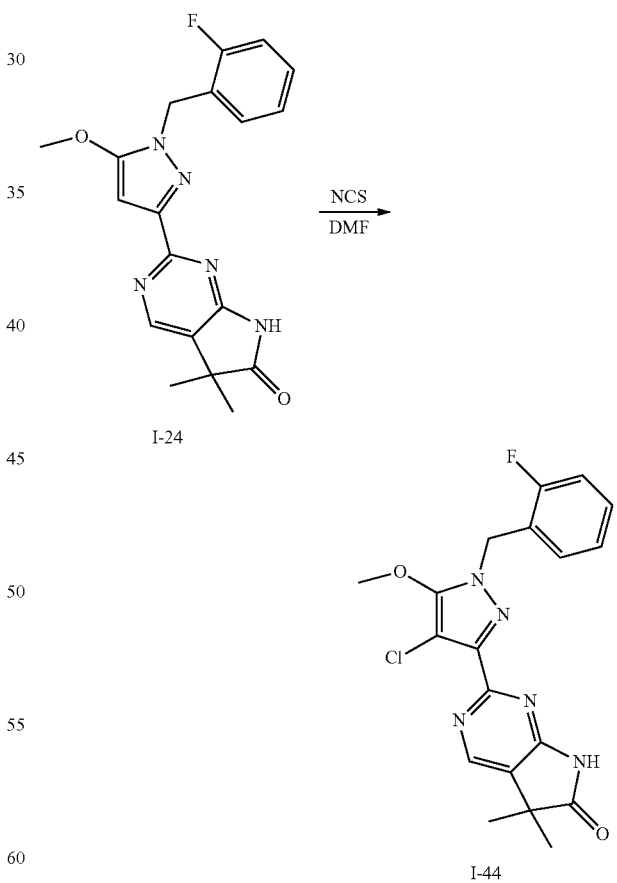

I-44

A mixture of Compound I-24 (1 equiv.) and N-chlorosuccinimide (1.5 equiv.) in DMF was stirred at room temperature overnight. The mixture was diluted with water and ethyl acetate. Phases were separated and the aqueous phase was extracted twice with ethyl acetate. The combined organic phase was washed with brine, dried over anhydrous magnesium sulfate, filtered and concentrated. The crude material was purified by silica gel chromatography (24 g ISCO, 30% to 100% ethyl acetate in hexane over 30 mins) to obtain Compound I-44 (21 mg, 35% yield) as a yellowish orange solid.

$^1$H NMR (500 MHz, DMSO-d$_6$) δ ppm 11.53 (s, 1H) 8.54 (s, 1H) 7.36-7.44 (m, 1H) 7.18-7.27 (m, 3H) 5.32 (s, 2H) 4.04 (s, 3H) 1.34 (s, 6H). m/z=402.1 (M+H).

Compound I-45

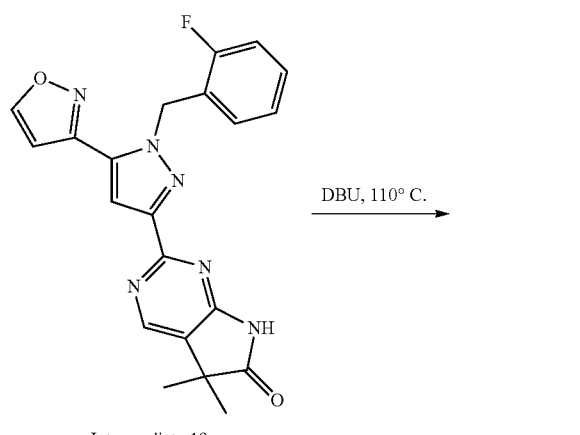

Intermediate 19

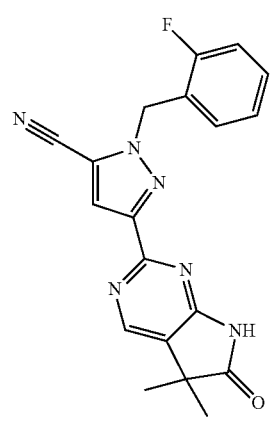

I-45

A mixture of 2-(1-(2-fluorobenzyl)-5-(isoxazol-3-yl)-1H-pyrazol-3-yl)-5,5-dimethyl-5H-pyrrolo[2,3-d]pyrimid in-6(7H)-one (1 equiv, Intermediate 19) and DBU (27 equiv.) was stirred at 110° C. for 42 h. After cooling, the reaction mixture was diluted with DCM and 1 N HCl. Phases were separated and the aqueous phase was extracted with DCM twice. The combined organic phase was dried over anhydrous magnesium sulfate, filtered and concentrated. The crude material was purified by reverse phase HPLC (C18 column, 5% to 95% acetonitrile in water with 0.1% formic acid over 20 mins) to obtain Compound I-45 (23 mg, 52% yield) as a white solid.

$^1$H NMR (500 MHz, DMSO-d$_6$) δ ppm 11.59 (s, 1H) 8.54 (s, 1H) 7.70 (s, 1H) 7.41-7.48 (m, 1H) 7.34-7.40 (m, 1H) 7.21-7.31 (m, 2H) 5.68 (s, 2H) 1.34 (s, 6H). m/z=363.1 (M+H).

Compound I-48

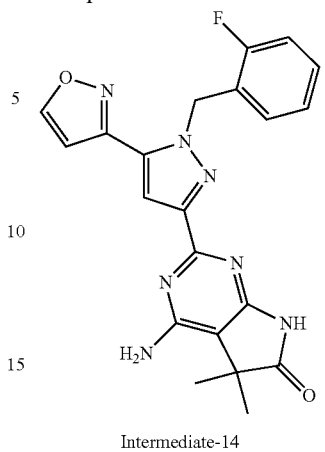

Intermediate-14

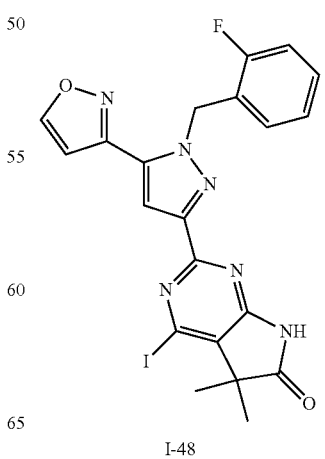

I-48

A mixture of 4-amino-2-(1-(2-fluorobenzyl)-5-(isoxazol-3-yl)-1H-pyrazol-3-yl)-5,5-dimethyl-5H-pyrrolo[2,3-d]pyrimidin-6(7H)-one (2.5 g, 5.96 mmol, Intermediate-14), diiodomethane (80 equiv.) and amyl nitrite (23 equiv.) was heated to 85° C. for 24 h. An excess amyl nitrite was removed in vacuuo. The resulting residue was purified by column chromatography using an EtOAc/Hexanes gradient to give Compound I-48 (927 mg, 29% yield) as a yellow solid: $^1$H NMR (500 MHz, DMSO-d6) δ ppm 9.09-9.12 (m, 1H) 7.56 (s, 1H) 7.34 (d, 2H) 7.20-7.25 (m, 1H) 7.11 (t, 1H) 6.85 (t, 1H) 5.94 (s, 2H) 1.38-1.42 (m, 6H).

Compound I-49

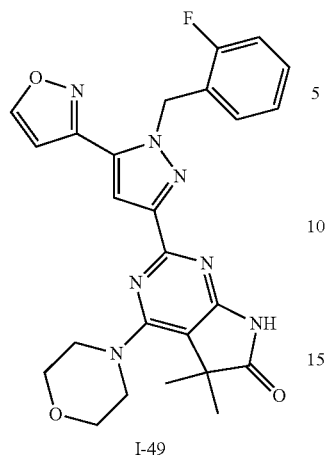

I-49

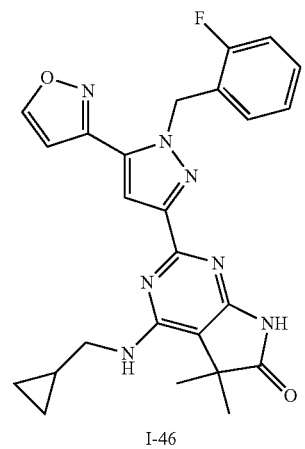

I-46

A mixture of 2-(1-(2-fluorobenzyl)-5-(isoxazol-3-yl)-1H-pyrazol-3-yl)-4-iodo-5,5-dimethyl-5H-pyrrolo[2,3-d]pyrimidin-6(7H)-one (Compound I-48, 200 mg, 0.38 mmol), DIPEA (4.0 equiv.) and morpholine (6.0 equiv.) in NMP (3.0 ml) was heated in microwave to 150° C. for 18 h. The mixture was diluted in ethyl acetate (100 ml) and washed with water (50 ml). The organic layer was dried, filtered and evaporated to give an oil. The oil was purified by column chromatography using an EtOAc/hexanes gradient, rinsed with a minimal amount of methanol-diethyl ether mixture and dried in vauco to give Compound I-49 (95 mg, 52% yield) as a white solid. $^1$H NMR (500 MHz, DMSO-$d_6$) δ ppm 9.09 (d, 1H) 7.51 (s, 1H) 7.29-7.37 (m, 1H) 7.18-7.27 (m, 2H) 7.10 (td, 1H) 6.83 (t, 1H) 5.90 (s, 2H) 3.68-3.79 (m, 8H) 1.39 (s, 6H).

Compound I-46

A mixture of 2-(1-(2-fluorobenzyl)-5-(isoxazol-3-yl)-1H-pyrazol-3-yl)-4-iodo-5,5-dimethyl-5H-pyrrolo[2,3-d]pyrimidin-6(7H)-one (Compound I-48, 200 mg, 0.38 mmol), DIPEA (4.0 equiv.) and cyclopropylmethanamine (6.0 equiv.) in NMP (3.0 ml) was heated in microwave to 150° C. for 18 h. The mixture was diluted in ethyl acetate (100 ml) and washed with water (50 ml). The organic layer was dried, filtered and evaporated in vacuo to give an oil. The oil was purified by column chromatography using an EtOAc/hexanes gradient, rinsed with a minimal amount of methanol-diethyl ether mixture and dried in vauco to give Compound I-46 (127 mg, 72% yield) as a yellow solid. $^1$H NMR (500 MHz, CHLOROFORM-d) δ ppm 8.33-8.36 (m, 1H) 7.18 (s, 1H) 7.03-7.11 (m, 1H) 6.88-6.93 (m, 1H) 6.83 (t, 1H) 6.70 (t, 1H) 6.50 (d, 1H) 5.88 (s, 2H) 4.40 (t, 1H) 3.42 (dd, 2H) 1.39 (s, 6H) 0.47-0.53 (m, 2H) 0.23 (q, 2H).

Compound I-47

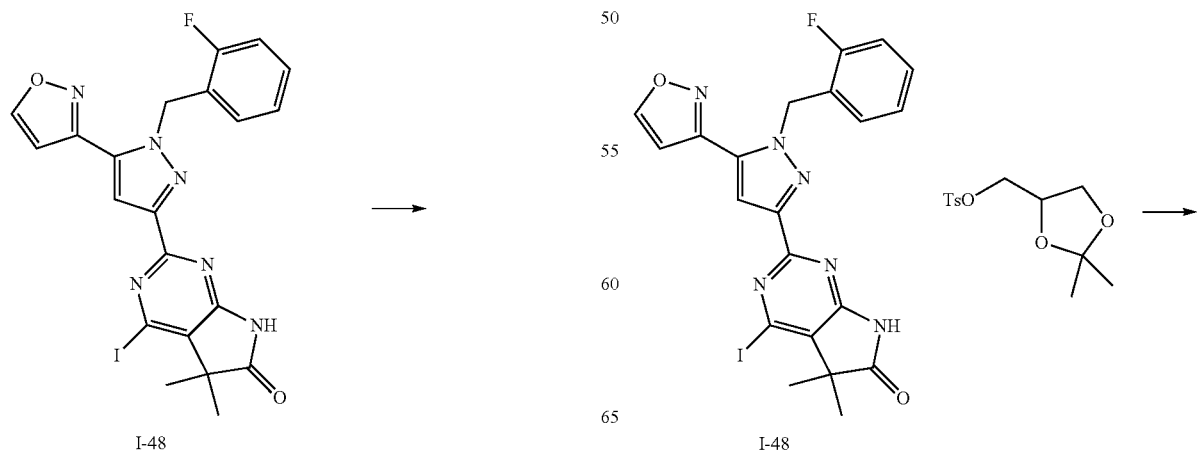

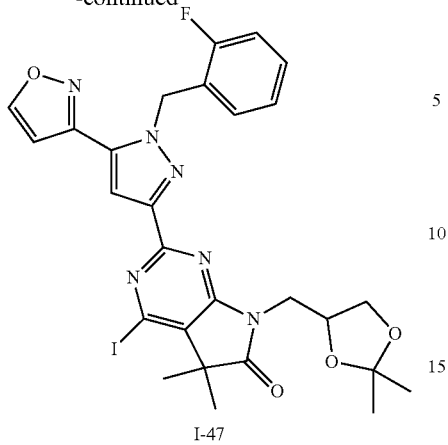

I-47

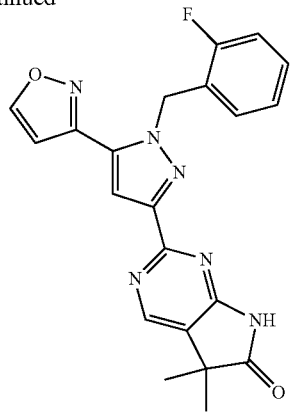

Intermediate-19

A mixture of Compound I-48 (101 mg, 0.19 mmol), potassium carbonate (1.5 equiv.) and (2,2-dimethyl-1,3-dioxolan-4-yl)methyl 4-methylbenzenesulfonate (3.0 equiv) in DMF (1 ml) was heated to 85° C. for 2 h. The mixture was diluted with ethyl acetate (100 ml) and washed with water (50 ml) and brine (50 ml). The organic layer was dried, filtered and evaporated in vacuo to give an oil. The oil was purified by column chromatography using EtOAc/hexanes gradient to give Compound I-47 (44 mg, 36% yield) as a white solid. $^1$H NMR (500 MHz, DMSO-$d_6$) δ ppm 9.10 (d, 1H) 7.63 (s, 1H) 7.30-7.35 (m, 2H) 7.19-7.28 (m, 1H) 7.09 (t, 1H) 6.79 (t, 1H) 5.97 (s, 2H) 4.40-4.50 (m, 2H) 3.92 (dd, 1H) 3.86 (dd, 1H) 3.76 (dd, 1H) 1.44 (d, 6H) 1.31 (s, 3H) 1.21 (s, 3H).

Compound I-50

The title compound was synthesized in 3 steps.

Step 1: Synthesis of 2-(1-(2-fluorobenzyl)-5-(isoxazol-3-yl)-1H-pyrazol-3-yl)-5,5-dimethyl-5H-pyrrolo[2,3-d]pyrimidin-6(7H)-one The hydrogenation of Compound I-48 (130 mg, 0.25 mmol) in acetic acid (22 ml, 0.01 M) was performed on an H-cube flow reactor equipped with 10% Pd/C CatCart at the flow rate of 0.7 ml/min. with an internal reactor temperature set at 80° C. and under the full hydrogen mode. The resulting solution was diluted in ethyl acetate (100 mL) and washed with 1N NaOH (50 ml). The organic layer was dried, filtered and evaporated to give an oil. The oil was purified by column chromatography using an EtOAc/hexanes gradient to give 2-(1-(2-fluorobenzyl)-5-(isoxazol-3-yl)-1H-pyrazol-3-yl)-5,5-dimethyl-5H-pyrrolo[2,3-d]pyrimidin-6(7H)-one (23 mg, 23% yield). $^1$H NMR (500 MHz, CHLOROFORM-d) δ ppm 8.38-8.40 (m, 1H) 8.33 (s, 1H) 7.35-7.37 (m, 1H) 7.08-7.15 (m, 1H) 6.92-6.98 (m, 1H) 6.88 (t, 1H) 6.75 (t, 1H) 6.53 (d, 1H) 5.95 (s, 2H) 1.43 (s, 6H).

Steps 2 and 3: Synthesis of Compound I-50

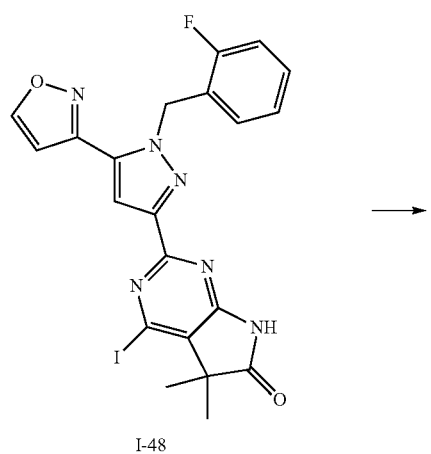

I-48

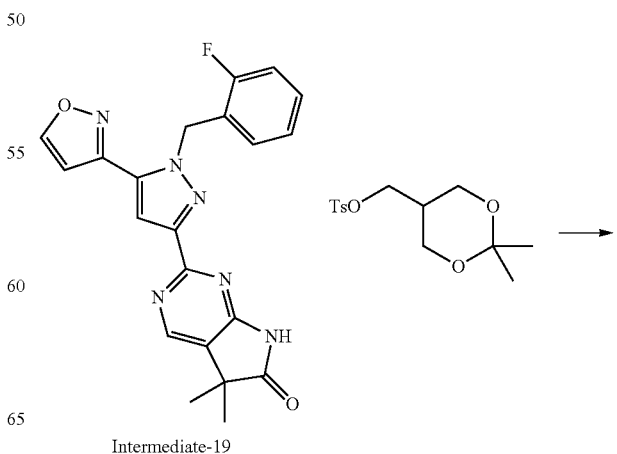

Intermediate-19

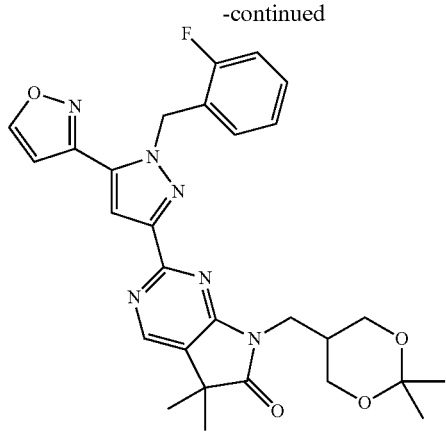

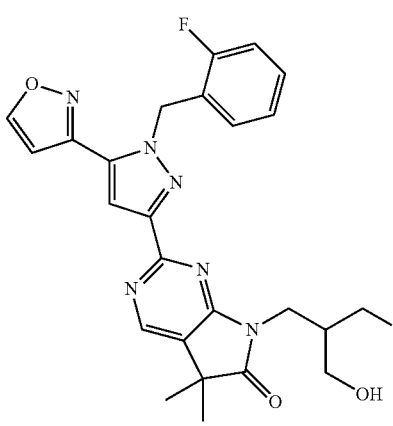

I-50

A mixture of 2-(1-(2-fluorobenzyl)-5-(isoxazol-3-yl)-1H-pyrazol-3-yl)-5,5-dimethyl-5H-pyrrolo[2,3-d]pyrimidin-6(7H)-one (57 mg, 0.14 mmol), postassium carbonate (2.0 equiv.) and (2,2-dimethyl-1,3-dioxan-5-yl)methyl 4-methylbenzenesulfonate (2.0 equiv.) in DMF (1.0 ml) was heated to 80° C. for 1 h. The mixture was diluted in ethyl acetate (50 ml) and washed with water (50 ml). The organic layer was dried, filtered and evaporated in vacuo to give an oil. The oil was purified by column chromatography using an EtOAc/hexanes gradient to give 7-((2,2-dimethyl-1,3-dioxan-5-yl)methyl)-2-(1-(2-fluorobenzyl)-5-(isoxazol-3-yl)-1H-pyrazol-3-yl)-5,5-dimethyl-5H-pyrrolo[2,3-d]pyrimidin-6(7H)-one a white solid. The solid was combined with HCl as a 4.0 M solution in dioxane (5.0 equiv) and DCM (1.0 ml). The mixture was stirred at rt for 2 h. The solvent was removed in vauco. The resulting residue was rinsed with a minimal amount of methanol and diethyl ether to give Compound I-50 (25 mg, 36% yield over two steps) as a light yellow solid. $^1$H NMR (500 MHz, DMSO-d$_6$) δ ppm 9.11 (d, 1H) 8.59 (s, 1H) 7.65 (s, 1H) 7.31-7.36 (m, 1H) 7.19-7.29 (m, 2H) 7.10 (t, 1H) 6.84 (t, 1H) 5.94 (s, 2H) 3.77 (d, 2H) 3.36-3.49 (m, 4H) 2.09-2.18 (m, 1H) 1.39 (s, 6H).

Compound I-51
The title compound was synthesized in 4 steps:

Step 1: Synthesis of ethyl 1-benzyl-5-hydroxy-1H-pyrazole-3-carboxylate

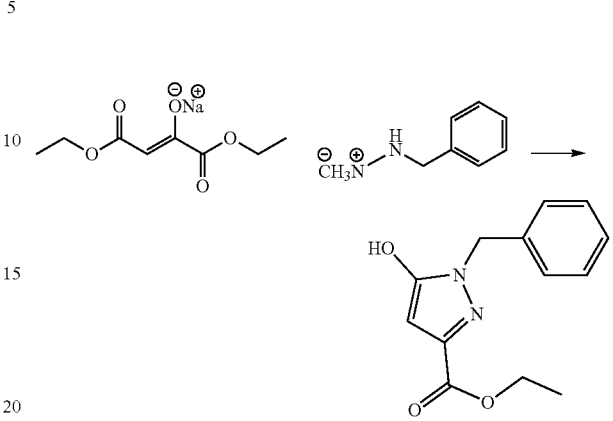

To a solution of sodium (Z)-1,4-diethoxy-1,4-dioxobut-2-en-2-olate (1 equiv.) and 2-benzylhydrazin-1-ium chloride (1.2 equiv.) in anhydrous benzene at 25° C. was added acetic acid (30 equiv.). The mixture was refluxed overnight. After cooling to ambient temperature, the reaction was concentrated under vacuum, and to it was added diethyl ether (100 ml). The resulting slurry was filtered, and the filter cake washed with diethyl ether (100 ml), collected, and dried under high vacuum to give ethyl 1-benzyl-5-hydroxy-1H-pyrazole-3-carboxylate (14.8 g, 126% yield) as a white crystalline powder. It was taken to the next step without purification. $^1$H NMR (500 MHz, DMSO-d6) δ ppm 7.32 (d, 3H), 7.27 (s, 1H), 7.17 (d, 2H), 5.85 (s, 1H), 5.15 (s, 2H), 4.20 (d, 2H), 1.25 (t, 3H).

Step 2: Synthesis of ethyl 1-benzyl-5-methoxy-1H-pyrazole-3-carboxylate

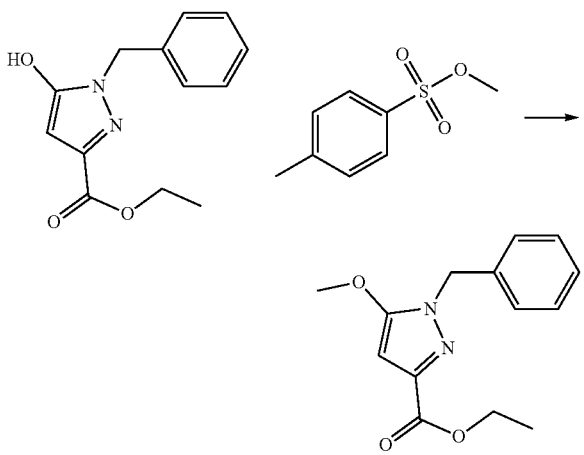

To a solution of ethyl 1-benzyl-5-hydroxy-1H-pyrazole-3-carboxylate (1 equiv.) and potassium carbonate (4 equiv.) in DMF was added methyl 4-methylbenzenesulfonate (1.5 equiv.) and reaction stirred overnight at 25° C. The purple solution was filtered through a celite pad and filter cake washed with ethyl acetate (75 ml). The filtrate was diluted with ethyl acetate (50 ml), washed with water (3×50 ml), dried over sodium sulfate, and concentrated to give an off white solid. Crude material was purified on a 120 g silica gel column using a 0-30% ethyl acetate hexane gradient to give ethyl 1-benzyl-5-methoxy-1H-pyrazole-3-carboxylate as a white solid. ¹H NMR (500 MHz, DMSO-d6) δ ppm 7.33 (d, 2H), 7.28 (s, 1H), 7.16 (d, 2H), 6.22 (s, 1H), 5.20 (s, 2H), 4.24 (d, 2H), 3.91 (s, 3H), 1.27 (t, 3H).

Step 3: Synthesis of
1-benzyl-5-methoxy-1H-pyrazole-3-carboximidamide
(Intermediate-24)

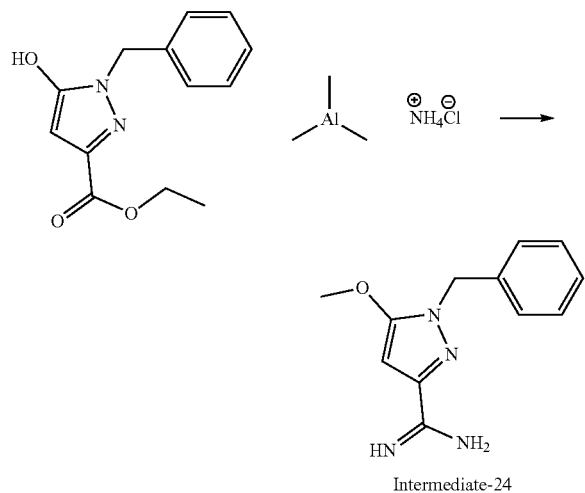

Intermediate-24

A suspension of ammonium chloride (5.5 equiv.) in toluene (100 mL) at 0 C was treated with trimethylaluminum (5 equiv.) as a 2M solution in toluene dropwise over 10 min. Suspension was warmed to 25° C. and stirred for 1 h. To it was added ethyl 1-benzyl-5-methoxy-1H-pyrazole-3-carboxylate (1 equiv.) as a solution in toluene (80 mL), and heated to 100° C. for 18 h. After cooling to ambient temperature a reaction was concentrated to 50 ml and cooled to 0 C. To it was added methanol (150 mL) slowly over the course of 20 min. The resultant white slurry was stirred at 0 C for 20 min, then warmed to 25° C. It was filtered through celite, and the filtere cake washed with methanol (3×100 ml). The filtrate was collected and concentrated to give crude 1-benzyl-5-methoxy-1H-pyrazole-3-carboximid-amide (15.3 g, 97% yield) as an off white solid.

Step 4: Synthesis of Compound I-51

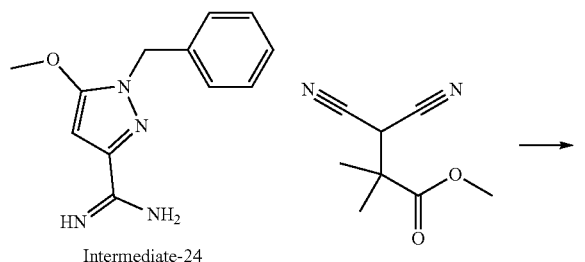

Intermediate-24

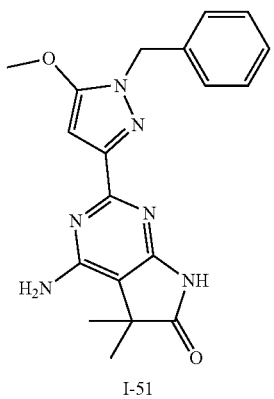

I-51

To a solution of 1-benzyl-5-methoxy-1H-pyrazole-3-carboximidamide (Intermediate-24, 1 equiv.) in t-BuOH (300 ml) was added methyl 3,3-dicyano-2,2-dimethylpropanoate (1.2 equiv.) and potassium hydrogencarbonate (4 equiv.). Reaction was stirred overnight at 80° C. After cooling to ambient temperature, solution was diluted with water (500 ml) and resultant precipitate collected by filtration. The filter cake was washed with water (50 ml) and ether (50 ml) and the filter cake dried to give the desired compound, Compound I-51 (10.9 g, 49% yield) as an off white solid. ¹H NMR (500 MHz, DMSO-d6) δ ppm 10.84 (s, 1H), 7.33 (m, 2H), 7.27 (s, 1H), 7.17 (d, 2H), 6.57 (br. s., 2H), 6.15 (s, 1H), 5.16 (s, 2H), 3.91 (s, 3H), 1.31 (s, 6H).

Compound I-52

The title compound was synthesized in 2 steps:

Step 1: Synthesis of 2-(1-benzyl-5-methoxy-1H-pyrazol-3-yl)-4-bromo-5,5-dimethyl-5H-pyrrolo[2,3-d]pyrimidin-6(7H)-one

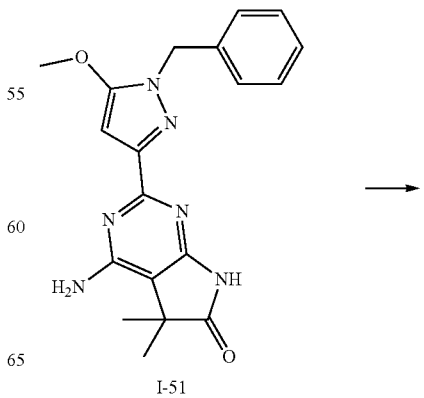

I-51

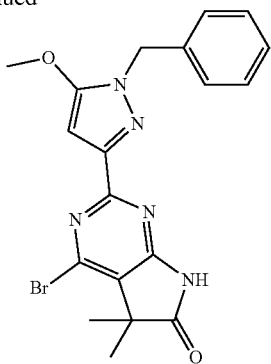

A mixture of 4-amino-2-(1-benzyl-5-methoxy-1H-pyrazol-3-yl)-5,5-dimethyl-5H-pyrrolo-[2,3-d]pyrimidin-6(7H)-one (Compound I-51, 1 equiv.), tert-butyl nitrite (2 equiv.), and copper(II) bromide (1.2 equiv.) in THF (318 ml) was stirred overnight at 65° C. After cooling to ambient temperature, reaction was concentrated, diluted with ethyl acetate (500 ml) and washed with aq. sat. EDTA (disodium) (2×100 ml). The organic layer was dried over sodium sulfate and concentrated to dryness to give 9 g of crude 2-(1-benzyl-5-methoxy-1H-pyrazol-3-yl)-4-bromo-5,5-dimethyl-5H-pyrrolo[2,3-d]pyrimidin-6(7H)-one as a yellow solid.

Step 2: Synthesis of Compound I-52

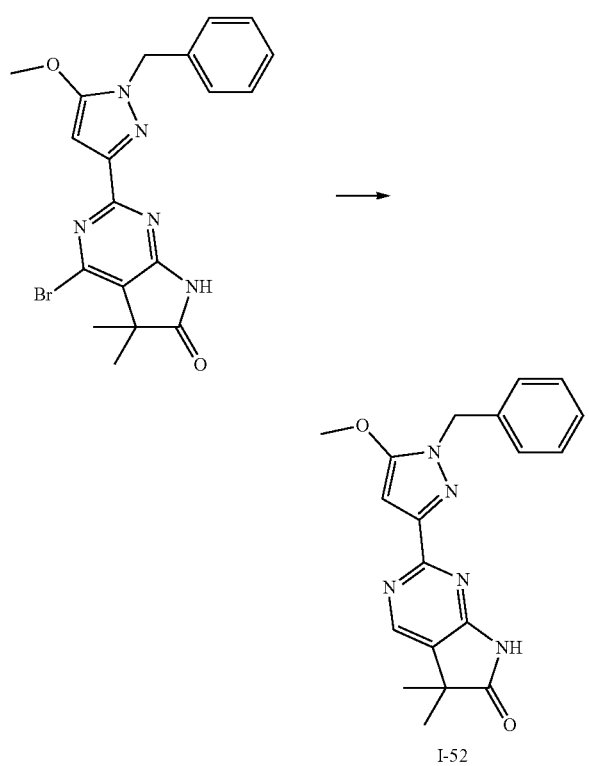

A mixture of 2-(1-benzyl-5-methoxy-1H-pyrazol-3-yl)-4-bromo-5,5-dimethyl-5H-pyrrolo-[2,3-d]pyrimidin-6(7H)-one (1 equiv.), zinc (10 equiv.), and acetic acid (15 equiv.) in THF (3 ml) was stirred at 80° C. for 2 h. After cooling to ambient temperature, reaction was filtered, and filtrate collected and concentrated. The crude material was purified via reverse phase HPLC utilizing a 30-80% acetonitrile water 0.1% formic acid gradient to deliver Compound I-52 (115 mg, 21% yield) as a white solid. $^1$H NMR (500 MHz, DMSO-d6) δ ppm 11.43 (s, 1H), 8.47 (s, 1H), 7.32 (m, 3H), 7.20 (d, 2H), 6.31 (s, 1H), 5.19 (s, 2H), 3.94 (s, 3H), 3.31 (s, 2H), 1.34 (s, 6H).

Compound I-53

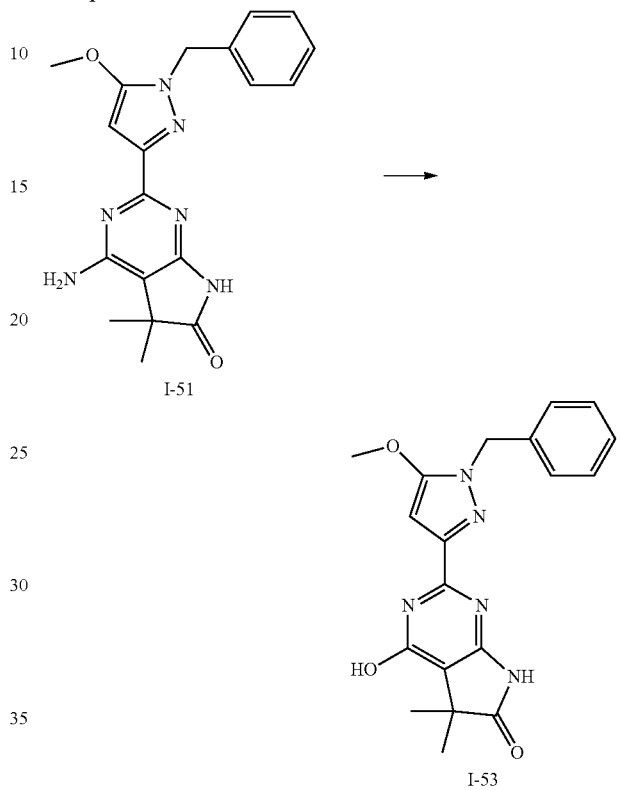

A solution of Compound I-51 (1 equiv.) in TFA was cooled to 0° C. To it was added water (100 ul) and sodium nitrite (1.5 equiv.) in one portion at which point gas evolved. The reaction was stirred for 20 min. at 0° C., after which it was quenched with the addition of water (2 ml). The resultant precipitate was collected by vacuum filtration, washed with water (4 ml) and ether (2 ml) and dried in vacuo to give 2-(1-benzyl-5-methoxy-1H-pyrazol-3-yl)-4-hydroxy-5,5-dimethyl-5H-pyrrolo[2,3-d]pyrimidin-6(7H)-one (60 mg, 80% yield) as a pale yellow solid. $^1$H NMR (500 MHz, DMSO-d6) δ ppm 11.99 (br. s., 1H), 10.99 (s, 1H), 7.30 (m, 5H), 6.38 (s, 1H), 5.21 (s, 2H), 3.93 (s, 3H), 1.29 (s, 6H).

Compound I-54

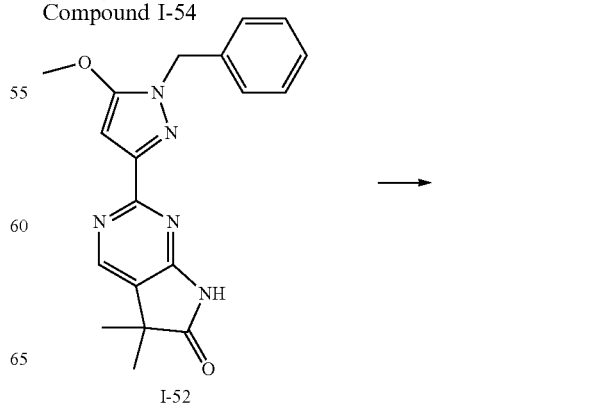

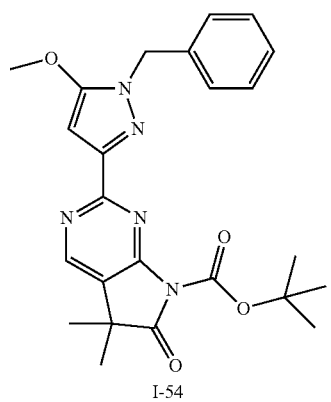

I-54

To a solution of Compound I-52 (1 equiv.), DMAP (1 equiv.), and TEA (1 equiv.) in DCM (3 ml) was added BOC-Anhydride 1M in THF (3 equiv.) at 0° C. After 30 min., reaction was allowed to warm to room temperature and stirred overnight. Reaction was diluted with ethyl acetate (5 ml), washed with 0.1N HCl (2×2 ml) and aqueous sodium bicarbonate (2 ml). The organic phase was dried over sodium sulfate, filtered and the solvent was removed in vacuo. The crude material was purified via silica gel chromatography utilizing a 0-100% ethyl acetate/hexanes gradient to deliver the desired compound, Compound I-54 (171 mg, 67% yield) as a white solid.

$^1$H NMR (500 MHz, DMSO-d6) δ ppm 8.70 (s, 1H), 7.33 (d, 2H), 7.28 (s, 1H), 7.20 (d, 2H), 6.32 (s, 1H), 5.21 (s, 2H), 3.94 (s, 3H), 1.60 (s, 9H), 1.42 (s, 6H)

Compound I-55

The title compound was synthesized in 2 steps:

Step 1: Synthesis of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20)

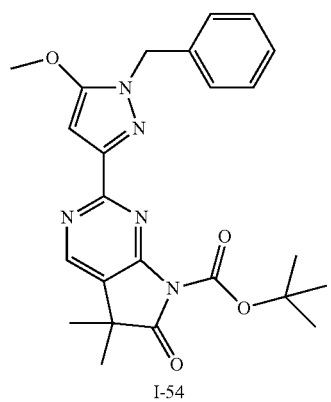

I-54

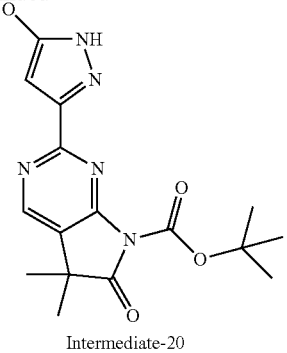

Intermediate-20

A solution of 2-(1-benzyl-5-methoxy-1H-pyrazol-3-yl)-5,5-dimethyl-6-oxo-5H-pyrrolo-[2,3-d]pyrimidine-7(6H)-carboxylate (Compound I-54, 1 equiv.), acetic acid (2 equiv.), and dihydroxypalladium (2 equiv.) in ethanol (10 ml) was added a balloon of hydrogen and stirred at room temperature overnight. Reaction was filtered through a pad of celite and washed with methanol (10 ml). The filtrate was collected and the solvent removed in vacuo to give tert-butyl 2-(5-methoxy-1H-pyrazol-3-yl)-5,5-dimethyl-6-oxo-5H-pyrrolo [2,3-d]pyrimidine-7(6H)-carboxylate (111 mg, 62% yield) of an off white solid.

Step 2: Synthesis of Compound I-55

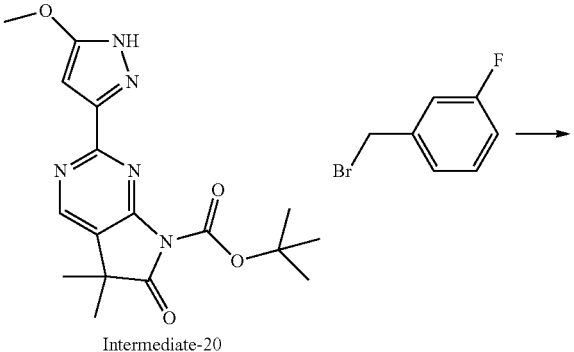

Intermediate-20

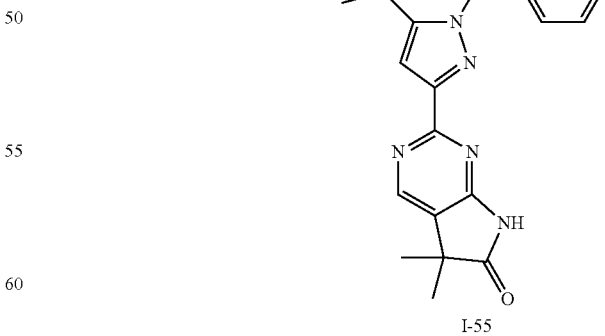

I-55

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-3-fluorobenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-55 (3.8 mg, 13% yield) as a white solid. $^1$H NMR (500 MHz, DMSO-d6) δ ppm 11.45 (s, 1H), 8.48 (s, 1H), 7.39 (d, 1H), 7.12 (t, 1H), 7.00 (m, 2H), 6.32 (s, 1H), 5.23 (s, 2H), 3.94 (s, 3H), 1.34 (s, 6H)

Compound I-56

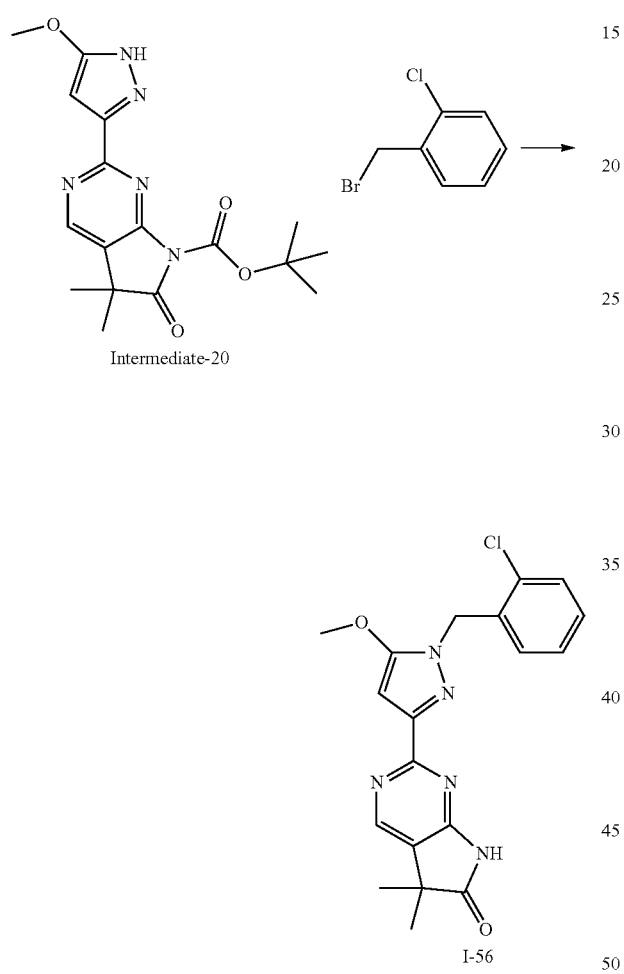

I-56

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-2-chlorobenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-56 (2 mg, 8% yield) as a white solid. $^1$H NMR (500 MHz, DMSO-d6) δ ppm 11.46 (s, 1H), 8.48 (s, 1H), 7.49 (d, 1H), 7.32 (td, 2H), 6.90 (dd, 1H), 6.35 (s, 1H), 5.28 (s, 2H), 3.95 (s, 3H), 1.34 (s, 6H)

Compound I-57

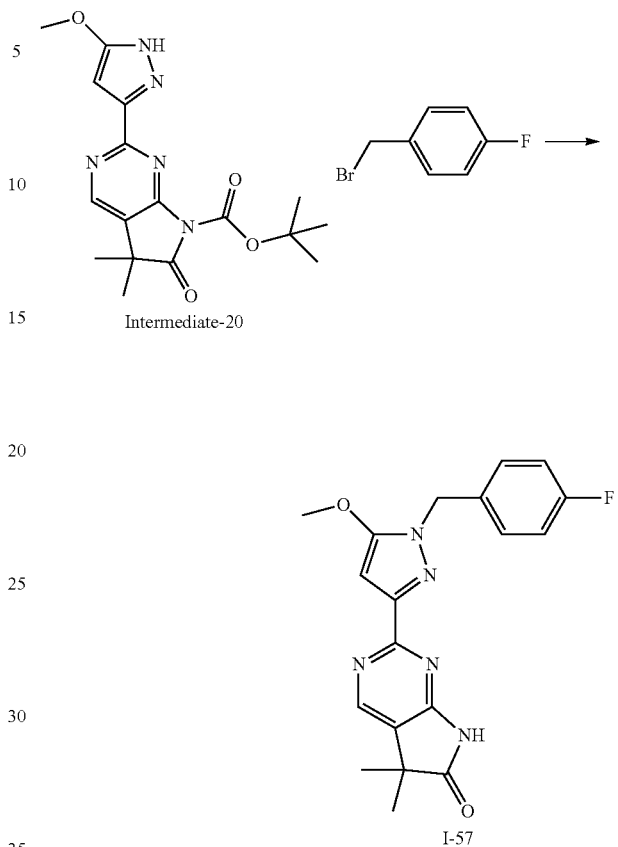

I-57

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-4-fluorobenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-57 (1.8 mg, 7% yield) as a white solid. $^1$H NMR (500 MHz, DMSO-d6) δ ppm 11.46 (s, 1H), 8.48 (s, 1H), 7.25 (dd, 2H), 7.18 (t, 2H), 6.31 (s, 1H), 5.18 (s, 2H), 3.94 (s, 3H), 1.34 (s, 6H)

Compound I-58

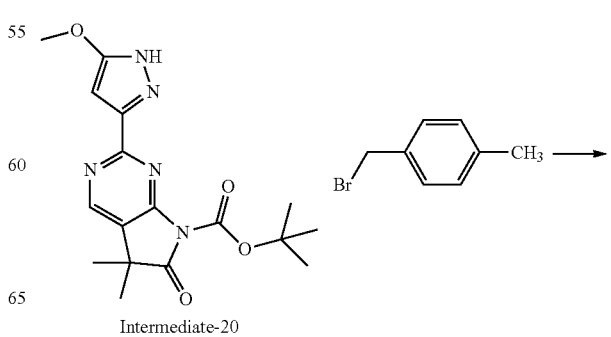

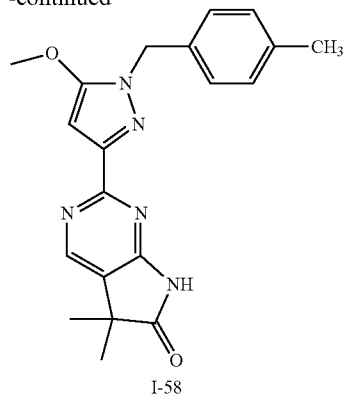

I-58

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-4-methylbenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-58 (3 mg, 12% yield) as a white solid. $^1$H NMR (500 MHz, DMSO-d6) δ ppm 11.46 (m, 1H), 8.47 (s, 1H), 7.11 (d, 4H), 6.29 (s, 1H), 5.13 (s, 2H), 3.93 (s, 3H), 2.26 (s, 3H), 1.34 (m, 6H)

Compound I-59

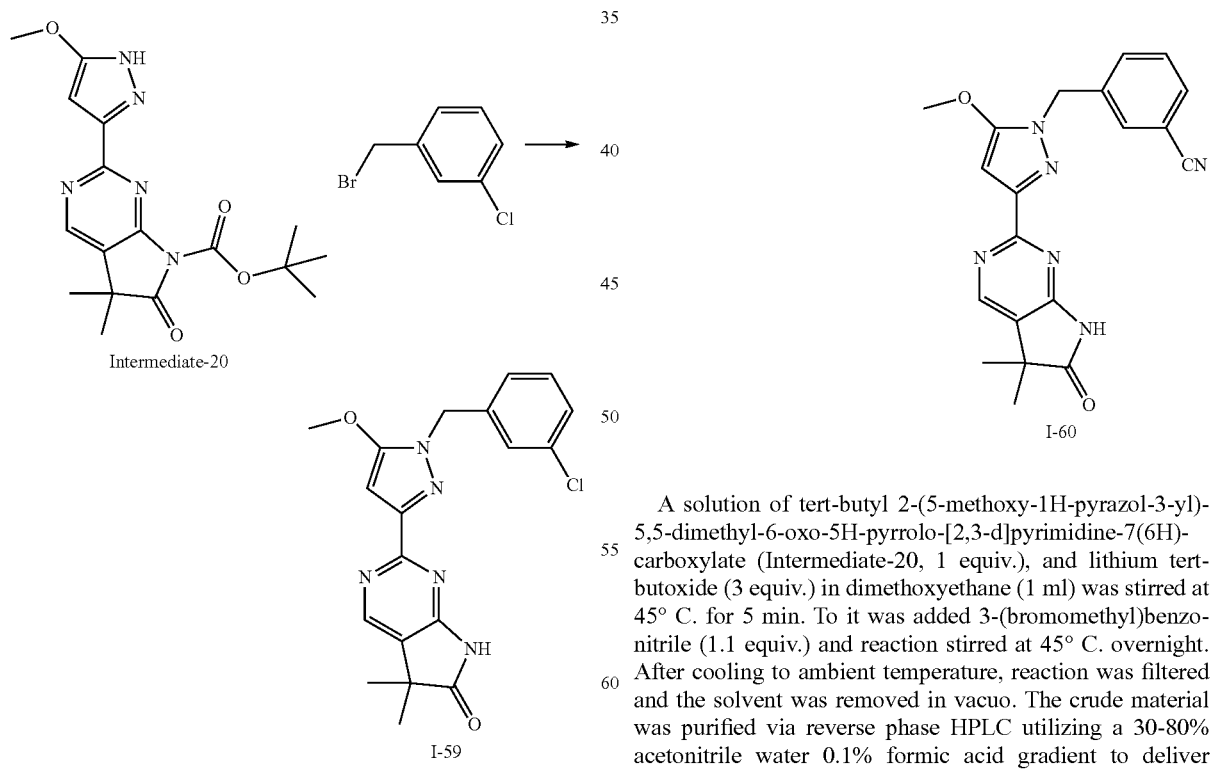

Intermediate-20

I-59

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-3-chlorobenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-59 (6.1 mg, 23% yield) as a white solid. $^1$H NMR (500 MHz, DMSO-d6) δ ppm 11.46 (s, 1H), 8.48 (s, 1H), 7.37 (m, 2H), 7.23 (s, 1H), 7.15 (d, 1H), 6.32 (s, 1H), 5.22 (s, 2H), 3.95 (s, 3H), 1.34 (s, 6H)

Compound I-60

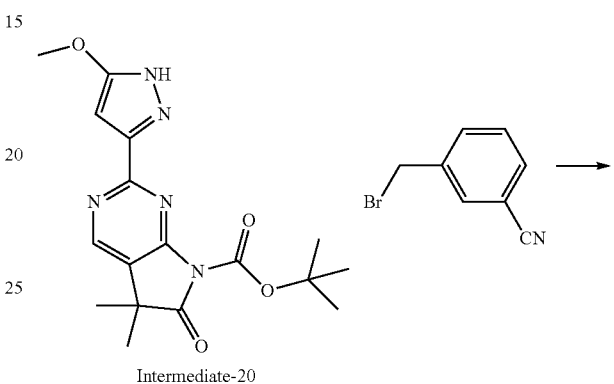

Intermediate-20

I-60

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 3-(bromomethyl)benzonitrile (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-60 (5 mg, 18% yield) as a white solid. $^1$H NMR (500 MHz, DMSO-d6) δ ppm 11.45 (s, 1H), 8.48 (s, 1H), 7.77 (d, 1H), 7.63 (s, 1H), 7.57 (t, 1H), 7.51 (d, 1H), 6.33 (s, 1H), 5.28 (s, 2H), 3.95 (s, 3H), 1.34 (s, 6H)

Compound I-61

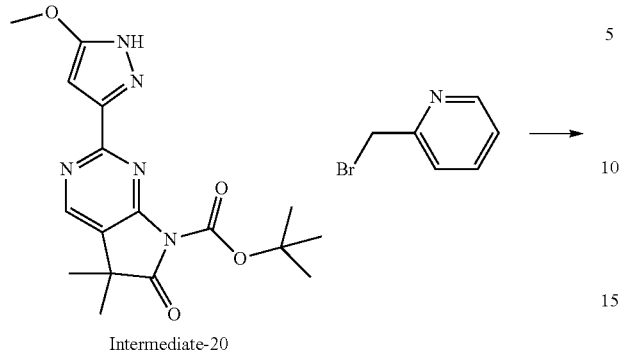
Intermediate-20

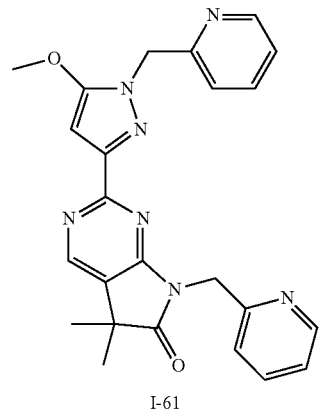
I-61

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 2-(bromomethyl)pyridine, HBr (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-61 (8.4 mg, 26% yield) as a white solid. $^1$H NMR (500 MHz, DMSO-d6) δ ppm 8.59 (s, 1H), 8.50 (d, 1H), 8.44 (d, 1H), 7.74 (d, 2H), 7.33 (d, 1H), 7.27 (dd, 2H), 6.93 (d, 1H), 6.34 (s, 1H), 5.28 (s, 2H), 5.05 (s, 2H), 3.90 (s, 3H), 1.43 (s, 6H)

Compound I-62

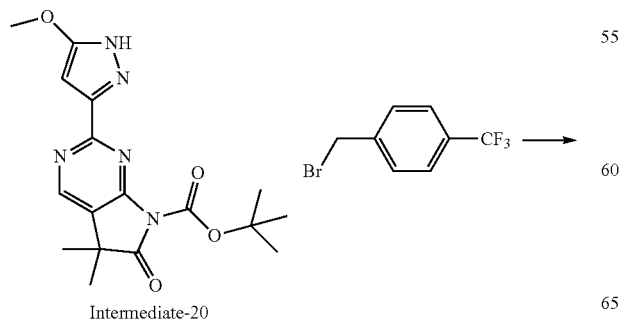
Intermediate-20

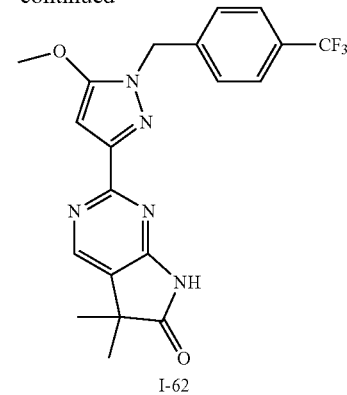
I-62

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-4-(trifluoromethyl)benzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-62 (7 mg, 23% yield) as a white solid. $^1$H NMR (500 MHz, CHLOROFORM-d) δ ppm 8.30 (m, 1H) 7.47 (d, 2H) 7.25 (d, 2H) 7.19 (s, 1H) 6.37 (m, 1H) 5.29 (s, 2H) 3.88 (s, 3H) 1.41 (s, 6H)

Compound I-63

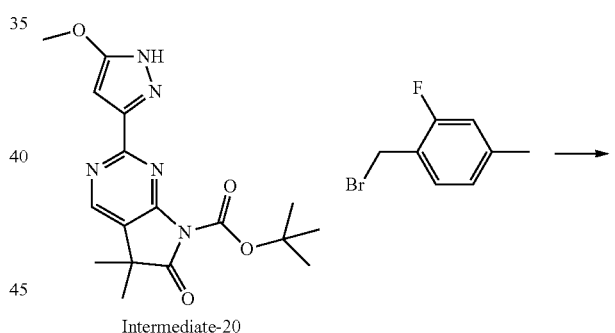
Intermediate-20

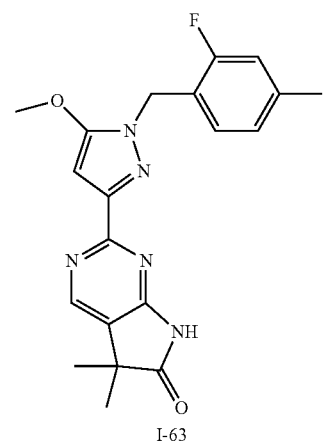
I-63

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 1-(bromomethyl)-2-fluoro-4-methylbenzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-63 (4.8 mg, 17% yield) as a white solid. ¹H NMR (500 MHz, DMSO-d6) δ ppm 11.46 (s, 1H), 8.47 (s, 1H), 7.02 (m, 3H), 6.30 (s, 1H), 5.18 (s, 2H), 3.94 (s, 3H), 2.29 (s, 3H), 1.34 (s, 6H)

Compound I-64

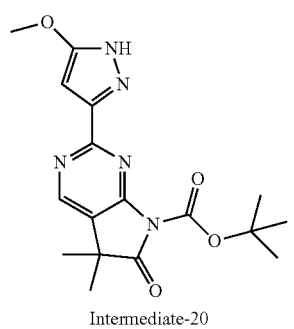

Intermediate-20

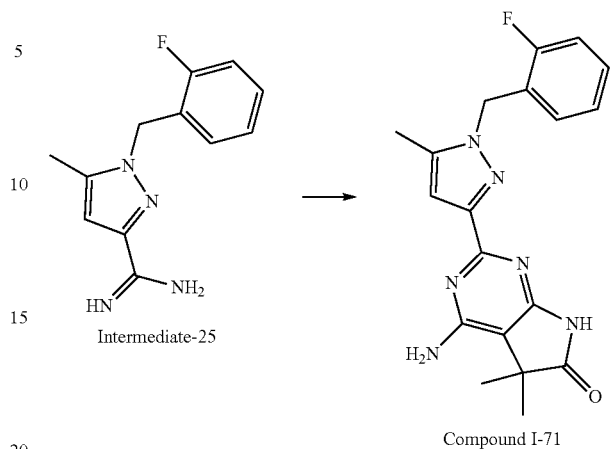

I-64

A solution of tert-butyl 2-(5-methoxy-1H-pyrazol-3-yl)-5,5-dimethyl-6-oxo-5H-pyrrolo-[2,3-d]pyrimidine-7(6H)-carboxylate (Intermediate-20, 1 equiv.), and lithium tert-butoxide (3 equiv.) in dimethoxyethane (1 ml) was stirred at 45° C. for 5 min. To it was added 4-(bromomethyl)-2-fluoro-1-(trifluoromethyl)benzene (1.1 equiv.) and reaction stirred at 45° C. overnight. After cooling to ambient temperature, reaction was filtered and the solvent was removed in vacuo. The crude material was purified via reverse phase HPLC utilizing a 30-80% acetonitrile water 0.1% formic acid gradient to deliver Compound I-64 (4.8 mg, 17% yield) as a white solid.

¹H NMR (500 MHz, DMSO-d6) δ ppm 11.46 (s, 1H), 8.47 (s, 1H), 7.02 (m, 3H), 6.30 (s, 1H), 5.18 (s, 2H), 3.94 (s, 3H), 2.29 (s, 3H), 1.34 (s, 6H)

Compound I-71

Intermediate-25

Compound I-71

A light yellow solution of 1-(2-fluorobenzyl)-5-methyl-1H-pyrazole-3-carboximidamide, methyl 3,3-dicyano-2,2-dimethylpropanoate (Intermediate 25, 3.0 equiv. the synthesis of this intermediate was previously described in patent application publication WO2014144100) and potassium bicarbonate (3.0 equiv.) in t-butanol was heated at 80° C. for 16 hours. The resultant beige color suspension was diluted with water and filtered to collect a tan solid. Purification via silica gel chromatography (10-35% acetonitrile/methanol (7:1) in dichloromethane gradient) afforded Compound I-71 (180 mg, 87%) as a white solid. ¹H-NMR (500 MHz, DMSO-d₆) δ ppm 10.9 (s, 1H), 7.36 (m, 1H), 7.24 (m, 1H), 7.16 (app. t, 1H), 6.95 (app. t, 1H), 6.60 (br s, 2H), 6.57 (s, 1H), 5.38 (s, 2H), 2.28 (s, 3H), 1.30 (s, 6H).

Compound I-72

The title compound was synthesized in 2 steps:

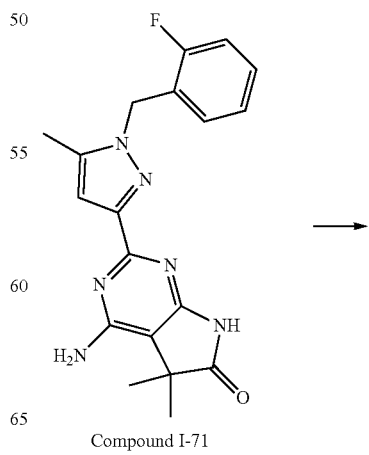

Compound I-71

289

-continued

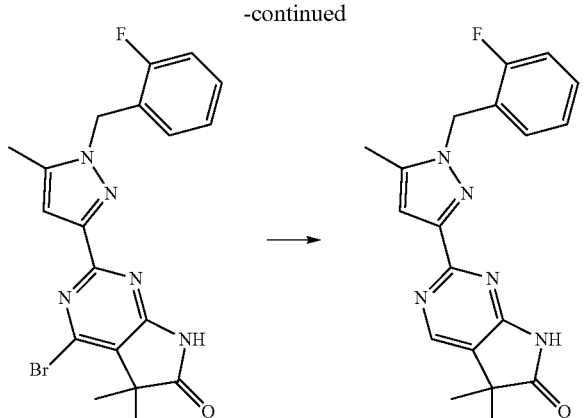

Compound I-72

Step 1: Synthesis of 4-bromo-2-(1-(2-fluorobenzyl)-
5-methyl-1H-pyrazol-3-yl)-5,5-dimethyl-5H-pyrrolo
[2,3-d]pyrimidin-6(7H)-one A suspension of 4-amino-2-(1-(2-fluorobenzyl)-5-methyl-1H-pyrazol-3-yl)-5,5-dimethyl-5H-pyrrolo[2,3-d]pyrimidin-6(7H)-one and copper(II) bromide (Compound I-71, 1.0 equiv.) in dichloromethane was treated with t-butyl nitrite (1.5 equiv.). The resultant mixture in a sealed vial was heated at 50° C. for 13 hours. During this time additional portions of t-butyl nitrite (2.0 equiv. total) were added to drive the reaction to completion. The reaction mixture was cooled to ambient temperature, filtered and partitioned between water and dichloromethane. The organic phases were washed with brine, dried over sodium sulfate, filtered, and the solvent was removed in vacuo to afford 4-bromo-2-(1-(2-fluorobenzyl)-5-methyl-1H-pyrazol-3-yl)-5,5-dimethyl-5H-pyrrolo[2,3-d]pyrimidin-6(7H)-one which was used in the next step without further purification.

Step 2: Synthesis of Compound I-72

A solution of 4-bromo-2-(1-(2-fluorobenzyl)-5-methyl-1H-pyrazol-3-yl)-5,5-dimethyl-5H-pyrrolo[2,3-d]pyrimidin-6(7H)-one in ethanol was treated with palladium on carbon (0.1 equiv., 20% on carbon with 50 wt % water) and stirred under a hydrogen atmosphere (balloon) for 17 hours. The reaction mixture was filtered through Celite with the aid of MeOH and the filtrate was concentrated in vacuo. Purification via silica gel chromatography (5-10% acetonitrile/methanol (7:1) in dichloromethane gradient) afforded Compound I-72 (30 mg, 52%) as a light tan solid. $^1$H-NMR (400 MHz, DMSO-$d_6$) δ ppm 11.5 (s, 1H), 8.47 (s, 1H), 7.37 (m, 1H), 7.25 (m, 1H), 7.17 (app. t, 1H), 7.00 (app. t, 1H), 6.70 (s, 1H), 5.41 (s, 2H), 2.31 (s, 3H), 1.33 (s, 6H).

290

Compound I-73
The title compound was synthesized in 5 steps:

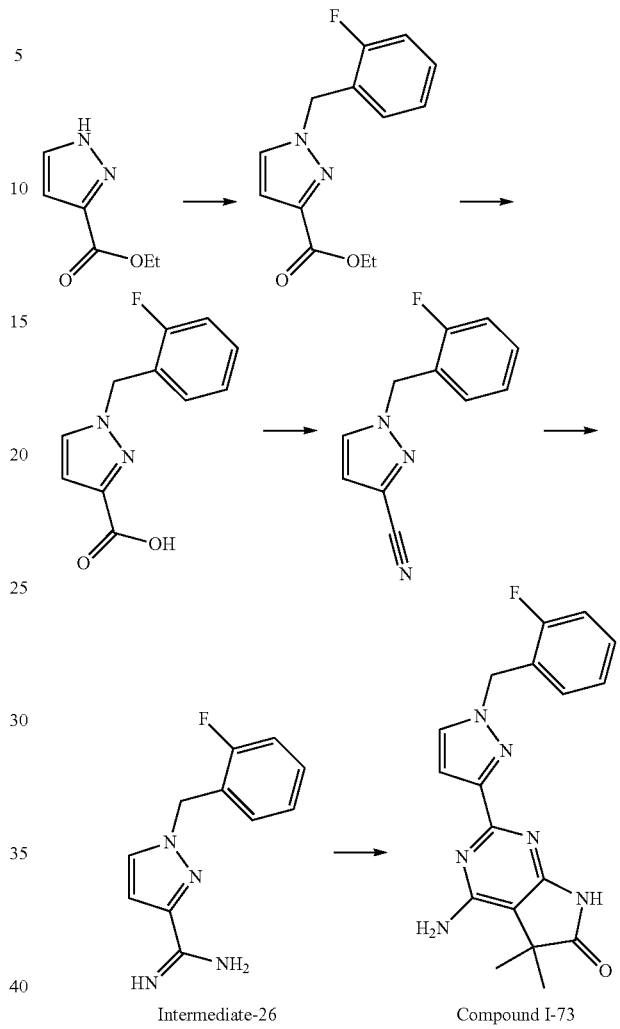

Intermediate-26    Compound I-73

Step 1. Synthesis of ethyl
1-(2-fluorobenzyl)-1H-pyrazole-3-carboxylate

To a suspension of sodium hydride (1.1 equiv., 60 wt % in mineral oil) in THF at 0° C. was added ethy 1H-pyrazole-3-carboxylate. After 5 min, 1-(bromomethyl)-2-fluorobenzene (1.1 equiv.) was added and the reaction mixture was stirred at ambient temperature for 25 hours. During this time additional portions of 1-(bromomethyl)-2-fluorobenzene (0.4 equiv. total) and sodium hydride (0.4 equiv. total) were added to drive the reaction to completion. 1N HCl solution was added and the resulting mixture was extracted with ethyl acetate. The organic phase was dried over sodium sulfate, filtered, and the solvent was removed in vacuo. Purification by silica gel chromatography (10-50% ethyl acetate/hexanes gradient) yielded ethyl 1-(2-fluorobenzyl)-1H-pyrazole-3-carboxylate (>99%).

Step 2. Synthesis of
1-(2-fluorobenzyl)-1H-pyrazole-3-carboxylic acid

To a solution of ethyl 1-(2-fluorobenzyl)-1H-pyrazole-3-carboxylate in THF/water (3:1 ratio) was added lithium hydroxide (2.0 equiv.). After 20 hours, the volatile organics were removed in vacuo and the resultant mixture was acidified to pH 3 with 1N HCl solution. 1-(2-Fluorobenzyl)-1H-pyrazole-3-carboxylic acid was collected by vacuum filtration (95%).

Step 3. Synthesis of 1-(2-fluorobenzyl)-1H-pyrazole-3-carbonitrile

To a suspension of 1-(2-fluorobenzyl)-1H-pyrazole-3-carboxylic acid, 2-methylpropan-2-amine (3 equiv.), and triethylamine (2 equiv.) in ethyl acetate was added n-propylphosphonic anhydride (T3P, 50 wt % solution in ethyl acetate, 3.0 equiv.). The resultant yellow solution was heated at 65° C. for 5 hours and 45 minutes. The solvent was removed in vacuo. Phosphoryl trichloride (10 equiv.) was added and the resulting mixture was stirred at 70° C. for 5 hours. The reaction was quenched by carefully pouring into a mixture of water and ice, neutralized to pH 7 by addition of saturated sodium bicarbonate solution/solid sodium bicarbonate and extracted with ethyl acetate. The combined organic phases were dried over sodium sulfate, filtered, and the solvent was removed in vacuo to yield 1-(2-fluorobenzyl)-1H-pyrazole-3-carbonitrile (>99%) as a brown oil which was used in the next step without further purification.

Step 4. Synthesis of 1-(2-fluorobenzyl)-1H-pyrazole-3-carboximidamide (Intermediate-26)

To 1-(2-fluorobenzyl)-1H-pyrazole-3-carbonitrile was added sodium methoxide (1.0 equiv., 0.5 N in MeOH). The reaction was stirred at ambient temperature for 3 hours 20 minutes and then at 60° C. for 3 hours. Ammonium chloride (5.0 equiv.) was added and the reaction mixture was stirred for 40 hours. During this time additional portions of sodium methoxide (3.0 equiv. total) and ammonium chloride (5.0 equiv. total) were added to increase conversion to product. The crude mixture was concentrated in vacuo and partitioned between half-saturated sodium bicarbonate and ethyl acetate. The aqueous phase was extracted with dichloromethane/iPrOH (4:1). The organic phases were dried over sodium sulfate, filtered, and the solvent was removed in vacuo. The crude product was contaminated with starting material due to incomplete reaction. This material was re-subjected to similar conditions to afford 1-(2-fluorobenzyl)-1H-pyrazole-3-carboximidamide (>99%).

Step 5. Synthesis of Compound I-73

A yellow suspension of 1-(2-fluorobenzyl)-1H-pyrazole-3-carboximidamide (Intermediate-26), methyl 3,3-dicyano-2,2-dimethylpropanoate (2.5 equiv.) and potassium bicarbonate (2.5 equiv.) in t-butanol was heated at 80° C. for 14 hours. The resultant thick tan suspension was diluted with water and filtered to collect Compound I-73 (1.3 g, 78%) as a white solid. $^1$H-NMR (500 MHz, DMSO-$d_6$) δ ppm 10.9 (s, 1H), 7.85 (d, 1H), 7.38 (m, 1H), 7.23 (m, 1H), 7.19 (m, 2H), 6.75 (d, 1H), 6.59 (br s, 2H), 5.44 (s, 2H), 1.30 (s, 6H).

Compound I-74
The title compound was synthesized in 2 steps:

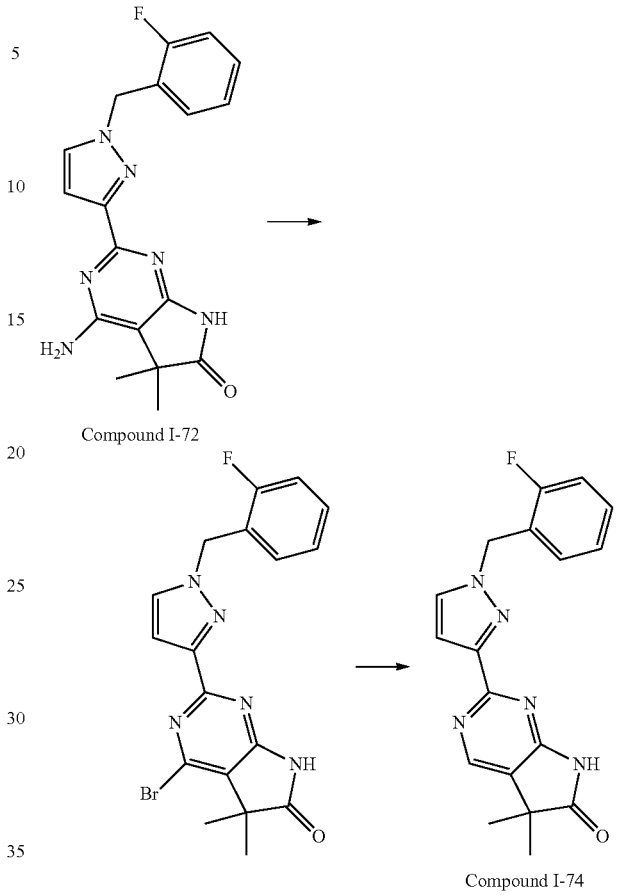

Step 1: Synthesis of 4-bromo-2-(1-(2-fluorobenzyl)-1H-pyrazol-3-yl)-5,5-dimethyl-5H-pyrrolo[2,3-d]pyrimidin-6(7H)-one A suspension of 4-amino-2-(1-(2-fluorobenzyl)-1H-pyrazol-3-yl)-5,5-dimethyl-5H-pyrrolo[2,3-d]pyrimidin-6 (7H)-one and copper(II) bromide (Compound I-72, 1.2 equiv.) in THF was treated with t-butyl nitrite (2.0 equiv.). The resultant mixture in a sealed vial was heated at 65° C. for 19 hours. The reaction mixture was cooled to ambient temperature, filtered and partitioned between water and dichloromethane. The organic phases were washed with saturated ammonium chloride solution, and brine, dried over sodium sulfate, filtered, and the solvent was removed in vacuo to afford 4-bromo-2-(1-(2-fluorobenzyl)-1H-pyrazol-3-yl)-5,5-dimethyl-5H-pyrrolo[2,3-d]pyrimidin-6(7H)-one which was used in the next step without further purification.

Step 2: Synthesis of Compound I-74

A solution of 4-bromo-2-(1-(2-fluorobenzyl)-1H-pyrazol-3-yl)-5,5-dimethyl-5H-pyrrolo[2,3-d]pyrimidin-6(7H)-one in THF was treated with zinc dust (20 equiv.) and acetic acid (24 equiv.). The resultant mixture in a sealed vial was heated at 85° C. for 23 hours. After cooling to ambient temperature, the reaction mixture was filtered through Celite with the aid of ethyl acetate and the filtrate was washed with 1N NaOH solution. The combined organic phases were washed with brine, dried over sodium sulfate, filtered and concentrated in vacuo. Purification via preparative HPLC (30-80% acetonitrile/water gradient with 0.1% formic acid) afforded Compound I-74 (38 mg, 48% over 2 steps) as a white solid. ¹H-NMR (500 MHz, DMSO-d₆) δ ppm 11.4 (s, 1H), 8.47 (s, 1H), 7.92 (d, 1H), 7.39 (m, 1H), 7.26-7.18 (m, 3H), 6.87 (d, 1H), 5.48 (s, 2H), 1.33 (s, 6H).

Compound I-75

The title compound was synthesized in 2 steps:

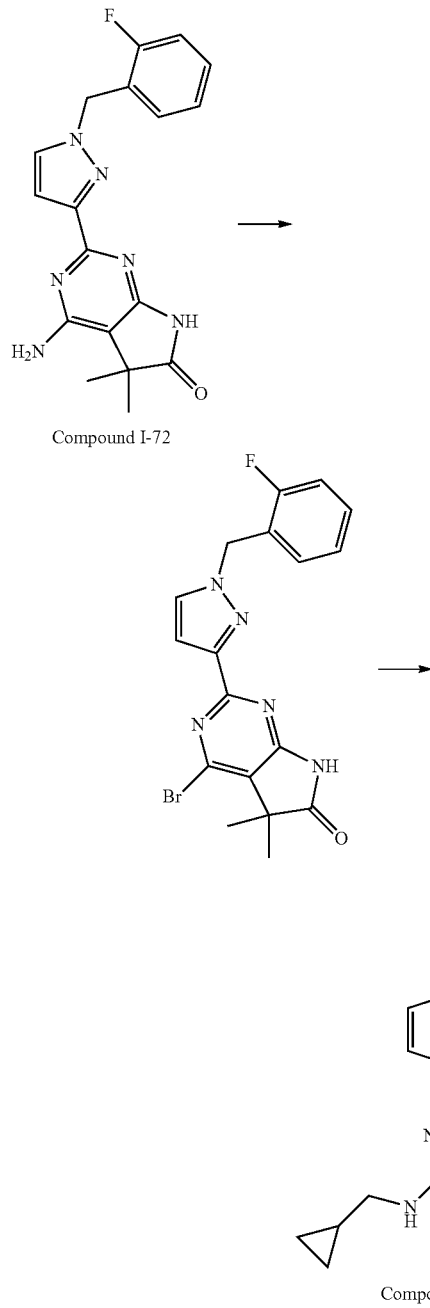

Step 1: Synthesis of 4-bromo-2-(1-(2-fluorobenzyl)-1H-pyrazol-3-yl)-5,5-dimethyl-5H-pyrrolo-[2,3-d]pyrimidin-6(7H)-one A suspension of 4-amino-2-(1-(2-fluorobenzyl)-1H-pyrazol-3-yl)-5,5-dimethyl-5H-pyrrolo-[2,3-d]pyrimidin-6(7H)-one and copper(II) bromide (Compound I-72, 1.2 equiv.) in dichloromethane was treated with t-butyl nitrite (2.0 equiv.). The resultant mixture in a sealed vial was heated at 50° C. for 23 hours. During this time additional portion of t-butyl nitrite (0.5 equiv.) was added to drive the reaction to completion. The reaction mixture was cooled to ambient temperature, filtered and partitioned between water and dichloromethane. The organic phases were washed with half-saturated ammonium chloride solution and brine, dried over sodium sulfate, filtered, and the solvent was removed in vacuo to afford 4-bromo-2-(1-(2-fluorobenzyl)-1H-pyrazol-3-yl)-5,5-dimethyl-5H-pyrrolo[2,3-d]pyrimidin-6(7H)-one which was used in the next step without further purification.

Step 2: Synthesis of Compound I-75

A solution of 4-bromo-2-(1-(2-fluorobenzyl)-1H-pyrazol-3-yl)-5,5-dimethyl-5H-pyrrolo[2,3-d]pyrimidin-6(7H)-one in N-methyl pyrrolidinone (NMP) was treated with cyclopropylmethanamine (10 equiv.). The resultant mixture was heated at 85° C. for 2 days. Purification via preparative HPLC (30-80% acetonitrile/water gradient with 0.1% formic acid) afforded Compound I-75 (10 mg, 56% over 2 steps) as a white solid. ¹H-NMR (500 MHz, DMSO-d₆) δ ppm 10.9 (s, 1H), 7.84 (d, 1H), 7.38 (m, 1H), 7.25-7.17 (m, 3H), 6.78 (d, 1H), 6.59 (t, 1H), 5.45 (s, 2H), 3.35 (t, 2H), 1.33 (s, 6H), 1.13 (m, 1H), 0.39 (m, 2H), 0.30 (m, 2H).

Compound I-76

The title compound was synthesized in 2 steps:

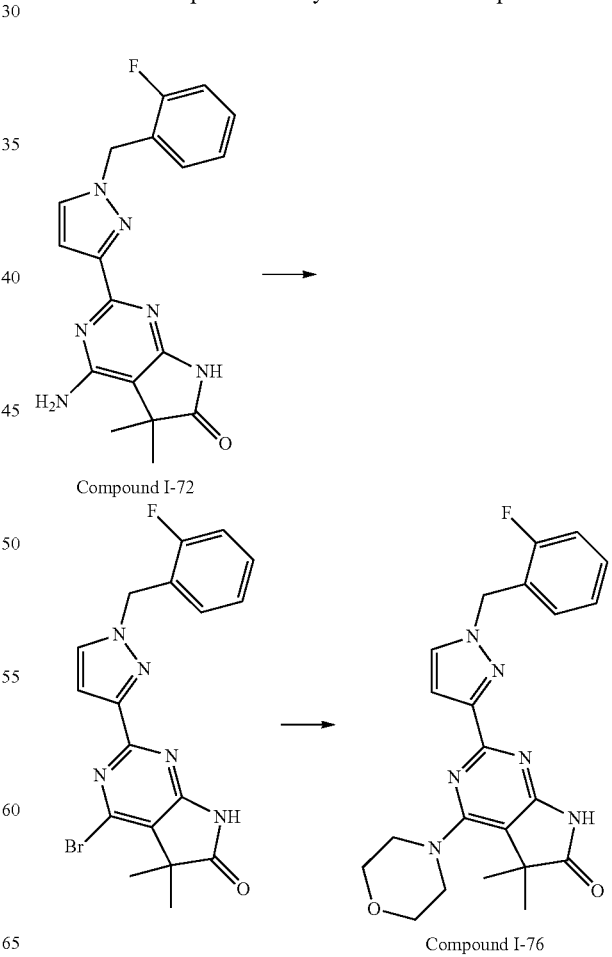

Step 1: Synthesis of 4-bromo-2-(1-(2-fluorobenzyl)-1H-pyrazol-3-yl)-5,5-dimethyl-5H-pyrrolo[2,3-d]pyrimidin-6(7H)-one A suspension of 4-amino-2-(1-(2-fluorobenzyl)-1H-pyrazol-3-yl)-5,5-dimethyl-5H-pyrrolo[2,3-d]pyrimidin-6(7H)-one and copper(II) bromide (Compound I-72, 1.2 equiv.) in dichloromethane was treated with t-butyl nitrite (2.0 equiv.). The resultant mixture in a sealed vial was heated at 50° C. for 2 days. The reaction mixture was cooled to ambient temperature, filtered and partitioned between water and dichloromethane. The organic phases were washed with half-saturated ammonium chloride solution and brine, dried over sodium sulfate, filtered, and the solvent was removed in vacuo to afford 4-bromo-2-(1-(2-fluorobenzyl)-1H-pyrazol-3-yl)-5,5-dimethyl-5H-pyrrolo[2,3-d]pyrimidin-6(7H)-one which was used in the next step without further purification.

Step 2: Synthesis of Compound I-76

A solution of 4-bromo-2-(1-(2-fluorobenzyl)-1H-pyrazol-3-yl)-5,5-dimethyl-5H-pyrrolo[2,3-d]pyrimidin-6(7H)-one in N-methyl pyrrolidinone (NMP) was treated with morpholine (10 equiv.). The resultant mixture was heated at 85° C. for 45 hours. Purification via preparative HPLC (30-80% acetonitrile/water gradient with 0.1% formic acid) afforded Compound I-76 (22 mg, 46% over 2 steps) as a white solid. $^1$H-NMR (500 MHz, DMSO-$d_6$) δ ppm 11.2 (s, 1H), 7.87 (d, 1H), 7.38 (m, 1H), 7.23 (m, 1H), 7.18 (m, 2H), 6.83 (d, 1H), 5.46 (s, 2H), 3.72 (m, 4H), 3.66 (m, 4H), 1.37 (s, 6H).

Compound I-77

The title compound was synthesized in 2 steps:

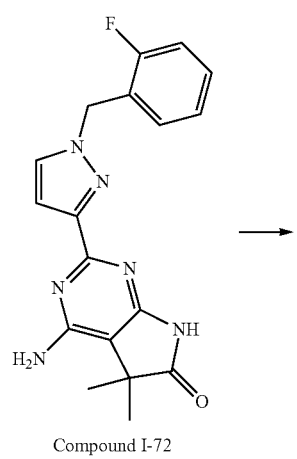

Compound I-72

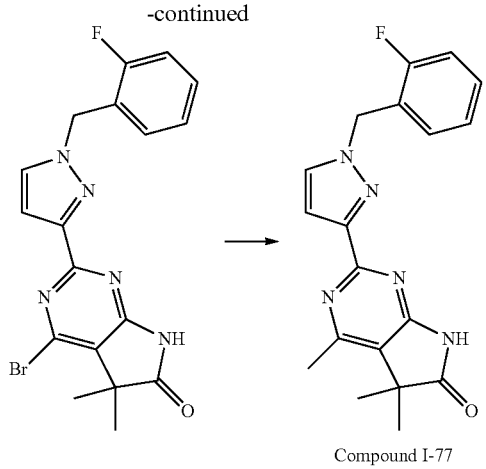

Compound I-77

Step 1: Synthesis of 4-bromo-2-(1-(2-fluorobenzyl)-1H-pyrazol-3-yl)-5,5-dimethyl-5H-pyrrolo[2,3-d]pyrimidin-6 (7H)-one A suspension of 4-amino-2-(1-(2-fluorobenzyl)-1H-pyrazol-3-yl)-5,5-dimethyl-5H-pyrrolo[2,3-d]pyrimidin-6 (7H)-one and copper(II) bromide (Compound I-72, 1.2 equiv.) in dichloromethane was treated with t-butyl nitrite (2.0 equiv.) and water (2.0 equiv). The resultant mixture in a sealed vial was heated at 50° C. for 30 hours. The reaction mixture was cooled to ambient temperature, filtered and partitioned between half-saturated ammonium chloride solution and dichloromethane. The organic phases were washed with brine, dried over sodium sulfate, filtered, and the solvent was removed in vacuo to afford 4-bromo-2-(1-(2-fluorobenzyl)-1H-pyrazol-3-yl)-5,5-dimethyl-5H-pyrrolo[2,3-d]pyrimidin-6(7H)-one which was used in the next step without further purification.

Step 2: Synthesis of Compound I-77

To a mixture of 4-bromo-2-(1-(2-fluorobenzyl)-1H-pyrazol-3-yl)-5,5-dimethyl-5H-pyrrolo[2,3-d]pyrimidin-6(7H)-one, cesium carbonate (1.5 equiv.), [1,1'-bis(diphenylphosphino)ferrocene]dichloropalladium(II) (complex with dichloromethane, 0.05 equiv.) was added dioxane/water (10:1, degassed by bubbling with nitrogen gas for 10 min). Trimethylboroxine (0.8 equiv.) was added and the reaction mixture was heated at 80° C. for 16 hours. Additional portions of [1,1'-bis(diphenylphosphino)ferrocene]-dichloropalladium(II) catalyst (0.05 equiv.) and trimethylboroxine (0.8 equiv.) were added and the reaction was heated at 100° C. for 24 hours. After cooling to ambient temperature, the mixture was partitioned between water and dichloromethane. The aqueous phase was extracted with dichloromethane/iPrOH (5:1). The organic phases were dried over sodium sulfate, filtered, and the solvent was removed in vacuo. Purification via silica gel chromatography (10% acetonitrile/methanol (7:1) in dichloromethane) afforded Compound I-77 (5.2 mg, 15% over 2 steps) as an off-white solid. $^1$H-NMR (500 MHz, DMSO-$d_6$) δ ppm 11.4 (s, 1H), 7.90 (d, 1H), 7.38 (m, 1H), 7.24 (m, 1H), 7.20 (m, 2H), 6.85 (d, 1H), 5.48 (s, 2H), 2.43 (s, 3H), 1.35 (s, 6H).

Compound I-78

The title compound was synthesized in 2 steps:

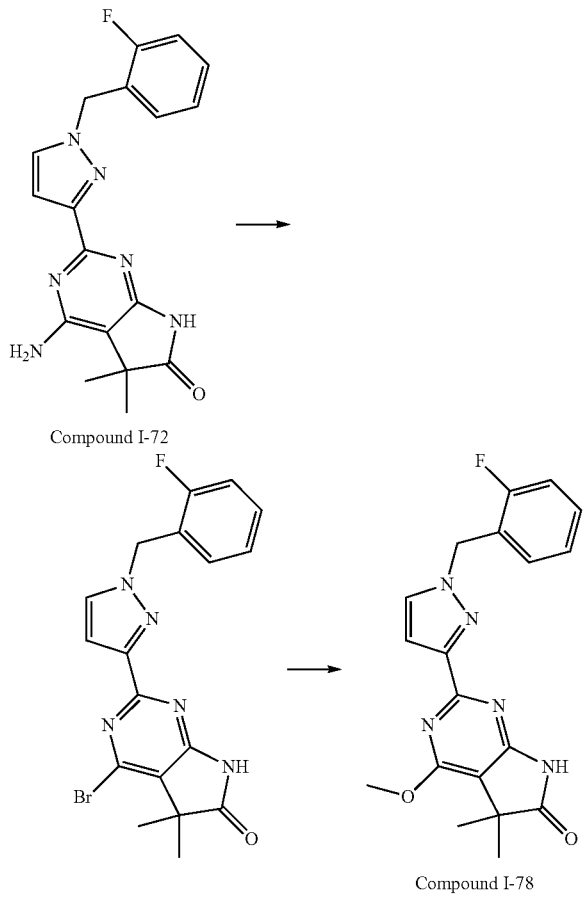

Compound I-72

Compound I-78

Step 1: Synthesis of 4-bromo-2-(1-(2-fluorobenzyl)-1H-pyrazol-3-yl)-5,5-dimethyl-5H-pyrrolo[2,3-d]pyrimidin-6(7H)-one A suspension of 4-amino-2-(1-(2-fluorobenzyl)-1H-pyrazol-3-yl)-5,5-dimethyl-5H-pyrrolo[2,3-d]pyrimidin-6(7H)-one and copper(II) bromide (Compound I-72, 1.2 equiv.) in dichloromethane was treated with t-butyl nitrite (2.0 equiv.) and water (2.0 equiv). The resultant mixture in a sealed vial was heated at 50° C. for 36 hours. The reaction mixture was cooled to ambient temperature, filtered and the solvent was removed in vacuo to afford 4-bromo-2-(1-(2-fluorobenzyl)-1H-pyrazol-3-yl)-5,5-dimethyl-5H-pyrrolo[2,3-d]pyrimidin-6(7H)-one which was used in the next step without further purification.

Step 2: Synthesis of Compound I-78

4-Bromo-2-(1-(2-fluorobenzyl)-1H-pyrazol-3-yl)-5,5-dimethyl-5H-pyrrolo[2,3-d]pyrimidin-6(7H)-one was treated with sodium methoxide (0.5 N in MeOH, 10 equiv.) and the resultant mixture was heated at 65° C. for 2 days. After cooling to ambient temperature, the mixture was concentrated in vacuo and partitioned between 1N HCl solution and dichloromethane/iPrOH (5:1). The organic phases were dried over sodium sulfate, filtered, and the solvent was removed in vacuo. The crude material was treated with sodium methoxide (25 wt % in MeOH, 95 equiv.) and heated at 65° C. for 2 hours 15 minutes. After cooling to ambient temperature, the mixture was concentrated in vacuo and partitioned between 1N HCl solution and dichloromethane/iPrOH (5:1). The organic phases were dried over sodium sulfate, filtered, and the solvent was removed in vacuo. Purification via preparative HPLC (30-80% acetonitrile/water gradient with 0.1% formic acid) afforded Compound I-78 (27 mg, 52% over 2 steps) as a white solid. $^1$H-NMR (500 MHz, DMSO-$d_6$) δ ppm 11.3 (s, 1H), 7.91 (d, 1H), 7.39 (m, 1H), 7.24 (m, 1H), 7.21 (m, 2H), 6.90 (d, 1H), 5.49 (s, 2H), 4.01 (s, 3H), 1.30 (s, 6H).

Compound I-79

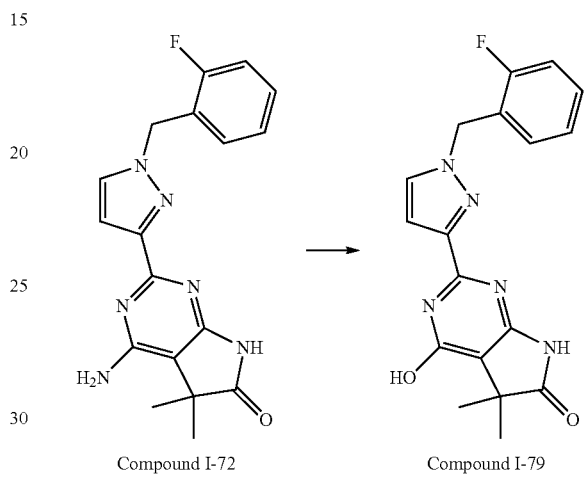

Compound I-72

Compound I-79

A solution of 4-amino-2-(1-(2-fluorobenzyl)-1H-pyrazol-3-yl)-5,5-dimethyl-5H-pyrrolo[2,3-d]pyrimidin-6(7H)-one in trifluoroacetic acid at 0° C. was treated water (Compound I-72, 26 equiv.) followed by sodium nitrite (1.5 equiv., added in two portions). Gas evolution was observed. After 20 minutes, water was added and the product was collected by vacuum filtration to afford Compound I-79 (28 mg, 95%) as a white solid. $^1$H-NMR (500 MHz, DMSO-$d_6$) δ ppm 12.1 (s, 1H), 11.0 (s, 1H), 8.02 (s, 1H), 7.40 (m, 1H), 7.29 (app. t, 1H), 7.24 (m, 1H), 7.20 (app. t, 1H), 7.00 (s, 1H), 5.50 (s, 2H), 1.28 (s, 6H).

Compound I-80

The title compound was synthesized in 7 steps:

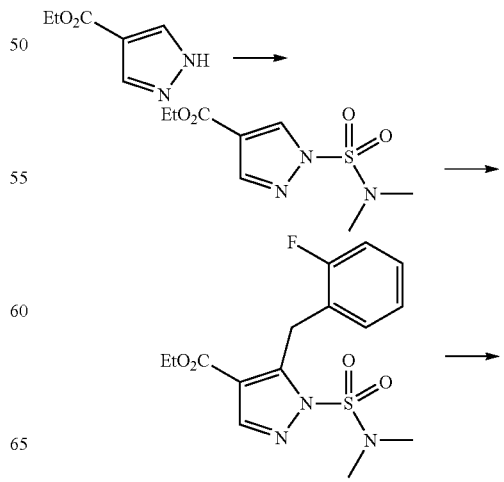

-continued

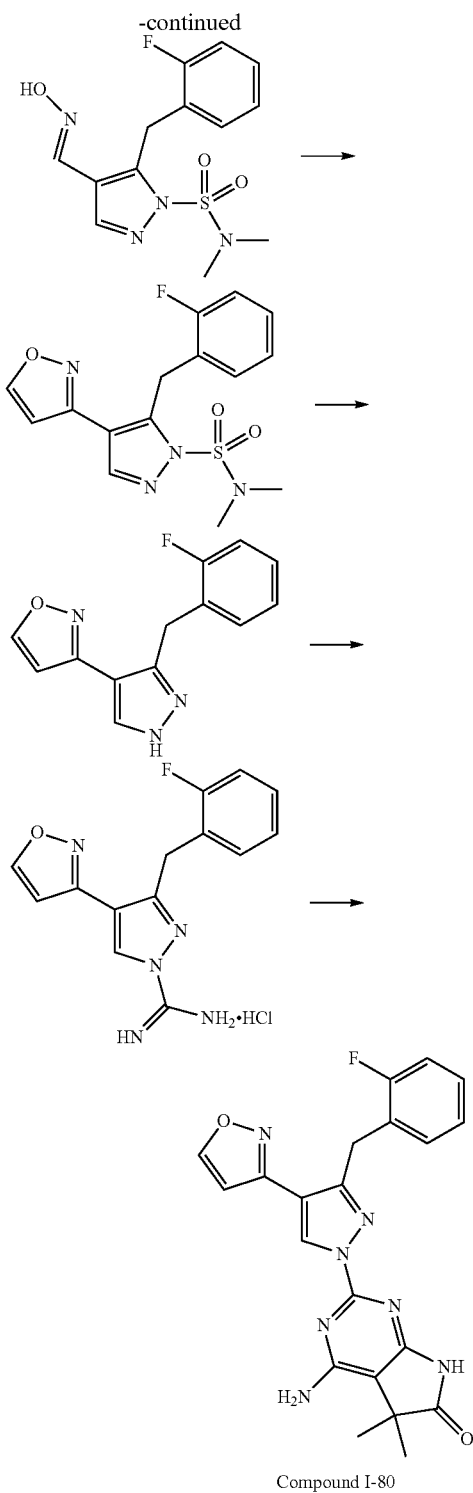

Compound I-80

Step 1: Synthesis of ethyl 1-(dimethylsulfamoyl)-1H-pyrazole-4-carboxylate

A stirred solution of ethyl 4-pyrazolecarboxylate in anhydrous acetonitrile under nitrogen was treated with dimethylsulfamoyl chloride (1.1 equiv.) and DABCO (1.1 equiv.) and stirred for 1 hour. The mixture was concentrated in vacuo and partitioned between water and ethyl acetate. The combined organic phases were washed with 10% citric acid solution, water and brine, dried over magnesium sulfate, filtered, and the solvent was removed in vacuo. Purification by silica gel chromatography (5% ethyl acetate in dichloromethane) yielded ethyl 1-(dimethylsulfamoyl)-1H-pyrazole-4-carboxylate as a white solid (99%).

Step 2: Synthesis of ethyl 1-(dimethylsulfamoyl)-5-[(2-fluorophenyl)methyl]-1H-pyrazole-4-carboxylate To a solution of diisopropylamine (1.2 equiv.) in anhydrous THF under nitrogen at −70° C. was added n-butyllithium (1.6 N, 1.1 equiv.). The solution was warmed to 0° C. for 5 minutes, recooled to −70° C. and added via cannula to a stirred solution of ethyl 1-(dimethylsulfamoyl)-1H-pyrazole-4-carboxylate, anhydrous HMPA (1.3 equiv.) in THF at −70° C. (temperature of the reaction mixture was kept below −65° C. during the addition). After stirring for 1 hour at −70° C., 2-fluorobenzyl bromide (1.3 equiv.) was added. After 2 hours at −70° C., the reaction was allowed to warmed to 0° C. over 30 minutes, recooled to −20° C. and quenched by addition of saturated ammonium chloride solution. The mixture was partitioned between water and ethyl acetate. The combined organic phases were washed with water and brine, dried over magnesium sulfate, filtered, and the solvent was removed in vacuo. Purification by silica gel chromatography (5-33% ethyl acetate in heptane) yielded ethyl 1-(dimethylsulfamoyl)-5-[(2-fluorophenyl)methyl]-1H-pyrazole-4-carboxylate as a white solid (58%).

Step 3: Synthesis of 5-[(2-fluorophenyl)methyl]-4-[(hydroxyimino)methyl]-N,N-dimethyl-1H-pyrazole-1-sulfonamide To a solution of 1-(dimethylsulfamoyl)-5-[(2-fluorophenyl)methyl]-1H-pyrazole-4-carboxylate in anhydrous THF at 3° C. was added lithium aluminum hydride (2.0 N in THF, 1.1 equiv.). The reaction was stirred at ambient temperature for 30 minutes and re-cooled to 0° C. The reaction was quenched by dropwise addition of water and 15% sodium hydroxide solution and filtered with the aid of THF and dichloromethane/THF (1:1). The combined filtrates were concentrated in vacuo, re-dissolved in dichloromethane, treated with N,N-diisopropylethylamine (3.0 equiv.) and cooled to 0° C. A solution of sulfur trioxide-pyridine complex (2.3 equiv.) in anhydrous DMSO was added via an addition funnel. The mixture was stirred at ambient temperature for 2 hours and then partitioned between water and ethyl acetate. The combined organic phases were washed with water and brine, dried over magnesium sulfate, filtered, and the solvent was removed in vacuo. The resultant pale yellow solid was dissolved in EtOH, treated with hydroxyamine (50% in water, 1.1 equiv.) and heated at 60° C. for 40 minutes. After cooling to ambient temperature, the mixture was concentrated in vacuo. Purification by silica gel chromatography (10% ethyl acetate in dichloromethane) yielded 5-[(2-fluorophenyl)methyl]-4-[(hydroxyimino)methyl]-N,N-dimethyl-1H-pyrazole-1-sulfonamide as a white solid (92%).

Step 4: Synthesis of 5-[(2-fluorophenyl)methyl]-N,N-dimethyl-4-(isoxazol-3-yl)-1H-pyrazole-1-sulfonamide A solution of 5-[(2-fluorophenyl)methyl]-4-[(hydroxyimino)methyl]-N,N-dimethyl-1H-pyrazole-1-sulfonamide in anhydrous DMF under nitrogen was treated with N-chlorosuccinimide (1.2 equiv.) and carefully heated to 40° C. At about 35° C. the mixture became orange in color and an exotherm was observed (cooling bath was applied). After stirring at 40° C. for 20 min, the mixture was cooled to ambient temperature and partitioned between water and ethyl acetate. The organic phases were washed with water and brine, dried over magnesium sulfate, filtered, and the solvent was removed in vacuo (<40° C.). The residue oil was purified by silica gel chromatography (3% ethyl acetate in dichloromethane). The product-rich fractions were gently concentrated to afford a pale yellow oil. This chlorooxime intermediate was dissolved in iPrOH (without heating) and added to a pressure bottle which had been charged with solid sodium bicarbonate (1.5 equiv.). Ethyl vinyl ether (3.1 equiv.) was added and the bottle was closed and heated to 50° C. for 6 hours. The pressure bottle was cooled on ice and the cap was removed. The contents were diluted with dichloromethane and filtered through Celite. The filtrate was concentrated to a pale yellow oil which was dissolved in EtOH and treated with 1.0N sodium hydroxide solution (1.0 equiv.) and stirred for 14 hours. The mixture was concentrated in vacuo and partitioned between water and dichloromethane. The organic phases were washed with saturated sodium bicarbonate solution and brine, dried over sodium sulfate, filtered, and the solvent was removed in vacuo. The residue yellow oil was purified by silica gel chromatography (0-2% ethyl acetate in dichloromethane) to yield a pale yellow solid which was triturated with petroleum ether/ether and dried to yield 5-[(2-fluorophenyl)methyl]-N,N-dimethyl-4-(isoxazol-3-yl)-1H-pyrazole-1-sulfonamide as a white solid (87%).

Step 5: Synthesis of 3-[3-(2-fluorobenzyl)-1H-pyrazol-4-yl]isoxazole

A solution of 5-[(2-fluorophenyl)methyl]-N,N-dimethyl-4-(isooxazol-3-yl)-1H-pyrazole-1-sulfonamide in dichloromethane under nitrogen at 0° C. was treated with trifluoroacetic acid (13 equiv.) dropwise via an addition funnel. The mixture was stirred at ambient temperature for 3 hours and then concentrated in vacuo (<40° C.). The residue was re-dissolved in dichloromethane and basicified to pH>9 with 10% potassium carbonate solution/solid potassium carbonate. The mixture was extracted with dichloromethane. The combined organic phases were washed with water and brine, dried over sodium sulfate, filtered, and the solvent was removed in vacuo. Purification by silica gel chromatography (67% ethyl acetate in dichloromethane) yielded 3-[3-(2-fluorobenzyl)-1H-pyrazol-4-yl]isoxazole (28 g, 96%) as a white solid. $^1$H-NMR (500 MHz, CDCl$_3$) δ ppm 8.96 (br s, 1H), 8.40 (d, 1H), 7.78 (s, 1H), 7.27-7.17 (m, 2H), 7.07-7.00 (m, 2H), 6.44 (d, 1H), 4.37 (s, 2H).

Step 6: Synthesis of 3-(2-fluorobenzyl)-4-(isoxazol-3-yl)-1H-pyrazole-1-carboximidamide hydrochloride A clear solution of 3-[3-(2-fluorobenzyl)-1H-pyrazol-4-yl]isoxazole and cyanamide (1.0 equiv.) in dioxane was treated with hydrogen chloride (4.0 N in dioxane, 1.8 equiv.). The resultant thick white suspension was warmed to 100° C. and stirred for 3 hours. The clear solution was cooled to ambient temperature and a white solid precipitated. The suspension was diluted with ether and the solid was collected by vacuum filtration and dried to yield 3-(2-fluorobenzyl)-4-(isoxazol-3-yl)-1H-pyrazole-1-carboximidamide hydrochloride (90%).

Step 7: Synthesis of Compound I-80

A white suspension of 3-(2-fluorobenzyl)-4-(isoxazol-3-yl)-1H-pyrazole-1-carboximidamide hydrochloride, methyl 3,3-dicyano-2,2-dimethylpropanoate (3.0 equiv.) and potassium bicarbonate (3.0 equiv.) in t-butanol was heated at 80° C. for 24 hours. The resultant thick yellow suspension was diluted with water and filtered to afford a light tan solid. The filtrate was extracted with dichloromethane. The combined organic phases were dried over sodium sulfate, filtered, and the solvent was removed in vacuo. The combined crude product was purified by silica gel chromatography (5-10% acetonitrile/methanol (7:1) in dichloromethane gradient) to yield Compound I-80 (140 mg, 36%) as a white solid. $^1$H-NMR (500 MHz, DMSO-d$_6$) δ ppm 11.1 (s, 1H), 8.95 (d, 1H), 8.91 (s, 1H), 7.25 (m, 1H), 7.16 (m, 2H), 7.07 (app. t, 1H), 7.02 (d, 1H), 6.97 (br s, 2H), 4.33 (s, 2H), 1.33 (s, 6H).

Compound I-81

The title compound was synthesized in 2 steps:

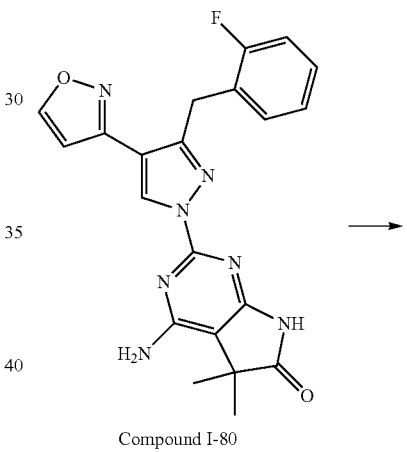

Compound I-80

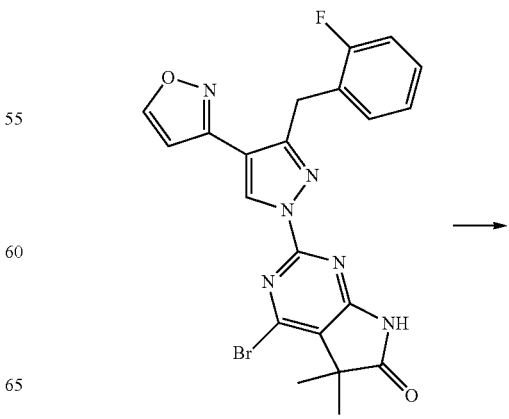

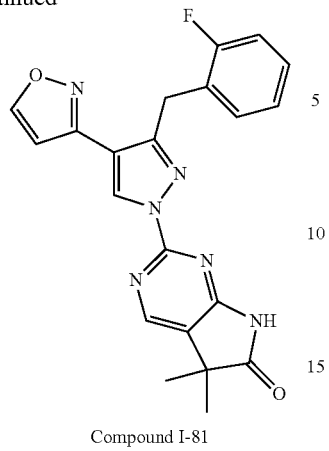

Compound I-81

Step 1: Synthesis of 4-bromo-2-(3-(2-fluorobenzyl)-4-(isoxazol-3-yl)-1H-pyrazol-1-yl)-5,5-dimethyl-5H-pyrrolo[2,3-d]pyrimidin-6(7H)-one A green solution of 4-amino-2-(3-(2-fluorobenzyl)-4-(isoxazol-3-yl)-1H-pyrazol-1-yl)-5,5-dimethyl-5H-pyrrolo[2,3-d]pyrimidin-6(7H)-one and copper(II) bromide (Compound I-80, 1.2 equiv.) in THF was treated with t-butyl nitrite (2.0 equiv.). The resultant mixture in a sealed vial was heated at 65° C. for 23 hours. The reaction mixture was cooled to ambient temperature, filtered and partitioned between water and dichloromethane. The organic phases were washed with saturated ammonium chloride solution and brine, dried over sodium sulfate, filtered, and the solvent was removed in vacuo to afford 4-bromo-2-(3-(2-fluorobenzyl)-4-(isoxazol-3-yl)-1H-pyrazol-1-yl)-5,5-dimethyl-5H-pyrrolo[2,3-d]pyrimidin-6(7H)-one as a thick green oil which was used in the next step without further purification.

Step 2: Synthesis of Compound I-81

A solution of 4-bromo-2-(3-(2-fluorobenzyl)-4-(isoxazol-3-yl)-1H-pyrazol-1-yl)-5,5-dimethyl-5H-pyrrolo[2,3-d]pyrimidin-6(7H)-one in THF was treated with zinc dust (20 equiv.) and acetic acid (24 equiv.). The resultant greenish grey suspension in a sealed vial was heated at 85° C. for 24 hours. After cooling to ambient temperature, the reaction mixture was filtered through Celite with the aid of ethyl acetate and the filtrate was washed with half-saturated sodium bicarbonate solution. The combined organic phases were washed with brine, dried over sodium sulfate, filtered and concentrated in vacuo. Purification via preparative HPLC (30-80% acetonitrile/water gradient with 0.1% trifluoroacetic acid) afforded Compound I-81 (51 mg, 41% over 2 steps) as a white solid.

$^1$H-NMR (500 MHz, DMSO-$d_6$) δ ppm 11.8 (s, 1H), 9.19 (s, 1H), 8.95 (d, 1H), 8.50 (s, 1H), 7.26 (m, 1H), 7.22-7.14 (m, 2H), 7.16 (d, 1H), 7.08 (app. td, 1H), 4.36 (s, 2H), 1.37 (s, 6H).

Compound I-82

The title compound was synthesized in 6 steps:

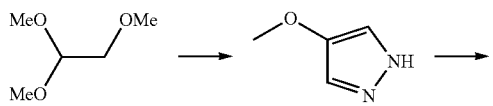

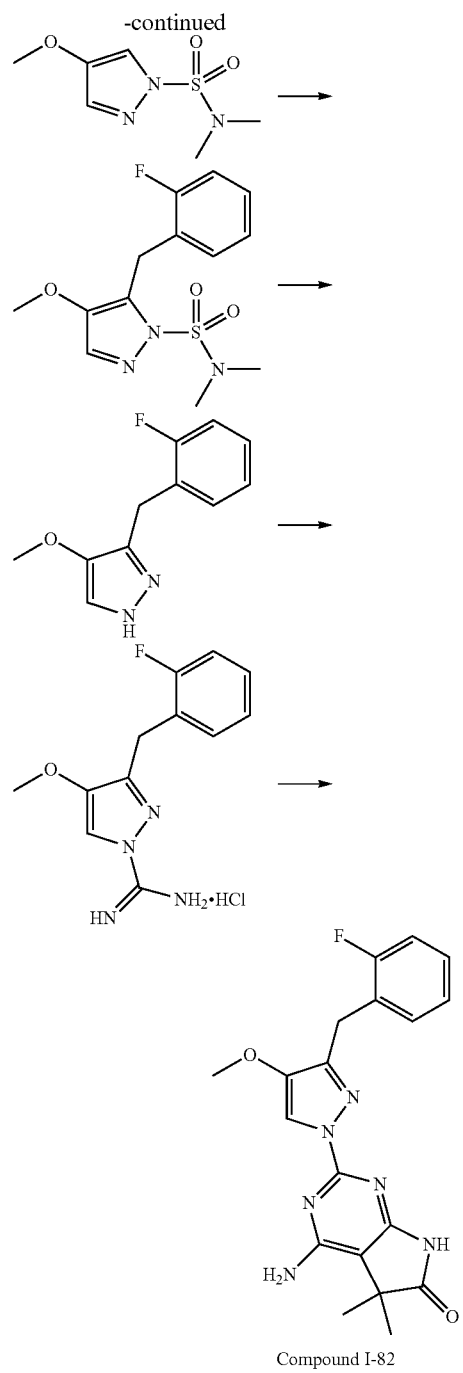

Compound I-82

Step 1: Synthesis of 4-methoxy-1H-pyrazole

To 1,1,2-trimethoxyethane (300 mmol, 1.0 equiv.) at 0° C. with stirring was added phosphorus pentachloride (300 mmol, 1.0 equiv.) portion-wise (temperature was kept below 20° C.). The mixture was stirred for 30 minutes at ambient temperature and re-cooled to 0° C. Anhydrous DMF (880 mmol, 2.9 equiv.) was added dropwise via addition funnel (temperature was kept below 20° C.) and the mixture was slowly warmed to 55° C. (<60° C., chilled with ice-bath if necessary). The reaction was maintained at 55° C. for 1 hour, cooled to 0° C. and quenched by slow addition of methanol (150 mL). The solution was maintained on an ice bath for several minutes, then added in portions to stirred ice-cold 50% aqueous potassium carbonate solution (240 mL) at a rate to keep temperature below 30° C. The mixture was stirred 5 minutes and extracted four times with dichloromethane (250 mL each). The combined extracts were dried over sodium sulfate and concentrated in vacuo to afford a crude viscous dark brown oil. The above intermediate was dissolved in 95% ethanol (250 mL), treated with hydrazine hydrate (300 mmol, 1.0 equiv.) and refluxed for 3 hours under nitrogen. The mixture was cooled to ambient temperature, filtered through Celite and the filtrate was concentrated in vacuo. Purification by silica gel chromatography (40-75% ethyl acetate in dichloromethane gradient) yielded 4-methoxy-1H-pyrazole (63%) as a light amber solid.

Step 2: Synthesis of 4-methoxy-N,N-dimethyl-1H-pyrazole-1-sulfonamide

DABCO (210 mmol, 1.1 equiv.) and dimethylsulfamoyl chloride (200 mmol, 1.1 equiv.) were sequentially added to a stirred solution of 4-methoxy-1H-pyrazole (180 mmol, 1.0 equiv.) in anhydrous acetonitrile (250 mL). The resultant suspension was stirred at ambient temperature for 16 hours, concentrated in vacuo and the residue was partitioned between water (200 mL) and ethyl acetate (200 mL). The aqueous phase was extracted with ethyl acetate (100 mL) and the combined organic phases were washed with 10% citric acid solution, water and brine (100 mL each), dried over magnesium sulfate, treated with silica gel (25 g). After stirring for 15 minutes, the mixture was filtered and concentrated in vacuo. Trituration from cold hexane (200 mL) containing ether (30 mL) afforded 4-methoxy-N,N-dimethyl-1H-pyrazole-1-sulfonamide (90%) as a pale yellow solid.

Step 3: Synthesis of 5-[(2-fluorophenyl)methyl]-N,N-dimethyl-4-methoxy-1H-pyrazole-1-sulfonamide A solution of 4-methoxy-N,N-dimethyl-1H-pyrazole-1-sulfonamide (130 mmol, 1.0 equiv.) in anhydrous 1,2-dimethoxyethane (500 mL) under nitrogen at −70° C. was treated with sec-butyllithium (1.3 N in cyclohexane, 130 mmol, 1.0 equiv.) (temperature of the reaction mixture was kept below −65° C. during the addition) After 45 minutes, the reaction was warmed to −30° C., and re-cooled to −70° C. 2-Fluorobenzyl bromide (150 mmol, 1.2 equiv.) was added dropwise. The turbid mixture was stirred for 30 minutes and then allowed to warm to 0° C. over 1 hour. After 30 minutes, the reaction mixture was quenched with ice-cold saturated aqueous sodium bicarbonate solution (500 mL). The mixture was extracted with ethyl acetate and the combined extracts were washed with water and brine, dried over magnesium sulfate, filtered and concentrated in vacuo to afford crude 5-[(2-fluorophenyl)methyl]-N,N-dimethyl-4-methoxy-1H-pyrazole-1-sulfonamide as a pale amber oil which was used in the next step without further purification.

Step 4: Synthesis of 5-[(2-fluorophenyl)methyl]-4-methoxy-1H-pyrazole

A stirred solution of 5-[(2-fluorophenyl)methyl]-N,N-dimethyl-4-methoxy-1H-pyrazole-1-sulfonamide in dichloromethane (200 mL) under nitrogen was treated with trifluoroacetic acid (200 mL) and refluxed for 5 h. The pale amber solution was concentrated in vacuo and the residual oil was taken up in 20% aqueous potassium carbonate solution (200 mL) and extracted with dichloromethane. The combined organic phases were washed with water and brine, dried over sodium sulfate and concentrated in vacuo. Purification via silica gel chromatography (2-67% ethyl acetate/dichloromethane gradient) afforded a pale yellow solid. Recrystallization from ethyl acetate/heptane yielded 5-[(2-fluorophenyl)methyl]-4-methoxy-1H-pyrazole (17 g, 68% over 2 steps) as a pale beige solid. $^1$H-NMR (500 MHz, CDCl$_3$) δ ppm 10.3 (br s, 1H), 7.22-7.15 (m, 2H), 7.12 (s, 1H), 7.07-7.00 (m, 2H), 3.97 (s, 2H), 3.72 (s, 3H).

Step 5: Synthesis of 3-(2-fluorobenzyl)-4-methoxy-1H-pyrazole-1-carboximidamide hydrochloride An orange solution of 5-[(2-fluorophenyl)methyl]-4-methoxy-1H-pyrazole and cyanamide (1.0 equiv.) in dioxane was treated with hydrogen chloride (4.0 N in dioxane, 1.1 equiv.). The resultant thick beige suspension was warmed to 100° C. and stirred for 3.5 hours. The reaction became an orange solution within 15 minutes and a light tan suspension upon further heating. The reaction was cooled to ambient temperature, diluted with ether and the solid was collected by vacuum filtration and dried to yield 3-(2-fluorobenzyl)-4-methoxy-1H-pyrazole-1-carboximidamide hydrochloride (98% as a 6.6:1.0 mixture of regioisomers).

Step 6: Synthesis of Compound I-82

A tan suspension of 3-(2-fluorobenzyl)-4-methoxy-1H-pyrazole-1-carboximidamide hydrochloride, methyl 3,3-dicyano-2,2-dimethylpropanoate (3.0 equiv.) and potassium bicarbonate (3.0 equiv.) in t-butanol was heated at 80° C. for 17 hours. The reaction mixture was was diluted with water and filtered to afford an off-white solid. Trituration with ether afforded pure Compound I-82 as a white solid. The filtrate was extracted with dichloromethane/iPrOH (5:1). The combined organic phases were dried over sodium sulfate, filtered, and the solvent was removed in vacuo. The combined crude product was purified by silica gel chromatography (5-20% acetonitrile/methanol (7:1) in dichloromethane gradient) to yield additional amounts of the title compound. The total yield was (540 mg, 67%). $^1$H-NMR (500 MHz, DMSO-d$_6$) δ ppm 11.0 (s, 1H), 8.01 (s, 1H), 7.29-7.21 (m, 2H), 7.16-7.10 (m, 2H), 6.85 (br s, 2H), 3.91 (s, 2H), 3.74 (s, 3H), 1.31 (s, 6H).

Compound I-38

The title compound was synthesized in 2 steps:

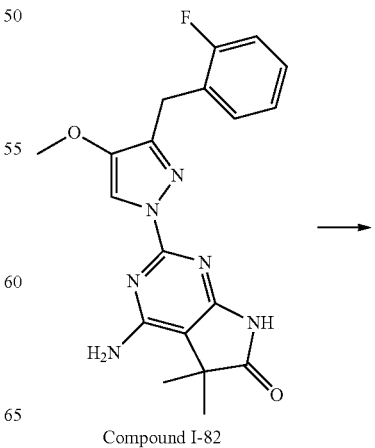

Compound I-82

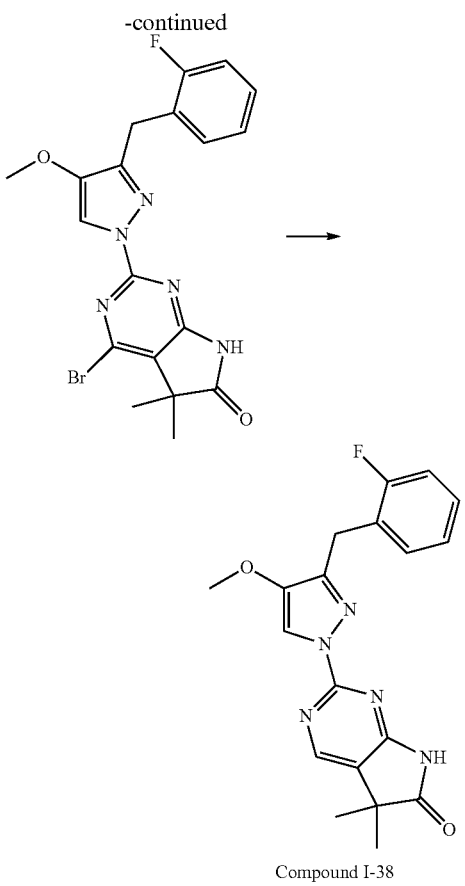

Compound I-38

Step 1: Synthesis of 4-bromo-2-(3-(2-fluorobenzyl)-4-methoxy-1H-pyrazol-1-yl)-5,5-dimethyl-5H-pyrrolo[2,3-d]pyrimidin-6(7H)-one A green solution of 4-amino-2-(3-(2-fluorobenzyl)-4-methoxy-1H-pyrazol-1-yl)-5,5-dimethyl-5H-pyrrolo[2,3-d]pyrimidin-6(7H)-one and copper(II) bromide (Compound I-82, 1.2 equiv.) in THF was treated with t-butyl nitrite (2.0 equiv.). The resultant mixture in a sealed vial was heated at 65° C. for 18 hours. The reaction mixture was cooled to ambient temperature, filtered and partitioned between water and dichloromethane. The organic phases were washed with saturated ammonium chloride solution and brine, dried over sodium sulfate, filtered, and the solvent was removed in vacuo to afford 4-bromo-2-(3-(2-fluorobenzyl)-4-methoxy-1H-pyrazol-1-yl)-5,5-dimethyl-5H-pyrrolo[2,3-d]pyrimidin-6(7H)-one as a green foam solid which was used in the next step without further purification.

Step 2: Synthesis of Compound I-38

A solution of 4-bromo-2-(3-(2-fluorobenzyl)-4-methoxy-1H-pyrazol-1-yl)-5,5-dimethyl-5H-pyrrolo[2,3-d]pyrimidin-6(7H)-one in THF was treated with zinc dust (20 equiv.) and acetic acid (24 equiv.). The resultant greenish grey suspension in a sealed vial was heated at 85° C. for 16 hours. After cooling to ambient temperature, the reaction mixture was filtered through Celite with the aid of ethyl acetate and the filtrate was washed with 1N sodium hydroxide solution and brine, dried over sodium sulfate, filtered and concentrated in vacuo. Purification via preparative HPLC (30-80% acetonitrile/water gradient with 0.1% trifluoroacetic acid) afforded Compound I-38 (55 mg, 56% over 2 steps) as a white solid. $^1$H-NMR (500 MHz, DMSO-d$_6$) δ ppm 11.6 (s, 1H), 8.40 (s, 1H), 8.18 (s, 1H), 7.30-7.24 (m, 2H), 7.18-7.11 (m, 2H), 3.94 (s, 2H), 3.78 (s, 3H), 1.34 (s, 6H).

Compound I-83

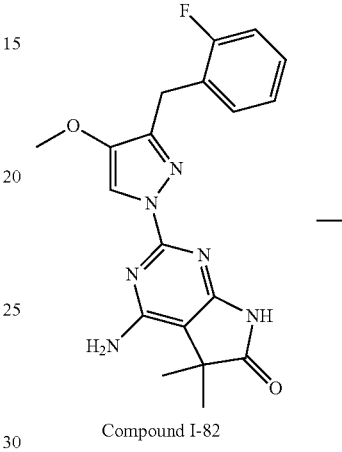

Compound I-82

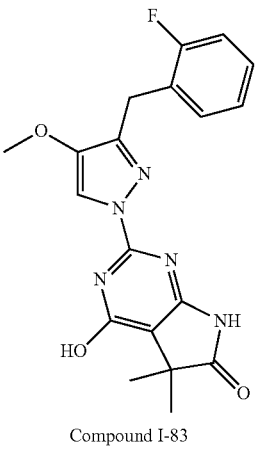

Compound I-83

A solution of 4-amino-2-(3-(2-fluorobenzyl)-4-methoxy-1H-pyrazol-1-yl)-5,5-dimethyl-5H-pyrrolo[2,3-d]pyrimidin-6(7H)-one in trifluoroacetic acid at 0° C. was treated water (25 equiv.) followed by sodium nitrite (Compound I-82, 1.1 equiv., added in four portions). Gas evolution was observed. After 14 minutes, additional amount of sodium nitrite (0.1 equiv.) was added and the reaction was stirred for 5 minutes. Water was added and the product was collected by vacuum filtration to afford Compound I-83 (200 mg, 98%) as a light tan solid. $^1$H-NMR (500 MHz, DMSO-d$_6$) δ ppm 12.5 (s, 1H), 11.3 (s, 1H), 8.02 (s, 1H), 7.27 (m, 2H), 7.14 (m, 2H), 3.94 (s, 2H), 3.77 (s, 3H), 1.29 (s, 6H).

Compound I-84

The title compound was synthesized in 6 steps:

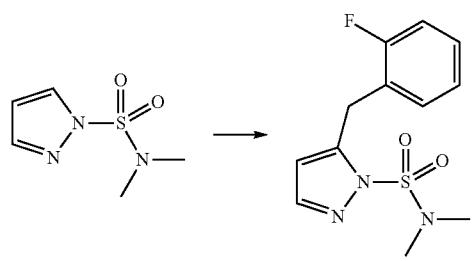

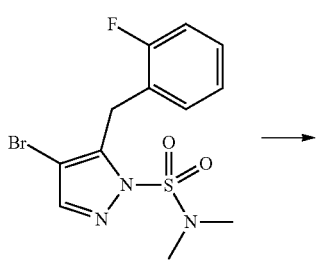

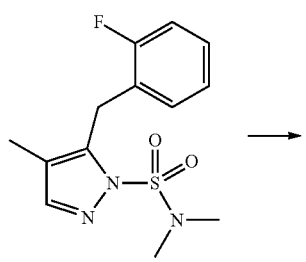

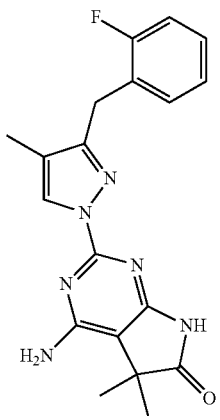

Compound I-84

Step 1: Synthesis of 5-[(2-fluorophenyl)methyl]-N,N-dimethyl-1H-pyrazole-1-sulfonamide A solution of N,N-dimethyl-1H-pyrazole-1-sulfonamide (150 mmol, 1.0 equiv.) in anhydrous THF (250 mL) under nitrogen at −72° C. was treated with sec-butyllithium (1.4 N in cyclohexane, 170 mmol, 1.1 equiv.) (temperature of the reaction mixture was kept below −60° C. during the addition). Additional 50 mL of THF was added to facilitate stirring. 2-Fluorobenzyl bromide (170 mmol, 1.1 equiv.) was added dropwise. The mixture was allowed to warm to ambient temperature over 1 hour and stirred for an additional hour. The reaction was cooled on ice and quenched with ice-cold saturated aqueous sodium bicarbonate solution (100 mL). The mixture was concentrated in vacuo to remove volatile organics, partitioned between water and ethyl acetate. The combined extracts were washed with water and brine, dried over magnesium sulfate, filtered and concentrated in vacuo. Purification via silica gel chromatography (3-40% ethyl acetate/heptane gradient) afforded 5-[(2-fluorophenyl)methyl]-N,N-dimethyl-1H-pyrazole-1-sulfonamide (89%) as a pale yellow oil.

Step 2: Synthesis of 4-bromo-5-[(2-fluorophenyl)methyl]-N,N-dimethyl-1H-pyrazole-1-sulfonamide A solution of 5-[(2-fluorophenyl)methyl]-N,N-dimethyl-1H-pyrazole-1-sulfonamide in anhydrous acetonitrile under nitrogen was treated with N-bromosuccinimide (NBS) (1.2 equiv.) and heated at 65° C. for 80 minutes. After cooling to ambient temperature, saturated sodium bicarbonate solution was added. The mixture was concentrated in vacuo to remove volatile organics and partitioned between water and dichloromethane. The combined organic phases were washed with brine, dried over sodium sulfate and concentrated in vacuo. Trituration with petroleum ethers afforded 4-bromo-5-[(2-fluorophenyl)methyl]-N,N-dimethyl-1H-pyrazole-1-sulfonamide (96%) as a white solid.

Step 3: Synthesis of 5-(2-fluorobenzyl)-N,N,4-trimethyl-1H-pyrazole-1-sulfonamide To a mixture of 4-bromo-5-[(2-fluorophenyl)methyl]-N,N-dimethyl-1H-pyrazole-1-sulfonamide, cesium carbonate (1.5 equiv.), [1,1′-bis(diphenylphosphino)ferrocene]-dichloropalladium(II) (complex with dichloromethane, 0.05 equiv.) was added dioxane/water (10:1, degassed by bubbling with nitrogen gas for 10 min). Trimethylboroxine (0.8 equiv.) was added and the reaction mixture was heated at 80° C. for 20 hours. Additional portions of cesium carbonate (0.5 equiv.), [1,1'-bis(diphenylphosphino)ferrocene]dichloropalladium(II) catalyst (0.02 equiv.) and trimethylboroxine (0.4 equiv.) were added and the reaction was heated at 80° C. for 2 days. After cooling to ambient temperature, the mixture was partitioned between water and ethyl acetate. The organic phases were washed with brine, dried over sodium sulfate, filtered, and the solvent was removed in vacuo. Purification via silica gel chromatography (10-20% ethyl acetate/hexanes gradient) afforded 5-(2-fluorobenzyl)-N,N,4-trimethyl-1H-pyrazole-1-sulfonamide (71%, 84% purity, contaminated with des-bromo side-product) as a clear oil.

Step 4: Synthesis of
5-(2-fluorobenzyl)-4-methyl-1H-pyrazole

A stirred solution of 5-(2-fluorobenzyl)-N,N, 4-trimethyl-1H-pyrazole-1-sulfonamide in dichloromethane under nitrogen was treated with trifluoroacetic acid (25 equiv.) and heated at 50° C. for 8.5 hours. The pale amber solution was concentrated in vacuo and the residual oil was taken up dichloromethane and basicified with 15% aqueous potassium carbonate solution. The combined organic phases were washed with water and brine, dried over sodium sulfate and concentrated in vacuo. Purification via silica gel chromatography (5-10% acetonitrile/MeOH (7:1) in dichloromethane gradient). Re-purified by preparative HPLC (30-80% acetonitrile/water gradient with 0.1% formic acid) to afford 5-(2-fluorobenzyl)-4-methyl-1H-pyrazole as a clear oil.

Step 5: Synthesis of 3-(2-fluorobenzyl)-4-methyl-1H-pyrazole-1-carboximidamide hydrochloride A clear solution of 5-[(2-fluorophenyl)methyl]-4-methyl-1H-pyrazole and cyanamide (1.1 equiv.) in dioxane was treated with hydrogen chloride (4.0 N in dioxane, 1.1 equiv.). The resultant white suspension was warmed to 100° C. and stirred for 2 hours. The reaction became a clear solution within 5 minutes. The reaction was cooled to ambient temperature, concentrated to half volume and diluted with ether. The resultant solid was collected by vacuum filtration and dried to yield 3-(2-fluorobenzyl)-4-methyl-1H-pyrazole-1-carboximidamide hydrochloride (93% as a 10:1.0 mixture of regioisomers) as a light tan solid.

Step 6: Synthesis of Compound I-84

A tan suspension of 3-(2-fluorobenzyl)-4-methyl-1H-pyrazole-1-carboximidamide hydrochloride, methyl 3,3-dicyano-2,2-dimethylpropanoate (3.0 equiv.) and potassium bicarbonate (3.0 equiv.) in t-butanol was heated at 80° C. for 19.5 hours. The reaction mixture was diluted with water and extracted with dichloromethane/iPrOH (5:1). The combined organic phases were dried over sodium sulfate, filtered, and the solvent was removed in vacuo. The combined crude product was purified by silica gel chromatography (5-20% acetonitrile/MeOH (7:1) in dichloromethane gradient) to yield Compound I-84 (330 mg, 68%) as a pale yellow solid.

$^1$H-NMR (500 MHz, DMSO-$d_6$) δ ppm 11.0 (s, 1H), 8.15 (s, 1H), 7.27 (m, 1H), 7.19 (m, 2H), 7.15 (m, 1H), 6.85 (br s, 2H), 3.95 (s, 2H), 1.95 (s, 3H), 1.31 (s, 6H).

Compound I-85
The title compound was synthesized in 2 steps:

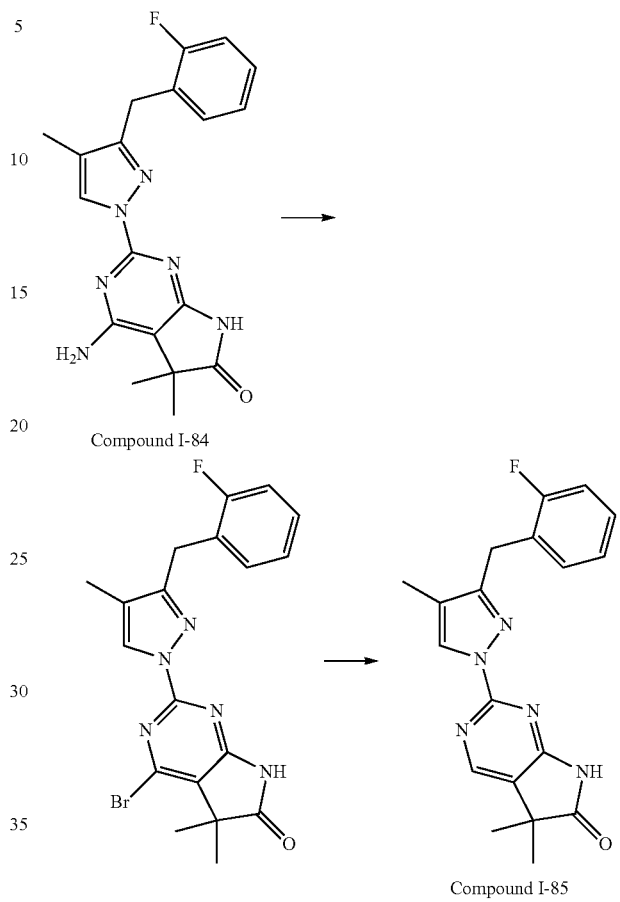

Step 1: Synthesis of 4-bromo-2-(3-(2-fluorobenzyl)-4-methyl-1H-pyrazol-1-yl)-5,5-dimethyl-5H-pyrrolo[2,3-d]pyrimidin-6(7H)-one A green solution of 4-amino-2-(3-(2-fluorobenzyl)-4-methyl-1H-pyrazol-1-yl)-5,5-dimethyl-5H-pyrrolo[2,3-d]pyrimidin-6(7H)-one and copper(II) bromide (1.2 equiv.) in THF was treated with t-butyl nitrite (2.0 equiv.). The resultant mixture in a sealed vial was heated at 65° C. for 27 hours. The reaction mixture was cooled to ambient temperature, filtered and partitioned between half-saturated ammonium chloride solution and dichloromethane. The organic phases were washed with brine, dried over sodium sulfate, filtered, and the solvent was removed in vacuo to afford 4-bromo-2-(3-(2-fluorobenzyl)-4-methyl-1H-pyrazol-1-yl)-5,5-dimethyl-5H-pyrrolo[2,3-d]pyrimidin-6(7H)-one as a green oil which was used in the next step without further purification.

Step 2: Synthesis of Compound I-85

A solution of 4-bromo-2-(3-(2-fluorobenzyl)-4-methyl-1H-pyrazol-1-yl)-5,5-dimethyl-5H-pyrrolo[2,3-d]pyrimidin-6(7H)-one in THF was treated with zinc dust (20 equiv.) and acetic acid (24 equiv.). The resultant greenish grey suspension in a sealed vial was heated at 85° C. for 24 hours. After cooling to ambient temperature, the reaction mixture was filtered through Celite with the aid of ethyl acetate and the filtrate was washed with 1N sodium hydroxide solution and brine, dried over sodium sulfate, filtered and concentrated in vacuo. Purification via preparative HPLC (30-80% acetonitrile/water gradient with 0.1% formic acid) afforded Compound I-85 (34 mg, 35% over 2 steps) as a white solid. $^1$H-NMR (500 MHz, DMSO-d$_6$) δ ppm 11.7 (s, 1H), 8.41 (s, 1H), 8.30 (s, 1H), 7.28 (m, 1H), 7.23 (m, 1H), 7.16 (m, 1H), 7.13 (m, 1H), 3.98 (s, 2H), 1.98 (s, 3H), 1.34 (s, 6H).

Compound I-86

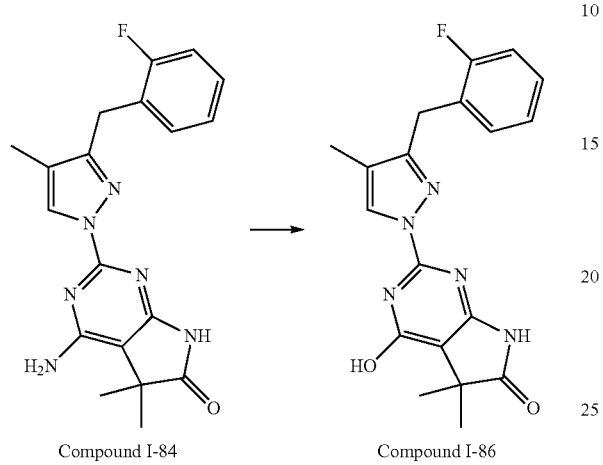

Compound I-84        Compound I-86

A solution of 4-amino-2-(3-(2-fluorobenzyl)-4-methyl-1H-pyrazol-1-yl)-5,5-dimethyl-5H-pyrrolo[2,3-d]pyrimidin-6(7H)-one in trifluoroacetic acid at 0° C. was treated water (Compound I-85, 26 equiv.) followed by sodium nitrite (1.5 equiv., added in two portions). Gas evolution was observed. After 20 minutes, water was added and the product was collected by vacuum filtration to afford Compound I-86 (45 mg, 96%) as a light tan solid. $^1$H-NMR (500 MHz, MeOH-d$_4$) δ ppm 8.45 (s, 0.6H, partially exchanged), 8.24 (s, 1H), 7.26 (m, 1H), 7.22 (m, 1H), 7.10 (m, 2H), 4.09 (s, 2H), 1.98 (s, 3H), 1.42 (s, 6H).

Compound I-87

The title compound was synthesized in 5 steps:

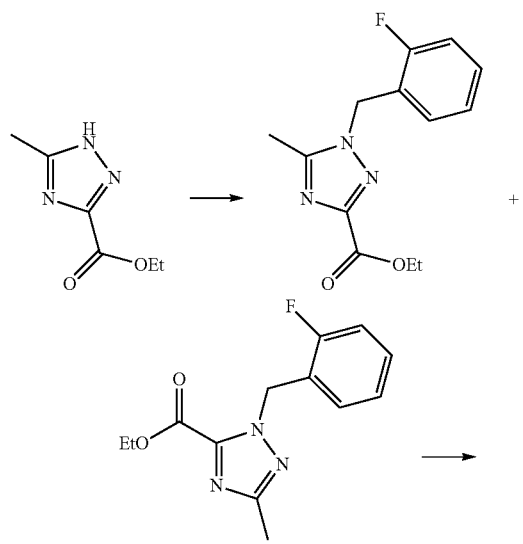

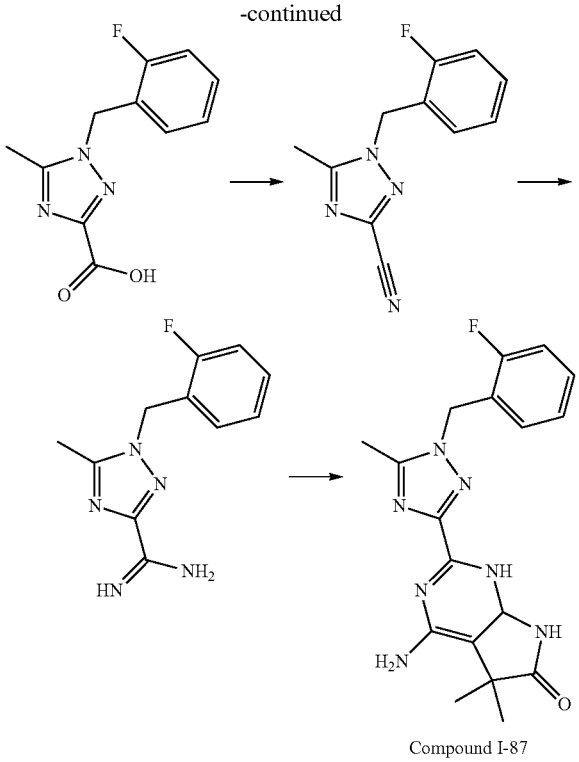

Compound I-87

Step 1: Synthesis of ethyl 1-(2-fluorobenzyl)-5-methyl-1H-1,2,4-triazole-3-carboxylate and ethyl 1-(2-fluorobenzyl)-3-methyl-1H-1,2,4-triazole-5-carboxylate A solution of ethyl 3-methyl-1H-1,2,4-triazole-5-carboxylate in anhydrous DMF was treated with sodium hydride (60 wt % in mineral oil, 1.2 equiv.) and stirred for 10 min. 2-Fluorobenzyl bromide (1.2 equiv.) was added. After 16 hours, water was added and the aqueous phase was extracted with ethyl acetate. The combined organic phases were washed with water and brine, dried over sodium sulfate, filtered, and the solvent was removed in vacuo. Purification by silica gel chromatography (10-50% ethyl acetate in hexanes gradient) yielded ethyl 1-(2-fluorobenzyl)-5-methyl-1H-1,2,4-triazole-3-carboxylate (58%) and ethyl 1-(2-fluorobenzyl)-3-methyl-1H-1,2,4-triazole-5-carboxylate (23%).

Step 2: Synthesis of 1-(2-fluorobenzyl)-5-methyl-1H-1,2,4-triazole-3-carboxylic acid To a solution of ethyl 1-(2-fluorobenzyl)-5-methyl-1H-1,2,4-triazole-3-carboxylate in THF/MeOH/water (3:1:1 ratio) was added lithium hydroxide (1.5 equiv.). After 3.5 hours, the reaction mixture was concentrated in vacuo to remove most of the volatile organics. The resultant mixture was diluted with water, acidified to pH 3-4 by addition of 1N HCl solution and extracted with dichloromethane/iPrOH (4:1). Note: The pH of aqueous phase became pH 7 after each extraction and was re-acidified to pH 3-4 before the next extraction. The combined organic phases were dried over sodium sulfate, filtered, and the solvent was removed in vacuo to give 1-(2-fluorobenzyl)-5-methyl-1H-1,2,4-triazole-3-carboxylic acid (99%).

Step 3: Synthesis of 1-(2-fluorobenzyl)-5-methyl-1H-1,2,4-triazole-3-carbonitrile To a suspension of 1-(2-fluorobenzyl)-5-methyl-1H-1,2,4-triazole-3-carboxylic acid, 2-methylpropan-2-amine (2.0 equiv.), and triethylamine (2.0 equiv.) in ethyl acetate was added n-propylphosphonic anhydride (T3P, 50 wt % solution in ethyl acetate, 3.0 equiv.). The resultant yellow solution was heated at 65° C. for 1 hour. The solvent was removed in vacuo. Phosphoryl trichloride (15 equiv.) was added and the resulting mixture was stirred at 80° C. for 24 hours. The reaction was quenched by carefully pouring into a mixture of water and ice, neutralized to pH 7 by addition of saturated sodium bicarbonate solution/solid sodium bicarbonate and extracted with dichloromethane. The combined organic phases were dried over sodium sulfate, filtered, and the solvent was removed in vacuo. Purification by silica gel chromatography (10-30% ethyl acetate in hexanes gradient) yielded 1-(2-fluorobenzyl)-5-methyl-1H-1,2,4-triazole-3-carbonitrile (84%) as a pale yellow oil.

Step 4: Synthesis of 1-(2-fluorobenzyl)-5-methyl-1H-1,2,4-triazole-3-carboximidamide A solution of 1-(2-fluorobenzyl)-5-methyl-1H-1,2,4-triazole-3-carbonitrile in methanol was treated sodium methoxide (25 wt % solution in MeOH, 5.0 equiv.) and stirred for 2 hours. Ammonium chloride (10 equiv.) was added. The reaction mixture was stirred at ambient temperature for 24 hours. The crude mixture was concentrated in vacuo and partitioned between half-saturated sodium bicarbonate solution/1N sodium hydroxide solution (30:1) and ethyl acetate. The organic phases were dried over sodium sulfate, filtered, and the solvent was removed in vacuo to afford 1-(2-fluorobenzyl)-5-methyl-1H-1,2,4-triazole-3-carboximidamide (97%) which was used without further manipulation.

Step 5: Synthesis of Compound I-87

A suspension of 1-(2-fluorobenzyl)-5-methyl-1H-1,2,4-triazole-3-carboximidamide, methyl 3,3-dicyano-2,2-dimethylpropanoate (3.0 equiv.) and potassium bicarbonate (3.0 equiv.) in t-butanol was heated at 80° C. for 4 hours. After cooling to ambient temperature, the reaction mixture was diluted with water. The resultant solid was collected by vacuum filtration and dried to afford Compound I-87 (230 mg, 82%) as a white solid. $^1$H-NMR (500 MHz, MeOH-d$_4$) δ ppm 7.39 (m, 1H), 7.28 (app. t, 1H), 7.19 (m, 2H), 5.52 (s, 2H), 2.57 (s, 3H), 1.43 (s, 6H).

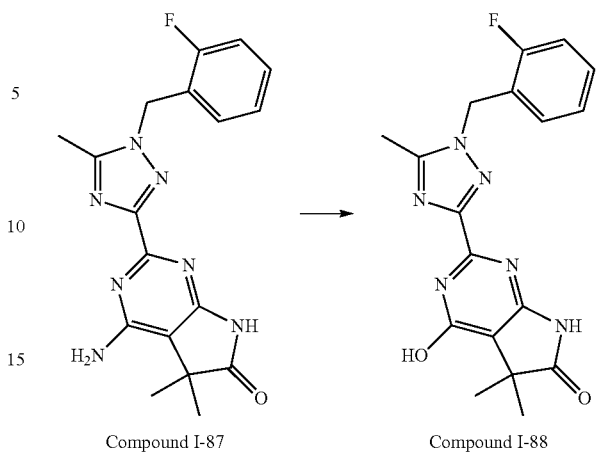

Compound I-87      Compound I-88

Compound I-88

A solution of 4-amino-2-(1-(2-fluorobenzyl)-5-methyl-1H-1,2,4-triazol-3-yl)-5,5-dimethyl-5H-pyrrolo[2,3-d]pyrimidin-6(7H)-one in trifluoroacetic acid at 0° C. was treated water (Compound I-87, 27 equiv.) followed by sodium nitrite (1.5 equiv.). Gas evolution was observed. After 20 minutes, water was added and the mixture was neutralized to pH 6-7 by addition of 1N or 3N sodium hydroxide solution. The product was collected by vacuum filtration and dried to afford Compound I-88 (35 mg, 85%) as a light tan solid. $^1$H-NMR (500 MHz, DMSO-d$_6$) δ ppm 12.2 (s, 1H), 11.1 (s, 1H), 7.42 (m, 1H), 7.28 (app. t, 1H), 7.24 (m, 2H), 5.51 (s, 2H), 2.55 (s, 3H), 1.28 (s, 6H).

Compound I-89

The title compound was synthesized in 2 steps:

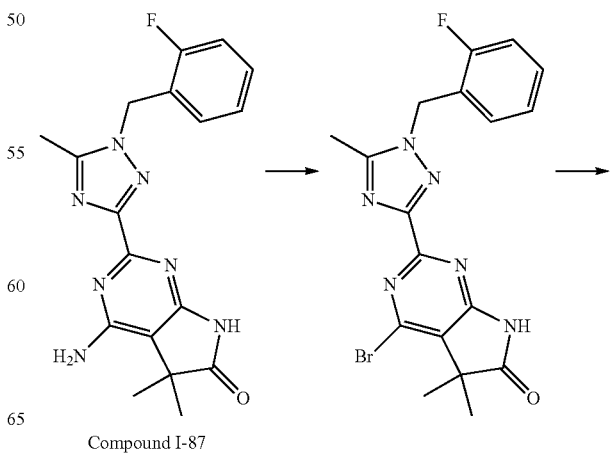

Compound I-87

-continued

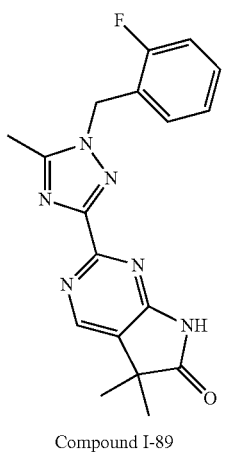

Compound I-89

Step 1: Synthesis of 4-bromo-2-(1-(2-fluorobenzyl)-5-methyl-1H-1,2,4-triazol-3-yl)-5,5-dimethyl-5H-pyrrolo[2,3-d]pyrimidin-6(7H)-one A dark red solution of 4-amino-2-(1-(2-fluorobenzyl)-5-methyl-1H-1,2,4-triazol-3-yl)-5,5-dimethyl-5H-pyrrolo[2,3-d]pyrimidin-6(7H)-one and copper(II) bromide (Compound I-87, 1.2 equiv.) in THF was treated with t-butyl nitrite (2.0 equiv.). The resultant mixture in a sealed vial was heated at 65° C. for 26 hours. The reaction mixture was cooled to ambient temperature, filtered and partitioned between half-saturated sodium bicarbonate solution and dichloromethane. The organic phases were washed with saturated ammonium chloride solution and brine, dried over sodium sulfate, filtered, and the solvent was removed in vacuo to afford 4-bromo-2-(1-(2-fluorobenzyl)-5-methyl-1H-1,2,4-triazol-3-yl)-5,5-dimethyl-5H-pyrrolo[2,3-d]pyrimidin-6(7H)-one as a green oil which was used in the next step without further purification.

Step 2: Synthesis of Compound I-89

A solution of 4-bromo-2-(1-(2-fluorobenzyl)-5-methyl-1H-1,2,4-triazol-3-yl)-5,5-dimethyl-5H-pyrrolo[2,3-d]pyrimidin-6(7H)-one in THF was treated with zinc dust (20 equiv.) and acetic acid (24 equiv.). The resultant greenish grey suspension in a sealed vial was heated at 85° C. for 21 hours. After cooling to ambient temperature, the reaction mixture was filtered through Celite with the aid of ethyl acetate and the filtrate was washed with 1N sodium hydroxide solution and brine, dried over sodium sulfate, filtered and concentrated in vacuo. Purification via silica gel chromatography (10-60% acetonitrile/MeOH (7:1) in dichloromethane gradient) afforded Compound I-89 (17 mg, 20% over 2 steps) as a white solid. $^1$H-NMR (500 MHz, DMSO-d$_6$) δ ppm 11.5 (s, 1H), 8.53 (s, 1H), 7.41 (m, 1H), 7.30-7.20 (m, 3H), 5.48 (s, 2H), 2.53 (s, 3H), 1.34 (s, 6H).

Compound I-90

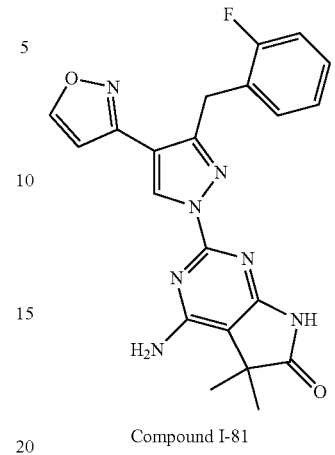

Compound I-81

Compound I-90

A solution of 2-(3-(2-fluorobenzyl)-4-(isoxazol-3-yl)-1H-pyrazol-1-yl)-5,5-dimethyl-5H-pyrrolo[2,3-d]pyrimidin-6(7H)-one (Compound I-81) in 1,8-diazabicyclo[5.4.0]undec-7-ene (DBU) (34 equiv.) as solvent was heated at 110-115° C. for 13 days. After cooling to ambient temperature, the reaction mixture was blown to dryness under a stream of nitrogen. Purification via preparative HPLC (30-80% acetonitrile/water gradient with 0.1% formic acid) afforded Compound I-90 (7.8 mg, 27%) as an off-white solid. $^1$H-NMR (500 MHz, DMSO-d$_6$) δ ppm 11.9 (s, 1H), 9.29 (s, 1H), 8.51 (s, 1H), 7.34 (m, 2H), 7.19 (m, 2H), 4.17 (s, 2H), 1.35 (s, 6H).

Compound I-91

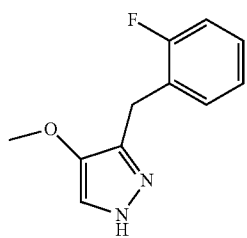

+

319
-continued

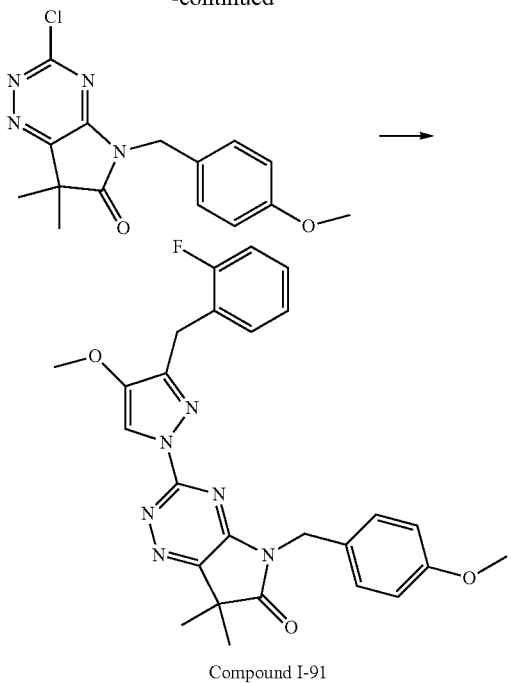

Compound I-91

A solution of 5-[(2-fluorophenyl)methyl]-4-methoxy-1H-pyrazole (1.1 equiv.) in N-methyl pyrrolidinone (NMP) was treated with sodium hydride (60 wt % in mineral oil, 1.3 equiv.). After 15 min, the mixture was added dropwise to a solution of 3-chloro-5-(4-methoxybenzyl)-7,7-dimethyl-5H-pyrrolo[2,3-e][1,2,4]triazin-6(7H)-one (ref. M. Follmann et al. US2013/210824) in NMP. The resulting mixture was stirred for 75 minutes and then partitioned between water and ethyl acetate. The combined organic phases were dried over sodium sulfate, filtered and concentrated in vacuo. Purification by silica gel chromatography (10-30% ethyl acetate in hexanes gradient) yielded Compound I-91 (78 mg, 91%) as clear oil.

$^1$H-NMR (500 MHz, MeOH-$d_4$) δ ppm 8.24 (s, 1H), 7.40 (s, 2H), 7.23 (m, 2H), 7.06 (m, 2H), 6.85 (d, 2H), 4.97 (s, 2H), 4.07 (s, 2H), 3.83 (s, 3H), 3.74 (s, 3H), 1.49 (s, 6H).

Synthesis of Intermediate-21

This intermediate was synthesized in several steps:

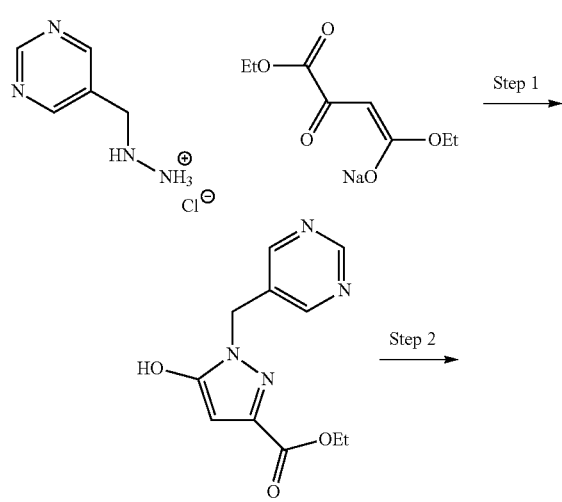

320
-continued

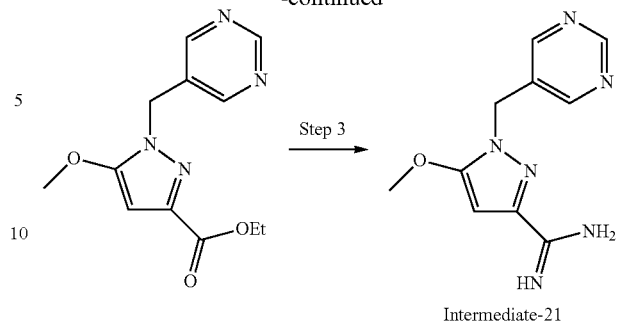

Intermediate-21

Step 1

A suspension of sodium (E)-1,4-diethoxy-3,4-dioxobut-1-en-1-olate (1.38 g, 6.55 mmol), 2-(pyrimidin-5-yl)acetimidamide hydrochloride (1.13 g, 6.55 mmol), and acetic acid (0.600 mL, 10.5 mmol) was heated at 90° C. for 30 minutes after which the reaction was allowed to cool to room temperature. Diethyl ether was added, leading to the formation of a precipitate. This solid was filtered and dried to afford ethyl 5-hydroxy-1-(pyrimidin-5-yl methyl)-1H-pyrazole-3-carboxylate (1.07 g, 66% yield) as a tan-pink solid with 90% purity.

Step 2

A suspension of ethyl 5-hydroxy-1-(pyrimidin-5-ylmethyl)-1H-pyrazole-3-carboxylate (411 mg, 1.66 mmol), p-toluenesulfonic acid methyl ester (462 mg, 2.48 mmol), and potassium carbonate (915 mg, 6.62 mmol) in N,N-Dimethylformamide (8 mL) was stirred at room temperature for 18 hours. The reaction mixture was diluted in water, extracted with 5:1 dichloromethane/isopropanol (5×30 mL), dried (sodium sulfate), filtered and concentrated to afford the crude product as a solution in N,N-Dimethylformamide. Lyophilization from water afforded ethyl 5-methoxy-1-(pyrimidin-5-ylmethyl)-1H-pyrazole-3-carboxylate (97.1 mg, 22% yield) as a tan solid.

Step 3: Preparation of Intermediate-21

To a 0° C. suspension of ammonium chloride (141 mg, 2.63 mmol) in toluene (3 mL) was added a 2M in toluene solution of trimethylaluminum (1.20 mL, 2.40 mmol). The reaction mixture was allowed to warm up to room temperature, then stirred for 1 h. A solution of ethyl 5-methoxy-1-(pyrimidin-5-ylmethyl)-1H-pyrazole-3-carboxylate (126 mg, 0.479 mmol) in toluene was then added, after which the resulting reaction mixture was heated to 100° C. for 18 h. The reaction mixture was cooled to 0° C., after which methanol was added. The resulting slurry was stirred at 0° C. for 20 min, then warmed up to room temperature. The suspension was filtered through celite and washed with methanol to afford crude 5-methoxy-1-(pyrimidin-5-ylmethyl)-1H-pyrazole-3-carboximidamide (130 mg, 117% yield due to trapped inorganic salts) as a tan-orange solid. No purification was necessary. $^1$H NMR: (500 MHz, CD$_3$OD): δ (ppm) 9.12 (s, 1H), 8.77 (s, 2H), 6.42 (s, 1H), 5.39 (s, 2H), 4.04 (s, 3H).

Compound I-92

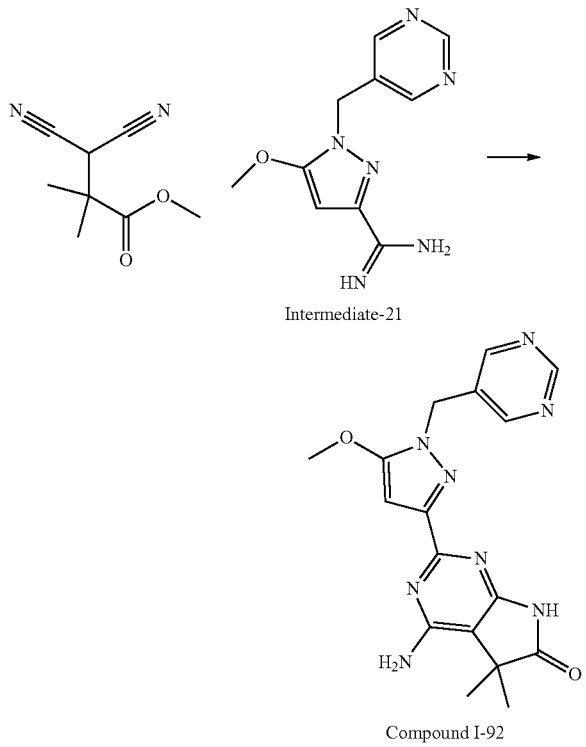

Intermediate-21

Compound I-92

A suspension of methyl 3,3-dicyano-2,2-dimethylpropanoate (Intermediate-21, 90.0 mg, 0.544 mmol), 5-methoxy-1-(pyrimidin-5-ylmethyl)-1H-pyrazole-3-carboximidamide (126 mg, 0.544 mmol), and sodium bicarbonate (45.7 mg, 0.544 mmol) in methanol (3 mL) was heated at 80° C. for 16 hours, after which the reaction mixture was diluted in water, concentrated, filtered to a solid. Purification was achieved by reverse phase HPLC utilizing a gradient of 5 to 95% acetonitrile in water (spiked with 0.1% trifluoroacetic acid) over 20 minutes to afford 4-amino-2-(5-methoxy-1-(pyrimidin-5-ylmethyl)-1H-pyrazol-3-yl)-5,5-dimethyl-5H-pyrrolo[2,3-d]pyrimidin-6(7H)-one (20.9 mg, 10% yield) as a tan solid after lyophilization. $^1$H NMR: (500 MHz, CD$_3$OD): δ (ppm) 9.12 (s, 1H), 8.77 (s, 2H), 6.45 (s, 1H), 5.39 (s, 2H), 4.04 (s, 3H), 1.47 (s, 6H).

Compound I-93

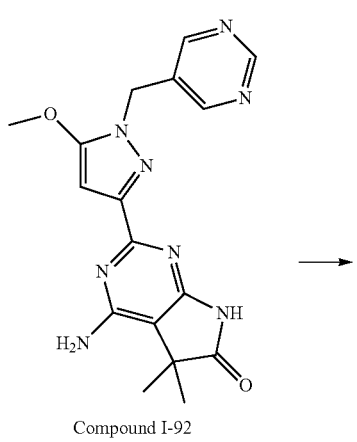

Compound I-92

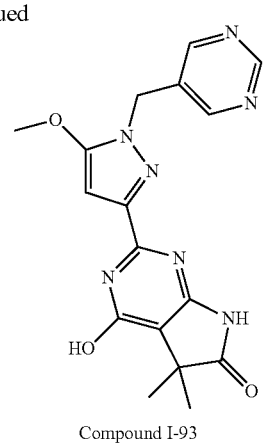

Compound I-93

To a solution of 4-amino-2-(5-methoxy-1-(pyrimidin-5-ylmethyl)-1H-pyrazol-3-yl)-5,5-dimethyl-5H-pyrrolo[2,3-d]pyrimidin-6(7H)-one (Compound I-92, 6.8 mg, 0.019 mmol) in trifluoroacetic acid (0.2 mL) at 0° C. was added water (20 3.33 mmol) followed by solid sodium nitrite (1.9 mg, 0.028 mmol). After 20 minutes, the reaction mixture was diluted in water (1 mL) then lyophilized to afford 4-hydroxy-2-(5-methoxy-1-(pyrimidin-5-ylmethyl)-1H-pyrazol-3-yl)-5,5-dimethyl-5H-pyrrolo[2,3-d]pyrimidin-6(7H)-one (6.8 mg, 100% yield) as a tan solid. No purification was necessary. $^1$H NMR: (500 MHz, CD$_3$OD): δ (ppm) 9.13 (s, 1H), 8.80 (s, 2H), 6.39 (s, 1H), 5.40 (s, 2H), 4.04 (s, 3H), 1.45 (s, 6H).

Compound I-94

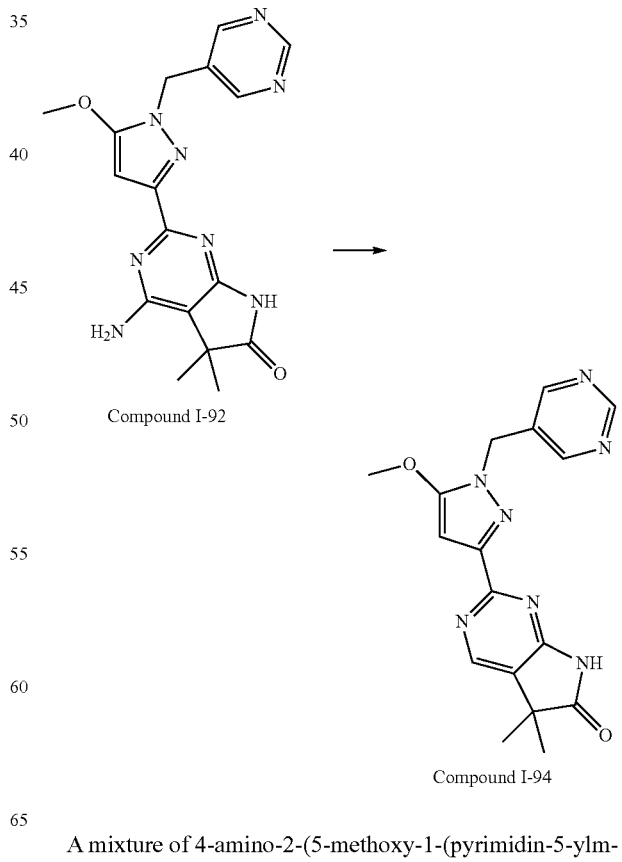

Compound I-92

Compound I-94

A mixture of 4-amino-2-(5-methoxy-1-(pyrimidin-5-ylmethyl)-1H-pyrazol-3-yl)-5,5-dimethyl-5H-pyrrolo[2,3-d]pyrimidin-6(7H)-one (Compound I-92, 17.3 mg, 0.047 mmol), tert-Butyl nitrite (0.011 ml, 0.094 mmol), and copper(II) bromide (12.7 mg, 0.0570 mmol) in tetrahydrofuran (1.5 mL) was heated at 65° C. for 16 hours. The reaction mixture was then filtered and concentrated to dryness to afford a crude mixture of 4-bromo-2-(5-methoxy-1-(pyrimidin-5-yl-methyl)-1H-pyrazol-3-yl)-5,5-dimethyl-5H-pyrrolo[2,3-d] pyrimidin-6(7H)-one and 4-bromo-2-(4-bromo-5-methoxy-1-(pyrimidin-5-ylmethyl)-1H-pyrazol-3-yl)-5,5-dimethyl-5H-pyrrolo[2,3-d]pyrimidin-6(7H)-one (34.4 mg). This crude mixture was suspended in a mixture of tetrahydrofuran (1.5 mL) and acetic acid (0.069 mL, 1.2 mmol), after which zinc dust (52.3 mg, 0.800 mmol) was added. The resulting suspension was heated to 80° C. for 4 hours, after which all of the brominated starting material had been consumed. The reaction mixture was filtered through celite then purified by reverse phase HPLC utilizing a gradient of 12 to 48% acetonitrile in water over 30 minutes (spiked with 0.1% trifluoroacetic acid) to afford 2-(5-methoxy-1-(pyrimidin-5-ylmethyl)-1H-pyrazol-3-yl)-5,5-dimethyl-5H-pyrrolo[2,3-d]pyrimidin-6(7H)-one (0.5 mg, 2% yield) as a tan solid. $^1$H NMR: (500 MHz, CD$_3$OD): δ (ppm) 9.10 (s, 1H), 8.77 (s, 2H), 8.44 (s, 1H), 6.44 (s, 1H), 5.37 (s, 2H), 4.04 (s, 3H), 1.46 (s, 6H).

Compound I-12

This compound was synthesized in 5 steps:

Step 1: Synthesis of 2-(2-fluorophenyl)-N-hydroxyacetimidamide

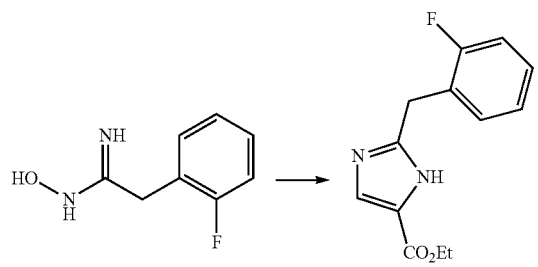

To a solution of hydroxylamine hydrochloride (2.2 equiv.) and 2-(2-fluorophenyl)acetonitrile (1 equiv.) in methanol and water (5:1 ratio) was added sodium bicarbonate (2.4 equiv.). After stirring at 70° C. for 20 h, the methanol was removed in vacuo and the resulting solution was diluted with water and dichloromethane (1:2 ratio). The layers were separated and the organic layer was washed with saturated aqueous sodium chloride. The organic layer was dried over magnesium sulfate, filtered, and the solvent was removed in vacuo to deliver the desired intermediate, 2-(2-fluorophenyl)-N-hydroxyacetimidamide (1.13 g, 90% yield) as a white solid.

Step 2: Synthesis of ethyl 2-(2-fluorobenzyl)-1H-imidazole-5-carboxylate

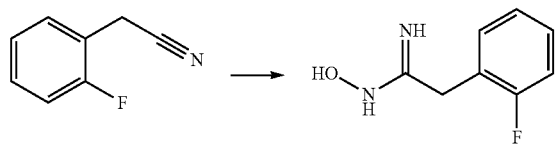 [SMILES: N#CCc1ccccc1F ; N=C(Cc1ccccc1F)NO]

A solution of ethyl propiolate (1.08 equiv.) and 2-(2-fluorophenyl)-N-hydroxyacetimidamide (1 equiv.) in ethanol was heated to 80° C. for 5 h, at which point the solvent was removed in vacuo. The resulting residue was brought up in diphenyl ether and heated to 170° C. for 14 h. The black reaction mixture was poured into hexanes (4×volume of diphenyl ether) and stirred for 24 h. The hexane was then decanted to give the crude product. Purification via silica gel chromatography (0-5% methanol in dichloromethane) delivered the desired intermediate, ethyl 2-(2-fluorobenzyl)-1H-imidazole-5-carboxylate (1.8 g, 27% yield) as a black solid.

Step 3: Synthesis of ethyl 2-(2-fluorobenzyl)-1-methyl-1H-imidazole-4-carboxylate

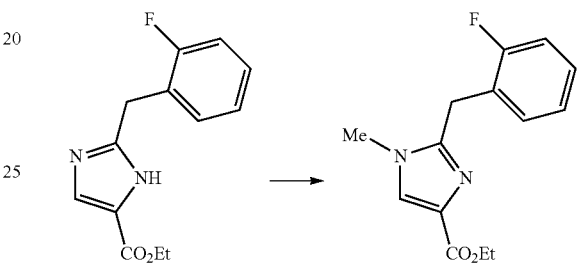

A suspension of ethyl 2-(2-fluorobenzyl)-1H-imidazole-5-carboxylate (1 equiv.) and cesium carbonate (1.2 equiv.) in acetonitrile was treated with iodomethane (1 equiv.). After stirring at room temperature for 2 h, the solvent was removed in vacuo and the black residue was diluted with dichloromethane and water (4:3 ratio). The layers were separated and the aqueous layer was extracted with dichloromethane (2×). The organics were dried over magnesium sulfate, filtered, and the solvent was removed in vacuo. Purification via silica gel chromatography (0-80% ethyl acetate in hexanes) delivered the desired intermediate, ethyl 2-(2-fluorobenzyl)-1-methyl-1H-imidazole-4-carboxylate (375 mg, 36% yield) as a dark oil.

Step 4: Synthesis of 2-(2-fluorobenzyl)-1-methyl-1H-imidazole-4-carboximidamide hydrochloride (Intermediate-29)

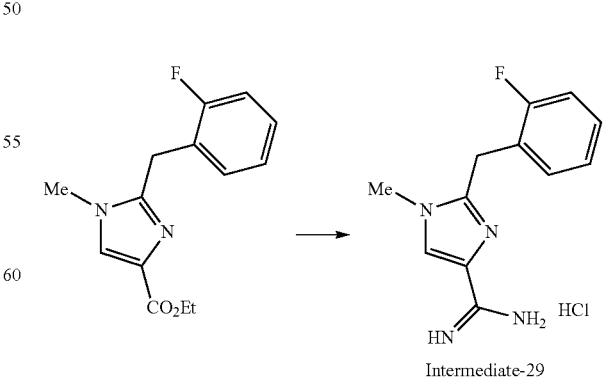

A suspension of ammonium chloride (5.5 equiv.) in toluene was treated with trimethylaluminum (5 equiv., 2N solution in toluene) over the course of 10 min. After stirring for 40 min, the solution was added to ethyl 2-(2-fluorobenzyl)-1-methyl-1H-imidazole-4-carboxylate (1 equiv.) and the resulting suspension was heated to 80° C. for 6 h. The reaction mixture was cooled to 0° C. and methanol was added dropwise. The reaction mixture was warmed to 23° C. and stirred for an additional 1 h. The resulting slurry was filtered through celite and then washed with 4:1 diethyl ether/methanol followed by 1:1 dichloromethane/methanol to deliver the desired intermediate, 2-(2-fluorobenzyl)-1-methyl-1H-imidazole-4-carboximidamide hydrochloride (240 mg, 73%) as a solid.

Step 5: Synthesis of Compound I-12

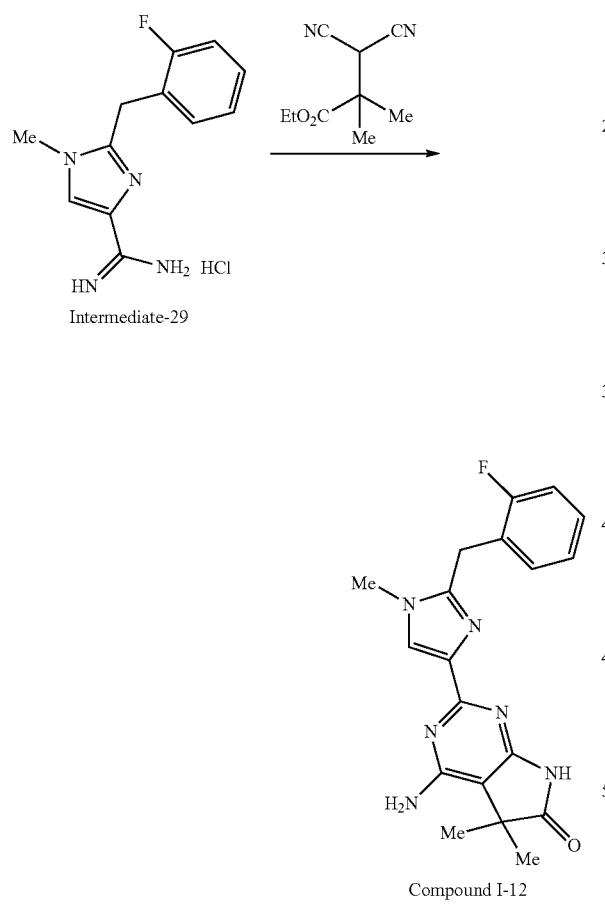

A suspension of 2-(2-fluorobenzyl)-1-methyl-1H-imidazole-4-carboximidamide hydrochloride (Intermediate-29), ethyl 3,3-dicyano-2,2-dimethylpropanoate (1.7 equiv.), and potassium bicarbonate (1.7 equiv.) in tert-butanol was heated to 80° C. for 60 h. Water was added to the suspension, and the solid was filtered off to deliver the desired compound, Compound I-12 (68 mg, 55% yield) as a tan solid. $^1$H-NMR (500 MHz, DMSO-$d_6$) δ ppm 10.75 (s, 1H), 7.57 (s, 1H), 7.32-7.28 (m, 1H), 7.21-7.13 (m, 3H), 6.43 (s, 2H), 4.08 (s, 2H), 3.62 (s, 3H), 1.29 (s, 6H).

Compound I-66

The title compound was prepared in 2 steps:

Step 1: Synthesis of 4-bromo-2-(2-(2-fluorobenzyl)-1-methyl-1H-imidazol-4-yl)-5,5-dimethyl-5H-pyrrolo[2,3-d]pyrimidin-6(7H)-one

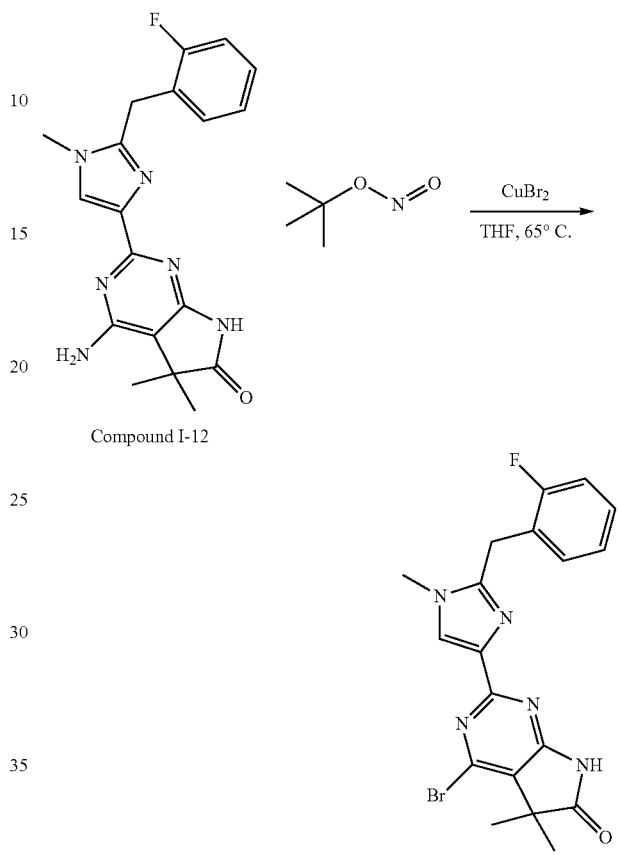

A mixture of Compound I-12 (1 equiv.), tert-butyl nitrite (3 equiv.) and copper(II) bromide (1.2 equiv.) in THF was heated to 50° C. for 4 h. After cooling, the insoluble salts were filtered off and washed with DCM. The filterate was partitioned with water and the separated aqueous phase was back extracted with DCM twice. The combined organic phase was dried over anhydrous magnesium sulfate, filtered and concentrated to give a green colored residue that was carried forward to the next step without any purification.

Step 2: Synthesis of Compound I-66

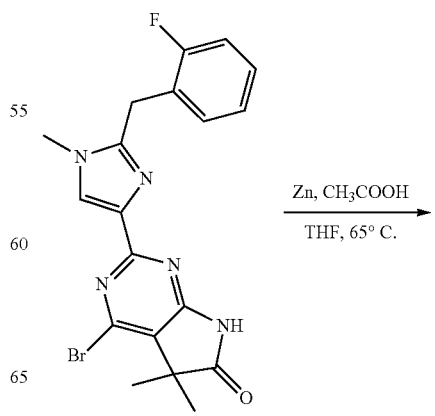

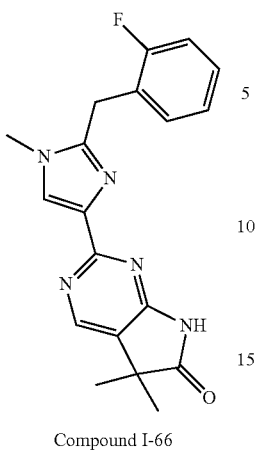

Compound I-66

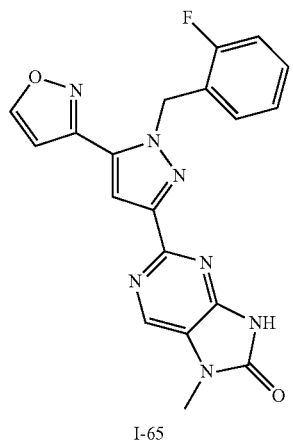

I-65

A mixture of crude 4-bromo-2-(2-(2-fluorobenzyl)-1-methyl-1H-imidazol-4-yl)-5,5-dimethyl-5H-pyrrolo[2,3-d]pyrimidin-6(7H)-one (1 equiv.), zinc dust (12 equiv.) and acetic acid (14 equiv.) in THF was heated to reflux overnight. After cooling, the reaction mixture was partitioned between ethyl acetate and saturated aqueous sodium bicarbonate solution. Layers were separated and the aqueous phase was extracted with ethyl acetate twice. The combined organic phase was dried over anhydrous magnesium sulfate, filtered and concentrated. The crude material was then purified by reverse phase HPLC (C18 column, 5% to 75% acetonitrile in water with 0.1% TFA over 20 mins) to obtain Compound I-66 (7 mg, 24% yield over two steps) as a white solid. $^1$H NMR (500 MHz, METHANOL-d$_4$) δ ppm 8.48 (1H, s) 8.13 (1H, s) 7.31-7.45 (2H, m) 7.16-7.27 (2H, m) 4.50 (2H, s) 3.82 (3H, s) 1.44-1.47 (6H, m). m/z=352.2 (M+H).

Compound I-65

A mixture of 2-(1-(2-fluorobenzyl)-5-(isoxazol-3-yl)-1H-pyrazol-3-yl)-N5-methylpyrimidine-4,5-diamine hydrochloride (1 equiv., this compound was previously described in patent application publication WO2012003405), di(1H-imidazol-1-yl)methanone (2 equiv.) and triethylamine (4 equiv.) in DMF was stirred at 60° C. for 2 h. After cooling, the resultant precipitate was filtered, washed with methanol and dried in vacuo to obtain Compound I-65 (6 mg, 41% yield) as a white solid. $^1$H NMR (500 MHz, DMSO-d$_6$) δ ppm 12.09 (1H, s) 9.09 (1H, d) 8.42 (1H, s) 7.55 (1H, s) 7.30-7.37 (1H, m) 7.27 (1H, d) 7.19-7.25 (1H, m) 7.12 (1H, td) 6.93 (1H, td) 5.90 (2H, s) 3.35 (3H, s). m/z=391.9 (M+H).

Compound I-67

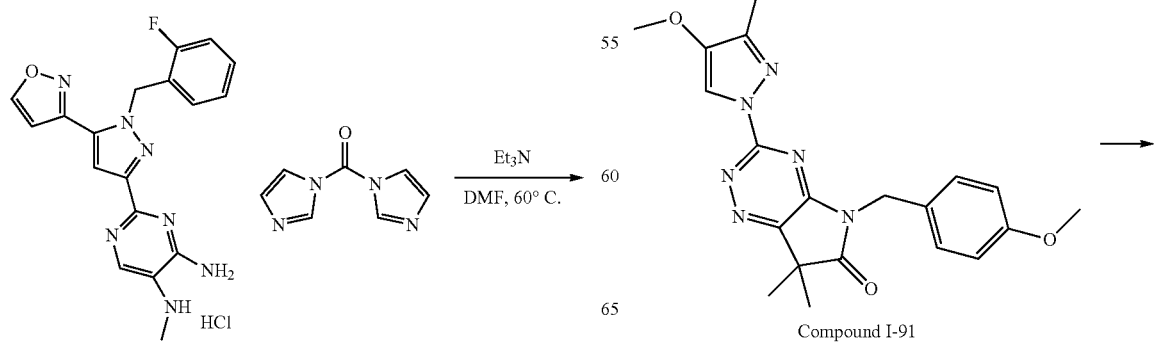

Compound I-91

-continued

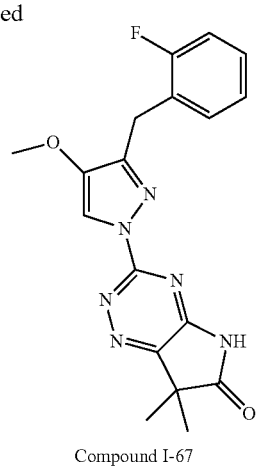

Compound I-67

A solution of 3-(3-(2-fluorobenzyl)-4-methoxy-1H-pyrazol-1-yl)-5-(4-methoxybenzyl)-7,7-dimethyl-5H-pyrrolo[2,3-e][1,2,4]triazin-6(7H)-one (Compound I-91) in toluene was treated with trifluoroacetic acid (110 equiv.) and anisole (10 equiv.). The reaction was heated at 100° C. in sealed vial for 11 days. The solvent was removed in vacuo and the crude mixture was purified directly by preparative HPLC (30-80% acetonitrile in water gradient with 0.1% formic acid) to yield Compound I-67 (3.6 mg, 16%) as an off-white solid. $^1$H-NMR (500 MHz, MeOH-$d_4$) δ ppm 8.53 (s, 0.16H, —NH proton partially exchanged), 8.23 (s, 1H), 7.23 (m, 2H), 7.06 (m, 2H), 4.05 (s, 2H), 3.82 (s, 3H), 1.51 (s, 6H).

Compound I-69

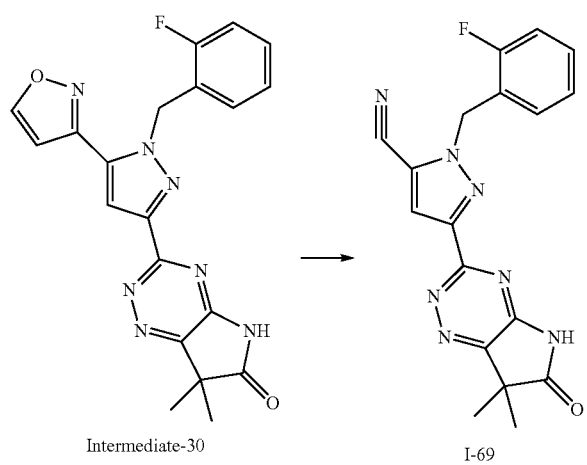

Intermediate-30    I-69

Intermediate-30 (60 mg, 0.15 mmol, the synthesis of this intermediate was previously described in patent application publication WO2014144100) and diazabicycloundecane (DBU, 0.50 mL, 3.32 mmol) were sealed in a 10 mL microwave reaction vial and heated at 150° C. for a total of 25 min. The vial contents were then diluted with ethyl acetate (100 mL) and washed in succession with 3N HCl (aq, 3×10 mL), water (10 mL), 10% aqueous NaHCO3 (2×10 mL), brine and finally dried over Na2SO4. The organic solution was filtered and concentrated by rotary evaporation. Purification over SiO2 using a gradient elution of hexane/ethyl acetate gave the product as a white solid (33 mg, 54% yield). $^1$H-NMR (400 MHz, CDCl$_3$) δ 8.81 (br s, 1H), 7.73 (s, 1H), 7.35 (q, 1H), 7.23 (t, 1H), 7.1-7.2 (m, 2H), 5.75 (s, 2H), 1.63 (s, 6H) ppm.

Compound I-70

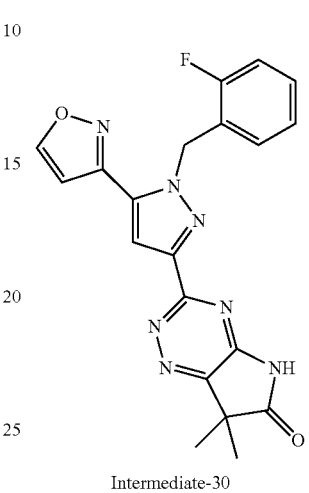

Intermediate-30

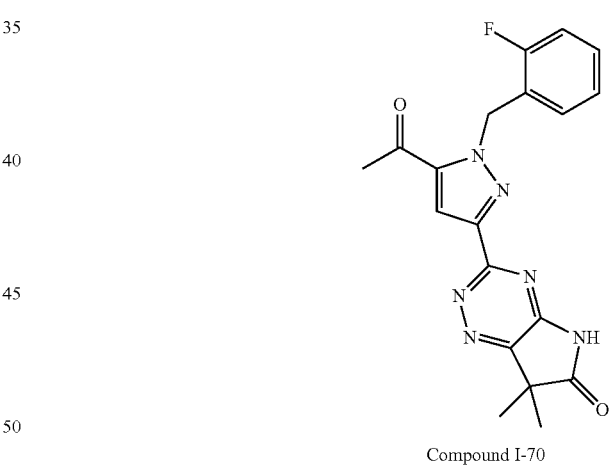

Compound I-70

A solution of Intermediate-30 (70 mg, 0.17 mmol) in 2% wt/wt sodium ethoxide/ethanol (5 mL, 1.47 mmol) was sealed in a 10 mL microwave reaction vial and heated at 150° C. for 5 min. The solvent was removed under vacuum, then the residue was taken up in water (30 mL) and the pH was taken to 3-4 with 3N HCl (aq). The aqueous solution was extracted with ethyl acetate and the combined organic layers were washed with brine, dried over Na2SO4, filtered and concentrated by rotary evaporation. Chromatography over SiO2 with a gradient elution of hexane/ethyl acetate gave Compound I-70 as a white solid (40 mg, 61% yield). $^1$H-NMR (400 MHz, CDCl$_3$) δ 8.54 (br s, 1H), 7.76 (s, 1H), 7.15 (q, 1H), 6.97 (t, 1H), 6.91 (t, 1H), 6.77 (s, 1H), 5.93 (s, 2H), 2.52 (s, 3H), 1.55 (s, 6H) ppm.

Compound I-68

This compound was prepared in two steps from Intermediate-31

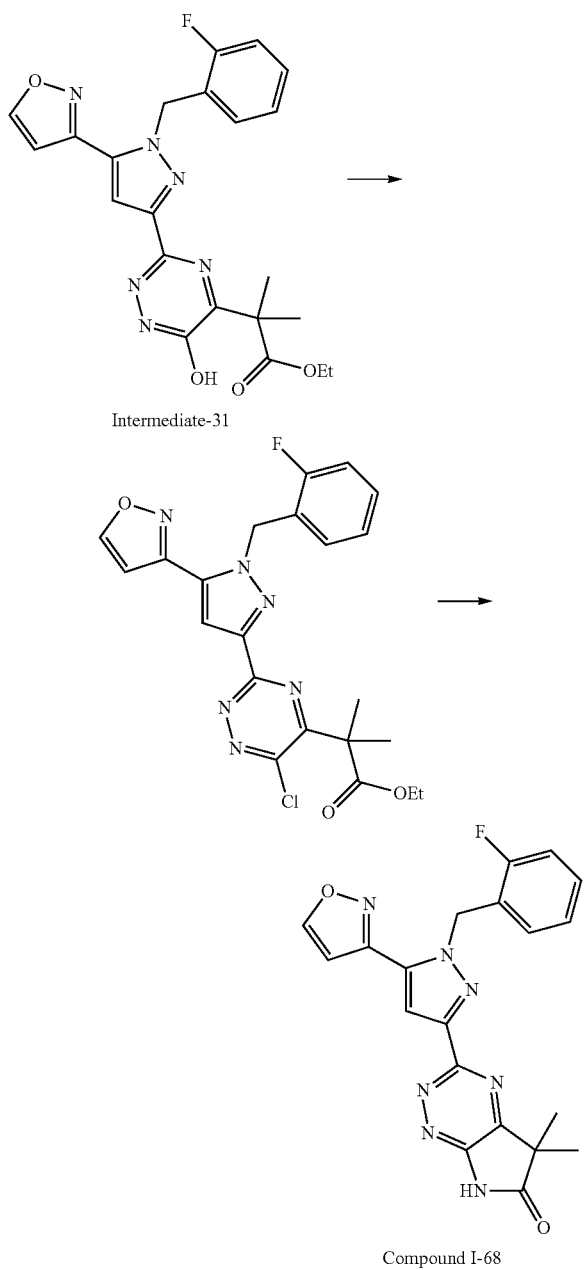

Intermediate-31

↓

↓

Compound I-68

Step 1: A sample of Intermediate-31 (54 mg, 0.12 mmol) in POCl$_3$ (1.0 mL, 10.7 mmol) was heated at 105° C. for 4 hr, then cooled to room temperature and the solvent was removed under vacuum. The residue was diluted with ethyl acetate, washed with 10% aqueous NaHCO$_3$ and brine, then dried over Na$_2$SO$_4$, filtered and concentrated to dryness by rotary evaporation. Purification over SiO$_2$ using a gradient elution of hexane/ethyl acetate gave the chlorinated intermediate as a white solid (40 mg, 73% yield). $^1$H-NMR (400 MHz, CDCl$_3$) δ 8.52 (d, 1H), 7.54 (s, 1H), 7.2-7.3 (m, 1H), 7.07 (t, 1H), 7.03 (t, 1H), 6.99 (t, 1H), 6.65 (d, 1H), 6.06 (s, 2H), 4.23 (q, 2H), 1.75 (s, 6H), 1.23 (t, 3H) ppm.

Step 2: The chlorinated intermediate (40 mg, 0.085 mmol) was sealed in a 10 mL microwave reaction vial with ammonia/dioxane solution (0.5 M, 5 mL, 2.5 mmol) and heated at 190° C. for 63 hr. The solution was concentrated under vacuum and the residue was purified over SiO2 using a gradient elution of hexane/ethyl acetate to give Compound I-68 as a white solid (20 mg, 59% yield). $^1$H-NMR (400 MHz, CDCl$_3$) δ 8.49 (br s, 1H), 7.54 (s, 1H), 7.27 (s, 1H), 7.22 (q, 1H), 7.05 (t, 1H), 6.99 (t, 1H), 6.86 (t, 1H), 6.64 (s, 1H), 6.06 (s, 2H), 1.60 (s, 6H) ppm.

Example 2A

Biological Activity Measurement by the sGC-HEK-cGMP Assay, with LC/MS Detection Human embryonic kidney cells (HEK293), endogenously expressing soluble guanylate cyclase (sGC), were used to evaluate the activity of test compounds. Compounds stimulating the sGC enzyme should cause an increase in the intracellular concentration of cGMP. HEK 293 cells were seeded in Dulbecco's Modification of Eagle's Medium supplemented with fetal bovine serum (10% final) and penicillin (100 U/mL)/streptomycin (100 μg/mL) in a 50 μL, volume at a density of 1.5×10$^4$ cells/well in a poly-D-lysine coated 384 well flat bottom plate. Cells were incubated overnight at 37° C. in a humidified chamber with 5% CO$_2$. Medium was aspirated and cells were washed with 1× Hank's Buffered Saline Salt Solution (50 μL). Cells were then incubated for 15 minutes at 37° C. with 50 μL of a 0.5 mM 3-isobutyl-1-methylxanthine (IBMX) solution. Test article and Diethylenetriamine NONOate (DETA-NONOate) solutions (x μM concentration for test article solution and 10 μM concentration for DETA-NONOate solution; wherein x is one of the following concentrations);

| |
|---|
| 30000 nM |
| 7500 nM |
| 1875 nM |
| 468.75 nM |
| 117.19 nM |
| 29.29 nM |
| 7.32 nM |
| 1.83 nM |
| 0.46 nM |
| 0.114 nM |
| 0.029 nM | were then added to the assay mixture and the resulting mixture incubated at 37° C. for 20 minutes. After the 20 minute incubation, the assay mixture was aspirated and 10% acetic acid containing 150 ng/mL+3-cGMP (internal standard for LCMS) (50 μL) was added to the cells. The plate was incubated at 4° C. for 30 minutes in the acetic acid solution to stop the reaction and lyse the cells. The plates were then centrifuged at 1,000 g for 3 minutes at 4° C. and the supernatant transferred to a clean reaction plate for LCMS analysis.

cGMP concentrations were determined from each sample using the LCMS conditions below (Table 2) and calculated standard curve. The standard curve was prepared in 10% acetic acid with 150 ng/mL+3cGMP (isotopically labelled cGMP with a weight 3 units higher than wild type) with the following final concentrations of cGMP in ng/mL: 1, 5, 10, 50, 100, 250, 500, 1000, 2000.

TABLE 2

LC/MS conditions, Example 2

| MS: | Thermo Vantage |
|---|---|
| Ion Mode: | ESI+ |
| Scan Type: | MRM |

| Compound: | Transition | Dwell Time (msec) | Collision Energy (V) | S Lens | Retention Time (min) |
|---|---|---|---|---|---|
| cGMP | 346 > 152 | 100 | 32 | 75 | 0.6 |
| (+3) cGMP IS | 349 > 155 | 100 | 32 | 75 | 0.6 |

| HPLC: | Waters Acquity UPLC |
|---|---|
| Column: | Thermo Hypersil Gold 2.1 × 50 mm 1.9 micron particle size |
| Flow Rate: | 750 uL/min |
| Column Temperature: | RT |
| Autosampler Temperature: | 6° C. |
| Injection Volume: | 20 uL |
| Mobile Phases: | A = 100% Water + 0.1% Formic Acid<br>B = 100% Acetonitrile + 0.1% Formic Acid |

| Gradient: | Time (min) | % A | % B |
|---|---|---|---|
| | 0 | 100 | 0 |
| | 0.2 | 100 | 0 |
| | 0.3 | 50 | 50 |
| | 0.7 | 50 | 50 |
| | 0.8 | 100 | 0 |

Data were normalized to a high control using the following equation: 100*(Sample—Low Control)/(High Control—Low Control), where the low control is the average of 16 samples treated with 1% DMSO, and the high control is the average of 16 samples treated with 30 μM of Compound Y depicted below. Data were fit using a 4-parameter fit (log(agonist) vs. response variable slope) using GraphPad Prism Software v.5. n=2 for all compounds. The Absolute $EC_{50}$ was interpolated from the curve fit and is defined as the concentration at which a given compound elicits 50% of the high control response. Compounds failing to elicit a minimum response of 50% are reported as >30 μM. For compounds run in duplicate or n higher than 2, the result herein given is the geometric mean of the several results obtained. Table 3A summarizes results obtained for selected compounds of the invention in this assay.

Compound Y

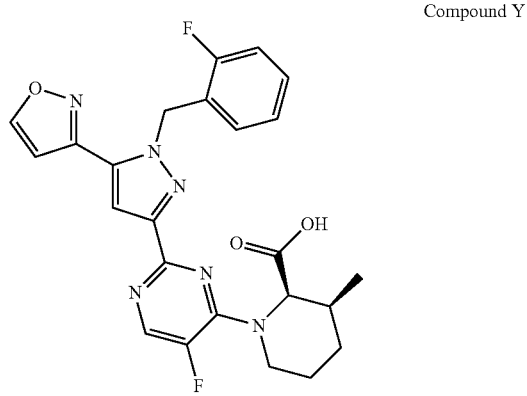 [SMILES: C[C@H]1CCCN(c2nc(-c3cc(-c4ccon4)n(Cc4ccccc4F)n3)ncc2F)[C@H]1C(=O)O]

TABLE 3A

Whole cell activity in the HEK assay with LC/MS detection (updated assay conditions, Example 2C).

| Compound | Absolute EC50 (nM) - binned (~) | Compound | Absolute EC50 (nM) - binned (~) |
|---|---|---|---|
| I-1 | A | I-14 | C |
| I-2 | C | I-15 | C |
| I-3 | C | I-22 | C |
| I-4 | C | I-16 | C |
| I-5 | B | I-17 | B |
| I-6 | B | I-18 | B |
| I-7 | C | I-20 | B |
| I-8 | B | I-19 | A |
| I-13 | B | I-21 | C |
| I-72 | C | I-71 | C |
| I-23 | B | | |

(~) Code definitions for the sGC enzyme activity values, expressed as Absolute $EC_{50}$ which is defined as the concentration at which a given compound elicits 50% of the high control response (Compound Y). Compounds failing to elicit a minimum response of 50% are reported as >30 μM or ND. EC50Abs ≤ 100 nM = A; 100 nM < EC50Abs ≤ 1000 nM = B; 1000 nM < EC50Abs = C.

Example 2B

Biological Activity Measurement by the cGMP GloSensor Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS) (10% final) and hygromycine (200 μg/ml). The day before assay, cells were plated in DMEM with 10% FBS in a 50 μL volume at a density of $1.5 \times 10^4$ cells/well in a poly-D-lysine coated 384-well flat white-bottom plate (Corning Cat No 35661). Cells were incubated overnight at 37° C. in a humidified chamber with 5% $CO_2$. The next day, medium was removed and cells were replaced with 40 μl/well of GloSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serally diluted at 4× dilutions to create 5× dose curve from which 10 ul was added to the wells (x uM concentration for test compound solution and 10 μM concentration for DETA-NONOate solution; wherein x is one of the following final concentrations).

| |
|---|
| 30000 nM |
| 7500 nM |
| 1875 nM |
| 468.75 nM |
| 117.19 nM |
| 29.29 nM |
| 7.32 nM |
| 1.83 nM |
| 0.46 nM |
| 0.114 nM |
| 0.029 nM |

For the kinetics studies, luminescense was measured right away for 0.2 sec per well with Envision (Perkin Elmer model No). For endpoint SAR screening, data were collected after 55 min incubation at room temperature.

Data analysis was carried out as indicated above in Example 2A.

TABLE 3B

Whole cell activity in the GloSensor cell-based assay, 384-well format (Example 2B)

| Compound | sGC_HEK_GloSensor EC50/IC50 Abs (Norm) (nM) Binned (~) |
|---|---|
| I-71 | B |
| I-72 | A |
| I-72 | B |
| I-12 | C |
| I-80 | A |
| I-24 | B |
| I-25 | B |
| I-81 | B |
| I-65 | ND |
| I-82 | A |
| I-26 | C |
| I-66 | C |
| I-27 | B |
| I-28 | B |
| I-38 | A |
| I-12 | A |
| I-29 | C |
| I-32 | B |
| I-31 | B |
| I-73 | B |
| I-51 | A |
| I-33 | C |
| I-74 | B |
| I-75 | B |
| I-76 | B |
| I-52 | B |
| I-34 | C |
| I-35 | C |
| I-36 | C |
| I-77 | C |
| I-84 | A |
| I-78 | C |
| I-85 | B |
| I-86 | B |
| I-54 | B |
| I-79 | C |
| I-83 | A |
| I-37 | C |
| I-39 | B |
| I-40 | A |
| I-87 | C |
| I-88 | C |
| I-92 | C |
| I-89 | C |
| I-55 | A |
| I-41 | B |
| I-42 | C |
| I-56 | B |
| I-57 | B |
| I-58 | A |
| I-59 | B |
| I-60 | B |
| I-43 | B |
| I-44 | A |
| I-45 | A |
| I-64 | C |
| I-63 | A |
| I-62 | C |
| I-91 | ND |
| I-70 | B |
| I-68 | C |
| I-69 | B |
| I-67 | B |

(~) Code definitions for the sGC enzyme activity values, expressed as Absolute $EC_{50}$ which is defined as the concentration at which a given compound elicits 50% of the high control response (Compound Y). Compounds failing to elicit a minimum response of 50% are reported as >30 μM or ND. EC50Abs ≤ 100 nM = A; 100 nM < EC50Abs ≤ 1000 nM = B; 1000 nM < EC50Abs = C.

Example 3A

Biological Activity Measurement by the Thoracic Aortic Rings Assay

Thoracic aortic rings are dissected from anesthetized (isoflurane) male Sprague-Dawley rats weighing 275-299 g. Tissues are immediately transferred to ice-cold Krebs-Henseleit solution, which has been aerated with 95% $O_2$ and 5% $CO_2$ for 30 minutes. Following removal of connective tissue, aortic sections are cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths containing Krebs Henseleit solution (10 mL) are heated to 37° C. and aerated with 95% $O_2$ and 5% $CO_2$. Rings are brought to an initial tension of 0.3-0.5 g and gradually raised to a resting tension of 1.0 g over 60 minutes. Rings are rinsed with Krebs Henseleit solution (heated to 37° C. and aerated with 95% $O_2$ and 5% CO2) at 15 minute intervals until a stable baseline is obtained. Rings are considered to be stable after a resting tension of 1.0 g is maintained (for approximately 10 minutes) without need for adjustment. Rings are then contracted with 100 ng/mL phenylephrine by adding 100 μL of a 10 μg/mL phenylephrine stock solution. Tissues achieving a stable contraction are then treated in a cumulative, dose dependent manner with test compounds prepared in dimethylsulfoxide (DMSO). In some cases, tissues are rinsed three times over a 5 minute period with Krebs-Heinseleit's solution (heated to 37° C. and aerated with 95% O2 and 5% CO2), allowed to stabilize at baseline, and then used for characterization of other test articles or DMSO effects. All data are collected using the HSE-ACAD software provided by Harvard Apparatus. Percent relaxation effects are calculated in Microsoft Excel using the recorded tension value of 100 ng/mL phenylephrine treatment as 0% inhibition and treatment with 100 μM 3-isobutyl-1-methyl-xanthine as 100% inhibition. EC50 values are calculated from concentration-response curves generated with Graph-Pad Prism Software.

Example 3B

Biological Activity Measurement by the Thoracic Aortic Rings Assay

As an alternative thoracic aortic rings assay, the procedure of Example 3 is used except that percent relaxation effects are calculated in Microsoft Excel using the recorded tension value of 100 ng/mL phenylephrine treatment as 0% inhibition and, after washing the tissue with buffer, the original resting tension of the tissue is used as 100% inhibition.

Example 4

Blood Pressure Change in Sprague-Dawley Rats

Male rats (250-350 g body weight, supplied by Harlan Laboratories) were anesthetized with ketamine/xylazine and a heparinized saline fluid filled catheter implanted into the right femoral artery. The catheter was exteriorized between the scapula, capped, and the animal allowed to recover for at least 7 days post surgery prior to any compound testing. Prior to testing animals were maintained on normal diet, with free access to drinking water, under a 12 hour light-dark cycle.

On the day of experimentation, under inhaled isoflurane anesthesia, the catheter was uncapped and connected to a tether (Instech Labs) and pressure transducer (Harvard Apparatus). Blood pressure and heart rate were subsequently captured and analyzed with a dedicated data capture system (PowerLab, ADInstruments). Data sampling rates were set at 1 cycle per second. Once connected, each rat was allowed to recover from anesthesia and baseline blood pressure and heart rate levels were established in these conscious, freely-moving animals. Once baseline was established either vehicle (0.5% methylcellulose or 100% PEG400) or test article was administered orally (PO, 10 mg/kg) and the effects on blood pressure and heart rate monitored for up to 24 hours.

Example 5

Purified Human Recombinant sGC α1β1 Enzyme Assay Performed in the Presence of Diethylenetriamine NONOate (DETA-NONOate), a Nitric Oxide Donor Purified human recombinant soluble guanylate cyclase enzyme α1β1(h sGC) obtained from Enzo Life Sciences (P/N: ALX-201-177) was used to evaluate the activity of test compounds. The assay reactions contained 0.1 M Tris (pH 8.0), 0.5 mg/mL BSA, 2 mM DTT, 4 mM $MgCl_2$, 30 uM DETA NONOate (Enzo Life Science P/N: ALX-430-014), and 12.5 ng/ml human soluble guanylate cyclase enzyme. Test compounds in DMSO were then added (in a 3-fold titration of compound over a 10-point curve starting at 30 uM final concentration, all samples had a 3% DMSO final concentration). Guanosine 5'-triphosphate (Sigma-Aldrich P/N: G8877) was added to a final concentration of 300 μM and enzyme reactions were incubated (100 μL, 384-well plate format) at 37° C. for 20 minutes. The controls contained 3% DMSO (low control), or 30 uM of Compound Y (high control). After the 20 minute incubation, the reaction was stopped with the addition of 100 μL of ice cold 20% acetic acid.

cGMP concentrations in all samples were determined using the cGMP HTRF (Cisbio P/N: 62GM2PEC) assay per manufacturer's instructions. A cGMP standard curve was fit using a 4-parameter fit (log(inhibitor) vs. response—variable slope) using GraphPad Prism Software v.6. Samples were diluted appropriately to ensure that values fell within the linear range of the standard curve.

Data were fit using a 4-parameter fit (log(agonist) vs. response variable slope) using GraphPad Prism Software v.6. The $EC_{50}$ was interpolated from the curve fit and is defined as the concentration at which the compound elicits 50% of the maximal response of the 30 uM of Compound Y, the high control compound.

TABLE 5

Enzyme data

| compound number | sGC_Enz_HTRF_a1b1 EC50/IC50 Abs (Norm) (nM) Binned |
|---|---|
| I-2 | C |
| I-3 | B |
| I-5 | B |

EC50Abs < 100 nM = A
≤100 nM < EC50Abs < 1000 nM = B
≤1000 nM = C

Example 6

Animal Model Descriptions

Lamb Model of Pulmonary Hemodynamics Using Inhaled sGC Stimulator

It is possible to test whether inhalation of novel dry-powder microparticle formulations containing sGC stimulators would produce selective pulmonary vasodilation in lambs with acute pulmonary hypertension by following a published procedure ("Inhaled Agonists of Soluble Guanylate Cyclase Induce Selective Pulmonary Vasodilation", Oleg V. et al, *American J of Resp and Critical Care Medicine*, Vol 176, 2007, p 1138).

It is also possible to evaluate the combined administration of the microparticles of sGC stimulator and inhaled nitric oxide (iNO) in this system. Finally, it is possible to examine whether inhaling microparticles of an sGC stimulator would produce pulmonary vasodilation when the response to iNO (inducible nitric oxide synthase) is impaired.

Protocol: In awake, spontaneously breathing lambs instrumented with vascular catheters and a tracheostomy tube, U-46619 is infused intravenously to increase mean pulmonary arterial pressure to 35 mm Hg. Inhalation of microparticles composed of either BAY 41-2272, BAY 41-8543, or BAY 58-2667 and excipients (dipalmitoylphosphatidylcholine, albumin, lactose) produced dose dependent pulmonary vasodilation and increased transpulmonary cGMP release without significant effect on mean arterial pressure. Inhalation of microparticles containing BAY 41-8543 or BAY 58-2667 increased systemic arterial oxygenation. The magnitude and duration of pulmonary vasodilation induced by iNO were augmented after inhaling BAY 41-8543 microparticles. Intravenous administration of 1H-[1,2,4]oxadiazolo[4,3-a]quinoxalin-1-one (ODQ), which oxidizes the prosthetic heme group of sGC, markedly reduced the pulmonary vasodilator effect of iNO. In contrast, pulmonary vasodilation and transpulmonary cGMP release induced by inhaling BAY 58-2667 microparticles were greatly enhanced after treatment with ODQ. Thus, inhalation of microparticles containing agonists of sGC may provide an effective novel treatment for patients with pulmonary hypertension, particularly when responsiveness to iNO is impaired by oxidation of sGC. Note: BAY 41-2272, BAY 41-8543 are sGC stimulators whereas BAY 58-2667 is an sGC activator.

Electrical Field Stimulated Guinea Pig Tracheal Smooth Muscle In Vitro (ex vivo) Model for the Assessment of Bronchodilation.

It is possible to assess the bronchodilating effects of sGC stimulators by using the system described below. This system allows us to determine potency, efficacy and duration of action of several sGC stimulators, as well as to assess potential side effects such as blood pressure, or heart rate changes (see "Novel and Versatile Superfusion System. Its use in the Evaluation of Some Spasmogenic and Spasmolytic Agents Using Guinea pig isolated Tracheal Smooth Muscle.", R. A. Coleman et al., *J. Pharmacol. Methods,* 21, 71-86, 1989. See also "The role of soluble guanylyl cyclase in Chronic Obstructive Pulmonary Disease"; C Glynos et al.; *AJRCCM Articles in Press*; published on 10 Jul. 2013 as 10.1164/rccm/201210-1884OC.

Animals: Guinea pig, Dunkin Hartley, male, Full barrier-bred and certified free of specific micro-organisms on receipt 525-609 g on the experimental day, Harlan UK Ltd. Guinea pigs are housed in a group of 4 in solid-bottomed cages with Gold Flake bedding in a controlled environment (airflow, temperature and humidity). Food (FD1, Special Diet Services) and water are provided ad libitum.

Guinea Pig Tracheal Smooth Muscle Contraction in Response to EFS. Assessment of Compound Potency and Efficacy:

On each experimental day, a guinea pig is killed by exposure to a rising concentration of $CO_2$ and the trachea removed. The trachea is cleaned of extraneous tissue and cut open longitudinally in a line opposite the muscle, opened out and cut into strips 2-3 cartilage rings wide. A cotton loop is attached to one end of each tracheal strip and a length of cotton to the other end. Tracheal strips are then suspended between two platinum electrodes, using tissue holders, in a Myobath system (World Precision Instruments Stevenage, UK). The loop is attached over the hook at the bottom of the tissue holder and the other end attached to the arm of a FORT10 force transducer (World Precision Instruments Stevenage, UK) ensuring that the tissue is positioned between the two platinum electrodes. The whole assembly is then lowered into a 10 ml tissue bath containing modified Kreb's-Henseleit buffer, at 37° C., bubbled with Carbogen. A 1 g tension is applied to each piece of tissue and the tissue washed, followed by a 1 hour stabilization period. Once the tissues has been allowed to stabilize, the apparatus for electrical field stimulation is set to deliver a stimulation of frequency 80 Hz pulse width 0.1 ms, with a gated, uni-polar pulse, every 2 minutes using a DS8000 8 channel digital stimulator (World Precision Instruments Stevenage, UK). A voltage response curve is carried out on each tracheal strip at 2, 4, 6, 7, 8, 10, 12 V and a sub-maximal voltage then selected to apply to each tissue during the remainder of the experiment. Guinea pig tracheal smooth muscle (GPTSM) contraction is induced using sub-maximal Electrical Field Stimulation (EFS) (It is also possible to induce contraction by using a spasmogen substance, such as methacholine or histamine as described in Coleman et al.*). Compounds are dissolved in 100% DMSO at $3 \times 10^{-2}$M and aliquots stored at −200 C. A separate aliquot is used for each experiment. Tissues are washed with Kreb's buffer and stimulated using the previously determined sub-maximal voltage for 1 hour to establish a stable baseline contraction prior to assessment of compound activity.

A cumulative dose response curve (DRC) to each test substance is then performed and changes in smooth muscle contraction measured. The effect of each test substance in each experiment is expressed as a percentage inhibition of the baseline contraction, normalized to the relevant vehicle controls. The experiment is performed three times, using tissue from three different animals. The data from all three experiments are pooled, the DRC plotted, and the test substance potency and efficacy determined. The potency of Ipratropium bromide is assessed alongside the test compounds and the IC50 determined to be 0.86 nM (95% Cl, 0.78-0.94), in agreement with data previously produced in the system.

Mouse Model for Diseases in Which Altered CFTR-Function is Causally Involved

These diseases comprise cystic fibrosis, pancreatic disorders, gastrointestinal disorders, liver disorders, cystic fibrosis-related diabetes (CFRO), dry eye, dry mouth and Sjoegren's syndrome.

By using transgenic mice expressing or not expressing the delta F508CFTR channel it is possible to measure differences on nasal potential difference and salivation in the presence of a test sGC stimulator by using the literature protocol described below (see WO2011095534).

Salivary Secretion Assay in Delta(.6.)50S-CFTR Mice

15 Male and female homozygous, heterozygous .6.50S-CFTR (backcrossed on the FVB genetic background for more than 12 generations, originally obtained from Erasmus University, Rotterdam; 10-14 weeks old and weighing 1S-36 g of both sexes were used in this assay. Solutions of Vardenafil in concentrations of 0.07, 0.14 and 0.42 mg/kg BW were 20 prepared in sterile saline, whereas the sGC stimulator BAY 41-2272 was dissolved to 0.01, 0.03, 0.1 and 0.3 mg/kg BW in a solvent containing 50% ddH20, 40% PEG 400 (polyethylene glycol 400) and 10% ethanol. The substances or the appropriate vehicles were administered to mice via intraperitoneal injection (5 ml/kg BW) 60 min prior to the salivary secretion assay. After 60 min, mice were anaesthetized with a combination of 25 ketamine and diazepam. The solution was prepared to contain 1 ml of 5 mg/ml diazepam. and 1 ml of 100 mg/ml ketamine in 8 ml sterile saline. Anesthesia was induced by intraperitoneal injection of the solution (10 ml/kg BW). After anesthesia, mice were pretreated with a subcutaneous injection of 1 mM atropine (50 1-11) into the left cheek in order to avoid a cross-stimulation of cholinergic receptors. Small strips of Whatman filter 5 paper were placed inside the previously injected cheek for 4 min to absorb any saliva secreted after the injection of atropine. This first piece of filter paper was removed and replaced with a second pre-weighed filter paper. Thereafter, 50 1-11 of a solution containing 100 I-IM isoprenaline and 1 mM atropine was injected into the left cheek at the same site to induce the salivary secretion by adrenergic mechanisms. The time of the 10 isoprenaline injection was taken as time zero, and filter paper stripes were replaced every 10 minutes for a total collection period of 30 minutes. Each piece of filter paper was immediately placed and sealed in a pre-weighed vial. After all samples had been collected, each vial was re-measured and the weights of all samples were recorded. The difference in total weight of vial plus paper measured before and after collecting saliva 15 was taken as the net weight of saliva secreted during the collection period. The total amounts of salivary secretion were calculated as the weight of saliva divided by the number of minutes required for each collection and then normalized to the mass of the mouse in grams. Results are expressed in table 1 as the mean percentage increase of n mice compared to placebo treatment. Statistics was analyzed by one way ANOVA test 20 followed by post-hoc Bonferoni analysis; *//* means statistical significant with p values <0.05/<0.01/0.001 and n.s. means non-significant.

These animal studies were carried out with a number of sGC stimulators, sGC activators and PDE5 inhibitors. The results suggests that compounds of the invention are useful for the treatment of cystic fibrosis, pancreatic disorders, gastrointestinal disorders, liver disorders, Cystic Fibrosis-related diabetes (CFRO), dry eye, dry mouth and Sjoegren's syndrome.

Neuromuscular Disorders

It has previously been shown that neuronal Nitric Oxide Synthase (nNOS) mislocalization from the sarcolemmal membrane to the sarcoplasm is observed in a broad range of non-dystrophic neuromuscular conditions associated with impaired motility status and catabolic stress. One tool for the evaluation of muscle biopsies of patients with a variety of inherited and acquired forms of neuromuscular disorders is the assessment of sarcolemal localization of nNOS. It was found that the level of nNOS at the sarcolemma correlates with mobility and functional status.

An analogous assessment can be used to determine nNOS localization in animal models of nondystrophic myopathy following the literature protocols described below ("Loss of sarcolemmal nNOS is common in acquired and inherited neuromuscular disorders"; E. L. Finanger Hedderick et al., *Neurology*, 2011, 76(11), 960-967).

nNOS Mislocalization in Mouse Models of Acquired Muscle Atrophy

Two mouse models have been described that demonstrate muscle atrophy without compromised mobility: high-dose corticosteroids therapy and short-term starvation. Mice treated with steroids or starved for 48 hours showed significant decreases in overall body mass and in normalized wet skeletal muscle mass. Morphometric analysis of skeletal muscle specimens of both models demonstrated muscle atrophy, as defined by a significant decrease in mean minimal Feret fiber diameter as compared to age-matched controls (n=5 for each group). Immunofluorescence staining for dystrophin, α-sarcoglycan, and α-1-syntrophin showed normal dystrophin localization suggestive of an intact DGC complex However, both steroid-treated and starved mice showed absent or severely reduced sarcolemmal nNOS staining. Real-time PCR for NOS family proteins (nNOS, eNOS, iNOS) revealed no significant differences in expression levels of any of the 3 transcripts in steroid-treated mice (n=8 for each group). Moreover, Western blot analysis for nNOS, iNOS, and eNOS showed no differences in protein levels.

These murine animal models could be used to assess the effects of sGC stimulators (for example an sGC stimulator of the invention) in the symptoms of muscle atrophy and related disease states.

Starved mice exhibited a 1-fold decrease of nNOS and iNOS transcript expression as compared to wild type mice (n=9 for controls, n=7 for starved). However, the protein level of nNOS, iNOS, and eNOS revealed no differences between control and starved mice (n=4 for each group). These data demonstrate that abnormal localization of nNOS occurs in mice with severe muscle atrophy even if overall mobility is preserved, supporting the notion that, in addition to impaired mobility, other triggers such as catabolic stress may be associated with sarcolemmal loss of nNOS.

Skeletal muscle nNOS localization is maintained during hibernation (studies with squirrels)

Skeletal muscle specimens from hibernating 13-lined ground squirrels have been used to evaluate the impact of immobility and catabolic stress on nNOS localization in the context of maintained muscle homeostasis and integrity. These animals are obligate hibernating mammals that are protected against skeletal muscle atrophy during hibernation. Despite hibernating for 5 months with almost complete immobility and no caloric intake, sarcolemmal expression of nNOS is preserved. These data together with patient and mouse data indicate that biochemical control of nNOS localization is complex and, importantly, that preserved sarcolemmal nNOS may be significant in maintaining muscle homeostasis.

These results also suggest that targeting aberrant NO signaling (for instance with sGC stimulators such as the ones here described) may prove beneficial for a broad group of patients with neuromuscular disorders.

Mouse Models of Muscular Dystrophy (BMD and DMD)

Becker muscular dystrophy (BMD), characterized by progressive skeletal muscle wasting, is caused by mutations of the muscle protein dystrophin. In a human study, Martin et al. (see "Tadalafil Alleviates Muscle Ischemia in Patients with Becker Muscular Dystrophy"; Elizabeth A. Martin et al., *Sci. Transl. Med.* 4, 162ra155 (2012); "Vascular-targeted therapies for Duchenne muscular dystrophy"; Ennen et al., *Skeletal Muscle*, 2013, 3:9) assessed exercise-induced attenuation of reflex sympathetic vasoconstriction in the muscles of 10 patients with BMD and 7-age matched healthy male controls. This is a protective mechanism that optimizes perfusion of skeletal muscle to meet the metabolic demands of exercise. Reflex vasoconstriction was induced by simulated orthostatic stress and was measured as the forearm muscles were rested or lightly exercised in the form of rhythmic handgrip. First, the investigators showed that exercise-induced attenuation of reflex vasoconstriction was defective in 9 out of 10 patients with BMD in whom the common dystrophin mutations disrupt targeting of neuronal NO synthase (nNOS) to the muscle sarcolemma. Then, in a double-blind randomized placebo-controlled crossover trial, the authors showed that normal blood flow regulation was restored in eight of nine patients by a single oral dose of 20 mg of tadalafil, a specific PDE5 inhibitor.

It is possible to assess the effects of drugs acting on the NO pathway by using a dystrophin-deficient mdx mouse model of related disease Duchenne muscular dystrophy (DMD). This model has also shown that inhibitors of phosphodiesterase 5 (PDE5) alleviate some features of the dystrophic phenotype including vasospasm of skeletal muscle micro-vessels that can lead to muscle injury and fatigue.

With exercise of healthy skeletal muscle, sarcolemmal nNOS derived NO attenuates local α-adrenergic vasoconstriction, thereby optimizing perfusion to meet the metabolic demands of the active muscle. This protective mechanism (termed functional sympatholysis) is lost in mdx mice (a model of BMD and DMD), nNOS null mice, and boys with DMD causing functional muscle ischemia. Repeated bouts of functional ischemia could accelerate use-dependent injury of muscle fibers already weakened by dystrophin deficiency In the mdx mouse, many features of the dystrophic phenotype can be improved by multiple strategies that boost NO signaling, including transgenic expression of nNOS, transgenic expression of dystrophin minigenes that restore sarcolemmal nNOS (and thereby restore functional sympatholysis), administration of the NOS substrate L-arginine (24, 25), treatment with NO-donating drugs, and phosphodiesterase 5A (PDE5A) inhibition with the drug tadalafil or sildenafil. These PDE5A inhibitors, which prolong the half-life of guanosine 3',5'-monophosphate (cGMP)—the downstream target of NO in vascular smooth muscle—were shown in the mdx mouse to alleviate muscle ischemia, as well as injury and fatigue, after a brief bout of exercise. Also, these drugs were shown to improve cardiac dynamics in mdx mice and to rescue dystrophic skeletal muscle and prolong survival in dystrophin-deficient zebra fish.

These findings support an essential role for sarcolemmal nNOS in modulating sympathetic vasoconstriction in exercising human skeletal muscles and suggests that targeting the aberrant NO pathway (for instance by using an sGC stimulator of the invention) may be a useful therapeutic approach for treating BMD and DMD in humans.

Sickle Cell Disease

Sickle-cell disease (SCD), or sickle-cell anemia (SCA) or drepanocytosis, is a hereditary blood disorder, characterized by red blood cells that assume an abnormal, rigid, sickle shape. Sickling decreases the cells' flexibility and results in a risk of various complications. The sickling occurs because of a mutation in the hemoglobin gene. Individuals with one copy of the defunct gene display both normal and abnormal hemoglobin. This is an example of co-dominance. In 1994, in the US, the average life expectancy of persons with this condition was estimated to be 42 years in males and 48 years in females, but today, thanks to better management of the disease, patients can live into their 70s or beyond.

Sickle-cell anemia is a form of sickle-cell disease in which there is homozygosity for the mutation that causes HbS. Sickle-cell anemia is also referred to as "HbSS", "SS disease", "hemoglobin S" or permutations of those names. In heterozygous people, that is, those who have only one sickle gene and one normal adult hemoglobin gene, the condition is referred to as "HbAS" or "sickle cell trait". Other, rarer forms of sickle-cell disease are compound heterozygous states in which the person has only one copy of the mutation that causes HbS and one copy of another abnormal hemoglobin allele. They include sickle-hemoglobin C disease (HbSC), sickle beta-plus-thalassemia (HbS/$\beta^+$) and sickle beta-zero-thalassemia)(HbS/($\beta^0$).

Although red blood cell (RBC) sickling and rheological abnormalities are central to the pathophysiology of sickle cell disease, vascular dysfunction resulting from complex interactions between sickled red blood cells (sRBC), endothelial cells, platelets and leukocytes play an equally important role. In sickle cell disease, endothelial activation is associated with sickle cell-mediated hypoxia-reperfusion events (see for example "Advances in understanding of the pathogenesis of cerebrovascular vasculopathy in sickle cell anemia", P. Connes et al., *Br. J. Haematol.* 2013, 161, 484-98). Red blood cell sickling and adhesion to endothelium initiate vaso-occlusion by impairing blood flow. The subsequent surge of inflammatory mediators and endothelial activation trigger a cascade of events leading to vascular damage. Pathophysiological responses to intermittent hypoxia-reperfusion from these vaso-occlusive events are demonstrated by an increased production of cytokines, leukocyte up-regulation and activation of pro-coagulant and adhesion molecules, with simultaneous inhibition of cytoprotective mediators.

Leukocytosis is correlated with nearly every manifestation of sickle cell disease, emphasizing the influential role of inflammation in the pathophysiology of sickle vasculopathy. Even at baseline, sickle cell disease patients exhibit elevations in pro-inflammatory cytokines, including C-reactive protein (CRP), tumor necrosis factor (TNF), interleukin-1 (IL-1) and interleukin-8 (IL-8). In vitro studies have shown that sRBC promote endothelial up-regulation of TNF-$\alpha$ and IL-1-$\beta$ (8-10). Microarray studies of activated monocytes have shown differential expression of genes involved in inflammation, heme metabolism, cell cycle regulation, antioxidant responses, and angiogenesis. More recently, it was shown that differential expression of nuclear factor $\kappa$-light-chain-enhancer of activated B cells (NF$\kappa$B/p65), Kruppel-like factor 2 (KLF2), and other transcription factors that regulate pathways of inflammation in sickle cell disease children at increased risk for stroke.

In transgenic mouse models (see "Novel Therapies Targeting the Endothelium in sickle cell disease", C. C. Hoppe, *Hemoglobin*, 35(5-6):530-546 (2011) and references cited therein), sickling inducing oxidative stress has been shown to affect microvascular regulatory mechanisms leading to endothelial activation and exaggerated inflammatory and pro-adhesive responses. Oxidative stress occurs through formation of reactive oxygen species (ROS). Depletion of NO occurs through hemoglobin (Hb) mediated scavenging, consumption by ROS and arginase-mediated substrate depletion. In sickle cell disease, the scavenger systems that normally remove circulating free Hb are saturated. Free Hb depletes NO, leading to endothelial dysfunction. Consequently, the normal balance of vasoconstriction and vasodilation is skewed towards vasoconstriction, endothelial activation, oxidative stress and proliferative vasculopathy.

Therapies directed at restoring NO homeostasis have shown promise in preliminary studies in patients with sickle cell disease. Previous in vitro studies and studies in other patient populations showed NO-mediated down-regulation of endothelial adhesion molecule expression. Following these observations, the use of inhaled NO was studied in sickle cell disease children presenting with VOE and found associated trends toward lower pain scores, decreased analgesic requirements and a shorter hospital stay.

These findings were reproduced in a recent randomized placebo controlled trial evaluating inhaled NO for the treatment of acute VOE in adult patients with sickle cell disease, showing that inhaled NO significantly reduced pain scores and was associated with a trend towards decreased use of parenteral morphine compared with placebos. Results from a completed phase II trial of adult sickle cell disease patients treated with inhaled NO for acute VOE have not yet been made available (clinicaltrials. gov NCT00023296). Another phase II trial of inhaled NO for VOE treatment in children with sickle cell disease is expected to be completed (clinicaltrials.gov NCT00094887). The possible therapeutic role of inhaled NO for ACS in sickle cell disease is currently being assessed in both children and adults in two separate French phase II/III trials comparing the use of inhaled NO to placebo or standard care in children with ACS (clinicaltrials.gov NCT01089439 and NCT00748423).

Dietary supplementation of the NO synthase substrate, L-arginine, has been studied extensively in sickle cell disease as a means of increase NO bioavailability. In sickle mice, oral L-arginine at high doses has been shown to decrease Gardos channel activity, dense cell formation and hemolysis, as well as functional improvements in vascular reactivity.

Sildenafil, an agent aimed at amplifying the effect of endogenous NO by inhibiting PDE5, a downstream mediator of NO, is used widely in the general population to treat primary PHT. Preliminary studies in sickle cell disease patients with severe PHT reported improvements in PAP and exercise capacity after treatment with sildenafil. A multicenter trial (Treatment of Pulmonary Hypertension and Sickle Cell Disease with Sildenafil Therapy, Walk-PHaSST) testing the safety and efficacy of sildenafil in sickle cell disease patients with Doppler-defined PHT was stopped prematurely due to a higher frequency of serious side effects, including increased rates of VOE, headache, and visual disturbance in the treatment group.

Nitrite and niacin have also been investigated for their direct NO donor properties. In a pilot phase I/II clinical trial, sodium nitrite infusions in adult sickle cell disease patients enhanced forearm blood flow, consistent with a NO donor mechanism of action. A larger phase I/II trial is now investigating whether nitrite infusions administered as adjunctive therapy during acute VOE will improve microvascular blood flow and tissue oxygenation (clinicaltrials.gov NCT01033227). The effect of niacin on improvement in endothelial-dependent vasodilation is also being assessed in a phase II randomized, controlled trial (clinicaltrials.gov NCT 00508989).

The above results suggest that targeting the aberrant NO pathway in sickle cell disease (for instance by using an sGC stimulator of the invention) may be a useful therapy for the treatment of the disease. Murine models of sickle cell anemia that could be used to assess the effect of sGC stimulators (e.g., an sGC stimulator of the invention) in this disease state, are described in *Blood,* 2001, 98(5), 1577-84; *J. Clin. Invest.* 2004, 114(8), 1136-45; and *Br. J. Haematol.,* 2004, 124(3), 391-402.

Bladder Dysfunction

It has been shown that the sGC activator BAY 60-2770 ameliorates overactive bladder in obese mice (see "The Soluble Guanylyl Cyclase Activator BAY 60-2770 ameliorates overactive bladder in obese mice", Luiz O Leiria et al., *The Journal of Urology,* 2013, doi:10.1016/j.juro.2013.09.020.). The animal model described in this publication can analogously be used to assess the effect of an sGC stimulator (for example, an sGC stimulator of the invention) on overactive bladder.

The same group of researchers have also described a rat model of bladder dysfunction (NO-deficient rats, F Z Monica et al., *Neurology and Urodynamics,* 30, 456-60, 2011) and have shown the protective effects of BAY-2272 (an sGC activator) in this model. The animal model described in this publication can analogously be used to assess the effect of an sGC stimulator (for example, an sGC stimulator of the invention) on bladder dysfunction related to detrusor smooth muscle overactivity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A compound of Formula I-c, or pharmaceutically acceptable salt thereof:

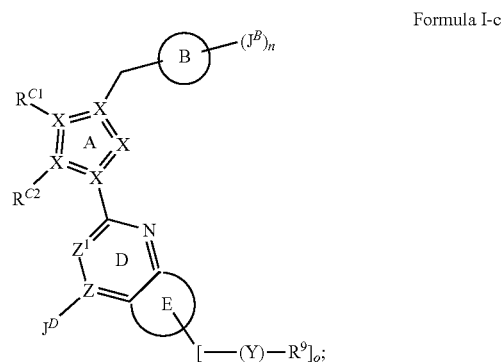

Formula I-c wherein:
ring A is a 5-membered heteroaryl ring; each instance of X is independently C or N and the bond between each two instances of X is either a single or a double bond so as to make ring A an aromatic heterocycle; wherein a minimum of 2 instances of X and a maximum of 3 instances of X in ring A can simultaneously be N;

ring B is selected from a phenyl, a 5 or 6-membered heteroaryl ring, containing 1 or 2 ring heteroatoms independently selected from N, O and S, a $C_{3-7}$ cycloalkyl ring and a 4 to 7-membered heterocyclic ring, containing up to 3 heteroatoms independently selected from O, N and S;

n is 0 or an integer selected from 1, 2 and 3;

each $J^B$ is independently selected from halogen, —CN, a $C_{1-6}$ aliphatic, —$OR^B$ and a $C_{3-8}$ cycloaliphatic group; wherein each said $C_{1-6}$ aliphatic and each said $C_{3-8}$ cycloaliphatic group is optionally and independently substituted with up to 3 instances of $R^3$;

each $R^B$ is independently selected from hydrogen, a $C_{1-6}$ aliphatic and a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —O($C_{1-4}$ alkyl) and —O($C_{1-4}$ haloalkyl);

each $R^{3a}$ is independently selected from halogen, —CN, $C_{1-4}$ alkyl, $C_{1-4}$ haloalkyl, —O($C_{1-4}$ alkyl) and —O($C_{1-4}$ haloalkyl);

$Z^1$ in ring D is CH or N; Z is C or N; wherein if $Z^1$ is CH, then Z must be C; and if $Z^1$ is N, then Z may be C or N;

each $J^D$ is independently selected from $J^A$, —CN, —$NO_2$, —$OR^D$, —$SR^D$, —$C(O)R^D$, —$C(O)OR^D$, —$OC(O)R^D$, —$C(O)N(R^D)_2$, —$N(R^D)_2$, —$N(R^d)C(O)R^D$, —$N(R^d)C(O)OR^D$, —$N(R^d)C(O)N(R^D)_2$, —$OC(O)N$ ($R^D$)$_2$, —SO$_2$R$^D$, —SO$_2$N(R$^D$)$_2$, —N(R$^d$)SO$_{2}$R$^D$, —N(R$^d$)SO$_2$NHR$^D$, —N(R$^d$)SO$_2$NHC(O)OR$^D$, —N(R$^d$)SO$_2$NHC(O)R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring and a 5 to 10-membered heteroaryl ring; wherein each said 4 to 8-membered heterocyclic ring and each said 5 to 10-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^D$ moiety, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of R$^{5d}$;

J$^A$ is selected from a lone pair on nitrogen, hydrogen, halogen, oxo, methyl, hydroxyl, methoxy, trifluoromethyl, trifluoromethoxy and —NR$^a$R$^b$; wherein R$^a$ and R$^b$ are each independently selected from hydrogen, C$_{1-6}$ alkyl and a 3-6 cycloalkyl ring; or wherein R$^a$ and R$^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;

each R$^D$ is independently selected from hydrogen, a C$_{1-6}$ aliphatic, —(C$_{1-6}$ aliphatic)-R$^f$, a C$_{3-8}$ cycloaliphatic ring, a 4 to 10-membered heterocyclic ring, and a 5 to 6-membered heteroaryl ring; wherein each said 4 to 10-membered heterocyclic ring and each said 5 to 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 10-membered heterocyclic ring, each said phenyl and each said 5 to 6-membered heteroaryl ring is optionally and independently substituted with up to 5 instances of R$^{5a}$; wherein when any R$^D$ is one of a C$_{1-6}$ aliphatic or a —(C$_{1-6}$ aliphatic)-R$^f$ group, one or two —CH$_2$— units that form said C$_{1-6}$ aliphatic chains may, optionally, be replaced by a group independently selected from —N(R$^d$)—, —CO— and –O—;

each R$^d$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl and a 5 to 6-membered heteroaryl ring; wherein each said 4 to 8-membered heterocyclic ring and each said 5 or 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$; wherein when any R$^d$ is one of a C$_{1-6}$ aliphatic or a —(C$_{1-6}$ aliphatic)-R$^f$ group, one or two —CH$_2$— units that form said C$_{1-6}$ aliphatic chains may, optionally, be replaced by a group independently selected from —N(R$^{dd}$)—, —CO— and —O—;

each R$^{dd}$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl and a 5 to 6-membered heteroaryl ring; wherein each said 4 to 8-membered heterocyclic ring and each said 5 or 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$;

each R$^f$ is independently selected from a C$_{1-3}$ alkyl, a C$_{3-8}$ cycloaliphatic ring, a 4 to 10-membered heterocyclic ring, phenyl and a 5 to 6-membered heteroaryl ring; wherein each said 4 to 10-membered heterocyclic ring and each said 5 to 6-membered heteroaryl ring contains between 1 and 4 heteroatoms independently selected from O, N and S; and wherein each said C$_{3-8}$ cycloaliphatic ring, each said 4 to 10-membered heterocyclic ring, each said phenyl and each said 5 to 6-membered heteroaryl ring is optionally and independently substituted by up to 5 instances of R$^{5c}$;

when J$^D$ is —C(O)N(R$^D$)$_2$, —N(R$^D$)$_2$, —N(R$^d$)C(O)N(R$^D$)$_2$, —OC(O)N(R$^D$)$_2$ or —SO$_2$N(R$^D$)$_2$, the two R$^D$ groups together with the nitrogen atom attached to the two R$^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O and S, in addition to the nitrogen atom to which the two R$^D$ groups are attached; and wherein each said 4 to 8-membered heterocyclic ring and each said 5-membered heteroaryl ring is optionally and independently substituted by up to 5 instances of R$^5$;

when J$^D$ is —N(R$^d$)C(O)R$^D$, the R$^D$ group together with the carbon atom attached to the R$^D$ group, with the nitrogen atom attached to the R$^d$ group, and with the R$^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O and S, in addition to the nitrogen atom to which the R$^d$ group is attached; and wherein each said 4 to 8-membered heterocyclic ring and each said 5-membered heteroaryl ring is optionally and independently substituted by up to 5 instances of R$^5$;

when J$^D$ is —N(R$^d$)C(O)OR$^D$, the R$^D$ group together with the oxygen atom attached to the R$^D$ group, with the carbon atom of the —C(O)— portion of the —N(R$^d$)C(O)OR$^D$ group, with the nitrogen atom attached to the R$^d$ group, and with said R$^d$ group, may form a 4 to 8-membered heterocyclic ring; wherein said 4 to 8-membered heterocyclic ring optionally contains up to 2 additional heteroatoms independently selected from N, O and S, and is optionally and independently substituted by up to 5 instances of R$^5$;

when J$^D$ is —N(R$^d$)C(O)N(R$^D$)$_2$, one of the R$^D$ groups attached to the nitrogen atom, together with said nitrogen atom, and with the N atom attached to the R$^d$ group and said R$^d$ group may form a 4 to 8-membered heterocyclic ring; wherein said 4 to 8-membered heterocyclic ring optionally contains up to 2 additional heteroatoms independently selected from N, O and S, and is optionally and independently substituted by up to 5 instances of R$^5$;

when $J^D$ is —N($R^d$)SO$_2$$R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O and S, and is optionally and independently substituted by up to 5 instances of $R^5$;

each $R^5$ is independently selected from halogen, —CN, C$_{1-6}$ alkyl, —(C$_{1-6}$ alkyl)-$R^6$, —O$R^6$, —S$R^6$, —CO$R^6$, —OC(O)$R^6$, —C(O)O$R^6$, —C(O)N($R^6$)$_2$, —C(O)N($R^6$)SO$_2$$R^6$, —N($R^6$)C(O)$R^6$, —N($R^6$)C(O)O$R^6$, —N($R^6$)C(O)N($R^6$)$_2$, —N($R^6$)$_2$, —SO$_2$$R^6$, —SO$_2$OH, —SO$_2$NHOH, —SO$_2$N($R^6$)$_2$, —SO$_2$N($R^6$)COO$R^6$, —SO$_2$N($R^6$)C(O)$R^6$, —N($R^6$)SO$_2$$R^6$, —(C=O)NHO$R^6$, a C$_{3-8}$ cycloalkyl ring, a 4 to 7-membered heterocyclic ring, a 5 or 6-membered heteroaryl ring, phenyl, benzyl, an oxo group and a bicyclic group; wherein each of said 5 or 6-membered heteroaryl ring or 4 to 7-membered heterocyclic ring contains up to 4 ring heteroatoms independently selected from N, O and S; and wherein each of said C$_{1-6}$ alkyl, C$_{1-6}$ alkyl portion of the —(C$_{1-6}$ alkyl)-$R^6$ moiety, C$_{3-8}$ cycloalkyl ring, 4 to 7-membered heterocyclic ring, 5 or 6-membered heteroaryl ring, benzyl or phenyl group is optionally and independently substituted with up to 3 instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo;

two instances of $R^5$, attached to the same or different atoms of $J^D$, together with said atom or atoms to which they are attached, may optionally form a C$_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O and S; and wherein said C$_{3-8}$ cycloalkyl ring, 4 to 6-membered heterocyclic ring, phenyl or 5 or 6-membered heteroaryl ring is optionally and independently substituted by up to 3 instances of C$_{1-4}$ alkyl, C$_{1-4}$ haloalkyl, C$_{1-4}$ alkoxy, C$_{1-4}$ haloalkoxy, oxo, —C(O)O(C$_{1-4}$ alkyl), —C(O)OH, —NR(CO)O(C$_{1-4}$ alkyl), —CONH$_2$, —OH or halogen; wherein R is hydrogen or a C$_{1-2}$ alkyl;

each $R^{5a}$ is independently selected from halogen, —CN, C$_{1-6}$ alkyl, —(C$_{1-6}$ alkyl)$R^{6a}$, —O$R^{6a}$, —S$R^{6a}$, —CO$R^{6a}$, —OC(O)$R^{6a}$, —C(O)O$R^{6a}$, —C(O)N($R^{6a}$)$_2$, —C(O)N($R^{6a}$)SO$_2$$R^{6a}$, —N($R^{6a}$)C(O)$R^{6a}$, —N($R^{6a}$)C(O)O$R^{6a}$, —N($R^{6a}$)C(O)N($R^{6a}$)$_2$, —N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, —N($R^{6a}$)SO$_2$$R^{6a}$, —(C=O)NHO$R^{6a}$, a C$_{3-8}$ cycloalkyl ring, a 4 to 7-membered heterocyclic ring, a 5 or 6-membered heteroaryl ring, phenyl, benzyl, an oxo group and a bicyclic group; wherein each 5 or 6-membered heteroaryl ring or 4 to 7-membered heterocyclic ring contains up to 4 ring heteroatoms independently selected from N, O and S, wherein each of said C$_{1-6}$ alkyl, C$_{1-6}$ alkyl portion of the —(C$_{1-6}$ alkyl)$R^{6a}$ moiety, C$_{3-8}$ cycloalkyl ring, 4 to 7-membered heterocyclic ring, 5 or 6-membered heteroaryl ring, benzyl or phenyl group is optionally and independently substituted with up to 3 instances of halogen, C$_{1-4}$ alkyl, C$_{1-4}$ haloalkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo;

each $R^{5b}$ is independently selected from halogen, —CN, C$_{1-6}$ alkyl, —(C$_{1-6}$ alkyl)$R^{6a}$, —O$R^{6a}$, —S$R^{6a}$, —CO$R^{6a}$, —OC(O)$R^{6a}$, —C(O)O$R^{6a}$, —C(O)N($R^{6a}$)$_2$, —C(O)N($R^{6a}$)SO$_2$$R^{6a}$, —N($R^{6a}$)C(O)$R^{6a}$, —N($R^{6a}$)C(O)O$R^{6a}$, —N($R^{6a}$)C(O)N($R^{6a}$)$_2$, —N($R^{6a}$)$_2$, —SO$_2$$R^{6a}$, —SO$_2$OH, —SO$_2$NHOH, —SO$_2$N($R^{6a}$)$_2$, —SO$_2$N($R^{6a}$)COO$R^{6a}$, —SO$_2$N($R^{6a}$)C(O)$R^{6a}$, —N($R^{6a}$)SO$_2$$R^{6a}$, —(C=O)NHO$R^{6a}$, a C$_{3-8}$ cycloalkyl ring, a 4 to 7-membered heterocyclic ring, a 5 or 6-membered heteroaryl ring, phenyl, benzyl, an oxo group and a bicyclic group; wherein each 5 or 6-membered heteroaryl ring or 4 to 7-membered heterocyclic ring contains up to 4 ring heteroatoms independently selected from N, O and S, wherein each of said C$_{1-6}$ alkyl, C$_{1-6}$ alkyl portion of the —(C$_{1-6}$ alkyl)$R^{6a}$ moiety, C$_{3-8}$ cycloalkyl ring, 4 to 7-membered heterocyclic ring, 5 or 6-membered heteroaryl ring, benzyl or phenyl group is optionally and independently substituted with up to 3 instances of halogen, C$_{1-4}$ alkyl, C$_{1-4}$ haloalkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, C$_{1-4}$ alkyl, —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a C$_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O($C_{1-4}$ alkyl), —OH or halogen; wherein R is hydrogen or a $C_{1-2}$ alkyl;

each $R^{5c}$ is independently selected from halogen, —CN, $C_{1-6}$ alkyl, —($C_{1-6}$ alkyl)-$R^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, and a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5c}$ attached to the same or different atoms of $R^f$, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl or an oxo group; wherein each 5 or 6-membered heteroaryl ring and 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-$R^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$ (haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, 0 and S;

each $R^{6a}$ is independently selected from hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently selected from hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —C(O)$NH_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, 0 and S;

two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

ring E is a 5 to 7-membered heterocycle or a 5-membered heteroaryl ring; said heterocycle or heteroaryl ring containing up to 4 heteroatoms independently selected from N and O;

o is 0 or an integer selected from 1, 2, and 3;

Y is either absent or is a $C_{1-6}$ alkyl chain, optionally substituted by up to 6 instances of fluoro; and wherein Y is a $C_{1-6}$ alkyl chain, up to 3 methylene units of this alkyl chain, can be replaced by a group selected from —O—, —C(O)— and —N(($Y^1$)—$R^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from hydrogen, —$COR^{10}$, —C(O)$OR^{10}$, —C(O)N($R^{10}$)$_2$, —C(O)N($R^{10}$)$SO_2R^{10}$, —$SO_2R^{10}$, —$SO_2$N($R^{10}$)$_2$, —$SO_2$N($R^{10}$)$COOR^{10}$, —$SO_2$N($R^{10}$)C(O)$R^{10}$, —(C=O)NHO$R^{10}$ a $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and when $Y^1$ is present, each $R^{90}$ is independently selected from hydrogen, halogen, —CN, —$OR^{10}$, —$COR^{10}$, —OC(O)$R^{10}$, —C(O)$OR^{10}$, —C(O)N($R^{10}$)$_2$, —C(O)N($R^{10}$)$SO_2R^{10}$, —N($R^{10}$)C(O)$R^{10}$, —N($R^{10}$)C(O)$OR^{10}$, —N($R^{10}$)C(O)N($R^{10}$)$_2$, —N($R^{10}$)$_2$, —$SO_2R^{10}$, —$SO_2$N($R^{10}$)$_2$, —$SO_2$N($R^{10}$)$COOR^{10}$, —$SO_2$N($R^{10}$)C(O)$R^{10}$, —N($R^{10}$)$SO_2R^{10}$, —(C=O)NHO$R^{10}$, $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from hydrogen, halogen, a $C_{1-6}$ alkyl, —CN, —$OR^{10}$, —$COR^{10}$, —OC(O)$R^{10}$, —C(O)$OR^{10}$, —C(O)N($R^{10}$)$_2$, —C(O)N($R^{10}$)$SO_2R^{10}$, —N($R^{10}$)C(O)$R^{10}$, —N($R^{10}$)C(O)$OR^{10}$, —N($R^{10}$)C(O)N($R^{10}$)$_2$, —N($R^{10}$)$_2$, —$SO_2R^{10}$, —$SO_2$N($R^{10}$)$_2$, —$SO_2$N($R^{10}$)$COOR^{10}$, —$SO_2$N($R^{10}$)C(O)$R^{10}$, —N($R^{10}$)$SO_2R^{10}$, —(C=O)NHO$R^{10}$, $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^{10}$ is independently selected from hydrogen, a $C_{1-6}$ alkyl, —($C_{1-6}$ alkyl)-$R^{13}$, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{11a}$;

each $R^{13}$ is independently selected from a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring and 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from halogen, $C_{1-6}$ alkyl, —CN, —$OR^{12}$, —$COR^{12}$, —C(O)$OR^{12}$, —C(O)N($R^{12}$)$_2$, —N($R^{12}$)C(O)$R^{12}$, —N($R^{12}$)C(O)$OR^{12}$, —N($R^{12}$)C(O)N($R^{12}$)$_2$, —N($R^{12}$)$_2$, —$SO_2R^{12}$, —$SO_2$N($R^{12}$)$_2$ and —N($R^{12}$)$SO_2R^{12}$; wherein each of said $C_{1-6}$ alkyl is optionally and independently substituted by up to 6 instances of fluoro and/or 3 instances of $R^{121}$;

each $R^{11}$ independently selected from halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ and —N(R$^{12}$)SO$_2$R$^{12}$; wherein each of said $C_{1-6}$ alkyl is optionally and independently substituted by up to 6 instances of fluoro and/or 3 instances of $R^{121}$; and each $R^{11b}$ is independently selected from halogen, $C_{1-6}$ alkyl, oxo, —CN, —OR$^{12}$, —COR$^{12}$, —C(O)OR$^{12}$, —C(O)N(R$^{12}$)$_2$, —N(R$^{12}$)C(O)R$^{12}$, —N(S)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ and —N(R$^{12}$)SO$_2$R$^{12}$; wherein each of said $C_{1-6}$ alkyl is optionally and independently substituted by up to 6 instances of fluoro and/or 3 instances of $R^{121}$;

each $R^{12}$ is selected from hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

each $R^{121}$ is selected from hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ fluoroalkyl) or oxo;

$R^{C1}$ is either i) a ring C; or ii) is selected from hydrogen, halogen, oxo, —CN, $C_{1-6}$ aliphatic, —($C_{1-6}$ aliphatic)-R$^N$, —OR$^7$, —OC(O)R$^7$, —O(R$^7$)C(O)N(R$^7$)$_2$, —COR$^7$, —C(O)OR$^7$, —C(O)N(R$^7$)$_2$, —N(R$^7$)C(O)R$^7$, —N(R$^7$)C(O)OR$^7$, —N(R$^7$)C(O)N(R$^7$)$_2$, —N(R$^7$)$_2$, —SR$^7$, —S(O)R$^7$, —SO$_2$R$^7$, —SO$_2$N(R$^7$)$_2$, —C(O)N(R$^7$)SO$_2$R$^7$, —SO$_2$N(R$^7$)COOR$^7$, —SO$_2$N(R$^7$)C(O)R$^7$ and —N(R$^7$)SO$_2$R$^7$; wherein each said $C_{1-6}$ aliphatic, each $C_{1-6}$ aliphatic portion of said —($C_{1-6}$ aliphatic)-R$^N$, is optionally and independently substituted with up to 6 instances of fluoro and/or up to 2 instances of —CN, oxo, —OR$^8$, —N(R$^8$)$_2$, —N(R$^8$)C(O)R$^8$, —N(R$^8$)C(O)R$^8$, —N(R$^8$)C(O)N(R$^8$)$_2$, —SO$_2$R$^8$, —SO$_2$N(R$^8$)$_2$, —NHOR$^8$, —SO$_2$N(R$^8$)COOR$^8$, —SO$_2$N(R$^8$)C(O)R$^8$, —N(R$^8$)SO$_2$R$^8$;

wherein each $R^7$ is independently selected from hydrogen, $C_{1-6}$ alkyl, $C_{1-6}$ fluoroalkyl, a $C_{3-8}$ cycloalkyl ring, phenyl, a 4 to 7-membered heterocyclic ring and a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^8$ is independently selected from hydrogen, $C_{1-6}$ alkyl, $C_{1-6}$ fluoroalkyl, a $C_{3-8}$ cycloalkyl ring, a 4 to 7-membered heterocyclic ring and a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^N$ is independently selected from a phenyl ring, a monocyclic 5 or 6-membered heteroaryl ring, a monocyclic $C_{3-6}$ cycloaliphatic ring, and a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O and S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —OR$^M$, —SR$^M$, —N(R$^M$)$_2$, a $C_{3-8}$ cycloaliphatic ring and a 4 to 8-membered heterocyclic ring; wherein said 4 to 8-membered heterocyclic ring contains 1 or 2 heteroatoms independently selected from N, O and S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring and a 4 to 8-membered heterocyclic ring; wherein each said 4 to 8-membered heterocyclic ring contains between 1 and 3 heteroatoms independently selected from O, N and S; and wherein ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O and S;

wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to p instances of $J^C$; wherein p is 0 or an integer selected from 1, 2 and 3;

each $J^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring and a 4 to 8-membered heterocyclic ring; wherein said 4 to 8-membered heterocyclic ring contains 1 or 2 heteroatoms independently selected from N, O and S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7d}$; or alternatively, two $J^C$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O and S;

each $R^H$ is independently selected from hydrogen, a $C_{1-6}$ aliphatic, a $C_{3-8}$ cycloaliphatic ring and a 4 to 8-membered heterocyclic ring; wherein each said 4 to 8-membered heterocyclic ring contains between 1 and 3 heteroatoms independently selected from O, N and S; alternatively, two instances of $R^H$ linked to the same nitrogen atom of —N(R$^H$)$_2$, together with said nitrogen atom of —N(R$^H$)$_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O and S;

each $R^{7c}$ is independently selected from halogen, —CN, —NO$_2$, $C_{1-4}$ alkyl, $C_{1-4}$ haloalkyl, $C_{3-8}$ cycloalkyl ring, —OR$^{8b}$, —SR$^{8b}$, —N(R$^{8b}$)$_2$, —C(O)O(C$_{1-4}$ alkyl), —C(O)OH, —NR(CO)CO(C$_{1-4}$ alkyl) and an oxo group; wherein each said cycloalkyl group is optionally and independently substituted with up to 3 instances of halogen;

each $R^{7d}$ is independently selected from halogen, —CN, —NO$_2$, $C_{1-4}$ alkyl, $C_{1-4}$ haloalkyl, $C_{3-8}$ cycloalkyl ring, —C(O)O(C$_{1-4}$ alkyl), —C(O)OH, —OR$^{8c}$, —SR$^{8c}$, —N(R$^{8c}$)$_2$, and an oxo group; wherein each said cycloalkyl group is optionally and independently substituted with up to 3 instances of halogen;

each $R^{8b}$ is independently selected from hydrogen, $C_{1-6}$ alkyl, $C_{1-6}$ fluoroalkyl, a $C_{3-8}$ cycloalkyl ring, a 4 to 7-membered heterocyclic ring and a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo;

each $R^{8c}$ is independently selected from hydrogen, $C_{1-6}$ alkyl, $C_{1-6}$ fluoroalkyl, a $C_{3-8}$ cycloalkyl ring, a 4 to 7-membered heterocyclic ring and a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ haloalkyl) or oxo; and $R^{C2}$ is selected from hydrogen, halogen, —OH, —O(C$_{1-6}$ alkyl), —O(haloC$_{1-6}$ alkyl), —O(C$_{1-6}$ haloalkyl), —O(cyclopropyl), cyclopropyl, $C_{1-6}$ alkyl, $C_{1-6}$ haloalkyl and —CN;

provided that the compound is not one represented by Formula C-1 or Formula C-2 depicted below:

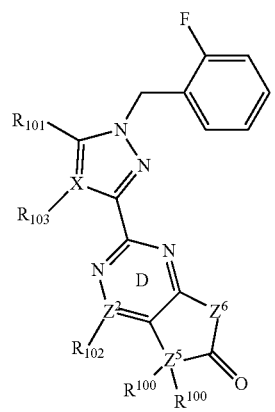

Formula C-1

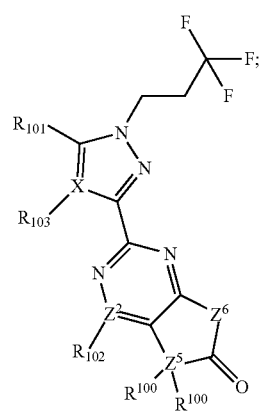

Formula C-2 wherein $Z^2$ is N or C; wherein when $Z^2$ is C, $R^{102}$ is selected from either —NH$_2$, —OH, halogen and hydrogen; or, alternatively, when $Z^2$ is N, $R^{102}$ is a lone pair on N;

$Z^5$ is C or N; wherein when $Z^5$ is C, each $R^{100}$ is independently selected from hydrogen, —CH$_3$, —CF$_3$, —CONH$_2$, —CONH(cyclopropyl), —COOH, —CN, —COO(C$_{1-3}$ alkyl), —NHCOOCH$_3$ and

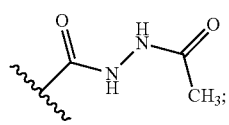 [SMILES: *C(=O)NNC(C)=O]

or, alternatively, when $Z^5$ is N, one of $R^{100}$ is hydrogen and the other is a lone pair on said N;

$R^{101}$ is selected from an isoxazole ring, oxo, —C(O)CH$_3$ and —CH$_2$OMe; wherein $R^{104}$ is selected from hydrogen, methyl, ethyl and isopropyl, said methyl optionally substituted with up to 3 fluorines;

$R^{103}$ is selected from hydrogen, methyl and —CN;

$Z^6$ is selected from NH or C; said C optionally substituted by methyl and ethyl ester;

also, provided that the compound is not one represented by Formula B represented below or a pharmaceutically acceptable salt thereof,

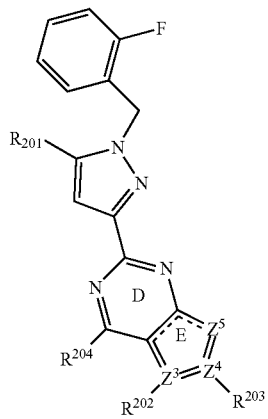

Formula B wherein ring E is a 5-membered, nitrogen containing, heteroaryl ring;

$R^{201}$ is an isoxazole, oxazole or thiazole ring;

$Z^3$ is a ring atom selected from N and C; wherein when $Z^3$ is N, $R^{202}$ is a lone pair on said N or hydrogen or methyl; when $Z^3$ is C, $R^{202}$ is a substituent selected from hydrogen, —OH, —NH$_2$, —OCO(tert-Bu), —NHCOMe and oxo;

$Z^4$ is a ring atom selected from N and C; wherein when $Z^4$ is N, $R^{203}$ is selected from a lone pair on said N, hydrogen and methyl; and wherein when $Z^4$ is C, $R^{203}$ is hydrogen, methyl or —CONH(tert-Bu);

$Z^5$ is a ring atom selected from N and CH;

$R^{204}$ is selected from hydrogen and —NH$_2$;

and provided the compound is not one of the compounds depicted below:

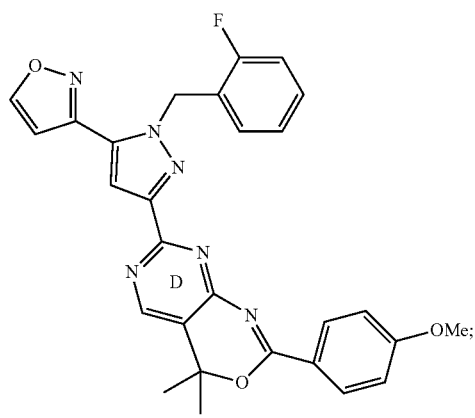

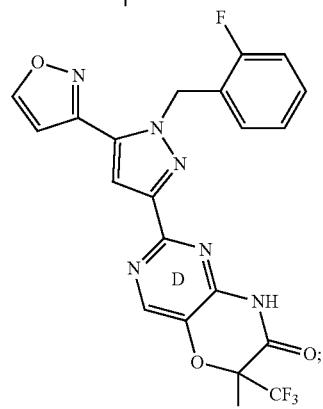

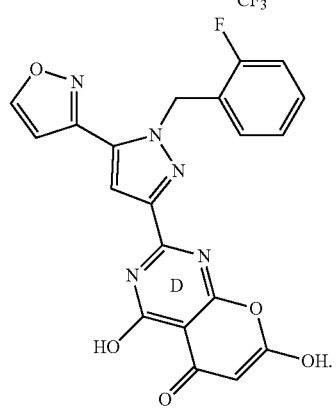

2. The compound according to claim 1, or a pharmaceutically acceptable salt thereof, wherein ring B is phenyl or a 5 to 6-membered heteroaryl ring containing 1 or 2 ring heteroatoms selected from N, O and S.

3. The compound according to claim 1, or a pharmaceutically acceptable salt thereof, wherein:

$R^{C1}$ is selected from hydrogen, halogen, oxo, —CN, C$_{1-6}$ aliphatic, —OR$^7$, —COR$^7$, —C(O)OR$^7$, —C(O)N(R$^7$)$_2$, —N(R$^7$)C(O)R$^7$, —N(R$^7$)$_2$, —SR$^7$, —S(O)R$^7$, —SO$_2$R$^7$, and —SO$_2$N(R$^7$)$_2$; wherein each said C$_{1-6}$ aliphatic is optionally and independently substituted with up to 6 instances of fluoro and up to 2 instances of —OR$^8$ or oxo; and $R^{C2}$ is selected from hydrogen and halogen.

4. The compound according to claim 1, or a pharmaceutically acceptable salt thereof, wherein the compound is represented by Formula I-e:

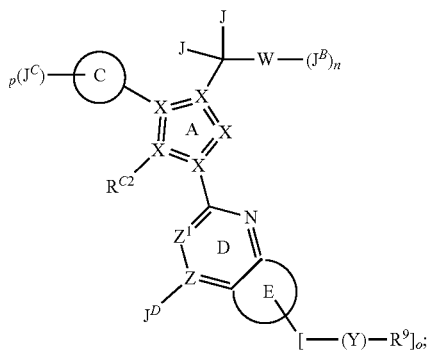

Formula I-e wherein p is 0 or an integer selected from 1 and 2;

ring C is a 5-membered heteroaryl ring containing up to 4 ring heteroatoms selected from N, O and S; wherein said 5-membered heteroaryl ring is not a 1,3,5-triazinyl ring; or alternatively, ring C is selected from a $C_{4-6}$ cycloalkyl ring and a 4 to 6-membered heterocyclic ring containing up to 2 ring heteroatoms selected from N, O and S;

each $J^C$ is independently selected from halogen or a $C_{1-4}$ aliphatic optionally and independently substituted by up to 3 instances of $C_{1-4}$ alkoxy, $C_{1-4}$ fluoroalkoxy, oxo, —C(O)O($C_{1-4}$ alkyl), —C(O)OH, —OH and halogen; and W is a phenyl and each J is hydrogen.

5. The compound according to claim 1, or a pharmaceutically acceptable salt thereof, wherein the compound is represented by Formula I-f or Formula I-g:

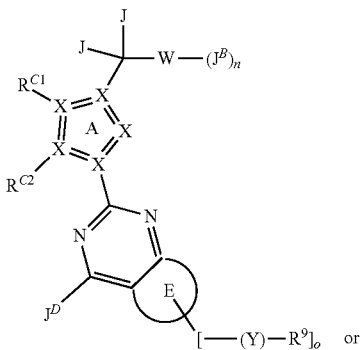

Formula I-f or

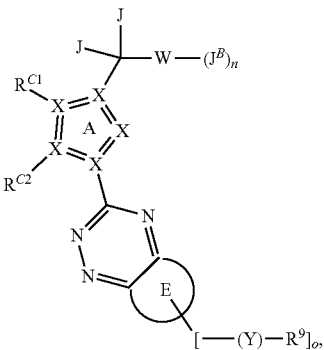

Formula I-g wherein W is ring B and each J is hydrogen.

6. The compound according to claim 1, or a pharmaceutically acceptable salt thereof, wherein $J^D$ is $J^A$, —N($R^D$)$_2$, —N($R^d$)SO$_2$NHR$^D$, —N($R^d$)SO$_2$NHCO(O)OR$^D$, or —N($R^d$)SO$_2$NHC(O)R$^D$.

7. The compound according to claim 1, or a pharmaceutically acceptable salt thereof, wherein the compound is represented by Formula I-h or Formula I-j:

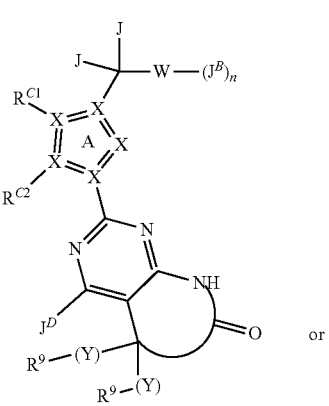

Formula I-h or

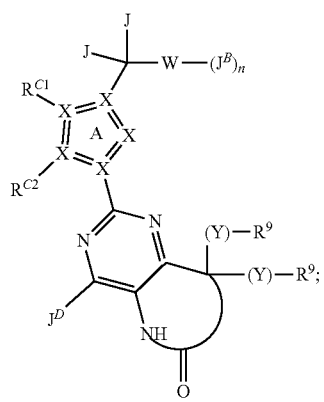

Formula I-j or Formula I-k or Formula I-m:
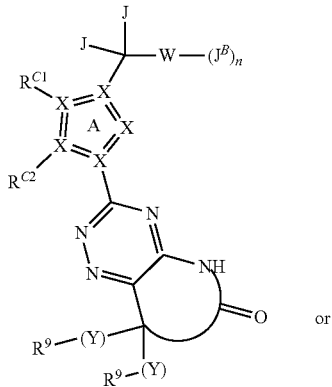
Formula I-k
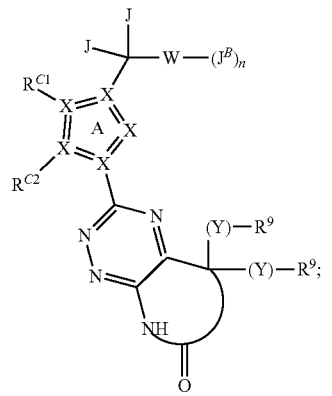
Formula I-m
wherein W is ring B and each J is hydrogen.
8. The compound according to claim 1, wherein the compound is one selected from those depicted in Table I:
TABLE I
I-1
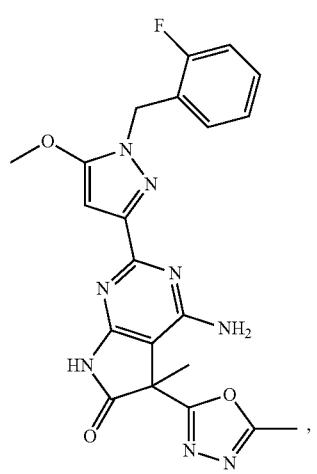
TABLE I-continued
I-2
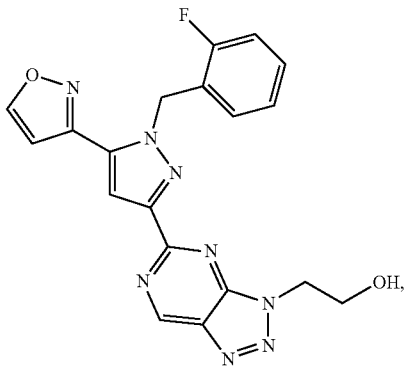 [SMILES: OCCn1nnc2cnc(-c3cc(-c4ccon4)n(Cc4ccccc4F)n3)nc21]
I-3
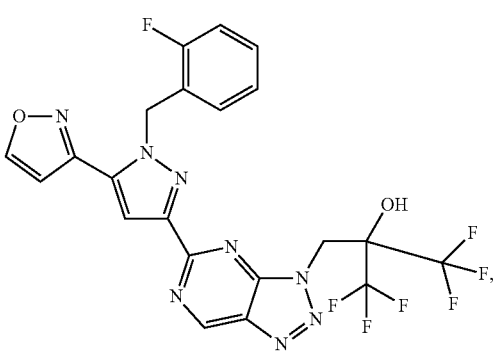 [SMILES: OC(Cn1nnc2cnc(-c3cc(-c4ccon4)n(Cc4ccccc4F)n3)nc21)(C(F)(F)F)C(F)(F)F]
I-4
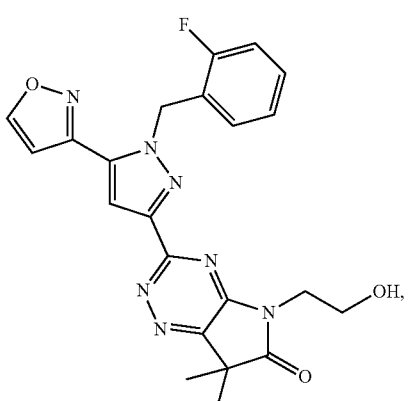
I-5
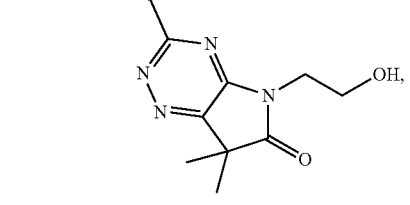

TABLE I-continued
I-6
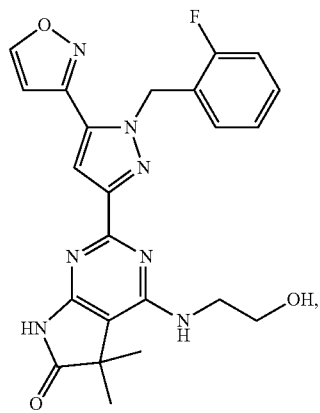 [SMILES: CC1(C)C(=O)Nc2nc(-c3cc(-c4ccon4)n(Cc4ccccc4F)n3)nc(NCCO)c21]
I-7
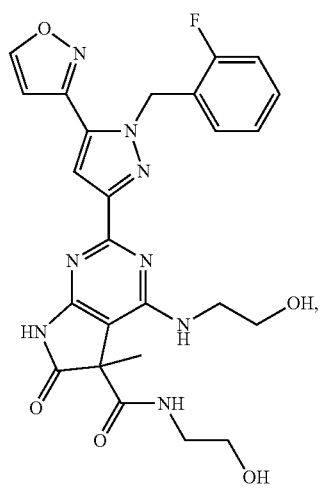 [SMILES: CC1(C(=O)NCCO)C(=O)Nc2nc(-c3cc(-c4ccon4)n(Cc4ccccc4F)n3)nc(NCCO)c21]
I-8
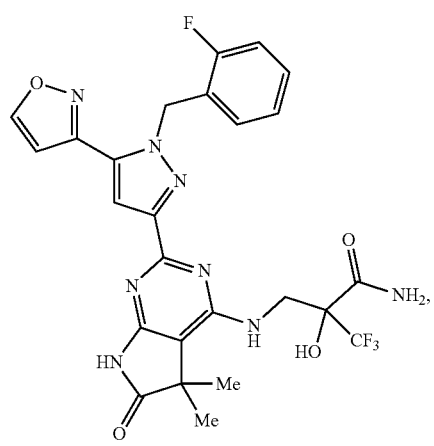 [SMILES: CC1(C)C(=O)Nc2nc(-c3cc(-c4ccon4)n(Cc4ccccc4F)n3)nc(NCC(O)(C(N)=O)C(F)(F)F)c21]
TABLE I-continued
I-9
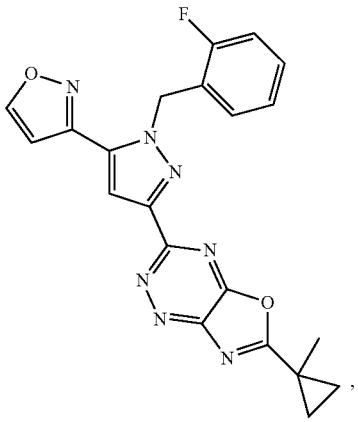 [SMILES: CC1(c2nc3nnc(-c4cc(-c5ccon5)n(Cc5ccccc5F)n4)nc3o2)CC1]
I-10
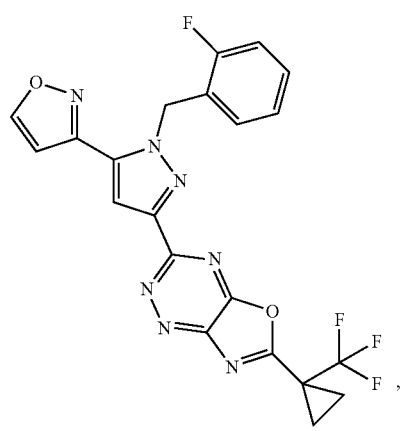 [SMILES: Fc1ccccc1Cn1nc(-c2nnc3nc(C4(C(F)(F)F)CC4)oc3n2)cc1-c1ccon1]
I-11
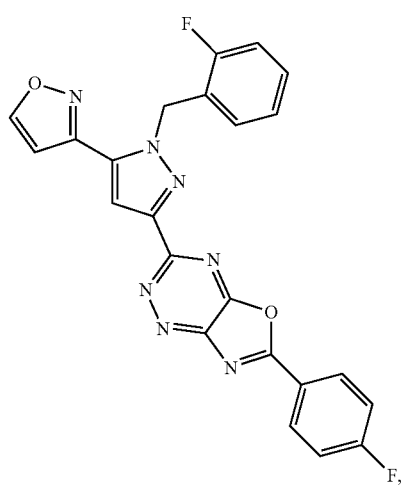 [SMILES: Fc1ccc(-c2nc3nnc(-c4cc(-c5ccon5)n(Cc5ccccc5F)n4)nc3o2)cc1]

TABLE I-continued
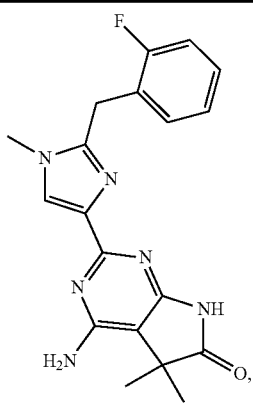
I-12
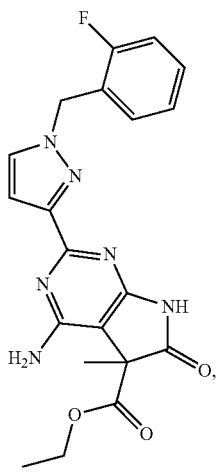 [SMILES: CCOC(=O)C1(C)C(=O)Nc2nc(-c3ccn(Cc4ccccc4F)n3)nc(N)c21]
I-13
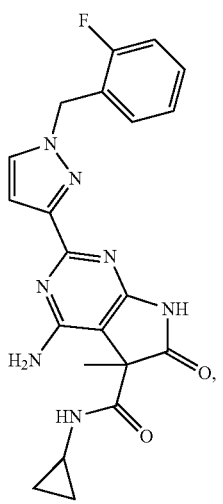 [SMILES: CC1(C(=O)NC2CC2)C(=O)Nc2nc(-c3ccn(Cc4ccccc4F)n3)nc(N)c21]
I-14
TABLE I-continued
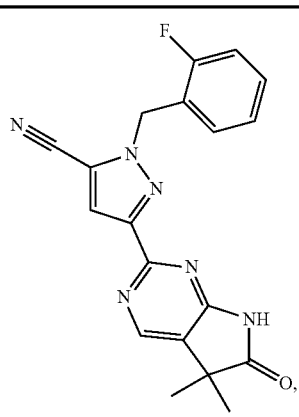
I-45
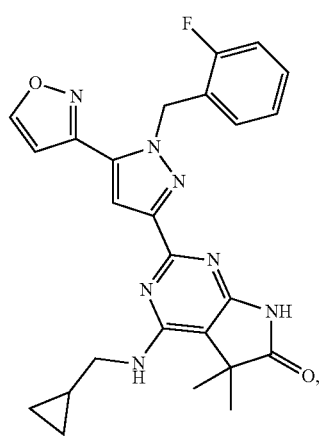 [SMILES: CC1(C)C(=O)Nc2nc(-c3cc(-c4ccon4)n(Cc4ccccc4F)n3)nc(NCC3CC3)c21]
I-46
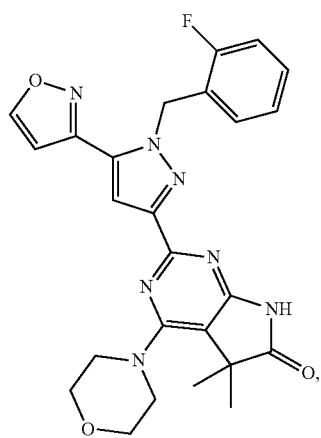 [SMILES: CC1(C)C(=O)Nc2nc(-c3cc(-c4ccon4)n(Cc4ccccc4F)n3)nc(N3CCOCC3)c21]
I-49

TABLE I-continued
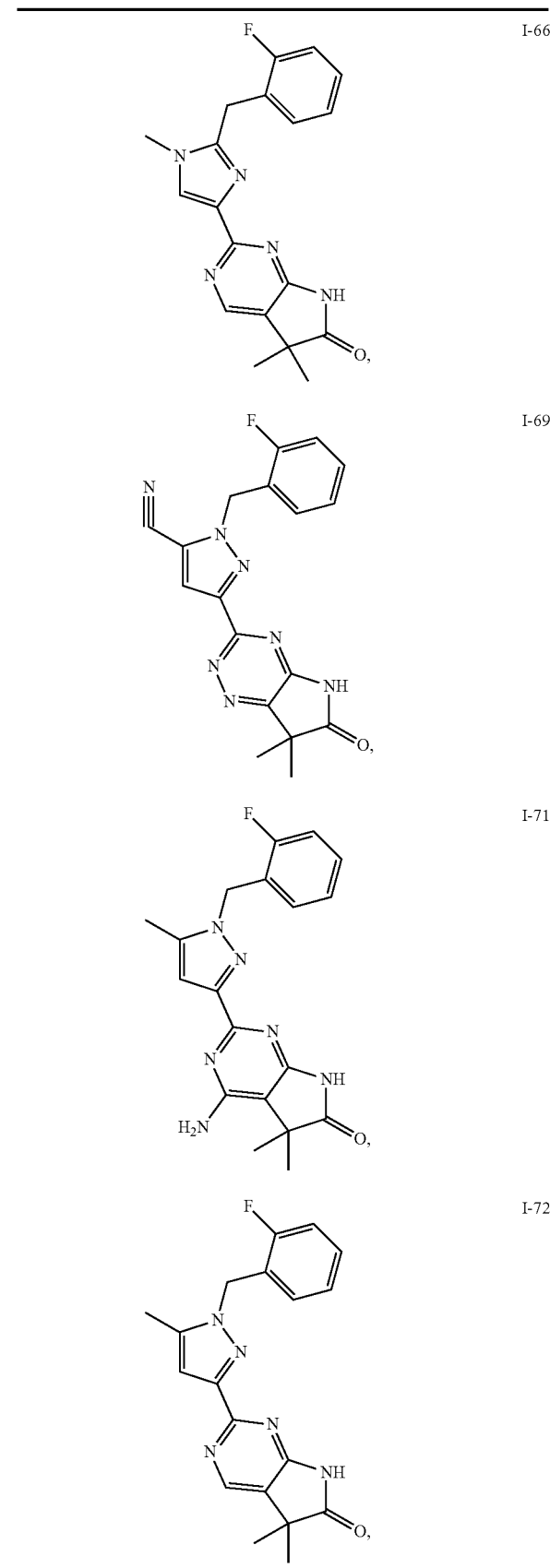
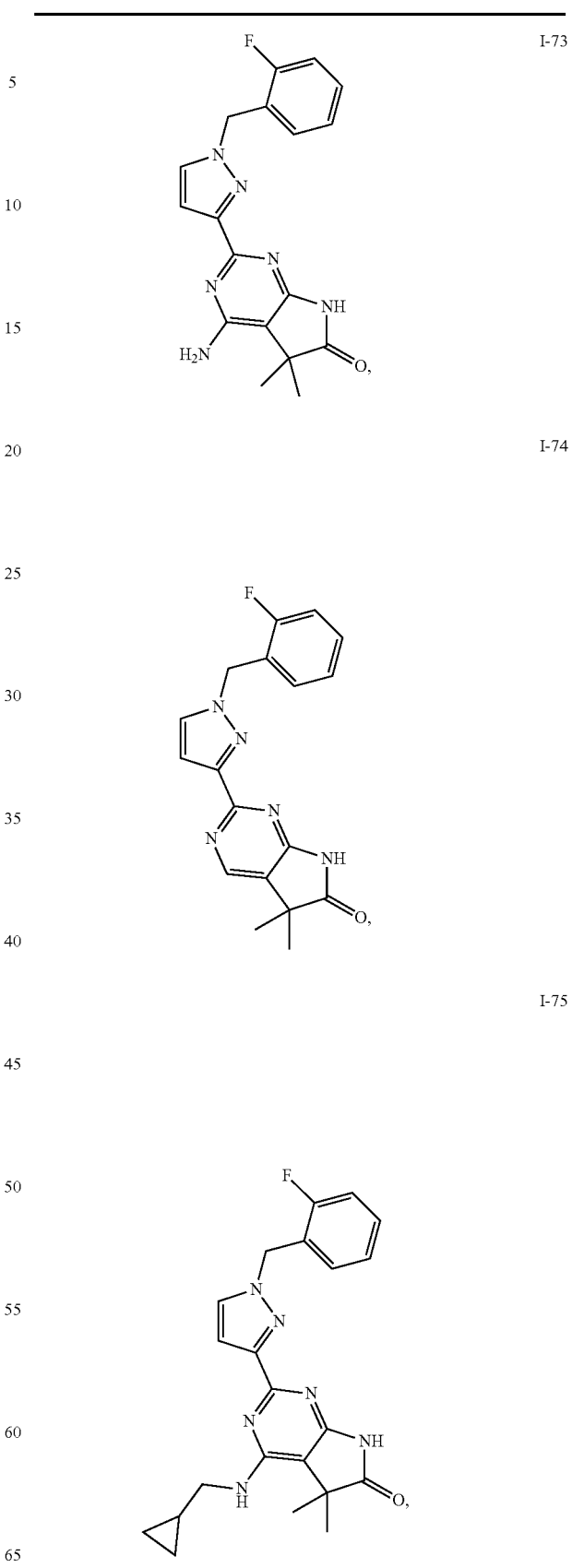

TABLE I-continued
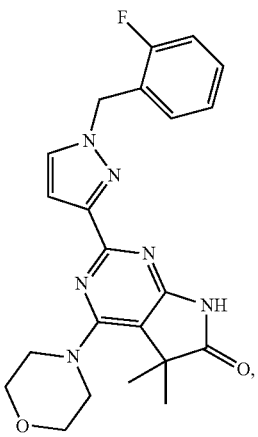 [SMILES: CC1(C)C(=O)Nc2nc(-c3ccn(Cc4ccccc4F)n3)nc(N3CCOCC3)c21]
I-76
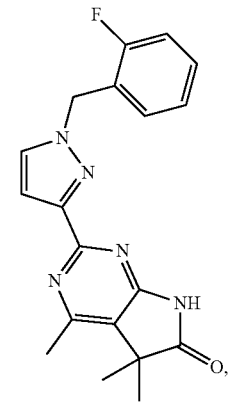 [SMILES: Cc1nc(-c2ccn(Cc3ccccc3F)n2)nc2c1C(C)(C)C(=O)N2]
I-77
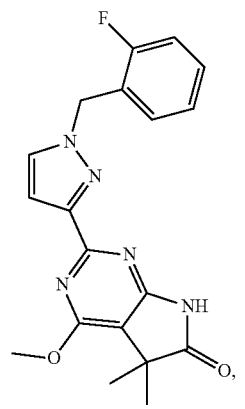 [SMILES: COc1nc(-c2ccn(Cc3ccccc3F)n2)nc2c1C(C)(C)C(=O)N2]
I-78
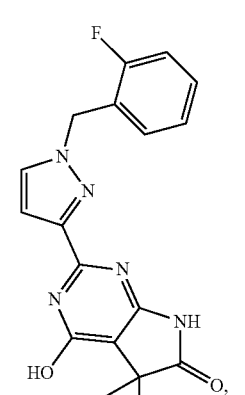
I-79
TABLE I-continued
I-80
I-81
I-84
I-85

TABLE I-continued
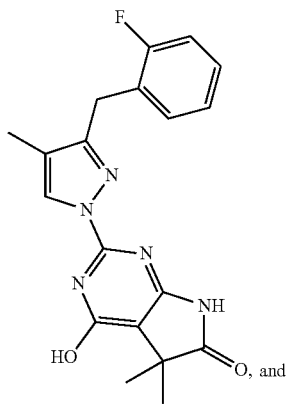 [SMILES: Cc1cn(-c2nc(O)c3c(n2)NC(=O)C3(C)C)nc1Cc1ccccc1F]
I-86
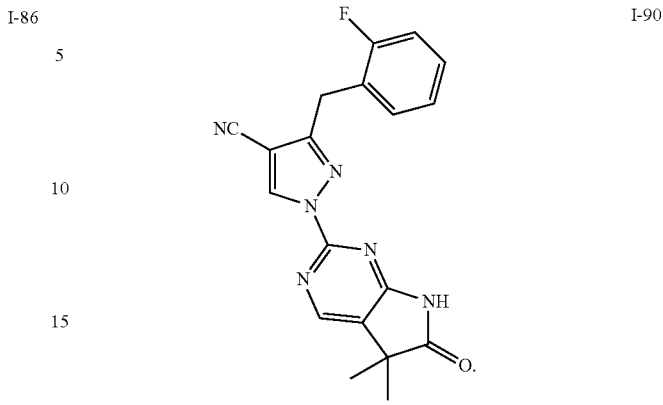
I-90
9. A pharmaceutical composition comprising a compound of claim 1, or a pharmaceutically acceptable salt thereof, and one or more excipients.
* * * * *